(12) United States Patent
Kubota et al.

(10) Patent No.: US 7,592,160 B2
(45) Date of Patent: Sep. 22, 2009

(54) PROCESSES FOR PRODUCING ISOMALTOSE AND ISOMALTITOL AND USE THEREOF

(75) Inventors: Michio Kubota, Okayama (JP);
Tomoyuki Nishimoto, Okayama (JP);
Tomohiko Sonoda, Okayama (JP);
Shigeharu Fukuda, Okayama (JP);
Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 887 days.

(21) Appl. No.: 10/492,932

(22) PCT Filed: Oct. 18, 2002

(86) PCT No.: PCT/JP02/10846

§ 371 (c)(1),
(2), (4) Date: Apr. 19, 2004

(87) PCT Pub. No.: WO03/033717

PCT Pub. Date: Apr. 24, 2003

(65) Prior Publication Data

US 2006/0240531 A1 Oct. 26, 2006

(30) Foreign Application Priority Data

Oct. 18, 2001 (JP) ............................. 2001-321182
Aug. 30, 2002 (JP) ............................. 2002-252609

(51) Int. Cl.
*C12P 19/44* (2006.01)
(52) U.S. Cl. ......................................... 435/74; 435/101
(58) Field of Classification Search .................. None
See application file for complete search history.

(56) References Cited

U.S. PATENT DOCUMENTS

| 4,521,252 | A | | 6/1985 | Miyake et al. |
| 5,679,781 | A | * | 10/1997 | Goldscher .................. 536/18.5 |
| 7,192,746 | B2 | * | 3/2007 | Kubota et al. .................. 435/97 |

FOREIGN PATENT DOCUMENTS

| EP | 0 138 687 A1 | 4/1985 |
| EP | 0 608 636 A1 | 8/1994 |
| EP | 0 875 585 A1 | 11/1998 |
| EP | 1229112 A1 | 8/2002 |
| EP | 1284286 A1 | 2/2003 |
| EP | 1335020 A1 | 8/2003 |
| EP | 1361274 A1 | 11/2003 |
| EP | 1 382 687 A1 | 1/2004 |
| EP | 1382687 A1 | 1/2004 |
| GB | 2 106 912 | 4/1983 |
| JP | 72598/83 | 4/1983 |
| JP | 145020/87 | 6/1987 |
| JP | 216493/88 | 9/1988 |
| JP | 101862/89 | 4/1989 |
| JP | 255988/02 | 9/2002 |
| WO | WO 99/27124 A1 | 6/1999 |
| WO | WO 01/90338 A1 | 11/2001 |
| WO | WO 02/10361 A1 | 2/2002 |
| WO | WO 02/40659 A1 | 5/2002 |
| WO | WO 02/055708 A1 | 7/2002 |
| WO | WO 02/088374 A1 | 11/2002 |

OTHER PUBLICATIONS

Cote, Gregory L. et al "Enzymically produced cyclic α-1,3-linked and α-1,6-linked oligosaccharides of D-glucose," European Journal of Biochemistry, (1994), vol. 226, pp. 641-648.
Iwai, Atsushi et al "Molecular Cloning and Expression of an Isomalto-Dextranase Gene from Arthrobacter globiformis T6," Journal of Bacteriology, Dec. 1994, vol. 176, pp. 7730-7734.
Sawai, Teruo et al, "A Bacterial Dextranase Releasing only Isomaltose from Dextrans," Journal of Biochemistry, (1974), vol. 75, pp. 105-112.
Sawai, Teruo et al "Purification and Some Properties of the Isomaltodextranase of Actinomadura Strain R10 and Comparison with that of Arthrobacter globiformis T6," Carbohydrate Research, (1981), vol. 89, pp. 289-299.
Yamamoto, Kazuya et al "Purification and Some Properties of Dextrin Dectranase from Acetobacter capsulatus ATCC 11894," Bioscience Biotechnology and Biochemistry, (1992), vol. 56(2), pp. 169-173.

* cited by examiner

*Primary Examiner*—Anand U Desai
(74) *Attorney, Agent, or Firm*—Browdy and Neimark, P.L.L.C.

(57) ABSTRACT

The present invention aims to provide a novel process for producing isomaltose and isomaltitol, and uses thereof, and it solves the object by establishing a process for producing isomaltose comprising a step of contacting a saccharide, having the α-1,4 glucosidic linkage as the linkage of non-reducing end and a glucose polymerization degree of at least two, with an α-isomaltosyl-transferring enzyme and an α-isomaltosylglucosaccharide-forming enzyme derived from a specific microorganism; a process for producing isomaltitol using the isomaltose produced by the above process; saccharide compositions comprising the isomaltose and/or the isomaltitol produced by the above processes; and uses thereof.

7 Claims, 50 Drawing Sheets

PROCESSES FOR PRODUCING ISOMALTOSE AND ISOMALTITOL AND USE THEREOF

CROSS-REFERENCE TO RELATED APPLICATIONS

This application is a 35 U.S.C. 371 application of PCT/JP02/10846, filed Oct. 18, 2002, which claims benefit of JP 2001-321182, filed Oct. 18, 2001 and JP 2002-252609, filed Aug. 30, 2002, all of which are herein incorporated by reference in their entirety.

TECHNICAL FIELD

The present invention relates to a novel process for producing isomaltose and isomaltitol, and uses thereof, more particularly, to a process for producing isomaltose and/or isomaltitol in a relatively high yield from a saccharide which has the α-1,4 glucosidic linkage as the linkage of non-reducing end and a glucose polymerization degree of at least two, and uses thereof.

BACKGROUND ART

Isomaltose is a rare saccharide that merely exists in nature in fermented foods in a slight amount, and it is known to be produced by conventional methods such as partial hydrolysis reactions using acid catalysts, enzymatic reactions using dextranase or isomaltodextranase, reverse-synthetic reactions for forming isomaltose from glucose using glucoamylase or acid catalysts, and glucose-transferring reactions for forming isomaltose from maltose or maltodextrins using α-glucosidase. However, the above conventional methods are far from a satisfactory industrial-scale production of isomaltose, because the isomaltose contents in the reaction mixtures, obtained by the above conventional processes, are only about 10 to about 25% (w/w) (the symbol "% (w/w)" is abbreviated as "%" throughout the specification, unless specified otherwise), on a dry solid basis (d.s.b.) and their purities are relatively low. To improve this drawback, for example, a column chromatography, disclosed in Japanese Patent Kokai No. 72,598/83, can be mentioned. According to the method, a relatively high purity isomaltose can be produced from material saccharide solutions with an isomaltose content of about 10 to about 25%, d.s.b. However, even if the method is employed, there still remains a problem of that the purity and the yield of the produced isomaltose inevitably depend on the isomaltose content in the material saccharide solutions used.

Under these circumstances, there has been required a novel process for producing isomaltose on an industrially scale and in a lesser cost and a higher yield.

While isomaltitol is a sugar alcohol having satisfactory non-reducibility, low sweetness, and moisture-retaining ability, and it is a useful sugar alcohol which has been extensively used in food products, cosmetics, pharmaceuticals, etc., in the form of a saccharide mixture with sorbitol, maltitol, and glucosyl-1,6-mannitol.

Isomaltitol can be theoretically prepared by hydrogenating, i.e., reducing the reducing group of paratinose or isomaltose, as a reducing oligosaccharide, into an alcohol group. In particular, although isomaltitol has been prepared from isomaltose in a relatively high yield, the desired industrial supply of material isomaltose has not been satisfactory. Isomaltose is known to be prepared by the methods such as partial hydrolytic reactions of dextrans using acid catalysts, enzymatic reactions using dextranase or isomaltodextranase, reverse-synthetic reaction for forming isomaltose from glucose using glucoamylase or acid catalysts, glucose-transferring reactions for forming isomaltose from maltose or maltodextrins using α-glucosidase. However, the above conventional methods are far from a satisfactory industrial-scale production of isomaltitol, because the isomaltose contents in the reaction mixtures, obtained by the above conventional processes, are only about 10 to about 25%, d.s.b., and the purity of isomaltitol, obtained by hydrogenating the above-identified isomaltose, is relatively low. To improve the drawback, for example, by applying column chromatography disclosed in Japanese Patent Kokai No. 72,598/83, a relatively high purity isomaltose can be obtained from material saccharide solutions with a relatively low isomaltose content of about 10% to about 25%, d.s.b., and then hydrogenated to obtain isomaltitol. Even in the process for producing isomaltitol, as a drawback, the yield and the cost of isomaltitol inevitably depend on the isomaltose content of the material saccharide solutions used, and this lowers the yield and increases the production cost of isomaltitol.

While in the case of producing isomaltitol from paratinose, the material paratinose is known to be prepared, for example, from sucrose through glucose-transferring reaction using α-glucosyl transferase. However, since the resulting reaction mixture comprises, as by products, trehalulose as an isomer of paratinose and others such as glucose and fructose as hydrolyzates of paratinose, the paratinose content in the reaction mixture could not be over about 85%, d.s.b. In producing isomaltitol from paratinose, glucosyl-1,6-mannitol is formed along with isomaltitol in a production ratio of, usually, 1:1 by weight, and this lowers the purity and the yield of isomaltitol as a drawback.

Under these circumstances, a novel process for producing isomaltitol on an industrial scale and in a lesser cost and a higher yield has been strongly required.

DISCLOSURE OF INVENTION

Considering the above prior arts, the object of the present invention is to establish a process for producing isomaltose and isomaltitol on an industrial scale and in a lesser cost and a higher yield, and uses thereof. Namely, the object of the present invention is to establish a process for producing isomaltose and isomaltitol on an industrial scale and in a lesser cost and a higher yield, saccharide mixtures comprising isomaltose and/or isomaltitol, and uses thereof.

During the present inventors had been eagerly studying on solving the above objects, it was reported in *European Journal of Biochemistry*, Vol. 226, pp. 641-648 (1994) a cyclic tetrasaccharide, having the structure of cyclo{→6)-α-D-glucopyranosyl-(1→3)-α-D-glucopyranosyl-(1→6)-α-D-glucopyranosyl-(1→3)-α-D-glucopyranosyl-(1→} (may be called "cyclotetrasaccharide" throughout the specification), having the structure of isomaltose intramolecularly, formed by contacting a hydrolyzing enzyme, i.e., alternanase, with alternan composed of four glucose molecules linked together via the alternating α-1,3 and α-1,6 bonds.

As previously disclosed in Japanese Patent Application No. 2000-229557 (International Publication No. WO 01/90338), the present inventors established a process for producing cyclotetrasaccharide using an α-isomaltosyl-transferring enzyme which forms cyclotetrasaccharide from amylaceous saccharides such as panose, and in Japanese Patent Application No. 2000-234937 (International Publication No. WO 02/10361), they established another process for producing cyclotetrasaccharide in a higher yield by allowing an α-isomaltosyl-transferring enzyme and an α-isomaltosylglucosaccharide-forming enzyme which forms α-isomaltosylglucosaccharide from maltooligosaccharides. Further, as disclosed in Japanese Patent Application No. 2001-130922 (International Publication No. WO 02/04166), the present inventors established another process for producing isomaltose in a higher yield by allowing an α-isomaltosylglucosaccharide-forming enzyme and an isomaltose-releasing enzyme to act on material starches.

Thereafter, the present inventors discovered α-isomaltosylglucosaccharides and an α-isomaltosylglucosaccharide-forming enzyme, which can be used in the above process for producing isomaltose, and also found that isomaltose is produced on an industrial scale and in a lesser cost and a higher yield by using these enzymes. The present inventors further studied the method for producing isomaltitol from isomaltose; they studied the enzymatic reaction mechanisms of such α-isomaltosylglucosaccharide-forming enzyme and α-isomaltosyl-transferring enzyme and found that the production yield of isomaltose is dramatically increased by allowing an α-isomaltosylglucosaccharide-forming enzyme and an α-isomaltose-releasing enzyme capable of releasing isomaltose to act on a saccharide having the α-1,4 glucosidic linkage as the linkage of non-reducing end and a glucose polymerization degree of at least two in the presence or the absence of α-isomaltosyl-transferring enzyme, and that isomaltitol is easily produced on an industrial scale and in an increased yield by hydrogenating the isomaltose thus obtained. The present inventors also established the uses of the isomaltitol thus obtained and accomplished this invention; they solved the above object by establishing a process for producing isomaltose comprising a step of contacting a saccharide, having the α-1,4 glucosidic linkage as the linkage of non-reducing end and a glucose polymerization degree of at least two, with one or more α-isomaltosylglucosaccharide-forming enzymes derived from *Bacillus globisporus* N75 strain (FERM BP-7591) (hereinafter may be called "N75 strain"), *Arthrobacter globiformis* A19 strain (FERM BP-7590) (hereinafter may be called "A19 strain"), and *Arthrobacter ramosus* S1 strain (FERM BP-7592) (hereinafter may be called "S1 strain"), which are disclosed in PCT/JP01/06412 (International Publication No. WO 02/10361) in the presence or the absence of α-isomaltosyl-transferring enzyme derived from *Bacillus globisporus* N75 strain (FERM BP-7591) and/or *Arthrobacter globiformis* A19 strain (FERM BP-7590) to form α-isomaltosylglucosaccharides having the α-1,6 glucosidic linkage as the linkage of non-reducing end and the α-1,4 glucosidic linkage other than the above linkage, and/or to form a saccharide with the structure of cyclo{→6)-α-D-glucopyranosyl-(1→3)-α-D-glucopyranosyl-(1→6)-α-D-glucopyranosyl-(1→3)-α-D-glucopyranosyl-(1→}, contacting the products thus obtained with isomaltose-releasing enzyme to form isomaltose, and collecting the produced isomaltose; saccharide mixtures with such isomaltose; and uses thereof. As regards the above-identified *Bacillus globisporus* N75 strain (FERM BP-7591), the microorganism was deposited on May 16, 2001, and has been maintained in International Patent Organism Depositary National Institute of Advanced Industrial Science and Technology, AIST Tsukuba Central 6, 1-1, Higashi 1-Chome, Tsukuba-shi, Ibaraki-ken, 305-8566, Japan. *Arthrobacter ramosus* S1 strain (FERM BP-7592) was deposited on May 16, 2001, and has been maintained in the above institute.

The present inventors further solved the object of the present invention by contacting a saccharide, having the α-1,4 glucosidic linkage as the linkage of non-reducing end and a glucose polymerization degree of at least two, with α-isomaltosylglucosaccharide-forming enzyme in the presence or the absence of α-isomaltosyl-transferring enzyme to form α-isomaltosylglucosaccharides, having the α-1,6 glucosidic linkage as the linkage of non-reducing end and α-1,4 glucosidic linkage other than the above linkage and having a glucose polymerization degree of at least three, and/or cyclotetrasaccharide; contacting the resulting saccharides with isomaltose-releasing enzyme to form isomaltose; hydrogenating the resulting mixtures containing isomaltose directly or after collecting isomaltose to form isomaltitol; and collecting the formed isomaltitol; saccharide mixtures containing isomaltitol; and uses thereof.

BEST MODE FOR CARRYING OUT THE INVENTION

Figure 1:
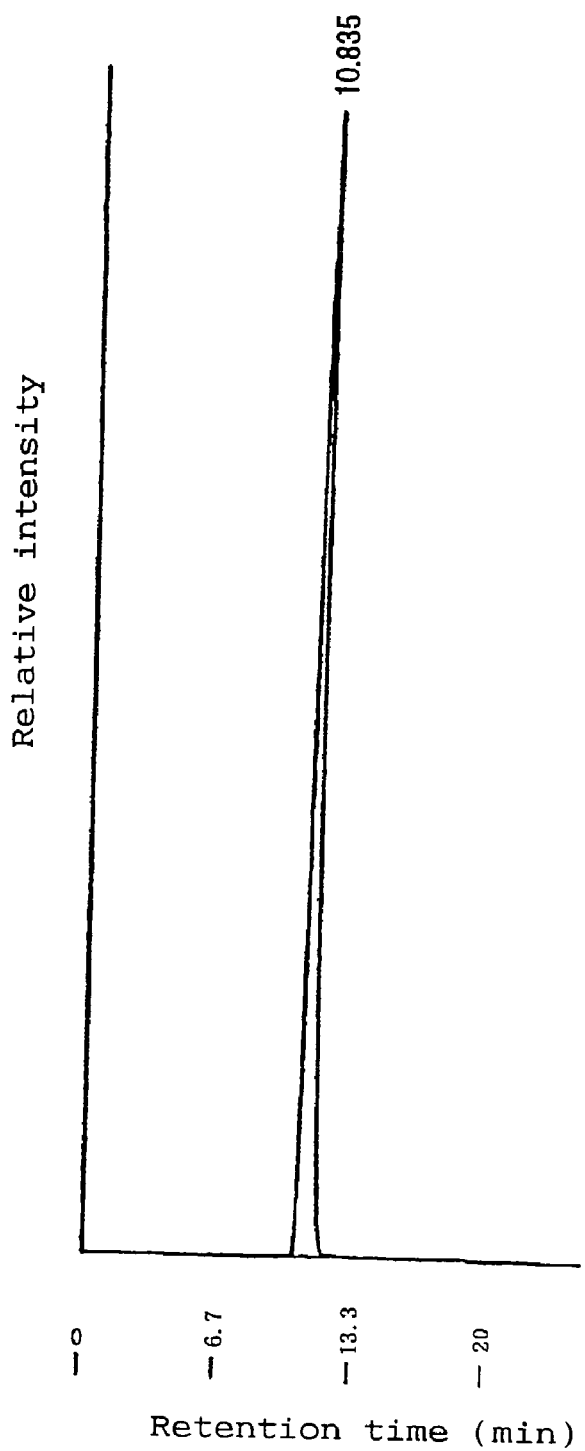
FIG. 1 is an elution pattern of a saccharide, obtained by the enzymatic reaction using α-isomaltosyl-transferring enzyme from a microorganism of the species *Bacillus globisporus* C9 strain, when determined on high-performance liquid chromatography.

The α-isomaltosylglucosaccharide-forming enzyme as referred to as in the present invention means those which forms α-isomaltosylglucosaccharides such as α-isomaltosylglucose (or panose), α-isomaltosylmaltose, α-isomaltosylmaltotriose, and α-isomaltosyltetraose; α-isomaltosylglucosaccharide-forming enzymes derived from microorganisms of the species *Bacillus globisporus* C9 strain (FERM BP-7143) (hereinafter may be called "C9 strain"), *Bacillus globisporus* C11 strain (FERM BP-7144) (hereinafter may be called "C11 strain"), Bacillus globisporus N75 strain (FERM BP-7591), and *Arthrobacter globiformis* A19 strain (FERM BP-7590), which are disclosed in PCT/JP01/06412 (International Publication No. WO 02/10361); and recombinant polypeptides having an activity of α-isomaltosylglucosaccharide-forming enzyme, which is disclosed in Japanese Patent Application No. 2001-5441 (International Publication No. WO 02/055708). Among these enzymes, those from *Bacillus globisporus* N75 strain (FERM BP-7591)

and *Arthrobacter globiformis* A19 strain (FERM BP-7590) are most preferably used in the present invention. As regards the above-identified *Bacillus globisporus* C9 strain (FERM BP-7143), and *Bacillus globisporus* C11 strain (FERM BP-7144) were deposited on Apr. 25, 2000, and have been maintained in National Institute of Bioscience and Human-Technology Agency of Industrial Science and Technology, now changed into International Patent Organism Depositary National Institute of Advanced Industrial Science and Technology, AIST Tsukuba Central 6, 1-1, Higashi 1-Chome, Tsukuba-shi, Ibaraki-ken, 305-8566, Japan.

The α-isomaltosylglucosaccharide-forming enzyme as referred to as in the present invention is a generic term for enzymes and polypeptides which have an activity of α-isomaltosylglucosaccharide-forming enzyme, and it is an enzyme which forms, via the α-glucosyl-transfer, a saccharide, having a glucose polymerization degree of at least three and having both the α-1,6 glucosidic linkage as the linkage of non-reducing end and the α-1,4 glucosidic linkage other than the above linkage, from a material saccharide having a glucose polymerization degree of at least two and having the α-1,4 glucosidic linkage as the linkage of non-reducing end, without substantially increasing the reducing power of the material saccharide used; has no dextran-forming ability; and which is inhibited by EDTA (ethylenediaminetetraacetic acid). More particularly, the above material saccharide, having both a glucose polymerization degree of at least two and the α-1,4 glucosidic linkage as the linkage of non-reducing end, includes, for example, one or more saccharides selected from maltooligosaccharides, maltodextrins, amylodextrins, amyloses, amylopectins, soluble starches, gelatinized starches, and glycogens. The above α-isomaltosylglucosaccharide-forming enzyme has the following physicochemical properties:

(1) Action

Forming a saccharide having a glucose polymerization degree of at least three and having both the α-1,6 glucosidic linkage as the linkage at the non-reducing end and the α-1,4 glucosidic linkage other than the above linkage, via the α-glucosyl-transfer from a material saccharide having a glucose polymerization degree of at least two and having the α-1,4 glucosidic linkage as the linkage at the non-reducing end, without substantially increasing the reducing power of the material saccharide;

(2) Molecular weight

Having a molecular weight of about 74,000 to about 160,000 daltons when determined on SDS-PAGE (sodium dodecyl sulfate polyacrylamide gel electrophoresis);

(3) Isoelectric point

Having an isoelectric point of about 3.8 to about 7.8 when determined on isoelectrophoresis using ampholine;

(4) Optimum temperature

Having an optimum temperature of about 40° C. to about 50° C. when incubated at a pH of 6.0 for 60 min;

Having an optimum temperature of about 45° C. to about 55° C. when incubated at a pH of 6.0 for 60 min in the presence of 1 mM $Ca^{2+}$;

Having an optimum temperature of 60° C. when incubated at a pH of 8.4 for 60 min; or Having an optimum temperature of 65° C. when incubated at a pH of 8.4 for 60 min in the presence of 1 mM $Ca^{2+}$;

(5) Optimum pH

Having an optimum pH of about 6.0 to about 8.4 when incubated at 35° C. for 60 min;

(6) Thermal stability

Having a thermostable region at temperatures of about 45° C. or lower when incubated at a pH of 6.0 for 60 min, Having a thermostable region at temperatures of about 50° C. or lower when incubated at a pH of 6.0 for 60 min in the presence of 1 mM $Ca^{2+}$, Having a thermostable region at temperatures of about 55° C. or lower when incubated at a pH of 8.0 for 60 min, and Having a thermostable region at temperatures of about 60° C. or lower when incubated at a pH of 8.0 for 60 min in the presence of 1 mM $Ca^{2+}$;

(7) pH Stability

Having a stable pH region at about 4.5 to about 10.0 when incubated at 4° C. for 24 hours; and (8) N-Terminal amino acid sequence tyrosine-valine-serine-serine-leucine-glycine-asparagine-leucine-isoleucine, histidine-valine-serine-alanine-leucine-glycine-asparagine-leucine-leucine, alanine-proline-leucine-glycine-valine-glutamine-arginine-alanine-glutamine-phenylalanine-glutamine-serine-glycine, or others.

The α-isomaltosyl-transferring enzyme used in the present invention means an enzyme, which forms cyclotetrasaccharide from α-isomaltosylglucosaccharides such as panose and isomaltosylmaltose, for example, α-isomaltosyl-transferring enzymes derived from *Bacillus globisporus* C9 strain (FERM BP-7143), *Bacillus globisporus* C11 strain (FERM BP-7144), *Bacillus globisporus* N75 strain (FERM BP-7591), *Arthrobacter globiformis* A19 strain (FERM BP-7590), and *Arthrobacter ramosus* S1 strain (FERM BP-7592), as well as recombinant polypeptides having an activity of α-isomaltosyl-transferring enzyme disclosed in PCT/JP01/10044 (International Publication No. WO 02/40659), which all have an α-isomaltosyl-transferring activity and are called as a general term of "α-isomaltosyl-transferring enzyme" in the present invention. Among these enzymes, those from *Bacillus globisporus* N75 strain (FERM BP-7591), *Arthrobacter globiformis* A19 strain (FERM BP-7590), and *Arthrobacter ramosus* S1 strain (FERM BP-7592) are most preferably used in the present invention. The α-isomaltosyl-transferring enzyme usable in the present invention has the following physicochemical properties:

(1) Action

Forming a cyclotetrasaccharide having the structure of cyclo{→6)-α-D-glucopyranosyl-(1→3)-α-D-glucopyranosyl-(1→6)-α-D-glucopyranosyl-(1→3)-α-D-glucopyranosyl-(1→} from a saccharide having a glucose polymerization degree of at least three and having both the α-1,6 glucosidic linkage as the linkage at the non-reducing end and the α-1,4 glucosidic linkage other than the above linkage;

(2) Molecular weight

Having a molecular weight of about 82,000 to about 136,000 daltons when determined on SDS-PAGE;

(3) Isoelectric point (pI)

Having a pI of about 3.7 to about 8.3 when determined on isoelectrophoresis using ampholine;

(4) Optimum temperature

Having an optimum temperature of about 45° C. to about 50° C. when incubated at a pH of 6.0 for 30 min;

(5) Optimum pH

Having an optimum pH of about 5.5 to about 6.5 when incubated at 35° C. for 30 min;

(6) Thermal stability

Having a thermostable range at temperatures of about 45° C. or lower when incubated at a pH of 6.0 for 60 min;

(7) pH Stability

Having a stable pH range at about 3.6 to about 10.0 when incubated at 4° C. for 24 hours.

(8) N-Terminal amino acid sequence isoleucine-aspartic acid-glycine-valine-tyrosine-histidine-alanine-proline, aspartic acid-threonine-leucine-serine-glycine-valine-phenylalanine-histidine-glycine-proline, or others.

The isomaltose-releasing enzyme used in the present invention means an enzyme, which has an action of releasing isomaltose from α-isomaltosylglucosaccharides or cyclotetrasaccharide, such as isomaltodextranase (EC 3.2.1.94) derived from microorganisms of the species *Arthrobacter globiformis* T6 (NRRL B-4425) reported in *Journal of Biochemistry*, Vol. 75, pp. 105-112 (1974); *Arthrobacter globiformis* (IAM 12103) which is distributed and available from Institute of Molecular and Cellular Biosciences, the University of Tokyo, Tokyo, Japan; and *Actinomadura* R10 (NRRL B-11411) disclosed in *Carbohydrate Research*, Vol. 89, pp. 289-299 (1981).

The saccharide usable in the present invention, which has the α-1,4 glucosidic linkage as the linkage of non-reducing end and a glucose polymerization degree of at least two, means one or more saccharides selected from maltooligosaccharides, maltodextrins, amylodextrins, amyloses, amylopectins, soluble starches, liquefied starches, gelatinized starches, and glycogens. Examples of material starches for the above-identified soluble starches, liquefied starches, and gelatinized starches are, for example, terrestrial starches such as corns, rices, and wheats; subterranean starches such as potatoes, sweet potatoes, and tapioca; and partial hydrolyzates thereof, i.e., partial starch hydrolyzates. Preferably, such partial starch hydrolyzates can be generally prepared by suspending the above terrestrial or subterranean starches in water into starch suspensions with a concentration, usually, of at least 10%, preferably, 15 to 65%, and more preferably, 20 to 50%; and liquefying the starch suspensions with acids or enzyme preparations. The liquefaction degree of the above terrestrial and subterranean starches is preferably set to a relatively low level, usually, a DE (dextrose equivalent) of less than 15, preferably, a DE of less than 10, and more preferably, DE of 9 to 0.1. In the case of liquefying the above terrestrial or subterranean starches with acids, for example, employed are methods which comprise the steps of liquefying the starches with acids such as hydrochloric acid, phosphoric acid, and oxalic acid; and then usually neutralizing the resulting mixtures with one or more alkalis such as calcium carbonate, calcium oxide, and sodium carbonate to adjust the mixtures to a desired pH. In the case of liquefying the above terrestrial or subterranean starches with an enzyme such as α-amylase, particularly, thermostable liquefying α-amylase can be preferably used as such an enzyme in the present invention. Isomaltose can be obtained in a higher yield by contacting saccharides, having the α-1,4 glucosidic linkage as the linkage of their non-reducing ends and a glucose polymerization degree of at least two, with α-isomaltosylglucosaccharide-forming enzyme in the presence or the absence of α-isomaltosyl-transferring enzyme to form cyclotetrasaccharide and/or α-isomaltosylglucosaccharides having the α-1,6 glucosidic linkage as the linkage of their non-reducing ends and the α-1,4 glucosidic linkage as a linkage other than that of their non-reducing ends; and contacting the formed saccharides with isomaltose-releasing enzyme to form isomaltose; and collecting the formed isomaltose. In the case of contacting the terrestrial or subterranean starches with α-isomaltosylglucosaccharide-forming enzyme in the presence or the absence of α-isomaltosyl-transferring enzyme, one or more enzymes selected from α-isomaltosyl-transferring enzyme, cyclomaltodextrin glucanotransferase (abbreviated as "CGTase" hereinafter), α-glucosidase, glucoamylase, and starch debranching enzyme including isoamylase and pullulanase can be used in combination; or one or more enzymes selected from α-isomaltosyl-transferring enzyme, CGTase, α-glucosidase, glucoamylase, and isoamylase can be used after the action of α-isomaltosylglucosaccharide-forming enzyme in the presence or the absence of α-isomaltosyl-transferring enzyme, whereby isomaltose can be formed in a relatively high yield. In particular, the production yield of isomaltose from cyclotetrasaccharide can be increased to 100% as the highest possible level by allowing isomaltose-releasing enzyme to act on cyclotetrasaccharide, prepared by contacting α-isomaltosylglucosaccharide-forming enzyme with saccharides, having α-1,4 glucosidic linkage as the linkage of non-reducing end and a glucose polymerization degree of at least two, in the presence of α-isomaltosyl-transferring enzyme. In practicing the present invention, the order of the enzymes used can be decided depending on the desired production yield of isomaltose, reaction time, reaction condition, etc., a plurality of enzymes can be used simultaneously; or a requisite amount of enzymes can be divided into portions and used at different timings. The pH for the enzymatic reactions of the enzymes used in the present invention is usually in the range of pH 4 to 10, preferably, pH 5 to 9. The temperature for the enzymatic reactions of the enzymes used in the present invention is usually in the range of 10 to 80° C., preferably, 30 to 70° C. The amount of enzymes used can be appropriately set depending on the reaction conditions and reaction times for each enzyme, and it is usually appropriately selected from 0.01 to 100 units/g substrate for α-isomaltosyl-transferring enzyme and α-isomaltosylglucosaccharide-forming enzyme, 1 to 10,000 units/g substrate for isomaltose-releasing enzyme and starch debranching enzyme, and 0.05 to 7,000 units/g substrate for CGTase, α-glucosidase, glucoamylase, and isoamylase. Varying depending on the amount of the enzymes used, the reaction time is appropriately set in view of the aimed production yield of isomaltose, usually, it is set to terminate the whole enzymatic reactions within 1 to 200 hours, preferably, 5 to 150 hours, and more preferably, 10 to 100 hours. The pH and temperature during each enzymatic reaction can be appropriately altered before completion of the enzymatic reactions of the present invention.

The content of isomaltose in the enzymatic reaction mixtures thus obtained usually reaches at least 30%, preferably, at least 40%, more preferably, at least 50%, and more preferably, 99% or more as the highest possible level. Particularly, enzymatic reaction mixtures having an isomaltose content of at least 50%, d.s.b., can be easily obtained by contacting α-isomaltosylglucosaccharide-forming enzyme, α-isomaltosyl-transferring enzyme, and isomaltose-releasing enzyme simultaneously or in this order with saccharides having the α-1,4 glucosidic linkage as the linkage of non-reducing end and a glucose polymerization degree of at least two. The above enzymatic reaction mixtures are usually subjected to conventional methods of filtration and centrifugation to remove insoluble impurities, followed by desalting to purify the resulting mixtures with ion exchangers in H- and OH-forms, and concentrating the resultants into syrups. The resulting syrups can be dried into solid or powdery products.

If necessary, the above syrups and products can be purified into high isomaltose content products by using one or more fractionations using column chromatography using ion-exchangers, activated charcoals, and silica gels, etc.; separations using organic solvents such as alcohols and acetone; and separation methods using membranes, which can be used in an appropriate combination. In particular, as an industrial scale production method for high isomaltose content products, column chromatography using ion-exchange resins is advantageously used; column chromatography using one or more strong-acid cation exchange resins in an alkaline metal form of $Na^+$, etc., or alkaline earth metal forms of $Ca^{2+}$, $Mg^{2+}$, etc., of styrene-divinylbenzene cross-linked copolymer resins with sulfonic group, as disclosed, for example, in Japanese Patent Kokai Nos. 23,799/83 and 72,598/83, facilitates the production of high isomaltose content products on an industrial scale and in a relatively high yield and low cost. Examples of commercialized products of the above-identified strong-acid cation exchange resins are "DOWEX 50W-X2™", "DOWEX 50W-X4™", and "DOWEX 50W-X8™", commercialized by Dow Chemical Co., Midland, Mich., USA; "AMBERLITE CG-120™" commercialized by Rohm & Hass Company, PA, USA; "XT-1022E™", commercialized by Tokyo Organic Chemical Industries, Ltd., Tokyo, Japan; "DIAION SK1B™", "DIAION SK102™", "DIAION SK104™", etc., which are cation exchangers commercialized by Mitsubishi Chemical Corporation, Tokyo, Japan. In practicing such column chromatography using the above ion-exchange resins, any one of fixed-bed, moving bed, and semi-moving methods can be employed. With these methods, isomaltose can be increased its purity, d.s.b., usually, up to 60% or more, preferably, 80% or more, and more preferably, 99% or more, as the highest possible purity, in a relatively high yield. High isomaltose content products other than the isomaltose with the highest possible purity usually comprise isomaltose and one or more saccharides selected from glucose, maltose, maltotriose, maltotetraose, other partial starch hydrolyzates, α-isomaltosylglucosaccharide, cyclotetrasaccharide, and α-glucosyl-(1→6)-α-glucosyl-(1→3)-α-glucosyl-(1→6)-glucose (hereinafter may be abbreviated as "ring-opened tetrasaccharide") in a total amount, excluding that of isomaltose, usually, of 1 to 60%, d.s.b. To industrially produce isomaltitol by hydrogenating isomaltose, the above-identified desalting and purification steps using ion-exchangers in H- and OH-forms can be omitted, if necessary.

By hydrogenating the resulting isomaltose or isomaltose-containing products in the presence of reducing catalysts, isomaltitol and high isomaltitol content products can be produced in a relatively high yield. For example, the Raney Nickel catalyst is added to a 40-60% aqueous isomaltose solution. The mixture is placed in a high-pressure vessel, filled with hydrogen, increased its inner pressure, and stirred at temperatures of 100 to 120° C. to hydrogenate the isomaltose until the hydrogen is no more consumed. In this case, isomaltose is reduced to isomaltitol, while reducing saccharides contained in isomaltose-containing products, such as glucose, maltose, maltotetraose, other partial starch hydrolyzates, reducing α-isomaltosylglucosaccharide, and ring-opened tetrasaccharide are simultaneously reduced to sugar alcohols. Cyclotetrasaccharide is a non-reducing saccharide which is not susceptible to hydrogenation. After removing the Raney nickel catalyst from the resulting isomaltitol solution, the resulting solution is decolored with activated charcoal, desalted for purification with ion-exchangers in H- and OH-forms, and concentrated into a syrupy product, and optionally further dried into a powdery product. In necessary, the syrupy product can be, for example, purified by one or more of the following methods alone or in an appropriate combination into a saccharide mixture with isomaltitol: Fractionation of column chromatography using ion-exchangers, activated charcoals, silica gels, etc.; crystallization; separation using organic solvents such as alcohols and acetone; and separation using membranes. The crystallization method for isomaltitol is usually effected by placing in a crystallizer a supersaturated solution of isomaltitol kept at 40 to 95° C., gradually adding a seed to the solution in an amount, usually, of 0.1 to 20%, and gradually cooling the mixture under gently stirring conditions to crystallize the contents and to form a massecuite. Thereafter, the resulting massecuite is subjected to conventional methods such as separation, block pulverization, fluidized-bed granulation, and spray drying to obtain a powdery crystalline isomaltitol, which is usually an anhydrous crystalline isomaltitol. The above separation means usually a method for separating massecuite into isomaltitol crystal and syrup by using a basket-type centrifuge, where a small amount of cooled water is optionally sprayed over the formed crystal for washing to facilitate the production of non-hygroscopic crystalline isomaltitol with a higher purity. As regards the other three methods among the above-identified methods, they have a characteristic of a higher yield of crystalline isomaltitol, although the purity of isomaltitol in the resulting massecuite with crystalline isomaltitol is not substantially improved because they do not separate syrup. Therefore, such massecuite usually comprises crystalline isomaltitol and one or more saccharides from sorbitol, maltitol, maltotriitol, maltotetraitol, sugar alcohols derived from other partial starch hydrolyzates and α-isomaltosylglucosaccharides, cyclotetrasaccharide, and α-glucosyl-(1→6)-α-glucosyl-(1→3)-α-glucosyl-(1→6)-sorbitol (hereinafter may be abbreviated as "reduced ring-opened tetrasaccharide"). In the case of spray drying, a massecuite with a concentration of 70 to 85% and a crystallization percentage of 25 to 60 is sprayed from a nozzle by a high-pressure pump; dried with air heated to a temperature, free of melting the formed powdery crystal, usually, a temperature of 60 to 100° C.; and aged by blowing air heated to 30 to 60° C. for about 1 to about 20 hours to facilitate the production of a non-hygroscopic or substantially-hygroscopic crystal with syrup. In the case of block pulverization, usually, a massecuite with a concentration of 85 to 95% and a crystallization percentage of about 10 to about 60% are allowed to stand for 0.5 to 5 days to crystallize and solidify the whole contents into a block, followed by pulverizing the block by the methods such as crushing and cutting, and drying the resultant to facilitate the production of a non-hygroscopic or substantially-hygroscopic crystal with syrup.

With these crystallization methods, isomaltitol with a purity, usually, of at least 40%, d.s.b., preferably, at least 60%, d.s.b., and more preferably, at least 99%, d.s.b., can be obtained in a higher yield. Also, saccharide mixtures with isomaltitol, which comprise maltitol and one or more saccharides from sorbitol, maltitol, maltotriitol, maltotetraitol, sugar alcohols prepared from other partial starch hydrolyzates and α-isomaltosylglucosaccharides, cyclotetrasaccharide, and reduced ring-opened tetrasaccharide in a total amount excluding that of isomaltitol, usually, of not higher than 70%, d.s.b., preferably, not higher than 60%, d.s.b., and more preferably, 1 to 50%, d.s.b., can be easily obtained. Among the aforementioned saccharide mixtures with isomaltitol, those, which comprise isomaltitol and one or more saccharides from cyclotetrasaccharide, reduced ring-opened tetrasaccharide, sorbitol, maltitol, maltotriitol, maltotetraitol, and sugar alcohols prepared from other partial starch hydrolyzates and α-isomaltosylglucosaccharide, are novel compositions.

Examples of the form of the isomaltitol and saccharide mixtures with isomaltitol obtained by the present process include various forms of liquids, pastes, syrups, granules, powders, and solids.

The isomaltose, isomaltitol, saccharide mixtures of isomaltose and/or isomaltitol, and crystalline isomaltitol (which all may be generally called "the saccharides of the present invention" hereinafter) produced by the process of the present invention have a high quality and elegant sweetness, and have a feature of that they do not substantially form acids, as a causative of dental caries, by dental caries-inducing microorganisms. Thus, the saccharides of the present invention can be preferably used as sweeteners which do not substantially induce dental caries. Varying to some extent depending on the purity of isomaltose and isomaltitol, the saccharides of the present invention have substantially non- or insubstantial-hygroscopicity, satisfactory free-flowing ability, and desired shelf-life, do not substantially induce the Maillard reaction even in the presence of amino compounds such as amino acids and proteins, do not substantially affect the coexisting ingredients, and do not substantially change color in themselves. The saccharide mixtures and products with crystalline isomaltitol according to the present invention can be advantageously used as a sugar coating for tablet in combination with one or more conventional binders such as pullulan, hydroxyethyl starch, and polyvinylpyrrolidone. The saccharides of the present invention have also useful properties of osmosis-controlling ability, filler-imparting ability, gloss-imparting ability, ability of saccharide-crystallization-preventing ability, substantial non-fermentability, and starch-retrogradation-preventing ability. Thus, the saccharides according to the present invention can be arbitrarily used as a sweetener, taste-improving agent, flavor-improving agent, flavor-retaining agent, quality-improving agent, stabilizer, filler-imparting agent in various compositions such as food products including health foods and health supplements, feeds, pet foods including bait for fish, cosmetics, pharmaceuticals, and favorite foods.

The saccharides according to the present invention can be also used as a seasoning for sweetening various products, and In necessary, they can be used in combination with one or more other sweeteners such as a corn syrup solid, glucose, fructose, lactosucrose, $\alpha,\alpha$-trehalose (alias trehalose), $\alpha,\beta$-trehalose (alias neotrehalose), $\beta,\beta$-trehalose, maltose, sucrose, isomerized sugar, honey, maple sugar. isomaltooligosaccharide, galactooligosaccharide, lactooligosaccharide, fructooligosaccharide, sorbitol, maltitol, lactitol, dihydrochalcone, stevioside, $\alpha$-glycosyl stevioside, rebaudioside, glycyrrhizin, L-aspartyl L-phenylalanine methyl ester, sucralose, acesulfame K, saccharin, glycine, and alanine. If necessary, one or more fillers such as dextrins, starches, and lactose can be suitably used in combination.

The saccharides, particularly, those comprising the crystalline isomaltitol powder according to the present invention can be used alone, and optionally they can be used in combination with one or more of appropriate fillers, excipients, binders, sweeteners to make them into different shapes of granules, spheres, short rods, plates, cubes, tablets, films, or sheets.

The saccharides of the present invention have a sweetness that well harmonize with other tastable substances having sour-, acid-, salty-, astringent-, delicious-, and bitter-tastes; and have a satisfactorily high acid- and heat-tolerance. Thus, they can be favorably used to sweeten, improve the taste, or improve the quality of various foods and beverages, for example, amino acids, peptides, soy sauce, powdered soy sauce, miso, "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), nucleotide seasonings, mixed seasoning, "mirin" (a sweet sake), "shin-mirin" (a synthetic mirin), table sugar, and coffee sugar. Also, the saccharide of the present invention can be arbitrarily used in "wagashi" (Japanese cakes) such as "senbei" (a rice cracker), "arare" (a rice cake cube), "okoshi" (a millet-and-rice cake), "mochi" (a rice paste) or the like, "manju" (a bun with a bean-jam), "uiro" (a sweet rice jelly), "an" (a bean jam) or the like, "yokan" (a sweet jelly of beans), "mizu-yokan" (a soft adzuki-bean jelly), "kingyoku" (a kind of yokan), jelly, pao de Castella, and "amedama" (a Japanese toffee); Western confectioneries such as a bun, biscuit, cracker, cookie, pie, pudding, butter cream, custard cream, cream puff, waffle, sponge cake, doughnut, Yorkshire pudding, chocolate, chewing gum, caramel, and candy; frozen desserts such as an ice cream and sherbet; syrups such as a "kajitsu-no-syrup-zuke" (a preserved fruit) and "korimitsu" (a sugar syrup for shaved ice); pastes such as a flour paste, peanut paste, fruit paste, and spread; processed fruits and vegetables such as a jam, marmalade, "syrup-zuke" (fruit pickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premixes for pickles and pickled products such as a "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relish) such as a "uni-no-shiokara" (a salted gut of sea urchin), "ika-no-shiokara" (a salted gut of squid), "su-konbu" (processed tangle), "saki-surume" (a dried squid strip), and "fugu-no-mirin-boshi" (a dried mirin-seasoned swellfish); "tsukudani" (foods boiled down in soy sauce) such as those of layer, edible wild plants, dried squid, small fish, and shellfish; daily dishes such as a "nimame" (cooked beans), potato salad, and "konbu-maki" (a tangle roll); milk products such as a yogurt and cheese; canned and bottled products such as those of meat, fish meat, fruit, and vegetables; alcoholic beverages such as sake, distilled spirit, shochu-based beverage, synthetic sake, liqueur, cocktail, and others; soft drinks such as a coffee, tea, cocoa, juice, isotonic beverage, carbonated beverage, sour milk beverage, and beverage containing lactic acid bacteria; instant food products such as an instant pudding mix, instant hot cake mix, "sokuseki-shiruko" (an instant mix of adzuki-bean soup with rice cake), and instant soup mix; and other foods and beverages such as solid foods for babies, foods for therapy, health/tonic drinks, peptide foods, frozen foods, and health foods. The saccharide of the present invention can be arbitrarily used to improve the taste preference of feeds and foods for animals and pets such as domestic animals, poultry, honey bees, silk warms, fishes, crustaceans including shrimps/prawns/lobsters, and crabs. In addition, the saccharides of the present invention can be used as a sweetener for solid products such as a tobacco, cigarette, tooth paste, lipstick/rouge, lip cream, internal liquid medicine, tablet, troche, cod liver oil in the form of a drop, cachou, oral refrigerant, or gargle. Also the saccharides can be used in the above products as a taste-improving agent, flavoring substance, quality-improving agent, stabilizer, or moisture-retaining agent.

The saccharides of the present invention are sugar alcohols which do not cause the Maillard reaction because of their non-reducibility. Therefore, the saccharides have no fear of deteriorating effective ingredients such as amino compounds and can be incorporated as a quality-improving agent and/or stabilizer into health foods and pharmaceuticals, which have effective ingredients, active components, or physiologically active substances, to obtain stabilized, high quality health foods or pharmaceuticals in the form of a liquid, paste, or solid. Examples of the above-identified effective ingredients and biologically active substances are lymphokines such as $\alpha$-, $\beta$- and $\gamma$-interferons, tumor necrosis factor-$\alpha$ (TNF-$\alpha$), tumor necrosis factor-$\beta$ (TNF-$\beta$), macrophage migration inhibitory factor, colony-stimulating factor, transfer factor, and interleukins; hormones such as insulin, growth hormone, prolactin, erythropoietin, and follicle-stimulating hormone; biological preparations such as BCG vaccine, Japanese encephalitis vaccine, measles vaccine, live polio vaccine, smallpox vaccine, tetanus toxoid, Trimeresurus antitoxin, and human immunoglobulin; antibiotics such as penicillin, erythromycin, chloramphenicol, tetracycline, streptomycin, and kanamycin sulfate; vitamins such as thiamine, riboflavin, L-ascorbic acid, $\alpha$-glycosyl ascorbic acid, cod liver oil, carotenoid, ergosterol, tocopherol, rutin, $\alpha$-glycosyl rutin, naringin, $\alpha$-glycosyl naringin, hesperidin, and $\alpha$-glycosyl hesperidin; enzymes such as lipase, elastase, urokinase, protease, $\beta$-amylase, isoamylase, glucanase, and lactase; extracts such as ginseng extract, bamboo leaf extract, Japanese plum extract, pine leaf extract, snapping turtle extract, chlorella extract, aloe extract, and propolis extract; viable microorganisms such as viruses, lactic acid bacteria, and yeasts; and royal jelly.

The methods for incorporating the saccharides of the present invention into the aforesaid compositions are those which can incorporate the saccharides into the compositions before completion of their processings, and which can be appropriately selected among the following conventional methods; mixing, dissolving, melting, soaking, penetrating, dispersing, applying, coating, spraying, injecting, crystallizing, and solidifying. The amount of the saccharides to be incorporated into each of the above compositions is usually in an amount of at least 0.1%, desirably, at least 1%, and more desirably, 2 to 99.9% by weight of each of the compositions.

The following experiments explain the process for producing isomaltose and isomaltitol according to the present invention:

EXPERIMENT 1

Preparation of Non-Reducing Cyclotetrasaccharide by Culturing

A liquid medium, consisting of 5% (w/v) of "PINE-DEX #1", a partial starch hydrolyzate commercialized by Matsutani Chemical Ind., Tokyo, Japan, 1.5% (w/v) of "ASAHIMEAST™", a yeast extract commercialized by Asahi Breweries, Ltd., Tokyo, Japan, 0.1% (w/v) of dipotassium phosphate, 0.06% (w/v) of sodium phosphate dodecahydrate, 0.05% (w/v) magnesium sulfate heptahydrate, and water, was placed in a 500-ml Erlenmeyer flask in an amount of 100 ml, sterilized by autoclaving at 121° C. for 20 min, cooled, and then seeded with a stock culture of *Bacillus globisporus* C9 strain (FERM BP-7143), followed by culturing under rotary-shaking conditions at 27° C. and 230 rpm for 48 hours and centrifuging the resulting culture to remove cells and to obtain a supernatant. The supernatant was autoclaved at 120° C. for 15 min and then cooled, and the resulting insoluble substances were removed by centrifugation to obtain a supernatant.

To examine the saccharides in the supernatant, they were separated by developing twice on silica gel thin-layer chromatography (abbreviated as "TLC" hereinafter) using, as a developer, a mixture solution of n-butanol, pyridine, and water (=6:4:1 by volume), and, as a thin-layer plate, "KIESELGEL™ 60", an aluminum plate (20×20 cm) for TLC commercialized by Merck & Co., Inc., Rahway, USA. The coloration of the separated total sugars by the sulfuric acid-methanol method and that of the reducing saccharides by the diphenylamine-aniline method detected a non-reducing saccharide positive at an Rf value of about 0.31 on the former detection method but negative on the latter detection method.

About 90 ml of the supernatant obtained in the above was adjusted to pH 5.0 and heated to 45° C. and then incubated for 24 hours after admixed with 1,500 units per gram of solids of "TRANSGLUCOSIDASE L AMANO™", an $\alpha$-glucosidase specimen commercialized by Amano Pharmaceutical Co., Ltd., Aichi, Japan; and 75 units per gram of solids of a glucoamylase commercialized by Nagase Biochemicals, Ltd., Kyoto, Japan. Thereafter, the resulting culture was adjusted to pH 12 by the addition of sodium hydroxide and boiled for two hours to decompose the remaining reducing sugars. After removing insoluble substances by filtration, the resulting solution was decolored and desalted with "DIAION PK218™" and "DIAION WA30™", cation exchange resins commercialized by Mitsubishi Chemical Industries, Ltd., Tokyo, Japan; and further desalted with "DIAION SK-1B™", commercialized by Mitsubishi Chemical Industries, Ltd., Tokyo, Japan, and "AMBERLITE IRA411™", an anion exchange resin commercialized by Japan Organo Co., Ltd., Tokyo, Japan. The resulting solution was decolored with an activated charcoal, membrane filtered, concentrated by an evaporator, and lyophilized in vacuo to obtain about 0.6 g, d.s.b., of a saccharide powder. The analysis of the saccharide powder on high-performance liquid chromatography (abbreviated as "HPLC" hereinafter) detected a single peak at an elution time of 10.84 min as shown in FIG. 1, and revealed that it had a purity of as high as 99.9% or higher. The above HPLC was run using "SHOWDEX KS-801™ column", Showa Denko K.K., Tokyo, Japan, at a column temperature of 60° C. and a flow rate of 0.5 ml/min of water, and "RI-8012", a differential refractometer commercialized by Tosoh Corporation, Tokyo, Japan. When measured for reducing power of the saccharide on the Somogyi-Nelson's method, the reducing power was below a detectable level, meaning that the saccharide was substantially a non-reducing saccharide.

EXPERIMENT 2

Structure Analysis of Non-reducing Saccharide

Figure 2:
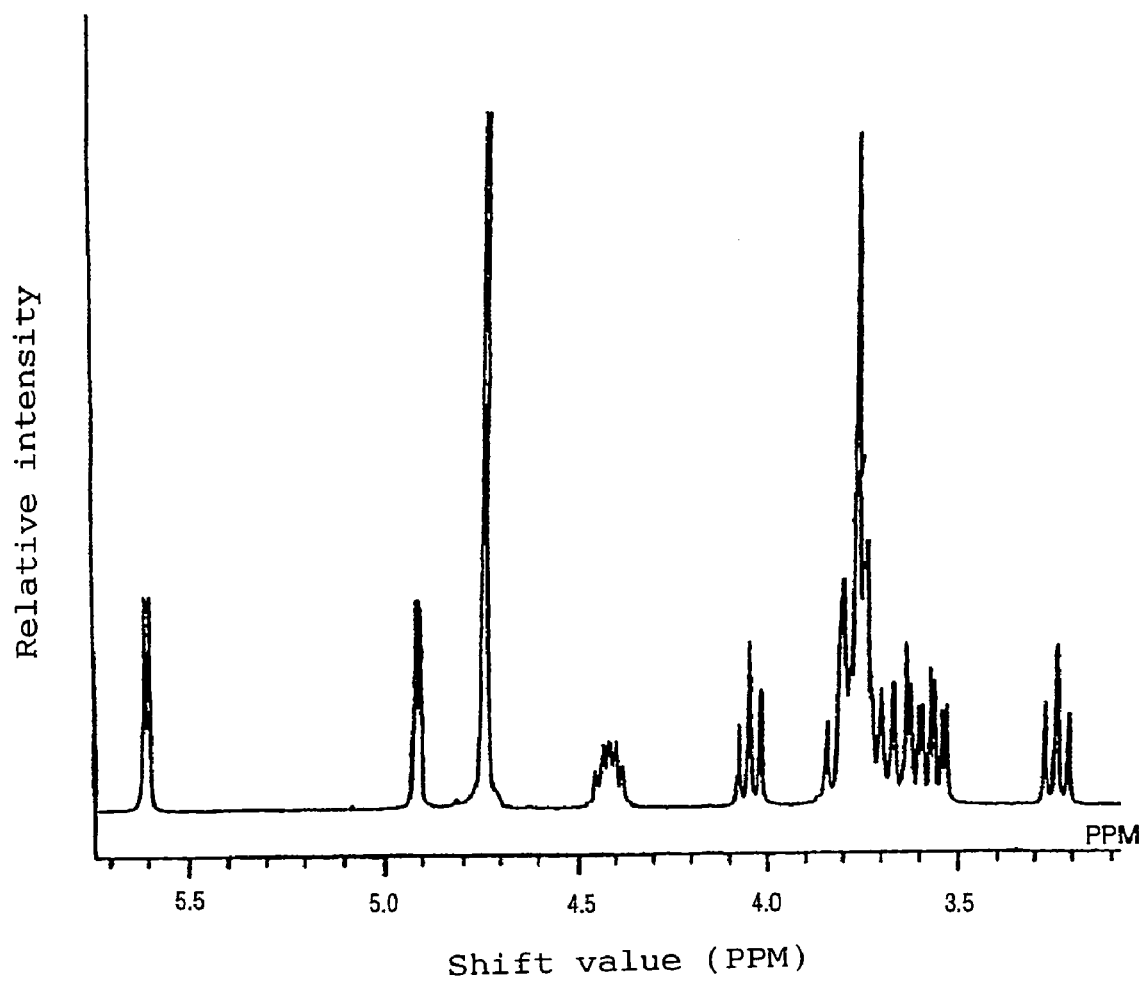
FIG. 2 is a spectrum of nuclear magnetic resonance ($^1$H-NMR) of cyclotetrasaccharide, obtained by the enzymatic reaction using α-isomaltosyl-transferring enzyme from a microorganism of the species *Bacillus globisporus* C9 strain.
Figure 3:
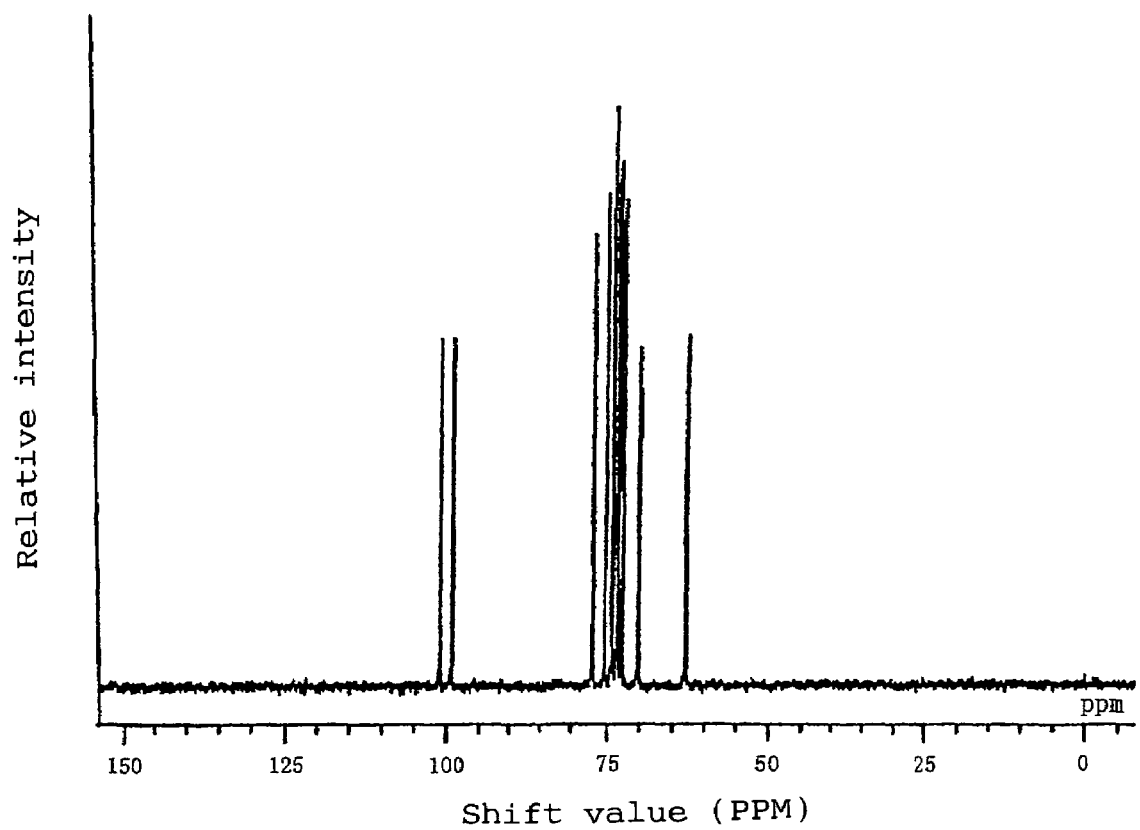
FIG. 3 is a spectrum of nuclear magnetic resonance ($^{13}$C-NMR) of cyclotetrasaccharide, obtained by the enzymatic reaction using α-isomaltosyl-transferring enzyme from a microorganism of the species *Bacillus globisporus* C9 strain.
Figure 4:
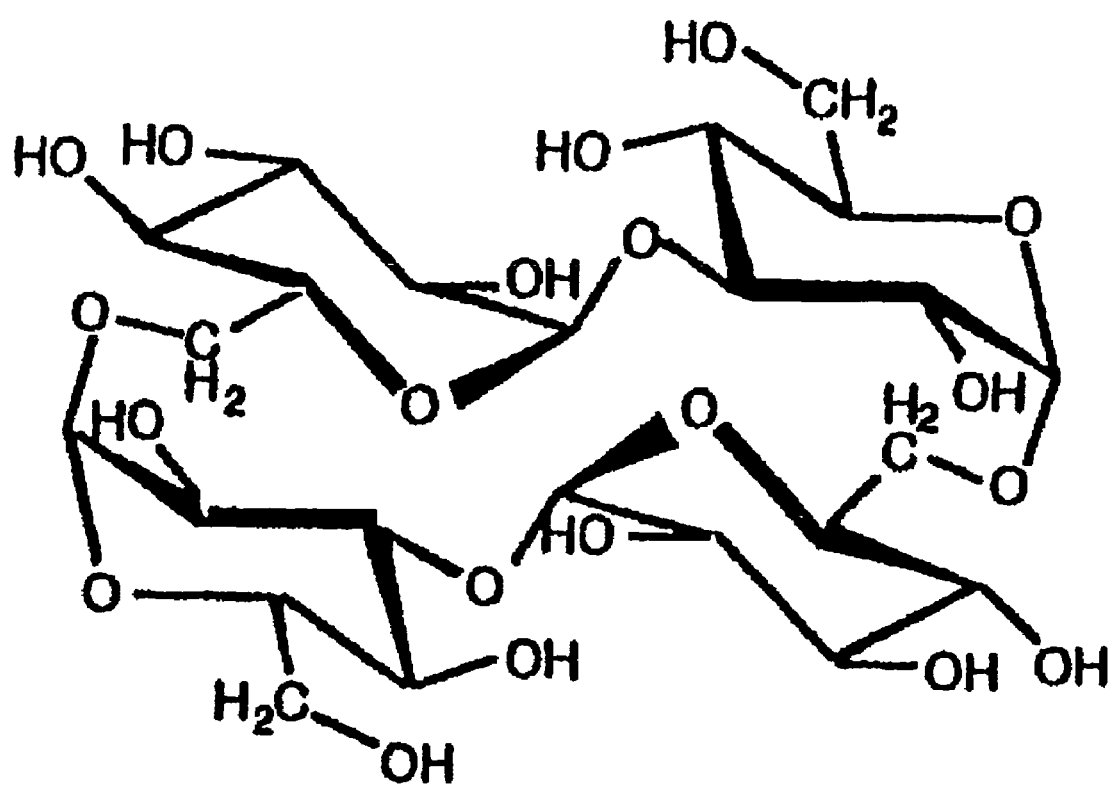
FIG. 4 represents the structure of cyclotetrasaccharide, i.e., cyclo{→6)-α-D-glucopyranosyl-(1→3)-α-D-glucopyranosyl-(1→6)-α-D-glucopyranosyl-(1→3)-α-D-glucopyranosyl-(1→}.

Fast atom bombardment mass spectrometry (called "FAB-MS") of a non-reducing saccharide, obtained by the method in Experiment 1, significantly detected a proton-addition-molecular ion with a mass number of 649, meaning that the saccharide had a mass number of 648. According to conventional manner, the saccharide was hydrolyzed with sulfuric acid and then analyzed for sugar composition on gas chromatography. As a result, D-glucose was detected only, revealing that the saccharide was composed of D-glucose molecules or a cyclotetrasaccharide composed of four D-glucose molecules based on the above mass number. Nuclear magnetic resonance analysis (called "NMR") of the saccharide gave a ¹H-NMR spectrum as shown in FIG. 2 and a ¹³C-NMR spectrum as shown in FIG. 3, and these spectra were compared with those of conventional saccharides, revealing that the spectra were coincided with those of a non-reducing cyclic saccharide, cyclo{→6)-α-D-glucopyranosyl-(1→3)-α-D-glucopyranosyl-(1→6)-α-D-glucopyranosyl-(1→3)-α-D-glucopyranosyl-(1→} disclosed in "*European Journal of Biochemistry*", pp. 641-648 (1994). The data confirmed that the saccharide obtained in this experiment is a cyclotetrasaccharide as shown in FIG. 4, i.e., cyclo{→6)-α-D-glucopyranosyl-(1→3)-α-D-glucopyranosyl-(1→6)-α-D-glucopyranosyl-(1→3)-α-D-glucopyranosyl-(1→}.

EXPERIMENT 3

Production of α-isomaltosylglucosaccharide-forming Enzyme from *Bacillus globisporus* C9 Strain A liquid culture medium, consisting of 4.0% (w/v) of "PINE-DEX #4™", a partial starch hydrolyzate commercialized by Matsutani Chemical Ind., Tokyo, Japan, 1.8% (w/v) of "ASAHIMEAST™", a yeast extract commercialized by Asahi Breweries, Ltd., Tokyo, Japan, 0.1% (w/v) of dipotassium phosphate, 0.06% (w/v) of sodium phosphate dodecahydrate, 0.05% (w/v) magnesium sulfate heptahydrate, and water, was placed in 500-ml Erlenmeyer flasks in an amount of 100 ml each, sterilized by autoclaving at 121° C. for 20 min, cooled, and then seeded with a stock culture of *Bacillus globisporus* C9 strain (FERM BP-7143), followed by culturing under rotary-shaking conditions at 27° C. and 230 rpm for 48 hours for a seed culture. About 20 L of a fresh preparation of the same liquid culture medium as used in the above seed culture were placed in a 30-L fermentor, sterilized by heating, and then cooled to 27° C. and inoculated with 1% (v/v) of the seed culture, followed by culturing at 27° C. and pH 6.0 to 8.0 for 48 hours under aeration-agitation conditions. After completion of the culture, the resulting culture, which had about 0.45 unit/ml of α-isomaltosylglucosaccharide-forming enzyme, about 1.5 units/ml of α-isomaltosyl-transferring enzyme, and about 0.95 unit/ml of a cyclotetrasaccharide-forming activity, was centrifuged at 10,000 rpm for 30 min to obtain about 18 L of a supernatant. When measured for enzymatic activity, the supernatant contained about 0.45 unit/ml of α-isomaltosylglucosaccharide-forming enzyme, i.e., a total enzymatic activity of about 8,110 units; about 1.5 units/ml of α-isomaltosyl-transferring enzyme, i.e., a total enzymatic activity of about 26,900 units; and about 0.95 unit/ml of cyclotetrasaccharide-forming enzyme, i.e., a total enzymatic activity of about 17,100 units. These activities were assayed as follows: The activity of α-isomaltosylglucosaccharide-forming enzyme was assayed by dissolving maltotriose in 100 mM acetate buffer (pH 6.0) to give a concentration of 2% (w/v) for a substrate solution, adding a 0.5 ml of an enzyme solution to a 0.5 ml of the substrate solution, enzymatically reacting the mixture solution at 35° C. for 60 min, suspending the enzymatic reaction by boiling the solution for 10 min, and quantifying maltose, among the isomaltosyl maltose and maltose formed mainly in the reaction mixture, on HPLC disclosed in Experiment 1. One unit activity of α-isomaltosylglucosaccharide-forming enzyme is defined as the enzyme amount that forms one micromole of maltose per minute under the above enzymatic reaction conditions. Throughout the specification, the enzymatic activity of α-isomaltosylglucosaccharide-forming enzyme means the unit(s) assayed as above.

The activity of α-isomaltosyl-transferring enzyme was assayed by dissolving panose in 100 mM acetate buffer (pH 6.0) to give a concentration of 2% (w/v) for a substrate solution, adding a 0.5 ml of an enzyme solution to 0.5 ml of the substrate solution, enzymatically reacting the mixture solution at 35° C. for 30 min, suspending the enzymatic reaction by boiling the solution for 10 min, and quantifying glucose, among the cyclotetrasaccharide and glucose formed mainly in the reaction mixture, by the glucose oxidase method. One unit activity of α-isomaltosyl-transferring enzyme is defined as the enzyme amount that forms one micromole of glucose per minute under the above enzymatic reaction conditions. Throughout the specification, the enzymatic activity of α-isomaltosyl-transferring enzyme means the unit(s) assayed as above.

The cyclotetrasaccharide-forming activity was assayed by dissolving "PINE-DEX #100™", a partial starch hydrolyzate commercialized by Matsutani Chemical Ind., Tokyo, Japan, in 50 mM acetate buffer (pH 6.0) to give a concentration of 2% (w/v) for a substrate solution, adding 0.5 ml of an enzyme solution to 0.5 ml of the substrate solution, enzymatically reacting the mixture solution at 35° C. for 60 min, suspending the enzymatic reaction by heating the solution at 100° C. for 10 min, and then further adding to the resulting solution one milliliter of 50 mM acetate buffer (pH 5.0) with 70 units/ml of "TRANSGLUCOSIDASE L AMANO™", an α-glucosidase commercialized by Amano Pharmaceutical Co., Ltd., Aichi, Japan, and 27 units/ml of glucoamylase, commercialized by Nagase Biochemicals, Ltd., Kyoto, Japan, followed by incubating the mixture at 50° C. for 60 min, inactivating the remaining enzymes by heating at 100° C. for 10 min, and quantifying cyclotetrasaccharide on HPLC described in Experiment 1. One unit activity of cyclotetrasaccharide-forming enzyme is defined as the enzyme amount that forms one micromole of cyclotetrasaccharide per minute under the above enzymatic reaction conditions. Throughout the specification, the activity of cyclotetrasaccharide-forming enzyme means the unit(s) assayed as above.

EXPERIMENT 4

Preparation of Enzyme from *Bacillus globisporus* C9 Strain

EXPERIMENT 4-1

About 18 L of the supernatant in Experiment 3 were salted out in 80% saturated ammonium sulfate and allowed to stand at 4° C. for 24 hours, and the formed sediments were collected by centrifugation at 10,000 rpm for 30 min, dissolved in 10 mM phosphate buffer (pH 7.5), and dialyzed against a fresh preparation of the same buffer to obtain about 400 ml of a crude enzyme solution with 8,110 units of an α-isomaltosylglucosaccharide-forming activity, 24,700 units of an α-isomaltosyl-transferring activity, and about 15,600 units of a cyclotetrasaccharide-forming activity. The crude enzyme solution was subjected to ion-exchange chromatography using 1,000 ml of "SEPABEADS FP-DA13 ™" gel, an ion-exchange resin commercialized by Mitsubishi Chemical Industries, Ltd., Tokyo, Japan. The α-isomaltosylglucosaccharide-forming enzyme and cyclotetrasaccharide were eluted as non-adsorbed fractions without adsorbing on the ion-exchange resin. The resulting enzyme solution was dialyzed against 10 mM phosphate buffer (pH 7.0) with 1 M ammonium sulfate, and the dialyzed solution was centrifuged to remove insoluble impurities, and subjected to affinity chromatography using 500 ml of "SEPHACRYL HR S-200™", a gel commercialized by Amersham Corp., Div., Amersham International, Arlington Heights, Ill., USA. Enzymatically active components adsorbed on the gel and, when sequentially eluted with a linear gradient decreasing from 1 M to 0 M of ammonium sulfate and a linear gradient increasing from 0 mM to 100 mM of maltotetraose, the α-isomaltosyl-transferring enzyme and the α-isomaltosylglucosaccharide-forming enzyme were separately eluted, i.e., the former was eluted with the linear gradient of ammonium sulfate at about 0 M and the latter was eluted with the linear gradient of maltotetraose at about 30 mM. Thus, fractions with an α-isomaltosyl-transferring activity and those with an α-isomaltosylglucosaccharide-forming activity were separatory collected. No cyclotetrasaccharide-forming activity was found in any of the above fractions but found in their mixture solution, and the fact revealed that the activity of forming cyclotetrasaccharide from partial starch hydrolyzates was exerted by the coaction of the activities of the above two types of enzymes.

Methods for separately purifying α-isomaltosylglucosaccharide-forming enzyme and α-isomaltosyl-transferring enzyme are described below:

EXPERIMENT 4-2

Purification of α-isomaltosylglucosaccharide-forming Enzyme

Factions of α-isomaltosylglucosaccharide-forming enzyme, obtained in Experiment 4-1, were pooled and dialyzed against 10 mM phosphate buffer (pH 7.0) containing 1 M ammonium sulfate. The dialyzed solution was centrifuged to remove insoluble impurities, and the resulting supernatant was fed to hydrophobic chromatography using 350 ml of "BUTYL-TOYOPEARL 650 M™", a gel for hydrophobic chromatography commercialized by Tosoh Corporation, Tokyo, Japan. The enzyme was adsorbed on the gel and eluted at about 0.3 M ammonium sulfate when eluted with a linear gradient decreasing from 1 M to 0 M of ammonium sulfate, followed by collecting fractions with the enzyme activity. The fractions were pooled and dialyzed against 10 mM phosphate buffer (pH 7.0) containing 1 M ammonium sulfate. The resulting dialyzed solution was centrifuged to remove insoluble impurities and fed to affinity chromatography using "SEPHACRYL HR S-200™" gel to purify the enzyme. The amount of enzyme activity, specific activity, and yield of α-isomaltosylglucosaccharide-forming enzyme in each purification step are in Table 1.

TABLE 1

| Purification step | Enzyme* activity (unit) | Specific activity of enzyme* (unit/mg protein) | Yield (%) |
| --- | --- | --- | --- |
| Culture supernatant | 8,110 | 0.12 | 100 |
| Dialyzed solution after salting out with ammonium sulfate | 7,450 | 0.56 | 91.9 |
| Eluate from ion-exchange column chromatography | 5,850 | 1.03 | 72.1 |
| Eluate from affinity column chromatography | 4,040 | 8.72 | 49.8 |
| Eluate from hydrophobic column chromatography | 3,070 | 10.6 | 37.8 |
| Eluate from affinity column chromatography | 1,870 | 13.6 | 23.1 |

Note:
The symbol "*" means α-isomaltosylglucosaccharide-forming enzyme.

The finally purified α-isomaltosylglucosaccharide-forming enzyme specimen was examined for purity on gel electrophoresis using a 7.5% (w/v) polyacrylamide gel and detected on the gel as a single protein band, i.e., a high purity enzyme specimen.

EXPERIMENT 4-3

Purification of α-isomaltosyl-transferring Enzyme

Fractions with α-isomaltosyl-transferring enzyme, which had been separated from the fractions with α-isomaltosylglucosaccharide-forming enzyme by affinity chromatography in Experiment 4-1, were pooled and dialyzed against 10 mM phosphate buffer (pH 7.0) containing 1 M ammonium sulfate. The resulting dialyzed solution was centrifuged to remove insoluble impurities and subjected to affinity chromatography using 350 ml of "BUTYL-TOYOPEARL 650M", a gel for hydrophobic chromatography commercialized by Tosoh Corporation, Tokyo, Japan, to purify the enzyme. The enzyme was adsorbed on the gel and eluted therefrom at a concentration of about 0.3 M ammonium sulfate when eluted with a linear gradient decreasing from 1 M to 0 M of ammonium sulfate, followed by collecting fractions with the enzyme activity. The fractions were pooled and dialyzed against 10 mM phosphate buffer (pH 7.0) containing 1 M ammonium sulfate. The resulting dialyzed solution was centrifuged to remove insoluble impurities and fed to affinity chromatography using "SEPHACRYL HR S-200" gel to purify the enzyme. The amount of enzyme activity, specific activity, and yield of α-isomaltosyl-transferring enzyme in each purification step are in Table 2.

TABLE 2

| Purification step | Enzyme* activity (unit) | Specific activity of enzyme* (unit/mg protein) | Yield (%) |
| --- | --- | --- | --- |
| Culture supernatant | 26,900 | 0.41 | 100 |
| Dialyzed solution after salting out with ammonium sulfate | 24,700 | 1.85 | 91.8 |
| Eluate from ion-exchange column chromatography | 19,400 | 3.41 | 72.1 |
| Eluate from affinity column chromatography | 13,400 | 18.6 | 49.8 |
| Eluate from hydrophobic column chromatography | 10,000 | 21.3 | 37.2 |
| Eluate from affinity column chromatography | 6,460 | 26.9 | 24.0 |

Note:
The symbol "*" means the α-isomaltosyl-transferring enzyme.

EXPERIMENT 5

Property of α-isomaltosylglucosaccharide-forming Enzyme and α-isomaltosyl-transferring Enzyme

EXPERIMENT 5-1

Property of α-isomaltosylglucosaccharide-forming Enzyme

A purified specimen of α-isomaltosylglucosaccharide-forming enzyme, obtained by the method in Experiment 4-2, was subjected to SDS-PAGE using a 7.5% (w/v) of polyacrylamide gel and then determined for molecular weight by comparing with the dynamics of standard molecular markers electrophoresed in parallel, commercialized by Japan Bio- Rad Laboratories Inc., Tokyo, Japan, revealing that the enzyme had a molecular weight of about 140,000±20,000 daltons.

Figure 5:
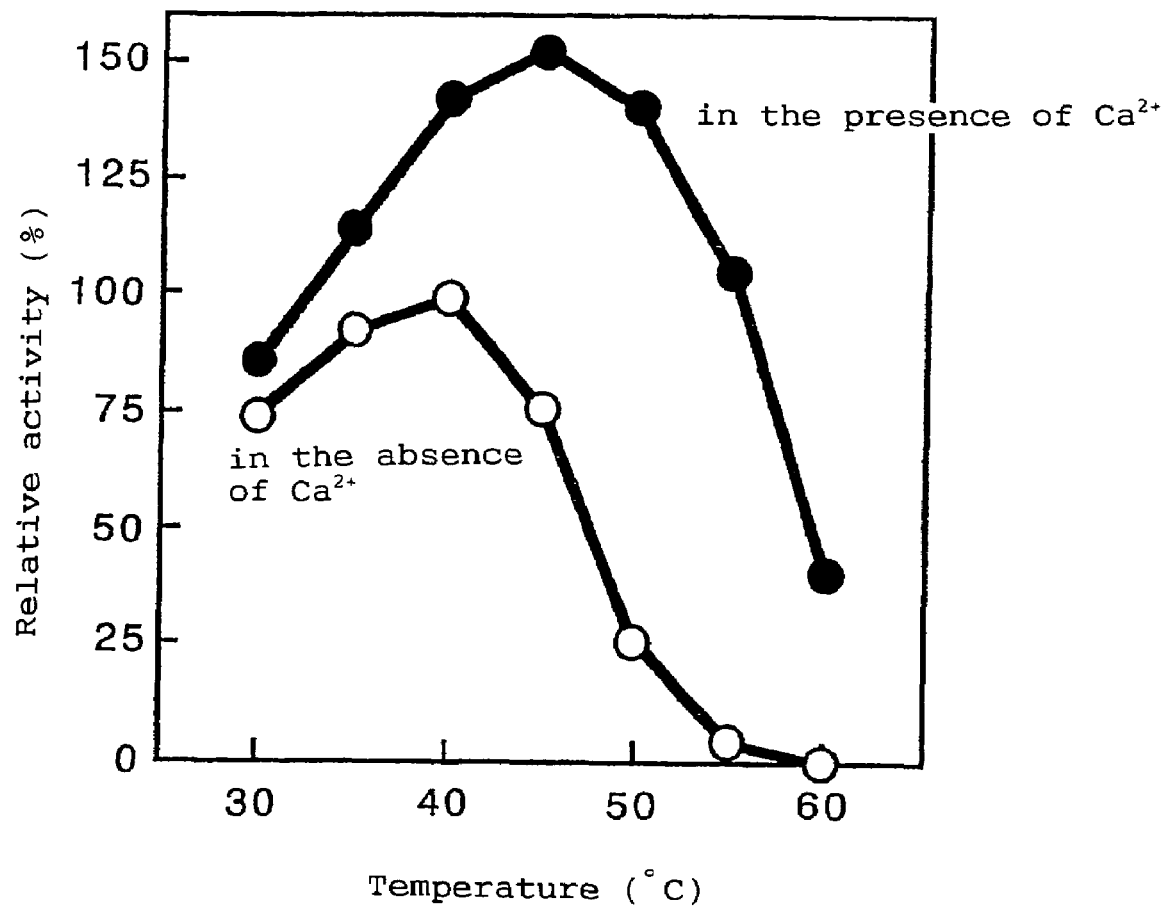
FIG. 5 shows the thermal influence on the enzymatic activity of α-isomaltosylglucosaccharide forming enzyme from a microorganism of the species *Bacillus globisporus* C9 strain.
Figure 6:
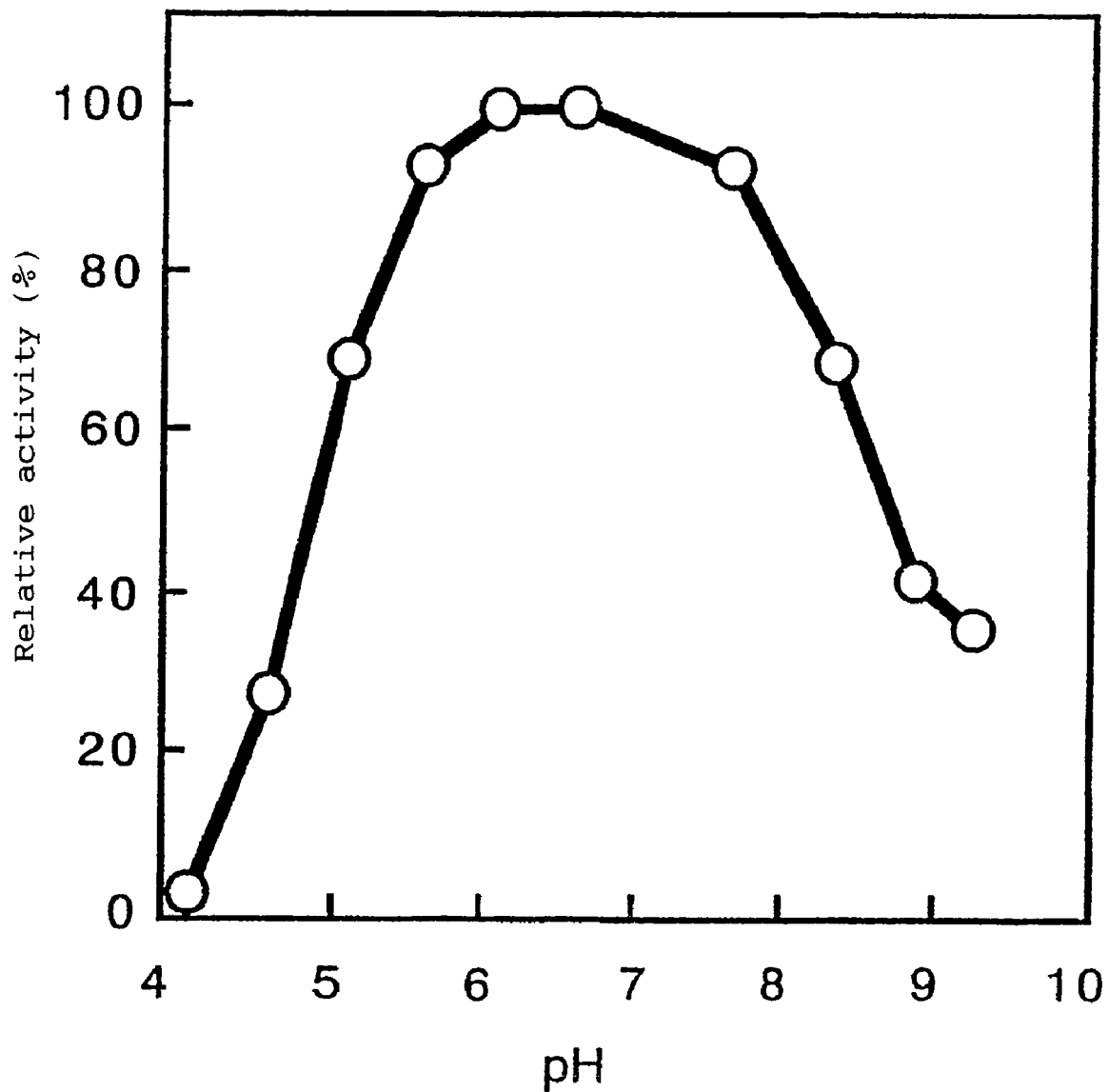
FIG. 6 shows the pH influence on the enzymatic activity of α-isomaltosylglucosaccharide-forming enzyme from a microorganism of the species *Bacillus globisporus* C9 strain.
Figure 7:
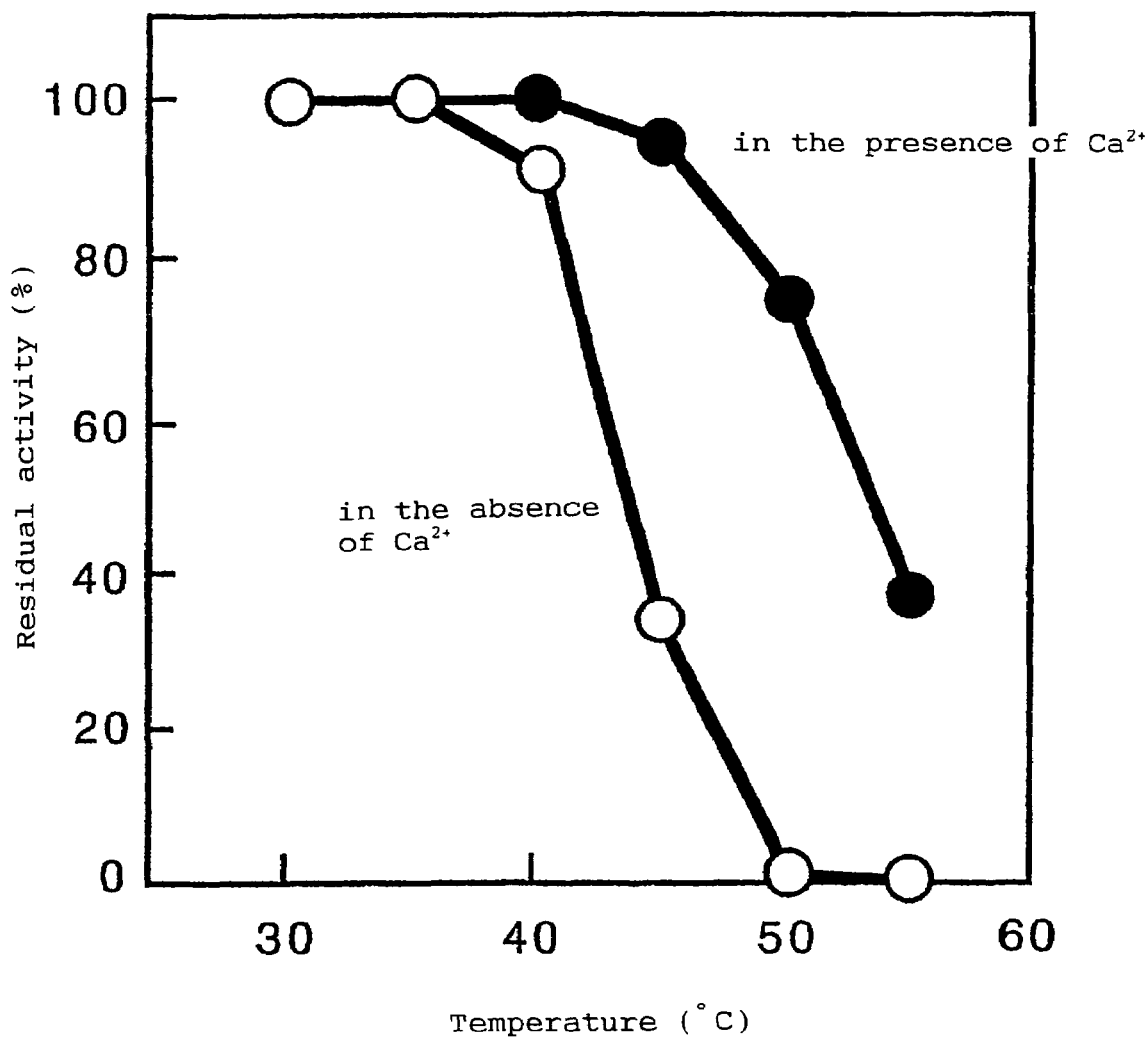
FIG. 7 shows the thermal stability of α-isomaltosylglucosaccharide-forming enzyme from a microorganism of the species *Bacillus globisporus* C9 strain.
Figure 8:
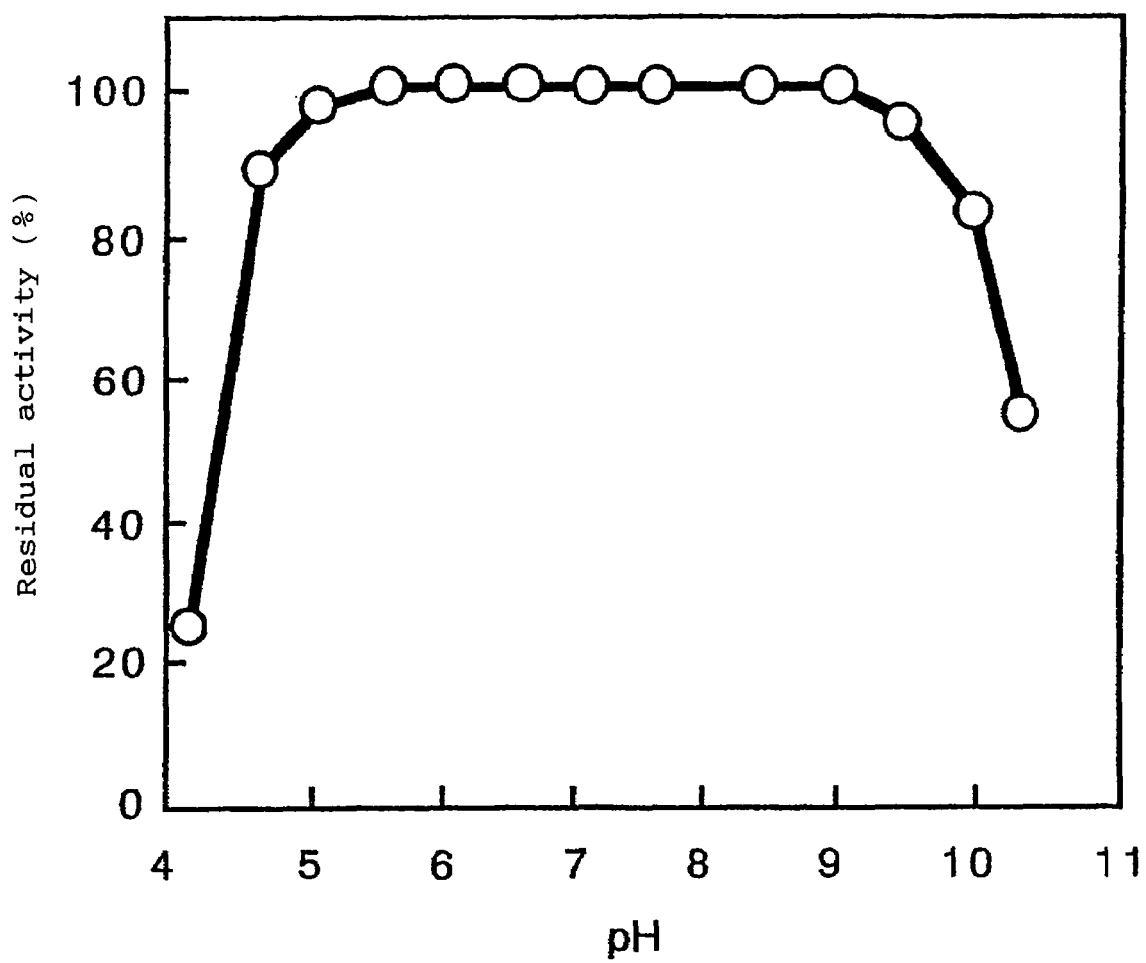
FIG. 8 shows the pH stability of α-isomaltosylglucosaccharide-forming enzyme from a microorganism of the species *Bacillus globisporus* C9 strain.

A fresh preparation of the above purified specimen was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 5.2±0.5. The influence of temperature and pH on the activity of α-isomaltosylglucosaccharide-forming enzyme was examined in accordance with the assay for its enzyme activity, where the influence of temperature was examined in the presence or the absence of 1 mM $Ca^{2+}$. These results are in FIG. 5 (influence of temperature) and FIG. 6 (influence of pH). The optimum temperature of the enzyme was about 40° C. (in the absence of $Ca^{2+}$) and about 45° C. (in the presence of 1 mM $Ca^{2+}$) when incubated at pH 6.0 for 60 min, and the optimum pH of the enzyme was about 6.0 to about 6.5 when incubated at 35° C. for 60 min. The thermal stability of the enzyme was determined by incubating the testing enzyme solutions in the form of 20 mM acetate buffer (pH 6.0) at prescribed temperatures for 60 min in the presence or the absence of 1 mM $Ca^{2+}$, cooling the resulting enzyme solutions with water, and assaying the remaining enzyme activity of each solution. The pH stability of the enzymes was determined by keeping the testing enzyme solutions in the form of an appropriate 50 mM buffer having a prescribed pH at 4° C. for 24 hours, adjusting the pH of each solution to 6.0, and assaying the remaining enzyme activity of each solution. These results are respectively in FIG. 7 (thermal stability) and FIG. 8 (pH stability). As a result, the enzyme had thermal stability of up to about 35° C. in the absence of $Ca^{2+}$ and about 40° C. in the presence of 1 mM $Ca^{2+}$, and pH stability of about 4.5 to about 9.0.

The influence of metal ions on the activity of α-isomaltosylglucosaccharide-forming enzyme was examined in the presence of 1 mM of each metal-ion according to the assay for its enzyme activity. The results are in Table 3.

TABLE 3

| Metal ion | Relative activity (%) | Metal ion | Relative activity (%) |
|---|---|---|---|
| None | 100 | $Hg^{2+}$ | 4 |
| $Zn^{2+}$ | 92 | $Ba^{2+}$ | 65 |
| $Mg^{2+}$ | 100 | $Sr^{2+}$ | 80 |
| $Ca^{2+}$ | 115 | $Pb^{2+}$ | 103 |
| $Co^{2+}$ | 100 | $Fe^{2+}$ | 98 |
| $Cu^{2+}$ | 15 | $Fe^{3+}$ | 97 |
| $Ni^{2+}$ | 98 | $Mn^{2+}$ | 111 |
| $Al^{3+}$ | 99 | EDTA | 20 |

As evident form the results in Table 3, the enzyme activity was strongly inhibited by $Hg^{2+}$, $Cu^{2+}$, and EDTA, and it was also inhibited by $Ba^{2+}$ and $Sr^{2+}$. It was also found that the enzyme was activated by $Ca^{2+}$ and $Mn^{2+}$.

Amino acid analysis on the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:1, i.e., tyrosine-valine-serine-serine-leucine-glycine-asparagine-leucine-isoleucine in the N-terminal region.

EXPERIMENT 5-2

Property of α-isomaltosyl-transferring Enzyme

A purified specimen of α-isomaltosyl-transferring enzyme, obtained by the method in Experiment 4-3, was subjected to SDS-PAGE using a 7.5% (w/v) of polyacrylamide gel and then determined for molecular weight by comparing with the dynamics of standard molecular markers electrophoresed in parallel, commercialized by Japan Bio-Rad Laboratories Inc., Tokyo, Japan, revealing that the enzyme had a molecular weight of about 112,000±20,000 daltons.

A fresh preparation of the above purified specimen was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 5.5±0.5.

Figure 9:
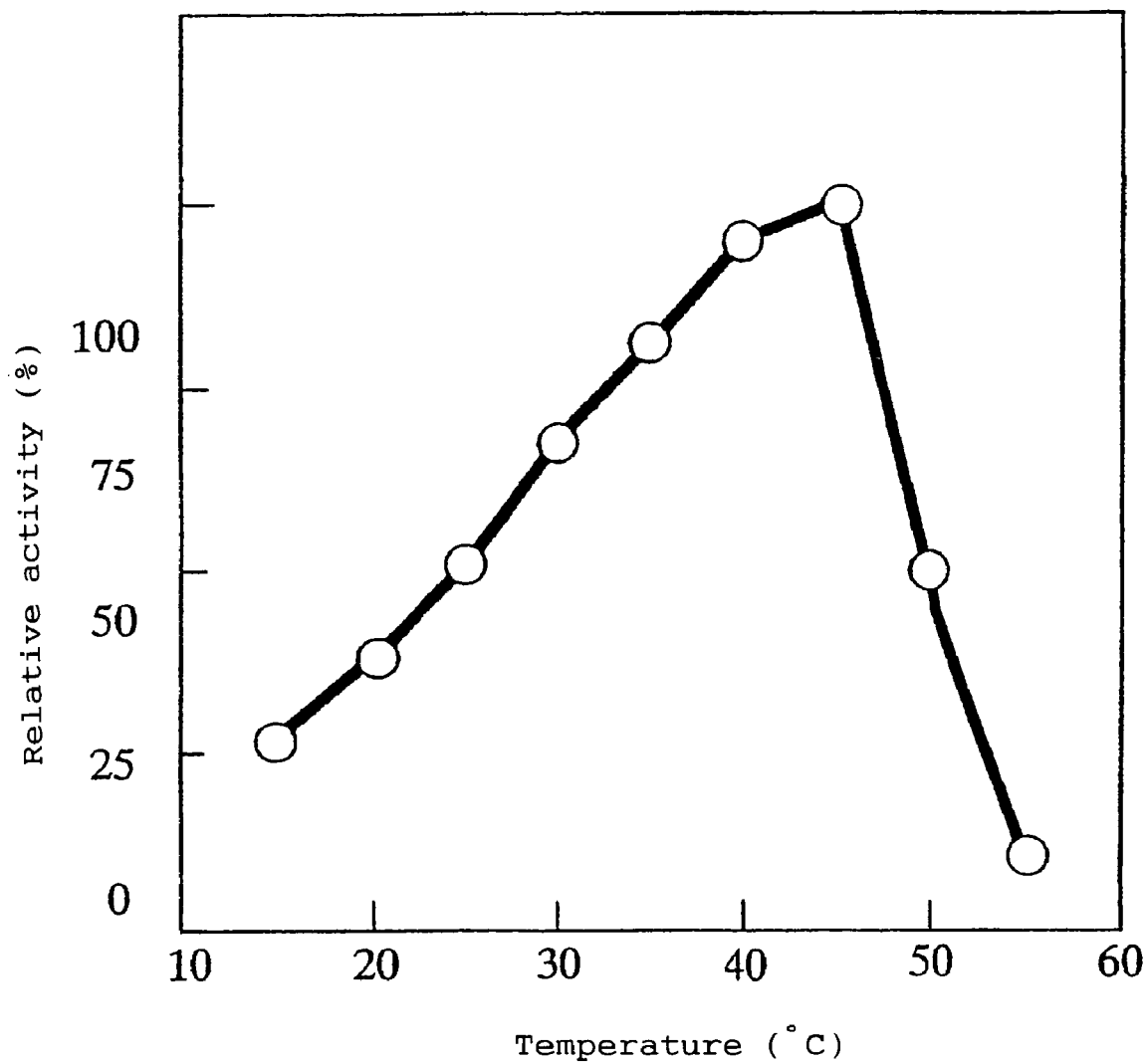
FIG. 9 shows the thermal influence on the enzymatic activity of α-isomaltosyl-transferring enzyme from a microorganism of the species *Bacillus globisporus* C9 strain.
Figure 10:
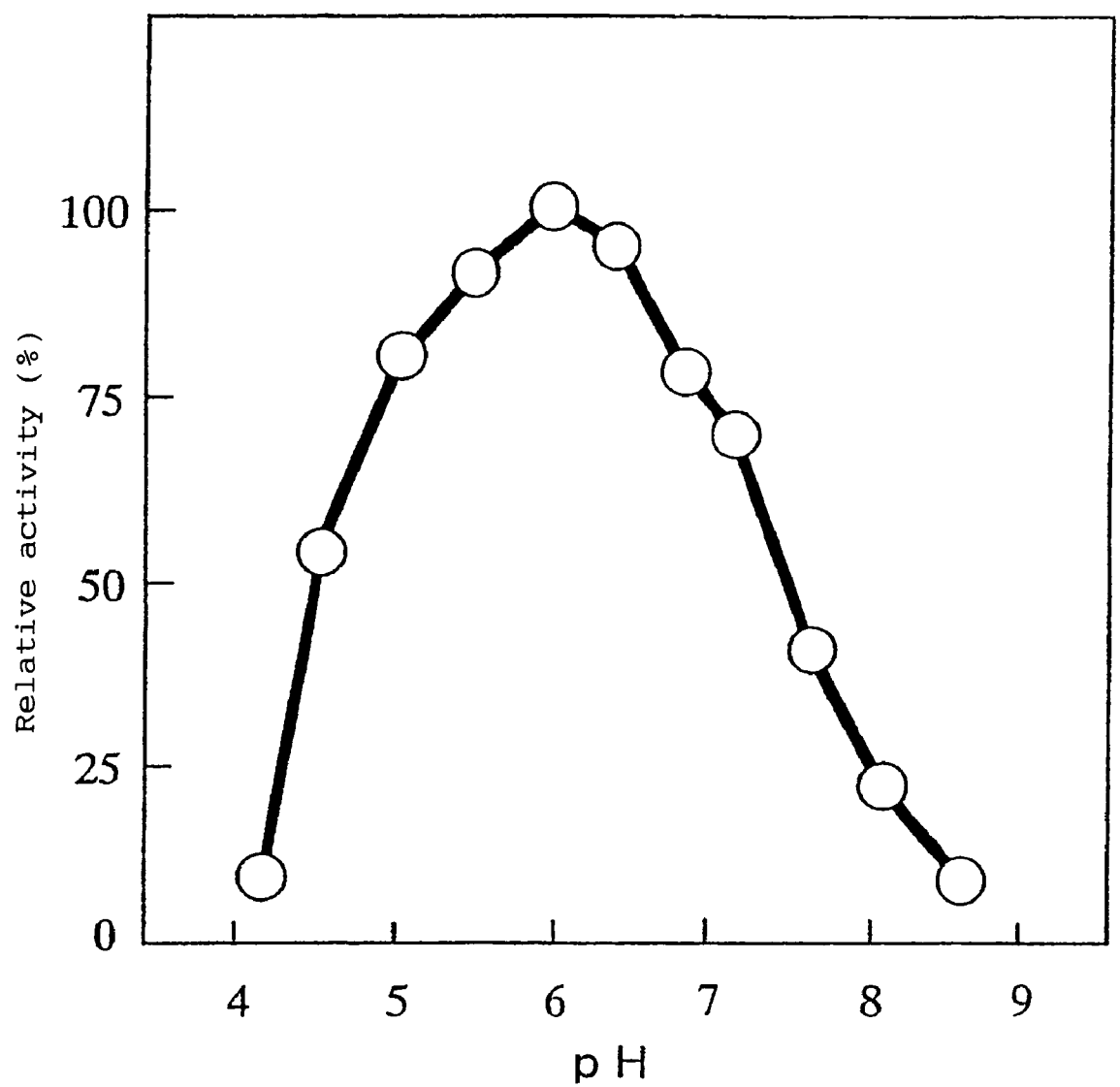
FIG. 10 shows the pH influence on the enzymatic activity of α-isomaltosyl-transferring enzyme from a microorganism of the species *Bacillus globisporus* C9 strain.
Figure 11:
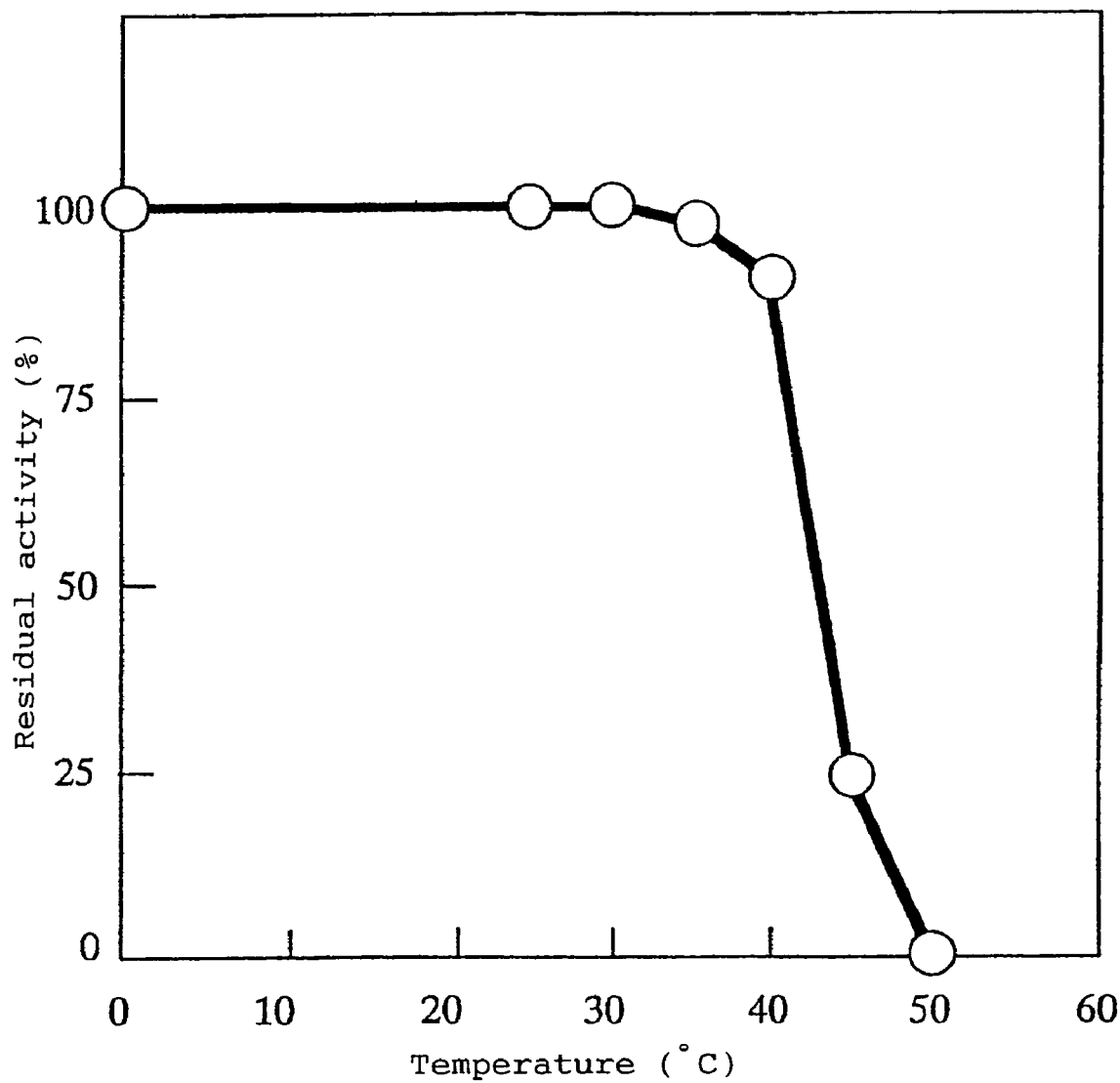
FIG. 11 shows the thermal stability of α-isomaltosyl-transferring enzyme from a microorganism of the species *Bacillus globisporus* C9 strain.
Figure 12:
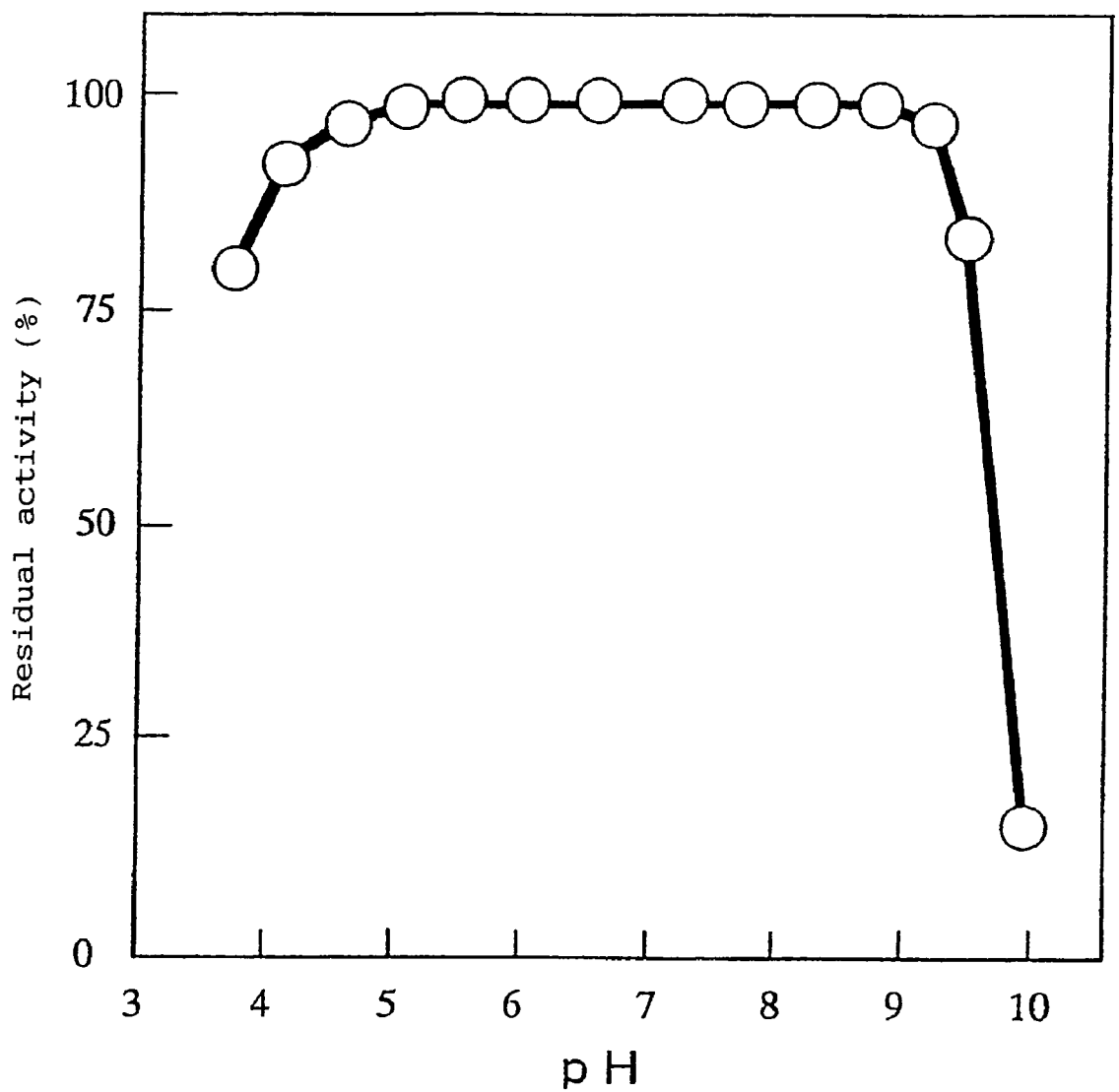
FIG. 12 shows the pH stability of α-isomaltosyl-transferring enzyme from a microorganism of the species *Bacillus globisporus* C9 strain.

The influence of temperature and pH on the activity of α-isomaltosyl-transferring enzyme was examined in accordance with the assay for its enzyme activity. These results are in FIG. 9 (influence of temperature) and FIG. 10 (influence of pH). The optimum temperature of the enzyme was about 45° C. when incubated at pH 6.0 for 30 min, and the optimum pH of the enzyme was about 6.0 when incubated at 35° C. for 30 min. The thermal stability of the enzyme was determined by incubating the testing enzyme solutions in the form of 20 mM acetate buffer (pH 6.0) at prescribed temperatures for 60 min, cooling the resulting enzyme solutions with water, and assaying the remaining enzyme activity of each solution. The pH stability of the enzyme was determined by keeping the testing enzyme solutions in the form of an appropriate 50 mM buffer having a prescribed pH at 4° C. for 24 hours, adjusting the pH of each solution to 6.0, and assaying the remaining enzyme activity of each solution. These results are respectively in FIG. 11 (thermal stability) and FIG. 12 (pH stability). As a result, the enzyme had thermal stability of up to about 40° C. and pH stability of about 4.0 to about 9.0.

The influence of metal ions on the activity of α-isomaltosyl-transferring enzyme was examined in the presence of 1 mM of each metal-ion according to the assay for its enzyme activity. The results are in Table 4.

TABLE 4

| Metal ion | Relative activity (%) | Metal ion | Relative activity (%) |
|---|---|---|---|
| None | 100 | $Hg^{2+}$ | 1 |
| $Zn^{2+}$ | 88 | $Ba^{2+}$ | 102 |
| $Mg^{2+}$ | 98 | $Sr^{2+}$ | 101 |
| $Ca^{2+}$ | 101 | $Pb^{2+}$ | 89 |
| $Co^{2+}$ | 103 | $Fe^{2+}$ | 96 |
| $Cu^{2+}$ | 57 | $Fe^{3+}$ | 105 |
| $Ni^{2+}$ | 102 | $Mn^{2+}$ | 106 |
| $Al^{3+}$ | 103 | EDTA | 104 |

As evident form the results in Table 4, the enzyme activity was strongly inhibited by $Hg^{2+}$, and it was also inhibited by $Cu^{2+}$. It was also found that the enzyme was not activated by $Ca^{2+}$ and not inhibited by EDTA.

Amino acid analysis on the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ. ID NO:2, i.e, isoleucine-aspartic acid-glycine-valine-tyrosine-histidine-alanine-proline-asparagine-glycine in the N-terminal region.

EXPERIMENT 6

Production of α-isomaltosylglucosaccharide-forming Enzyme from *Bacillus globisporus* C11 Strain A liquid nutrient culture medium, consisting of 4.0% (w/v) of "PINE-DEX #4", a partial starch hydrolyzate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water, was placed in 500-ml Erlenmeyer flasks in a volume of 100 ml each, autoclaved at 121° C. for 20 minutes to effect sterilization, cooled, inoculated with a stock culture of *Bacillus globisporus* C11 strain (FERM BP-7144), and incubated at 27° C. for 48 hours under rotary shaking conditions of 230 rpm. The resulting cultures were pooled and used as a seed culture. About 20 L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration-agitation conditions at 27° C. and a pH of 6.0 to 8.0. The resultant culture, having about 0.55 unit/ml of an α-isomaltosylglucosaccharide-forming activity, about 1.8 units/ml of an α-isomaltosyl-transferring activity, and about 1.1 units/ml of a cyclotetrasaccharide-forming activity, was centrifuged at 10,000 rpm for 30 min to obtain about 18 L of a supernatant. Measurement of the supernatant revealed that it had about 0.51 unit/ml of an α-isomaltosylglucosaccharide-forming enzyme activity, i.e., a total enzyme activity of about 9,180 units; about 1.7 units/ml of an α-isomaltosyl-transferring enzyme activity, i.e., a total enzyme activity of about 30,400 units; and about 1.1 units/ml of a cyclotetrasaccharide-forming enzyme activity, i.e., a total enzyme activity of about 19,400 units.

EXPERIMENT 7

Preparation of enzyme from *Bacillus globisporus* C11 Strain

EXPERIMENT 7-1

Purification of Enzyme from *Bacillus globisporus* C11 Strain

Eighteen litters of the supernatant, obtained in Experiment 6, were salted out in an 80% saturated ammonium sulfate solution and allowed to stand at 4° C. for 24 hours. Then, the salted out sediments were collected by centrifugation at 10,000 for 30 min, dissolved in 10 mM phosphate buffer (pH 7.5), dialyzed against a fresh preparation of the same buffer as used in the above to obtain about 416 ml of a crude enzyme solution. The crude enzyme solution was revealed to have 8,440 units of an α-isomaltosylglucosaccharide-forming enzyme activity, about 28,000 units of an α-isomaltosyl-transferring enzyme activity, and about 17,700 units of a cyclotetrasaccharide-forming enzyme activity. When subjected to ion-exchange chromatography using "SEPA-BEADS FP-DA13" gel, disclosed in Experiment 4-1, the above three types of enzymes were eluted as non-adsorbed fractions without adsorbing on the gel. The non-adsorbed fractions with those enzymes were pooled and dialyzed against 10 mM phosphate buffer (pH 7.0) containing 1 M ammonium sulfate, and the dialyzed solution was centrifuged to remove insoluble impurities. The resulting supernatant was fed to affinity chromatography using 500 ml of "SEPHACRYL HR S-200" gel to purify the enzyme. Active enzymes were adsorbed on the gel and sequentially eluted with a linear gradient decreasing from 1 M to 0 M of ammonium sulfate and a linear gradient increasing from 0 mM to 100 mM of maltotetraose, followed by collecting separate elutions of α-isomaltosyl-transferring enzyme and α-isomaltosylglucosaccharide-forming enzyme, respectively, where the former enzyme was eluted with the linear gradient of ammonium sulfate at a concentration of about 0.3 M and the latter enzyme was eluted with a linear gradient of maltotetraose at a concentration of about 30 mM. Therefore, fractions with the α-isomaltosylglucosaccharide-forming enzyme and those with the α-isomaltosyl-transferring enzyme were separately collected. Similarly as in the case of *Bacillus globisporus* C9 strain in Experiment 4, it was found that no cyclotetrasaccharide-forming activity was found in any fraction in this column chromatography, and that an enzyme mixture solution of both fractions of α-isomaltosylglucosaccharide-forming enzyme and α-isomaltosyl-transferring enzyme showed a cyclotetrasaccharide-forming enzyme activity, revealing that the activity of forming cyclotetrasaccharide from partial starch hydrolyzates was exerted in collaboration with the enzyme activities of the two types of enzymes.

Methods for separately purifying α-isomaltosylglucosaccharide-forming enzyme and α-isomaltosyl-transferring enzyme are explained below:

EXPERIMENT 7-2

Purification of α-isomaltosylglucosaccharide-forming Enzyme

A faction of α-isomaltosylglucosaccharide-forming enzyme, obtained in Experiment 7-1, was dialyzed against 10 mM phosphate buffer (pH 7.0) containing 1 M ammonium sulfate. The dialyzed solution was centrifuged to remove insoluble impurities, and the resulting supernatant was fed to hydrophobic chromatography using 350 ml of "BUTYL-TOYOPEARL 650 M", a gel commercialized by Tosoh Corporation, Tokyo, Japan. The enzyme adsorbed on the gel was eluted at about 0.3 M ammonium sulfate when eluted with a linear gradient decreasing from 1 M to 0 M of ammonium sulfate, followed by collecting fractions with the enzyme activity. The fractions were pooled and dialyzed against 10 mM phosphate buffer (pH 7.0) containing 1 M ammonium sulfate. The resulting dialyzed solution was centrifuged to remove insoluble impurities and fed to affinity chromatography using "SEPHACRYL HR S-200" gel to purify the enzyme. The amount of enzyme activity, specific activity, and yield of the α-isomaltosylglucosaccharide-forming enzyme in each purification step are in Table 5.

TABLE 5

| Purification step | Enzyme* activity (unit) | Specific activity of enzyme* (unit/mg protein) | Yield (%) |
|---|---|---|---|
| Culture supernatant | 9,180 | 0.14 | 100 |
| Dialyzed solution after salting out with ammonium sulfate | 8,440 | 0.60 | 91.9 |

TABLE 5-continued

| Purification step | Enzyme* activity (unit) | Specific activity of enzyme* (unit/mg protein) | Yield (%) |
|---|---|---|---|
| Eluate from ion-exchange column chromatography | 6,620 | 1.08 | 72.1 |
| Eluate from affinity column chromatography | 4,130 | 8.83 | 45.0 |
| Eluate from hydrophobic column chromatography | 3,310 | 11.0 | 36.1 |
| Eluate from affinity column chromatography | 2,000 | 13.4 | 21.8 |

Note:
The symbol "*" means α-isomaltosylglucosaccharide-forming enzyme.

The finally purified α-isomaltosylglucosaccharide-forming enzyme specimen was assayed for purity on gel electrophoresis using a 7.5% (w/v) polyacrylamide gel and detected on the gel as a single protein band, meaning a high purity enzyme specimen.

EXPERIMENT 7-3

Purification of α-isomaltosyl-transferring Enzyme

A faction of α-isomaltosyl-transferring enzyme, which had been separated from a fraction of α-isomaltosylglucosaccharide-forming enzyme by the affinity chromatography in Experiment 7-1, was dialyzed against 10 mM phosphate buffer (pH 7.0) containing 1 M ammonium sulfate. The dialyzed solution was centrifuged to remove insoluble impurities, and the resulting supernatant was fed to hydrophobic chromatography using 350 ml of "BUTYL-TOYOPEARL 650 M", a gel commercialized by Tosoh Corporation, Tokyo, Japan. The enzyme adsorbed on the gel and then it was eluted at about 0.3 M ammonium sulfate when eluted with a linear gradient decreasing from 1 M to 0 M of ammonium sulfate, followed by collecting fractions with the enzyme activity. The fractions were pooled and dialyzed against 10 mM phosphate buffer (pH 7.0) containing 1 M ammonium sulfate. The resulting dialyzed solution was centrifuged to remove insoluble impurities and fed to affinity chromatography using "SEPHACRYL HR S-200" gel to purify the enzyme. The amount of enzyme activity, specific activity, and yield of the α-isomaltosyl-transferring enzyme in each purification step are in Table 6.

TABLE 6

| Purification step | Enzyme* activity (unit) | Specific activity of enzyme* (unit/mg protein) | Yield (%) |
|---|---|---|---|
| Culture supernatant | 30,400 | 0.45 | 100 |
| Dialyzed solution after salting out with ammonium sulfate | 28,000 | 1.98 | 92.1 |
| Eluate from ion-exchange column chromatography | 21,800 | 3.56 | 71.7 |
| Eluate from affinity column chromatography | 13,700 | 21.9 | 45.1 |
| Eluate from hydrophobic column chromatography | 10,300 | 23.4 | 33.9 |
| Eluate from affinity column chromatography | 5,510 | 29.6 | 18.1 |

Note:
The symbol "*" means α-isomaltosyl-transferring enzyme.

EXPERIMENT 8

Property of α-isomaltosylglucosaccharide-forming Enzyme and α-isomaltosyl-transferring Enzyme

EXPERIMENT 8-1

Property of α-isomaltosylglucosaccharide-forming Enzyme

A purified specimen of α-isomaltosylglucosaccharide-forming enzyme, obtained by the method in Experiment 7-2, was subjected to SDS-PAGE using a 7.5% (w/v) of polyacrylamide gel and then determined for molecular weight by comparing with the dynamics of standard molecular markers electrophoresed in parallel, commercialized by Japan Bio-Rad Laboratories Inc., Tokyo, Japan, revealing that the enzyme had a molecular weight of about 137,000±20,000 daltons.

A fresh preparation of the same purified specimen as used in the above was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 5.2±0.5.

Figure 13:
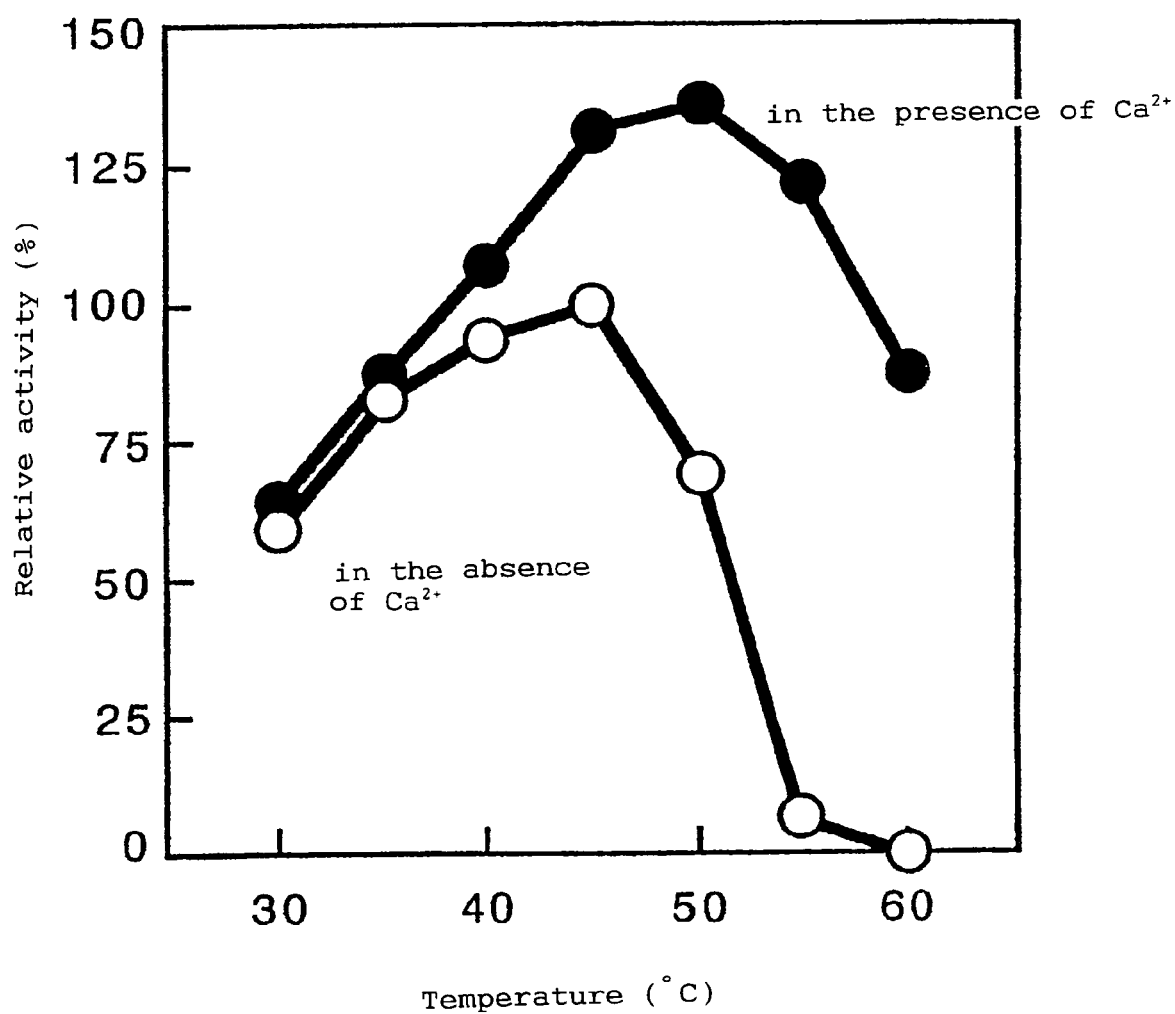
FIG. 13 shows the thermal influence on the enzymatic activity of α-isomaltosylglucosaccharide-forming enzyme from a microorganism of the species *Bacillus globisporus* C11 strain.
Figure 14:
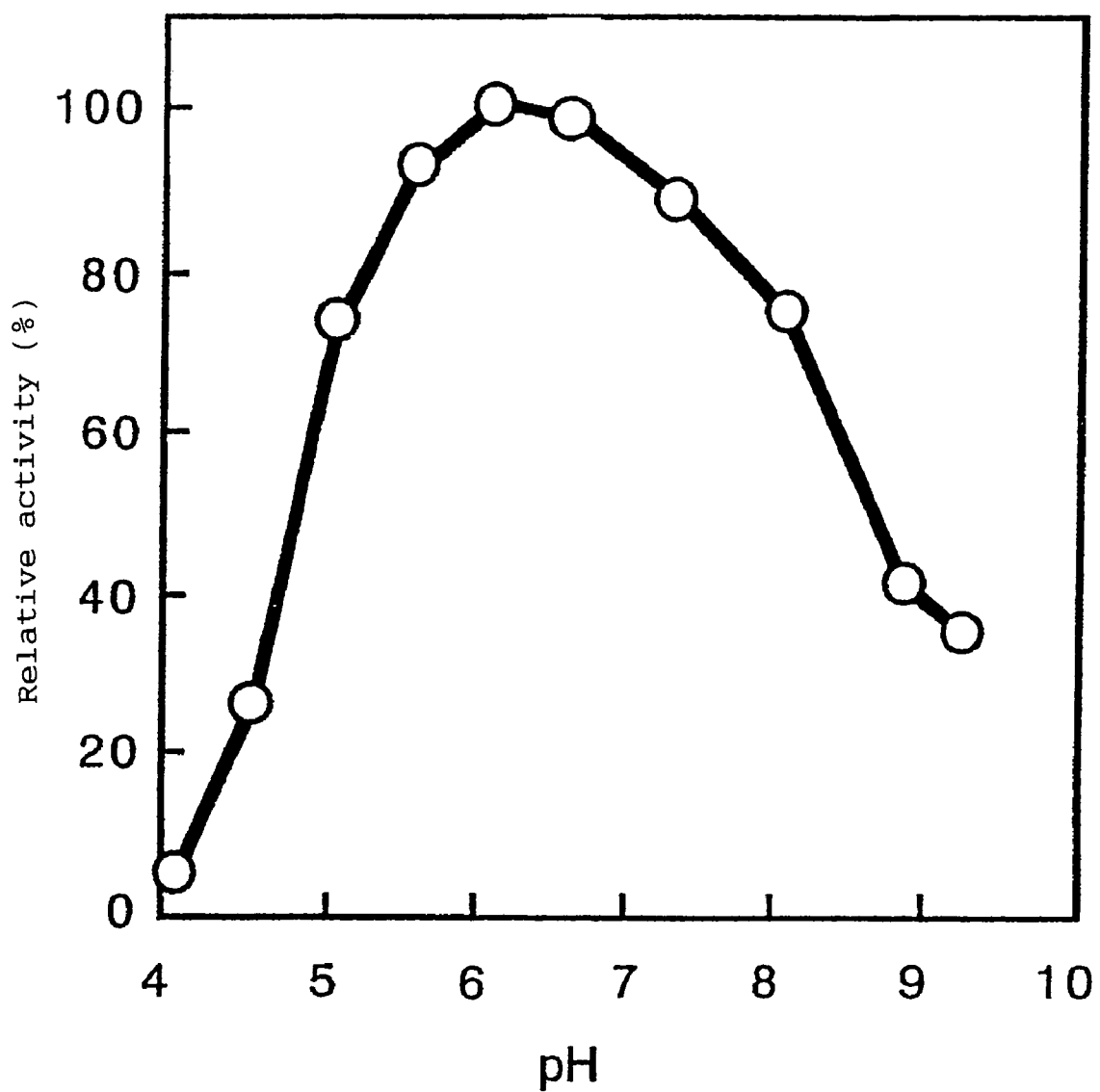
FIG. 14 shows the pH influence on α-isomaltosylglucosaccharide-forming enzyme from a microorganism of the species *Bacillus globisporus* C11 strain.
Figure 15:
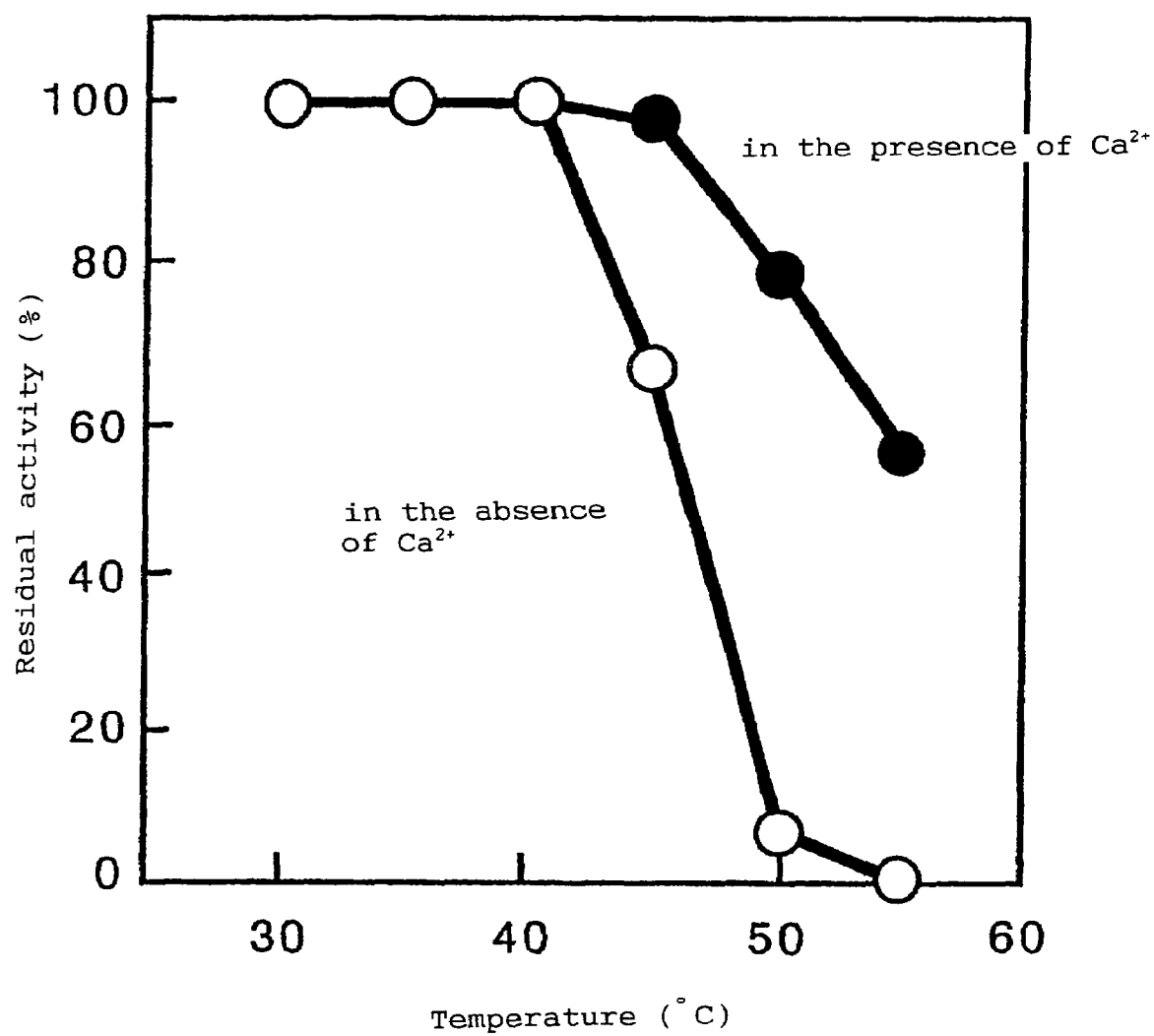
FIG. 15 shows the thermal stability of α-isomaltosylglucosaccharide-forming enzyme from a microorganism of the species *Bacillus globisporus* C11 strain.
Figure 16:
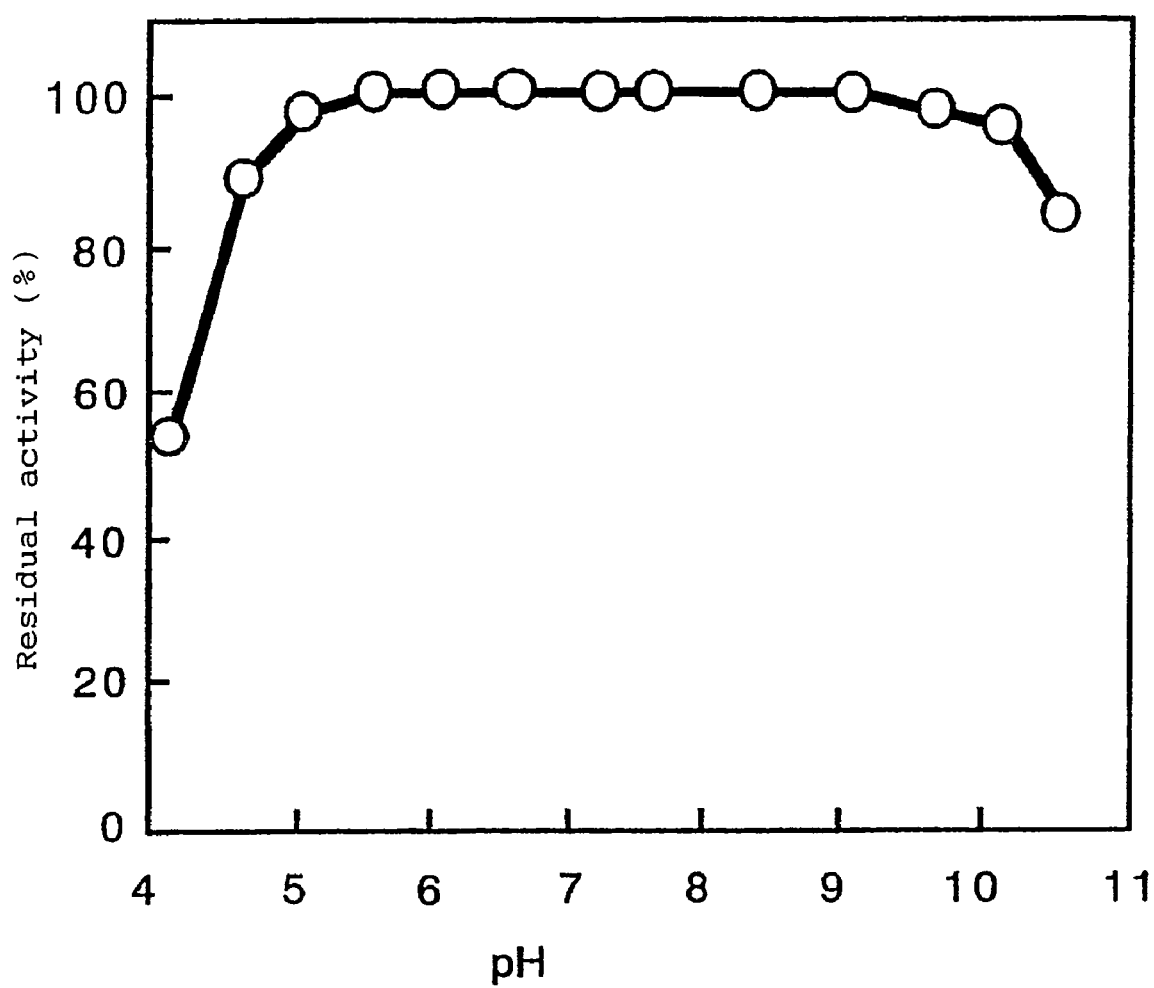
FIG. 16 shows the pH stability of α-isomaltosylglucosaccharide-forming enzyme from a microorganism of the species *Bacillus globisporus* C11 strain.

The influence of temperature and pH on the activity of α-isomaltosylglucosaccharide-forming enzyme was examined in accordance with the assay for its enzyme activity, where the influence of temperature was examined in the presence or the absence of 1 mM $Ca^{2+}$. These results are in FIG. 13 (influence of temperature) and FIG. 14 (influence of pH). The optimum temperature of the enzyme was about 45° C. in the absence of $Ca^{2+}$ and about 50° C. in the presence of 1 mM $Ca^{2+}$ when incubated at pH 6.0 for 60 min. The optimum pH of the enzyme was about 6.0 when incubated at 35° C. for 60 min. The thermal stability of the enzyme was determined by incubating the testing enzyme solutions in the form of 20 mM acetate buffer (pH 6.0) in the presence or the absence of 1 mM $Ca^{2+}$ at prescribed temperatures for 60 min, cooling the resulting enzyme solutions with water, and assaying the remaining enzyme activity of each solution. The pH stability of the enzyme was determined by keeping the testing enzyme solutions in the from of 50 mM buffers having prescribed pHs at 4° C. for 24 hours, adjusting the pH of each solution to 6.0, and assaying the remaining enzyme activity of each solution. These results are respectively in FIG. 15 (thermal stability) and FIG. 16 (pH stability). As a result, the enzyme had thermal stability of up to about 40° C. in the absence of $Ca^{2+}$ and up to about 45° C. in the presence of 1 mM $Ca^{2+}$. The pH stability of enzyme was about 5.0 to about 10.0.

The influence of metal ions on the activity of α-isomaltosyl-transferring enzyme was examined in the presence of 1 mM of each metal-ion according to the assay for its enzyme activity. The results are in Table 7.

TABLE 7

| Metal ion | Relative activity (%) | Metal ion | Relative activity (%) |
|---|---|---|---|
| None | 100 | $Hg^{2+}$ | 4 |
| $Zn^{2+}$ | 91 | $Ba^{2+}$ | 65 |
| $Mg^{2+}$ | 98 | $Sr^{2+}$ | 83 |
| $Ca^{2+}$ | 109 | $Pb^{2+}$ | 101 |
| $Co^{2+}$ | 96 | $Fe^{2+}$ | 100 |
| $Cu^{2+}$ | 23 | $Fe^{3+}$ | 102 |

TABLE 7-continued

| Metal ion | Relative activity (%) | Metal ion | Relative activity (%) |
|---|---|---|---|
| $Ni^{2+}$ | 93 | $Mn^{2+}$ | 142 |
| $Al^{3+}$ | 100 | EDTA | 24 |

As evident form the results in Table 7, the enzyme activity was strongly inhibited by $Hg^{2+}$, $Cu^{2+}$, and EDTA, and it was also inhibited by $Ba^{2+}$ and $Sr^{2+}$. It was also found that the enzyme was activated by $Ca^{2+}$ and $Mn^{2+}$. Amino acid analysis on the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:1, i.e, tyrosine-valine-serine-serine-leucine-glycine-asparagine-leucine-isoleucine in the N-terminal region. Comparison of the partial amino acid sequence in the N-terminal region with that derived from the α-isomaltosylglucosaccharide-forming enzyme from *Bacillus globisporus* C9 strain in Experiment 5-1 revealed that they were the same and the consensus N-terminal amino acid sequence, commonly found in these α-isomaltosylglucosaccharide-forming enzymes, was an amino acid sequence of tyrosine-valine-serine-serine-leucine-glycine-asparagine-leucine-isoleucine of SEQ ID NO:1 in the N-terminal region. Detailed method for assaying amino acid sequence is not shown in this specification because it is disclosed in detail in Japanese Patent Application No. 2001-519,441 (International Publication No. WO 02/055708), however, the α-isomaltosylglucosaccharide-forming enzyme has an amino acid sequence of 36-1284 amino acid residues shown in parallel in SEQ ID NO:21 similarly as that for the polypeptide, disclosed in the specification of the above-identified Japanese Patent Application No. 2001-5441.

EXPERIMENT 8-2

Property of α-isomaltosyl-transferring Enzyme

A purified specimen of α-isomaltosyl-transferring enzyme, obtained by the method in Experiment 7-3, was subjected to SDS-PAGE using a 7.5% (w/v) of polyacrylamide gel and then determined for molecular weight by comparing with the dynamics of standard molecular markers electrophoresed in parallel, commercialized by Japan Bio-Rad Laboratories Inc., Tokyo, Japan, revealing that the enzyme had a molecular weight of about 102,000±20,000 daltons.

A fresh preparation of the same purified specimen as used in the above was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 5.6±0.5.

Figure 17:
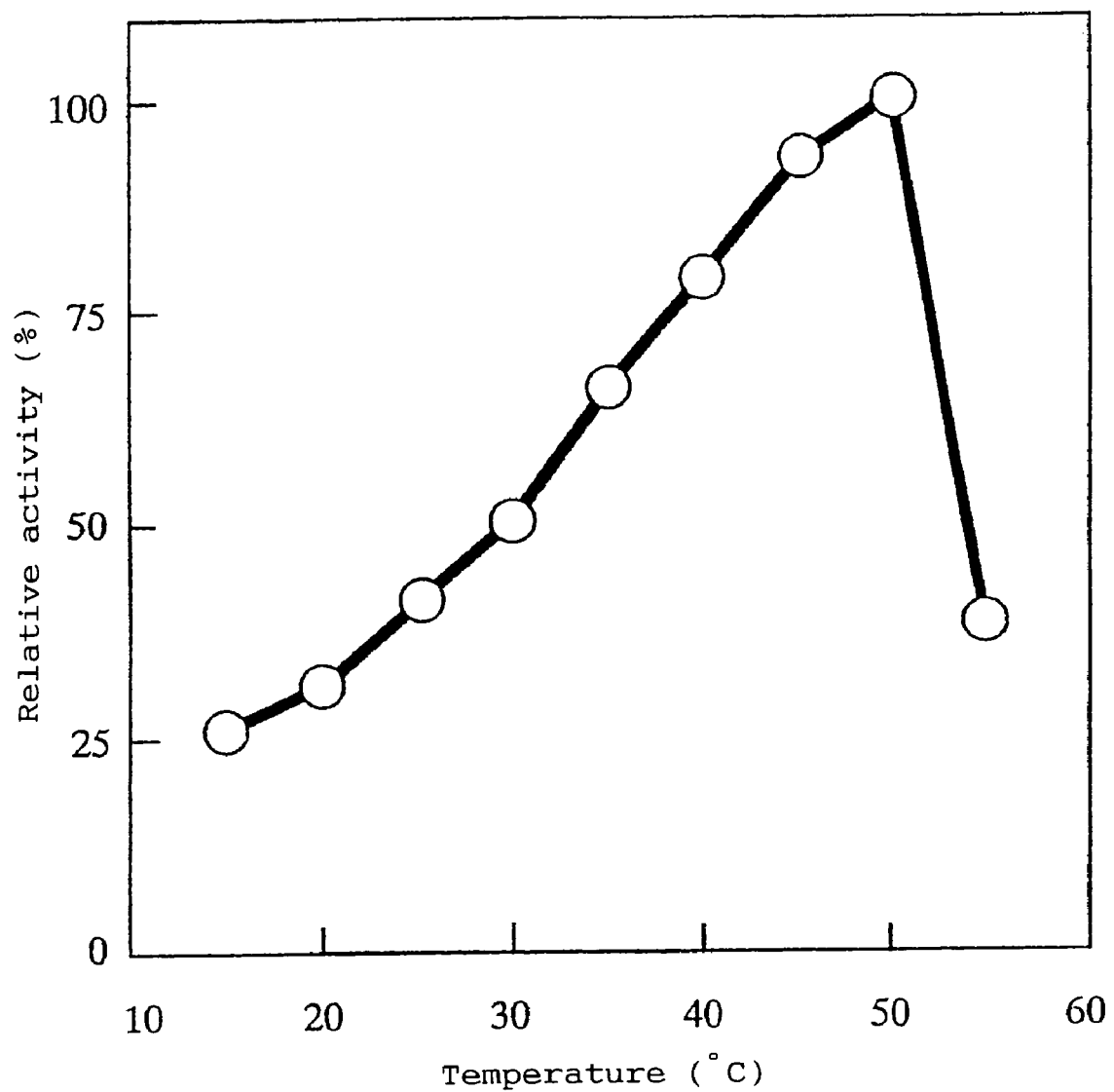
FIG. 17 shows the thermal influence on the enzymatic activity of α-isomaltosyl-transferring enzyme from a microorganism of the species *Bacillus globisporus* C11 strain.
Figure 18:
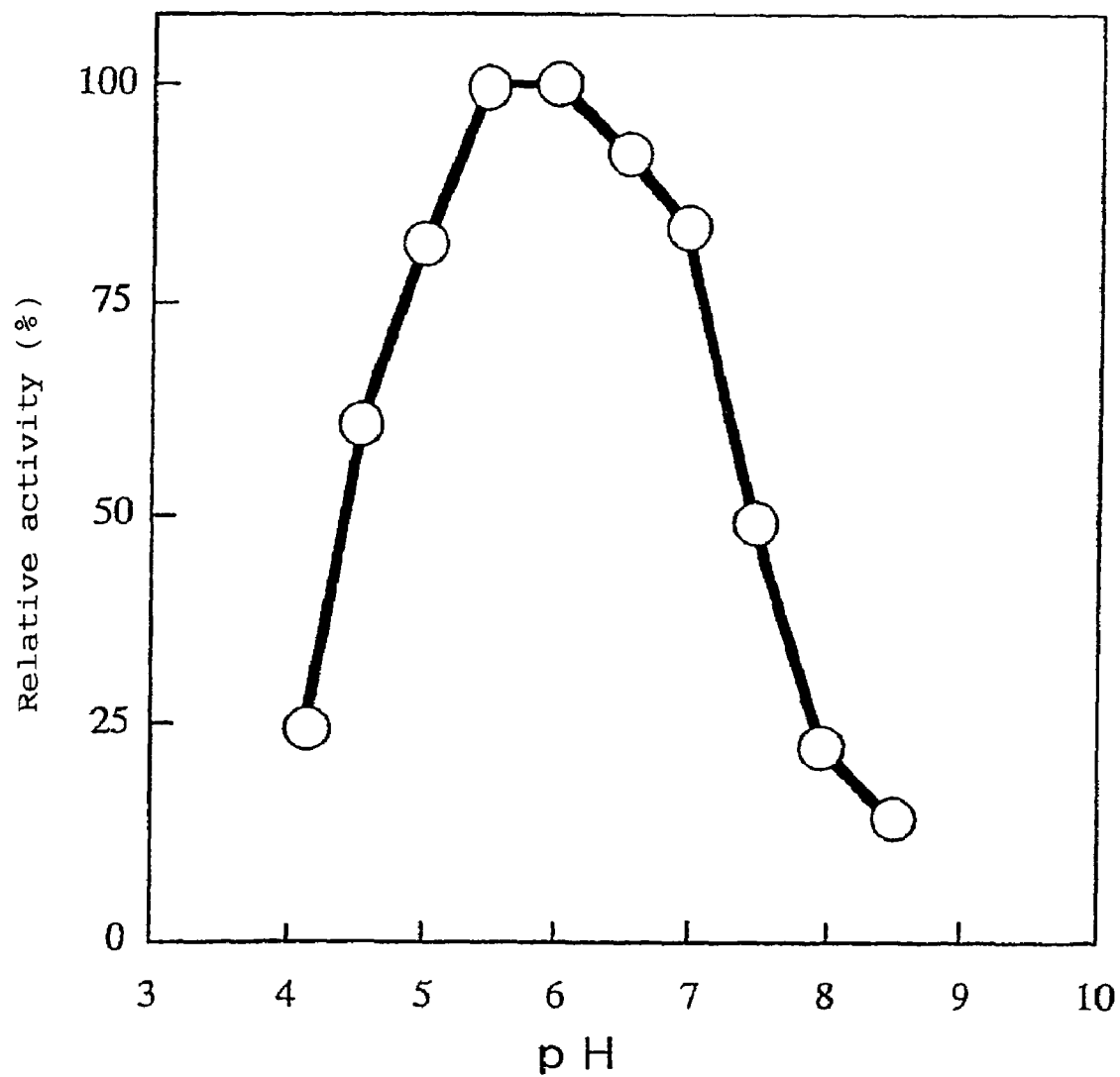
FIG. 18 shows the pH influence on the enzymatic activity of α-isomaltosyl-transferring enzyme from a microorganism of the species *Bacillus globisporus* C11 strain.
Figure 19:
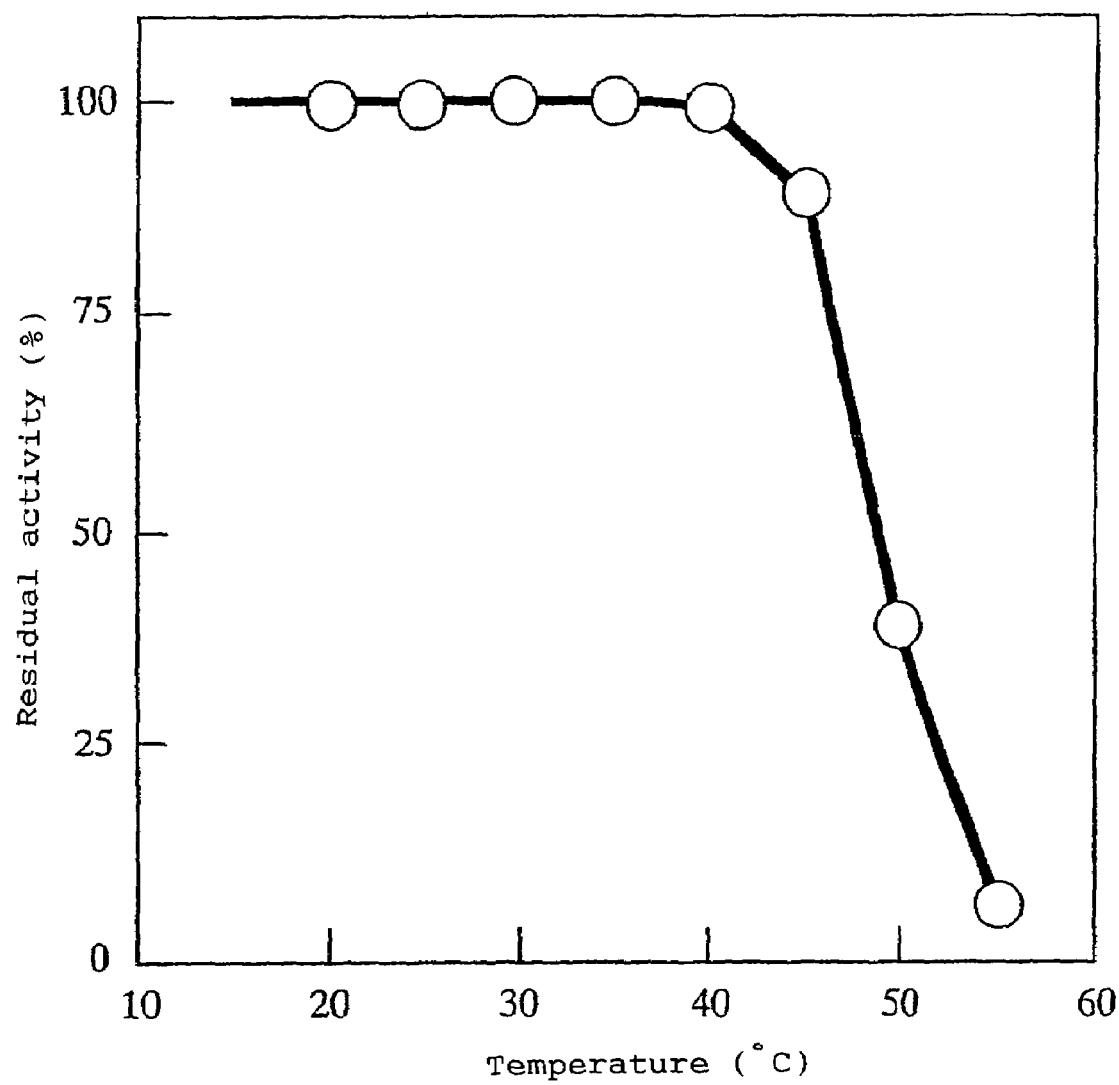
FIG. 19 shows the thermal stability of α-isomaltosyl-transferring enzyme from a microorganism of the species *Bacillus globisporus* C11 strain.
Figure 20:
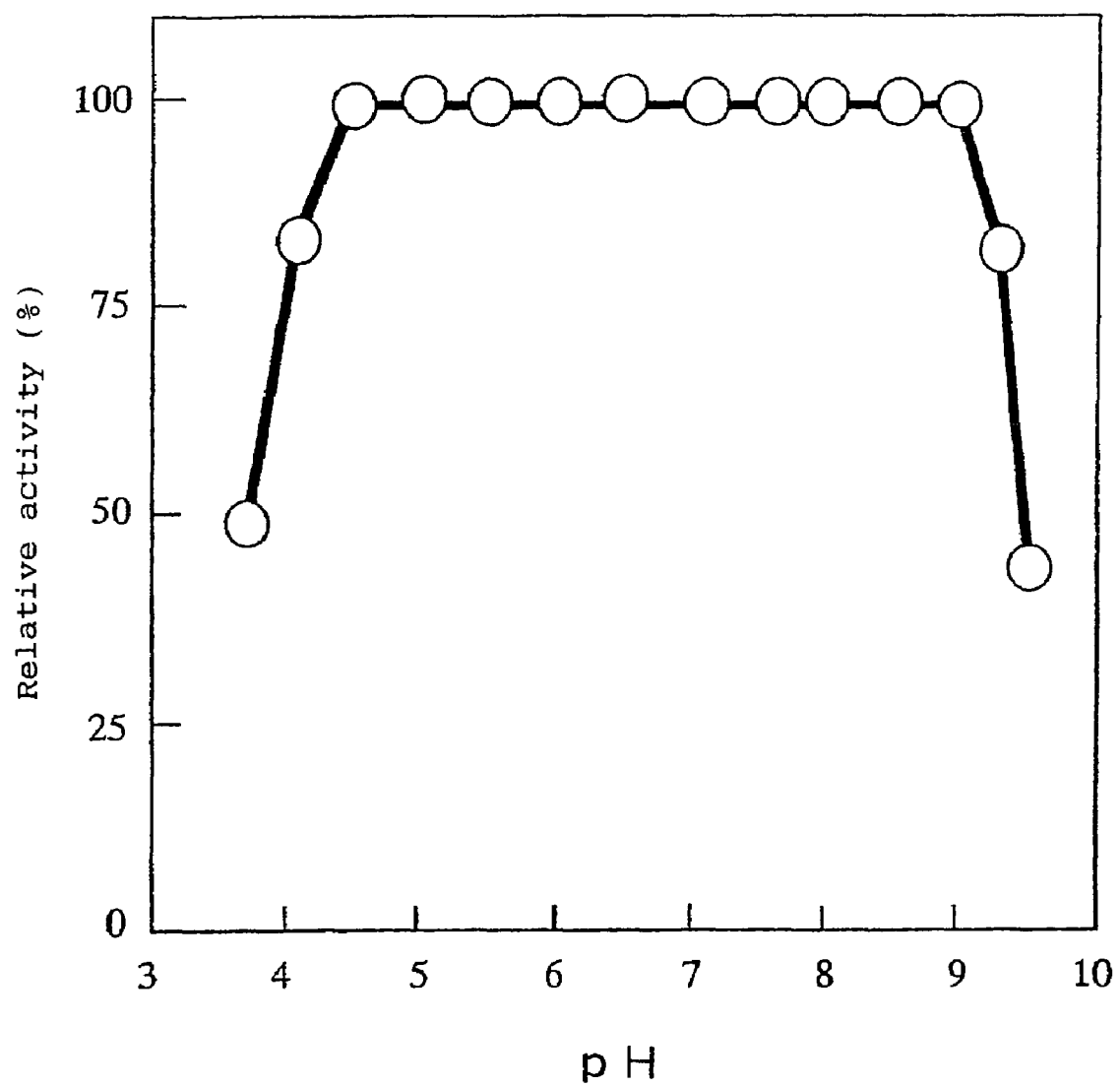
FIG. 20 shows the pH stability of α-isomaltosyl-transferring enzyme from a microorganism of the species *Bacillus globisporus* C11 strain.

The influence of temperature and pH on the activity of α-isomaltosyl-transferring enzyme was examined in accordance with the assay for its enzyme activity. These results are in FIG. 17 (influence of temperature) and FIG. 18 (influence of pH). The optimum temperature of the enzyme was about 50° C. when incubated at pH 6.0 for 30 min. The optimum pH of the enzyme was about 5.5 to about 6.0 when incubated at 35° C. for 30 min. The thermal stability of the enzyme was determined by incubating the testing enzyme solutions in the form of 20 mM acetate buffer (pH 6.0) at prescribed temperatures for 60 min, cooling the resulting enzyme solutions with water, and assaying the remaining enzyme activity of each solution. The pH stability of the enzyme was determined by keeping the testing enzyme solutions in the form of 50 mM buffers having prescribed pHs at 4° C. for 24 hours, adjusting the pH of each solution to 6.0, and assaying the remaining enzyme activity of each solution. These results are respectively in FIG. 19 (thermal stability) and FIG. 20 (pH stability). As a result, the enzyme had thermal stability of up to about 40° C. and pH stability of about 4.5 to about 9.0.

The influence of metal ions on the activity of α-isomaltosyl-transferring enzyme was examined in the presence of 1 mM of each metal-ion according to the assay for its enzyme activity. The results are in Table 8.

TABLE 8

| Metal ion | Relative activity (%) | Metal ion | Relative activity (%) |
|---|---|---|---|
| None | 100 | $Hg^{2+}$ | 2 |
| $Zn^{2+}$ | 83 | $Ba^{2+}$ | 90 |
| $Mg^{2+}$ | 91 | $Sr^{2+}$ | 93 |
| $Ca^{2+}$ | 91 | $Pb^{2+}$ | 74 |
| $Co^{2+}$ | 89 | $Fe^{2+}$ | 104 |
| $Cu^{2+}$ | 56 | $Fe^{3+}$ | 88 |
| $Ni^{2+}$ | 89 | $Mn^{2+}$ | 93 |
| $Al^{3+}$ | 89 | EDTA | 98 |

As evident form the results in Table 8, the enzyme activity was strongly inhibited by $Hg^{2+}$, and it was also inhibited by $Cu^{2+}$. It was also found that the enzyme was not activated by $Ca^{2+}$ and not inhibited by EDTA.

Amino acid analysis on the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:3, i.e., isoleucine-aspartic acid-glycine-valine-tyrosine-histidine-alanine-proline-tyrosine-glycine in the N-terminal region. Comparison of the partial amino acid sequence in the N-terminal region with that derived from the α-isomaltosyl-transferring enzyme from *Bacillus globisporus* C9 strain in Experiment 5-2 revealed that they had a consensus amino acid sequence of isoleucine-aspartic acid-glycine-valine-tyrosine-histidine-alanine-proline, as shown in SEQ ID NO:4 in their N-terminal regions. Detailed method for assaying amino acid sequence is not shown in this specification because it is disclosed in detail in Japanese Patent Application No. 2000-350142 (International Publication No. WO 02/40659), however, the α-isomaltosyl-transforming enzyme has an amino acid sequence of amino acid residues 30-1093 shown in parallel in SEQ ID NO:22 similarly as that disclosed in the specification of the above-identified Japanese Patent Application No. 2000-350142.

EXPERIMENT 9

Amino Acid Sequence of
α-isomaltosylglucosaccharide-forming Enzyme and
α-isomaltosyl-transferring Enzyme

EXPERIMENT 9-1

Internal Partial Amino Acid Sequence of
α-isomaltosylglucosaccharide-forming Enzyme A part of a purified specimen of α-isomaltosylglucosaccharide-forming enzyme, obtained by the method in Experiment 7-2, was dialyzed against 10 mM Tris-HCl buffer (pH 9.0), and the dialyzed solution was diluted with a fresh preparation of the same buffer as used in the above to give a concentration of about one milligram per milliliter. One milliliter of the dilute as a test sample was admixed with 10 μg of trypsin commercialized by Wako Pure Chemical Industries, Ltd., Tokyo, Japan, and incubated at 30° C. for 22 hours to hydrolyze the enzyme into peptides. To isolate the peptides, the resulting hydrolyzates were subjected to reverse-phase HPLC using "μ-Bondapak C18 column" with a diameter of 2.1 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 8% (v/v) to 40% (v/v) in 0.1% (v/v) trifluoroacetate over 120 min. The peptides eluted from the column were detected by monitoring the absorbance at a wavelength of 210 nm. Three peptide specimens named P64 with a retention time of about 64 min, P88 with a retention time of about 88 min, and P99 with a retention time of about 99 min, which had been well separated from other peptides, were separately collected and dried in vacuo and then dissolved in 200 μl of a solution of 0.1% (v/v) trifluoroacetate and 50% (v/v) acetonitrile. Each peptide specimen was subjected to a protein sequencer for analyzing amino acid sequence up to eight amino acid residues to obtain amino acid sequences of SEQ ID NOs:5 to 7. The analyzed internal partial amino acid sequences are in Table 9.

TABLE 9

| Peptide name | Internal partial amino acid sequence |
| --- | --- |
| P64 | aspartic acid-alanine-serine-alanine-asparagine-valine-threonine-threonine |
| P88 | tryptophane-serine-leucine-glycine-phenylalanine-methionine-asparagine-phenylalanine |
| P99 | asparagine-tyrosine-threonine-aspartic acid-alanine-tryptophane-methionine-phenylalanine |

EXPERIMENT 9-2

Internal Partial Amino Acid Sequence of α-isomaltosyl-transferring Enzyme

A part of a purified specimen of α-isomaltosyl-transferring enzyme, obtained by the method in Experiment 7-3, was dialyzed against 10 mM Tris-HCl buffer (pH 9.0), and the dialyzed solution was diluted with a fresh preparation of the same buffer as used in the above to give a concentration of about one milligram per milliliter. One milliliter of the dilute as a test sample was admixed with 10 μg of "Lysyl Endopeptidase" commercialized by Wako Pure Chemical Industries, Ltd., Tokyo, Japan, and allowed to react at 30° C. for 22 hours to form peptides. The resultant mixture was subjected to reverse-phase HPLC to separate the peptides using "μ-Bondapak C18 column" having a diameter of 2.1 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 8% (v/v) to 40% (v/v) in 0.1% (v/v) trifluoroacetate over 120 min. The peptides eluted from the column were detected by monitoring the absorbance at a wavelength of 210 nm. Three peptide specimens named P22 with a retention time of about 22 min, P63 with a retention time of about 63 min, and P71 with a retention time of about 71 min, which had been well separated from other peptides, were separately collected and dried in vacuo and then dissolved in 200 μl of a solution of 0.1% (v/v) trifluoroacetate and 50% (v/v) acetonitrile. Each peptide specimen was subjected to a protein sequencer for analyzing amino acid sequence up to eight amino acid residues to obtain amino acid sequences of SEQ ID NOs:8 to 10. The analyzed internal partial amino acid sequences are in Table 10.

TABLE 10

| Peptide name | Internal partial amino acid sequence |
| --- | --- |
| P22 | glycine-asparagine-glutamic acid-methionine-arginine-asparagine-glutamine-tyrosine |
| P63 | isoleucine-threonine-threonine-tryptophane-proline-isoleucine-glutamic acid-serine |
| P71 | tryptophane-alanine-phenylalanine-glycine-leucine-tryptophane-methionine-serine |

EXPERIMENT 10

Production of α-isomaltosylglucosaccharide-forming Enzyme from *Bacillus globisporus* N75 Strain A liquid nutrient culture medium, consisting of 4.0% (w/v) of "PINE-DEX #4", a partial starch hydrolyzate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water, was placed in 500-ml Erlenmeyer flasks in a volume of 100 ml each, autoclaved at 121° C. for 20 minutes to effect sterilization, cooled, inoculated with a stock culture of *Bacillus globisporus* N75 strain (FERM BP-7591), and incubated at 27° C. for 48 hours under rotary shaking conditions of 230 rpm for use as a seed culture. About 20 L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration-agitation conditions at 27° C. and pH 6.0 to 8.0. The resultant culture, having about 0.34 unit/ml of an α-isomaltosylglucosaccharide-forming enzyme activity, about 1.1 units/ml of an α-isomaltosyl-transferring enzyme activity, and about 0.69 unit/ml of a cyclotetrasaccharide-forming enzyme activity, was centrifuged at 10,000 rpm for 30 min to obtain about 18 L of a supernatant. Assay for enzyme activity of the supernatant revealed that it had about 0.33 unit/ml of an α-isomaltosylglucosaccharide-forming enzyme activity, i.e., a total enzyme activity of about 5,940 units; about 1.1 units/ml of an α-isomaltosyl-transferring enzyme activity, i.e., a total enzyme activity of about 19,800 units; and about 0.67 unit/ml of a cyclotetrasaccharide-forming enzyme activity, i.e., a total enzyme activity of about 12,100 units.

EXPERIMENT 11

Preparation of Enzyme from *Bacillus globisporus* N75 Strain

About 18 L of the supernatant obtained in Experiment 10 was salted out in a 60% saturated ammonium sulfate solution and allowed to stand at 4° C. for 24 hours. Then, the salted out sediments were collected by centrifugation at 10,000 for 30 min, dissolved in 10 mM Tris-HCl buffer (pH 8.3), and dialyzed against a fresh preparation of the same buffer as used in the above to obtain about 450 ml of a crude enzyme solution, revealing to have 4,710 units of α-isomaltosylglucosaccharide-forming enzyme, about 15,700 units of α-isomaltosyl-transferring enzyme, and about 9,590 units of cyclotetrasaccharide-forming enzyme. The crude enzyme solution was subjected to ion-exchange chromatography using "SEPABEADS FP-DA13" gel, disclosed in Experiment 4-1. The enzyme was adsorbed on the gel, while α-isomaltosyl-transferring enzyme was eluted as a non-adsorbed fraction without adsorbing on the gel. When eluted with a linear gradient increasing from 0 M to 1 M NaCl, α-isomaltosylglucosaccharide-forming enzyme was eluted at a concentration of about 0.25 M NaCl. Under these conditions, fractions with an α-isomaltosylglucosaccharide-forming enzyme activity and those with an α-isomaltosyl-transferring enzyme were separately fractionated and collected. Similarly as in the case of *Bacillus globisporus* C9 strain in Experiment 4 and *Bacillus globisporus* C11 strain in Experiment 7, it was revealed that no cyclotetrasaccharide-forming activity was found in any of the above fractions collected separately in this column chromatography, and an enzyme solution, obtained by mixing both fractions of α-isomaltosylglucosaccharide-forming enzyme and of α-isomaltosyl-transferring enzyme, showed a cyclotetrasaccharide-forming activity, and these facts revealed that the activity of forming cyclotetrasaccharide from partial starch hydrolyzates is exerted by the coaction of α-isomaltosylglucosaccharide-forming enzyme and α-isomaltosyl-transferring enzyme.

The following experiments are methods for separately purifying α-isomaltosylglucosaccharide-forming enzyme and α-isomaltosyl-transferring enzyme:

EXPERIMENT 11-2

Purification of α-isomaltosylglucosaccharide-forming Enzyme

Fractions with α-isomaltosylglucosaccharide-forming enzyme, obtained in Experiment 11-1, were pooled and dialyzed against 10 mM phosphate buffer (pH 7.0) containing 1 M ammonium sulfate, and the dialyzed solution was centrifuged to remove insoluble impurities and fed to affinity chromatography using 500 ml of "SEPHACRYL HR S-200" gel. The enzyme was adsorbed on the gel and then eluted therefrom sequentially with a linear gradient decreasing from 1 M to 0 M ammonium sulfate and with a linear gradient increasing from 0 mM to 100 mM maltotetraose. As a result, the α-isomaltosylglucosaccharide-forming enzyme adsorbed on the gel was eluted therefrom at a concentration of about 30 mM maltotetraose, followed by collecting fractions with the enzyme activity. The fractions were pooled and dialyzed against 10 mM phosphate buffer (pH 7.0) containing 1 M ammonium sulfate, and the dialyzed solution was centrifuged to remove insoluble impurities. The resulting supernatant was fed to hydrophobic chromatography using 350 ml of "BUTYL-TOYOPEARL 650M", a gel commercialized by Tosoh Corporation, Tokyo, Japan. The enzyme was adsorbed on the gel and then eluted with a linear gradient decreasing from 1 M to 0 M ammonium sulfate, resulting in an elution of the enzyme from the gel at a concentration of about 0.3 M ammonium sulfate and collecting fractions with the enzyme activity. The fractions were pooled and dialyzed against 10 mM phosphate buffer (pH 7.0) containing 1 M ammonium sulfate, and the dialyzed solution was centrifuged to remove insoluble impurities and purified on affinity chromatography using 350 ml of "SEPHACRYL HR S-200" gel. The amount of enzyme activity, specific activity, and yield of the α-isomaltosylglucosaccharide-forming enzyme in each purification step are in Table 11.

TABLE 11

| Purification step | Enzyme* activity (unit) | Specific activity of enzyme* (unit/mg protein) | Yield (%) |
|---|---|---|---|
| Culture supernatant | 5,940 | 0.10 | 100 |
| Dialyzed solution after salting out with ammonium sulfate | 4,710 | 0.19 | 79.3 |
| Eluate from ion-exchange column chromatography | 3,200 | 2.12 | 53.9 |
| Eluate from affinity column chromatography | 2,210 | 7.55 | 37.2 |
| Eluate from hydrophobic column chromatography | 1,720 | 10.1 | 29.0 |
| Eluate from affinity column chromatography | 1,320 | 12.5 | 22.2 |

Note:
The symbol "*" means α-isomaltosylglucosaccharide-forming enzyme.

The finally purified α-isomaltosylglucosaccharide-forming enzyme specimen was assayed for purity on gel electrophoresis using a 7.5% (w/v) polyacrylamide gel and detected on the gel as a single protein band, meaning a high purity enzyme specimen.

EXPERIMENT 11-3

Purification of α-isomaltosyl-transferring Enzyme

Fractions of α-isomaltosyl-transferring enzyme, which had been separated from fractions of α-isomaltosylglucosaccharide-forming enzyme by ion-exchange chromatography in Experiment 11-1, were pooled and dialyzed against 10 mM phosphate buffer (pH 7.0) containing 1 M ammonium sulfate, and the dialyzed solution was centrifuged to remove insoluble impurities. The resulting supernatant was fed to affinity column chromatography using 500 ml of "SEPHACRYL HR S-200", a gel commercialized by Amersham Corp., Div., Amersham International, Arlington Heights, Ill., USA. The enzyme was adsorbed on the gel and then eluted therefrom with a linear gradient decreasing from 1 M to 0 M of ammonium sulfate, resulting in an elution of the enzyme from the gel at a concentration of about 0.3 M ammonium sulfate and collecting fractions with the enzyme activity. The fractions were pooled and dialyzed against 10 mM phosphate buffer (pH 7.0) containing 1 M ammonium sulfate, and the dialyzed solution was centrifuged to remove insoluble impurities and purified on hydrophobic chromatography using 380 ml of "BUTYL-TOYOPEARL 650M" gel. The enzyme was adsorbed on the gel and then eluted therefrom with a linear gradient decreasing from 1 M to 0 M ammonium sulfate, resulting in an elution of the enzyme at a concentration of about 0.3 M ammonium sulfate. The fractions with the enzyme activity were pooled and dialyzed against 10 mM Tris-HCl buffer (pH 8.0), and the dialyzed solution was centrifuged to remove insoluble impurities. The resulting supernatant was fed to ion-exchange column chromatography using 380 ml of "SUPER Q-TOYOPEARL 650C" gel commercialized by Tosoh Corporation, Tokyo, Japan. The enzyme was not adsorbed on the gel and then eluted therefrom as non-adsorbed fractions which were then collected and pooled to obtain a finally purified enzyme preparation. The amount of enzyme activity, specific activity, and yield of the α-isomaltosylglucosaccharide-forming enzyme in each purification step are in Table 12.

TABLE 12

| Purification step | Enzyme* activity (unit) | Specific activity of enzyme* (unit/mg protein) | Yield (%) |
|---|---|---|---|
| Culture supernatant | 19,000 | 0.33 | 100 |
| Dialyzed solution after salting out with ammonium sulfate | 15,700 | 0.64 | 82.6 |
| Eluate from ion-exchange column chromatography | 12,400 | 3.56 | 65.3 |
| Eluate from affinity column chromatography | 8,320 | 11.7 | 43.8 |
| Eluate from hydrophobic column chromatography | 4,830 | 15.2 | 25.4 |
| Eluate from ion-exchange column chromatography | 3,850 | 22.6 | 20.3 |

Note:
The symbol "*" means α-isomaltosyl-transferring enzyme.

The finally purified α-isomaltosyl-transferring enzyme specimen was assayed for purity on gel electrophoresis using a 7.5% (w/v) polyacrylamide gel and detected on the gel as a single protein band, meaning a high purity enzyme specimen.

EXPERIMENT 12

Property of α-isomaltosylglucosaccharide-forming Enzyme and α-isomaltosyl-transferring Enzyme

EXPERIMENT 12-1

Property of α-isomaltosylglucosaccharide-forming Enzyme

A purified specimen of α-isomaltosylglucosaccharide-forming enzyme, obtained by the method in Experiment 11-2, was subjected to SDS-PAGE using a 7.5% (w/v) of polyacrylamide gel and then determined for molecular weight by comparing with the dynamics of standard molecular markers electrophoresed in parallel, commercialized by Japan Bio-Rad Laboratories Inc., Tokyo, Japan, revealing that the enzyme had a molecular weight of about 136,000±20,000 daltons.

A fresh preparation of the same purified specimen as used in the above was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 7.3±0.5.

Figure 21:
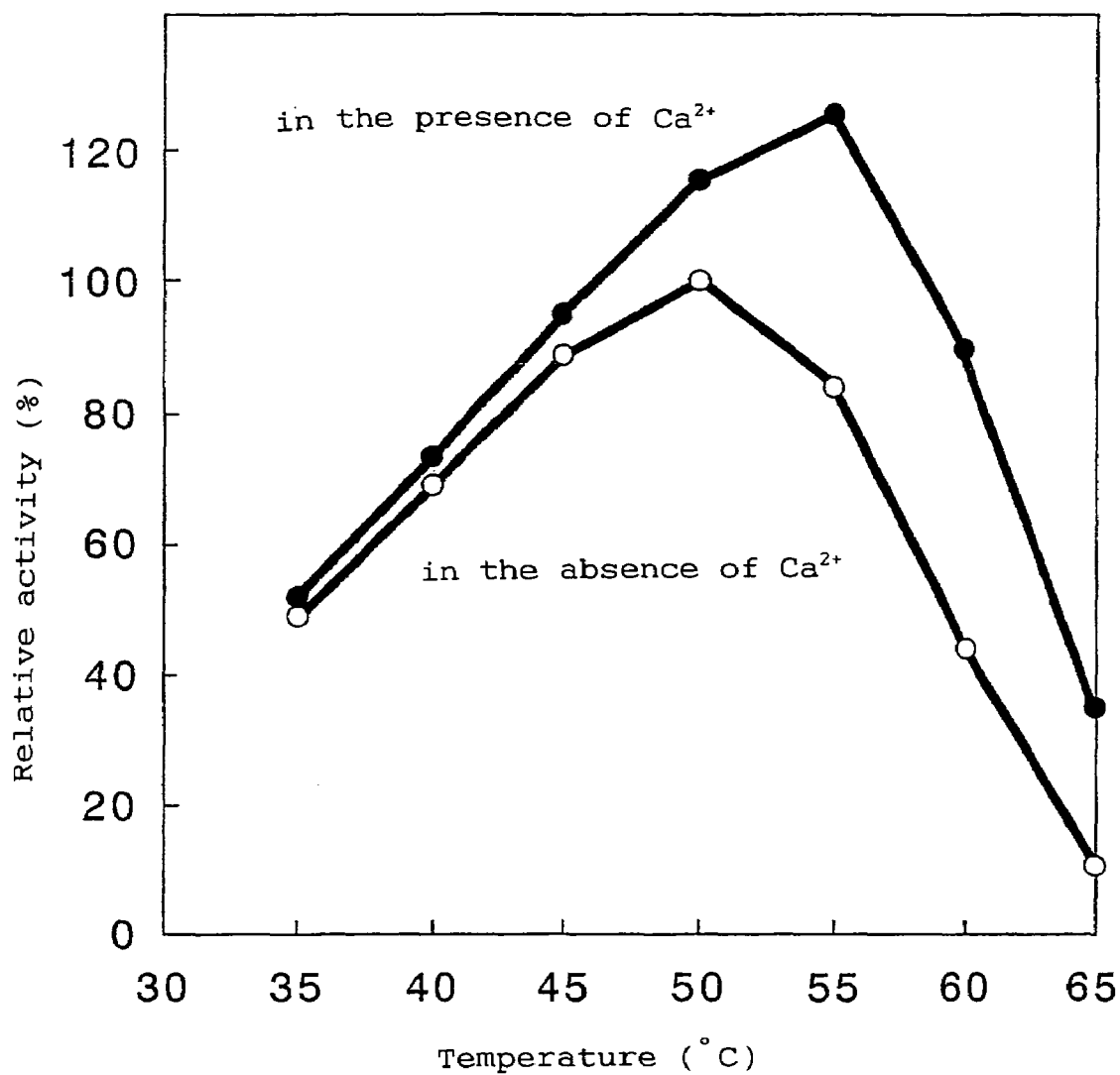
FIG. 21 shows the thermal influence on the enzymatic activity of α-isomaltosylglucosaccharide-forming enzyme from a microorganism of the species *Bacillus globisporus* N75 strain.
Figure 22:
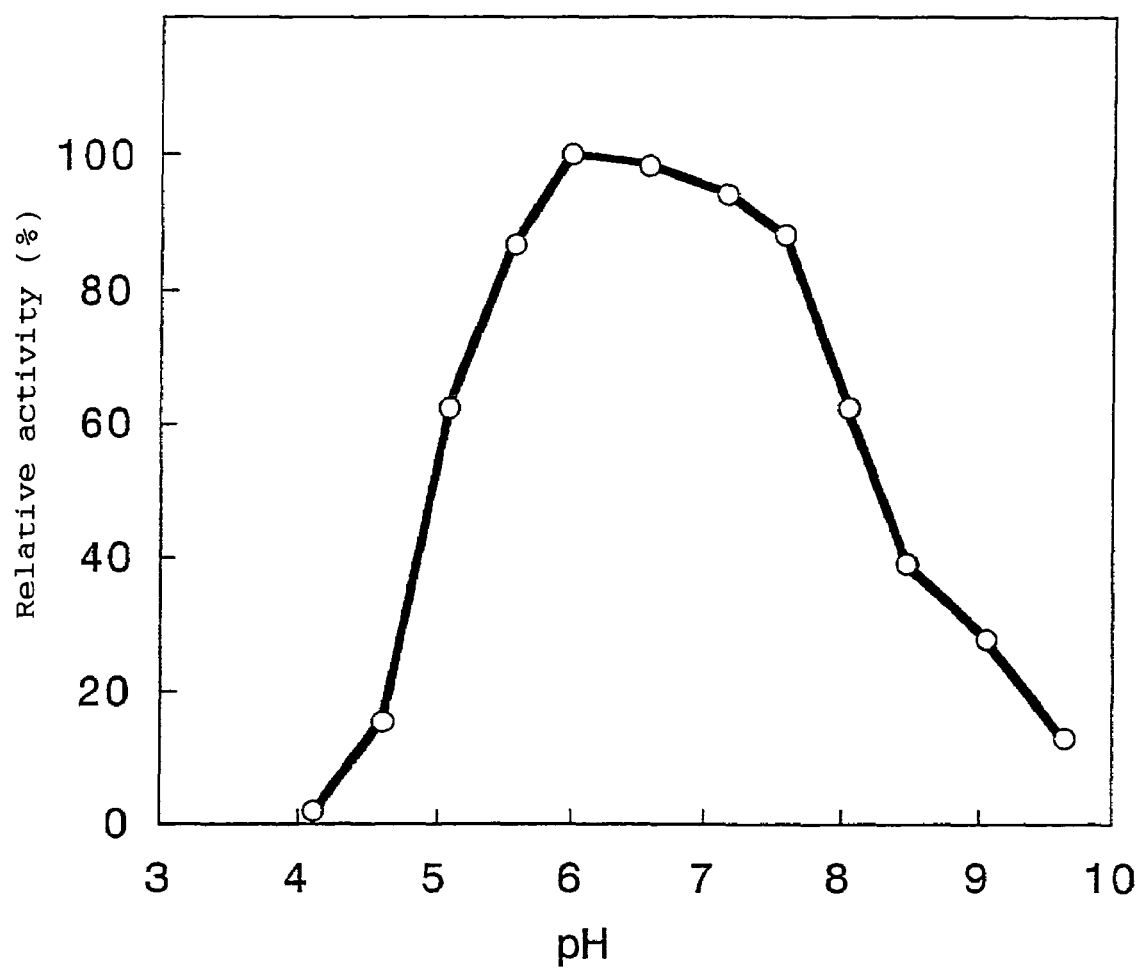
FIG. 22 shows the pH influence on the enzymatic activity of α-isomaltosylglucosaccharide-forming enzyme from a microorganism of the species *Bacillus globisporus* N75 strain.
Figure 23:
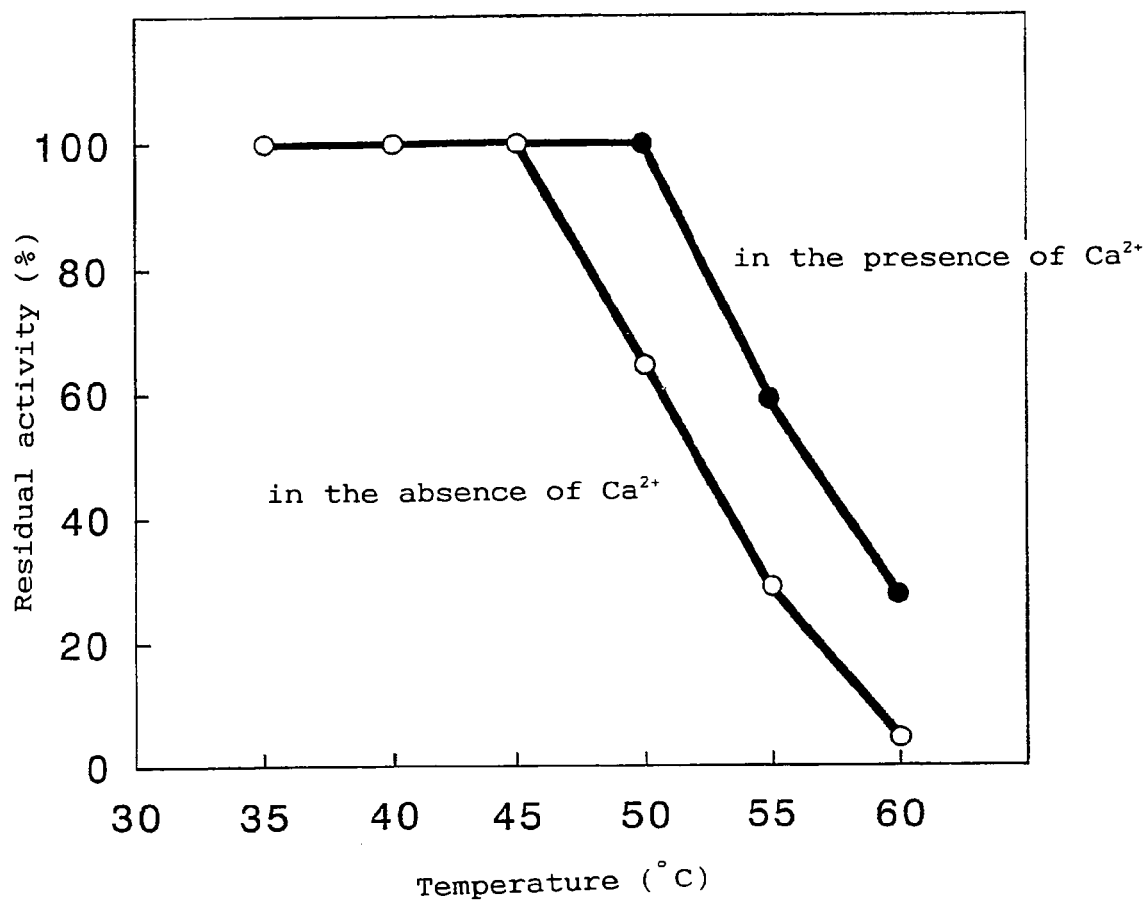
FIG. 23 shows the thermal stability of α-isomaltosylglucosaccharide-forming enzyme from a microorganism of the species *Bacillus globisporus* N75 strain.
Figure 24:
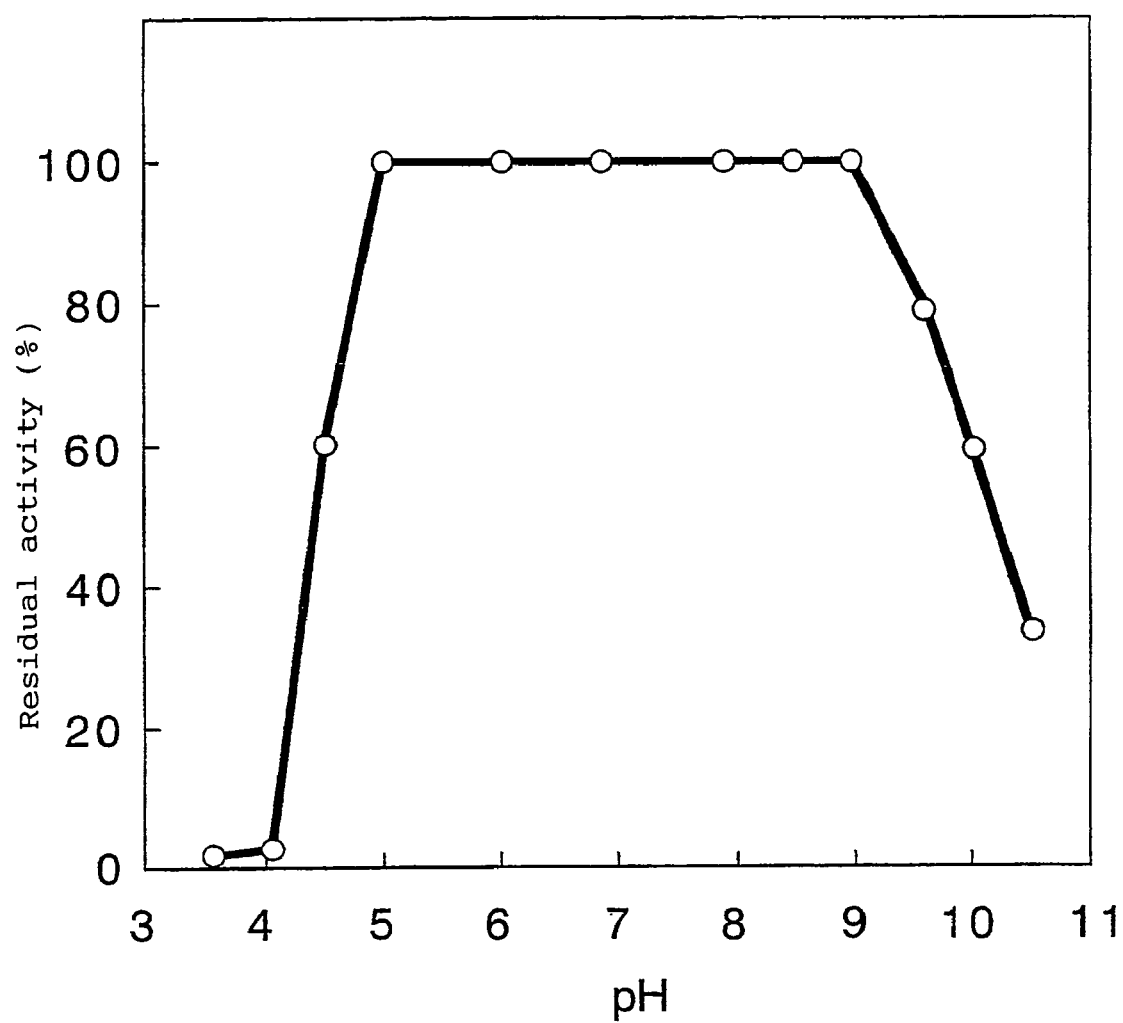
FIG. 24 shows the pH stability of α-isomaltosylglucosaccharide-forming enzyme from a microorganism of the species *Bacillus globisporus* N75 strain.

The influence of temperature and pH on the activity of α-isomaltosylglucosaccharide-forming enzyme was examined in accordance with the assay for its enzyme activity, where the influence of temperature was examined in the presence or the absence of 1 mM $Ca^{2+}$. These results are in FIG. 21 (influence of temperature) and FIG. 22 (influence of pH). The optimum temperature of the enzyme was about 50° C. and about 55° C. when incubated at pH 6.0 for 60 min in the absence of and in the presence of 1 mM $Ca^{2+}$, respectively. The optimum pH of the enzyme was about 6.0 when incubated at 35° C. for 60 min. The thermal stability of the enzyme was determined by incubating the testing enzyme solutions in the form of 20 mM acetate buffer (pH 6.0) at prescribed temperatures for 60 min in the absence of and in the presence of 1 mM $Ca^{2+}$, cooling the resulting enzyme solutions with water, and assaying the remaining enzyme activity of each solution. The pH stability of the enzyme was determined by keeping the testing enzyme solutions in the form of 50 mM buffers having prescribed pHs at 4° C. for 24 hours, adjusting the pH of each solution to 6.0, and assaying the remaining enzyme activity of each solution. These results are respectively in FIG. 23 (thermal stability) and FIG. 24 (pH stability). As a result, the enzyme had thermal stability of up to about 45° C. and about 50° C. in the absence of and in the presence of 1 mM $Ca^{2+}$, respectively, and had pH stability of about 5.0 to about 9.0.

The influence of metal ions on the activity of α-isomaltosylglucosaccharide-forming enzyme was examined in the presence of 1 mM of each metal-ion according to the assay for its enzyme activity. The results are in Table 13.

TABLE 13

| Metal ion | Relative activity (%) | Metal ion | Relative activity (%) |
|---|---|---|---|
| None | 100 | $Hg^{2+}$ | 1 |
| $Zn^{2+}$ | 82 | $Ba^{2+}$ | 84 |
| $Mg^{2+}$ | 96 | $Sr^{2+}$ | 85 |
| $Ca^{2+}$ | 108 | $Pb^{2+}$ | 86 |
| $Co^{2+}$ | 93 | $Fe^{2+}$ | 82 |
| $Cu^{2+}$ | 7 | $Fe^{3+}$ | 93 |
| $Ni^{2+}$ | 93 | $Mn^{2+}$ | 120 |
| $Al^{3+}$ | 98 | EDTA | 35 |

As evident form the results in Table 13, the enzyme activity was strongly inhibited by $Hg^{2+}$, $Cu^{2+}$, and EDTA. It was also found that the enzyme was activated by $Ca^{2+}$ and $Mn^{2+}$. Amino acid analysis on the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:11, i.e., histidine-valine-serine-alanine-leucine-glycine-asparagine-leucine-leucine in the N-terminal region. Comparison of the above partial amino acid sequence in the N-terminal region with that derived from the α-isomaltosylglucosaccharide-forming enzyme from Bacillus globisporus C11 strain in Experiment 8-1 revealed that they had a relatively high homology but differed in the amino acid residues 1, 4 and 9 in each of their partial amino acid sequences in their N-terminal regions. Detailed method for assaying amino acid sequence is not shown in this specification because it is disclosed in detail in Japanese Patent Application No. 2001-5441 (International Publication No. WO02/055708), however, the α-isomaltosylglucosaccharide-forming enzyme has an amino acid sequence of amino acid residues 36-1286 shown in parallel in SEQ ID NO:23 similarly as that disclosed in the specification of the above-identified Japanese Patent Application No. 2001-5441.

EXPERIMENT 12-2

Property of α-isomaltosyl-transferring Enzyme

A purified specimen of α-isomaltosyl-transferring enzyme, obtained by the method in Experiment 11-3, was subjected to SDS-PAGE using a 7.5% (w/v) of polyacrylamide gel and then determined for molecular weight by comparing with the dynamics of standard molecular markers electrophoresed in parallel, commercialized by Japan Bio-Rad Laboratories Inc., Tokyo, Japan, revealing that the enzyme had a molecular weight of about 112,000±20,000 daltons.

A fresh preparation of the same purified specimen as used in the above was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 7.8±0.5.

Figure 25:
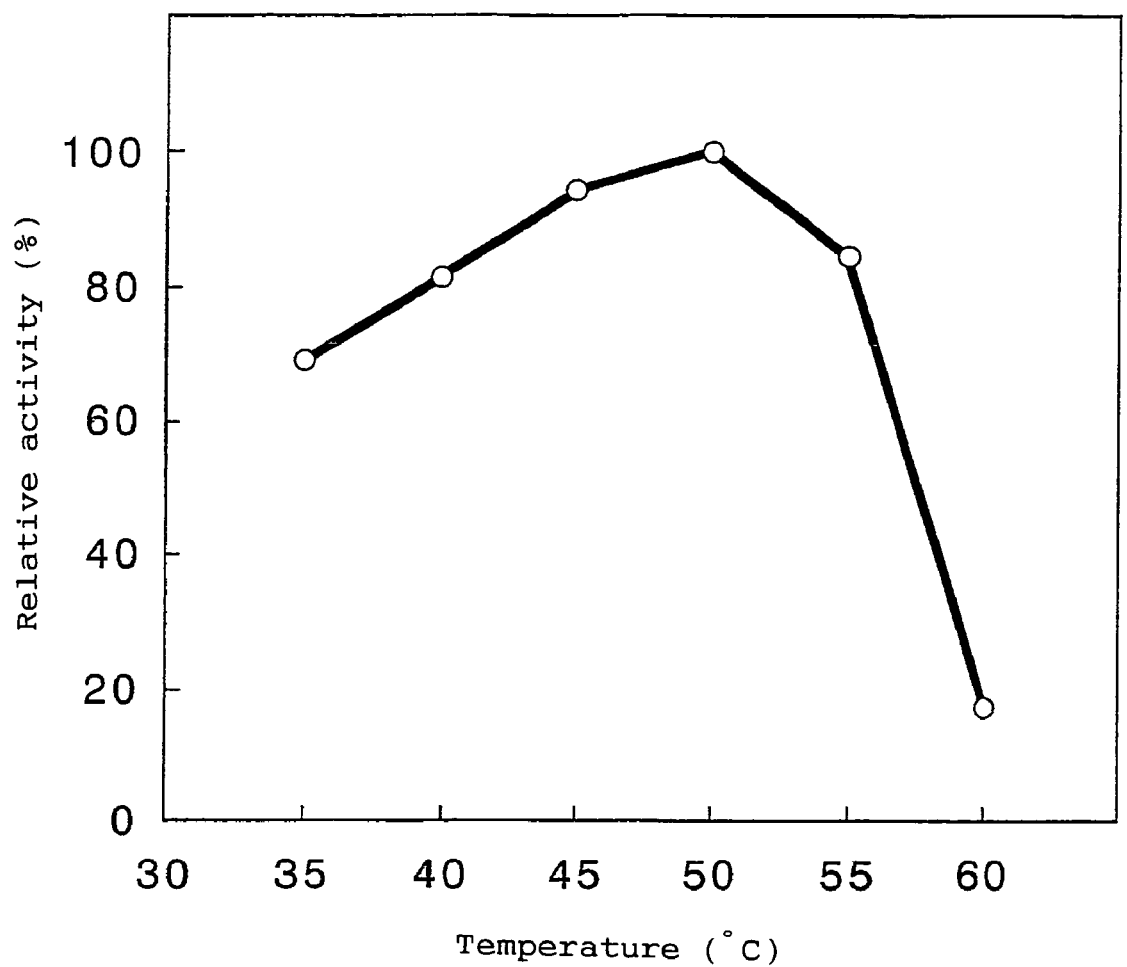
FIG. 25 shows the thermal influence on the enzymatic activity of α-isomaltosyl-transferring enzyme from a microorganism of the species *Bacillus globisporus* N75 strain.
Figure 26:
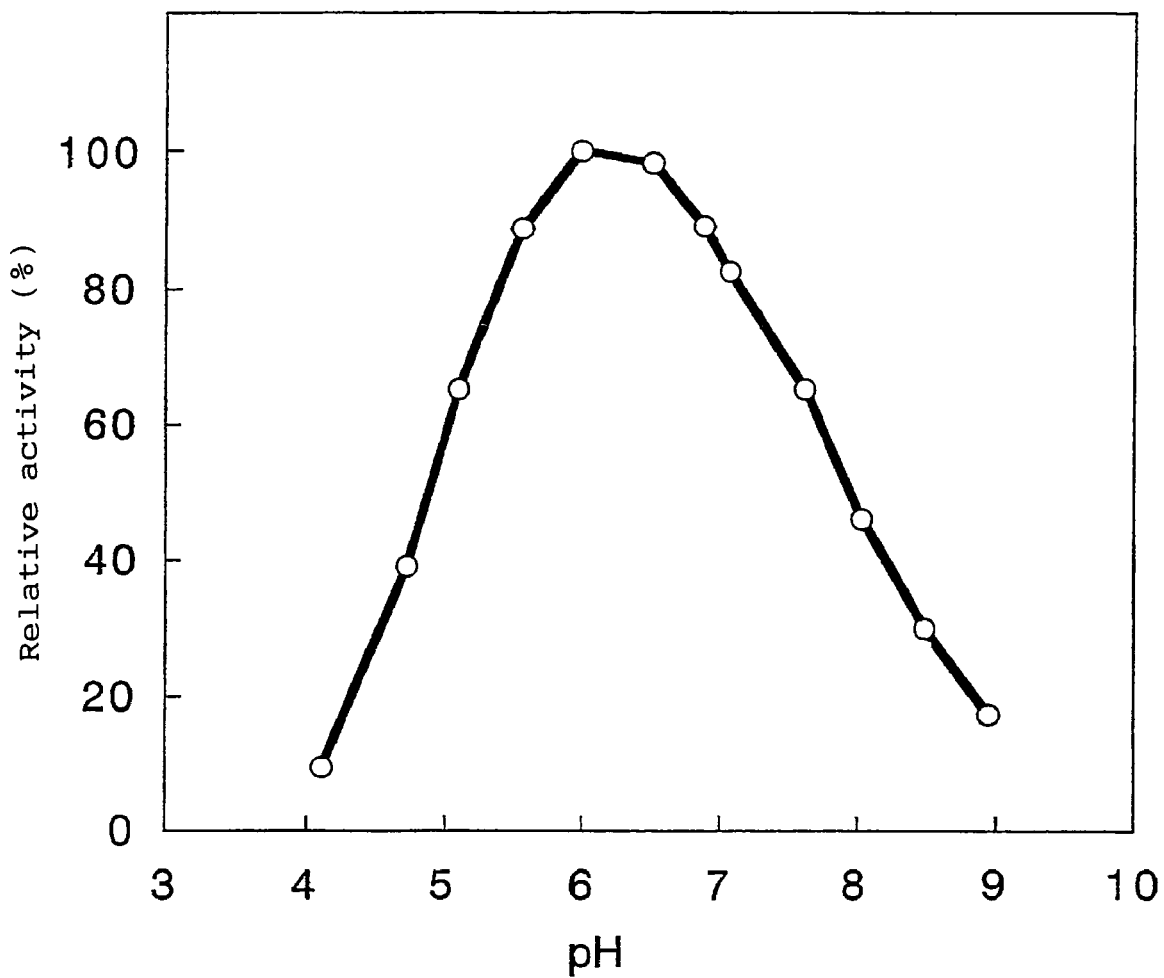
FIG. 26 shows the pH influence on the enzymatic activity of α-isomaltosyl-transferring enzyme from a microorganism of the species *Bacillus globisporus* N75 strain.
Figure 27:
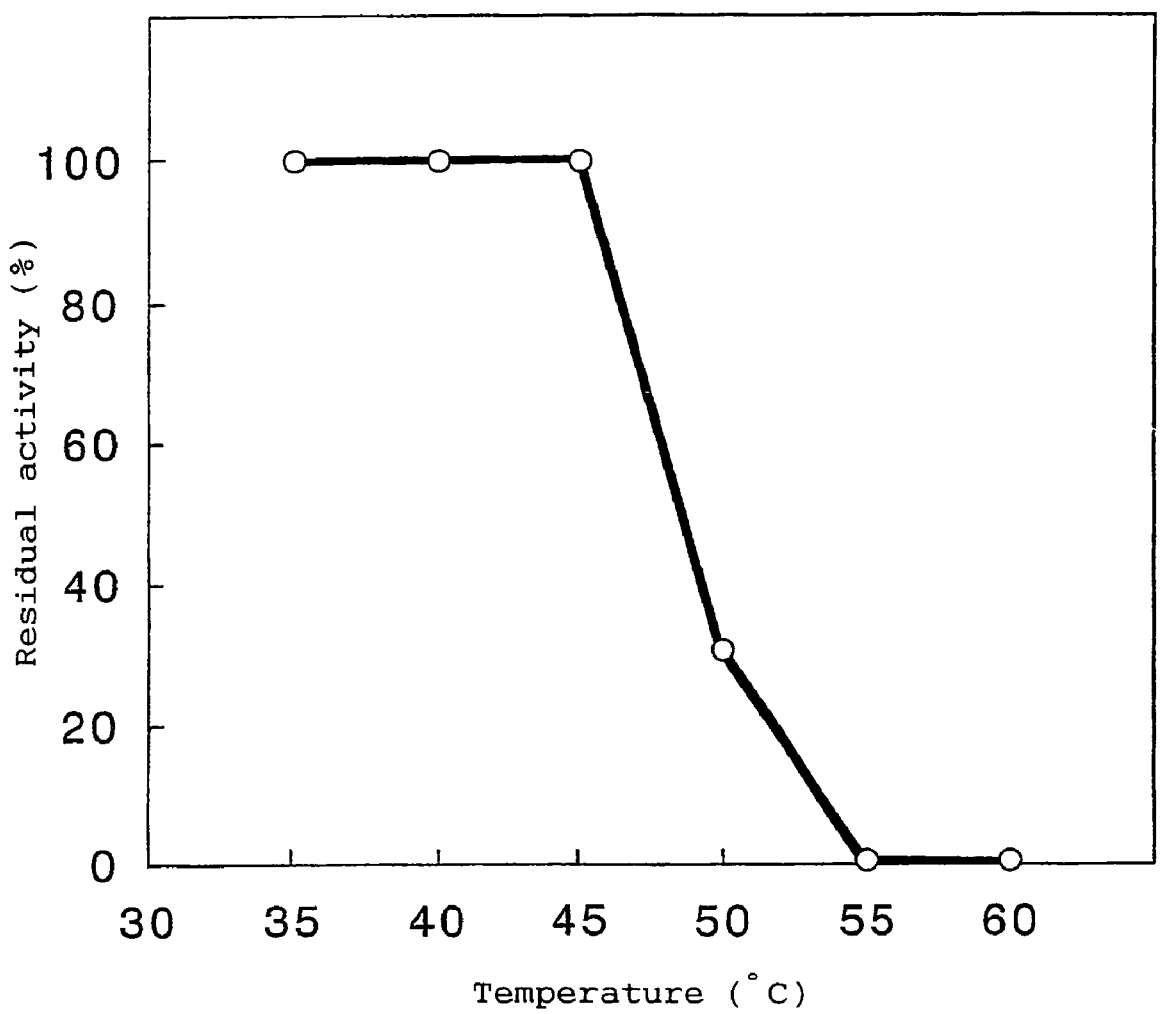
FIG. 27 shows the thermal stability of α-isomaltosyl-transferring enzyme from a microorganism of the species *Bacillus globisporus* N75 strain.
Figure 28:
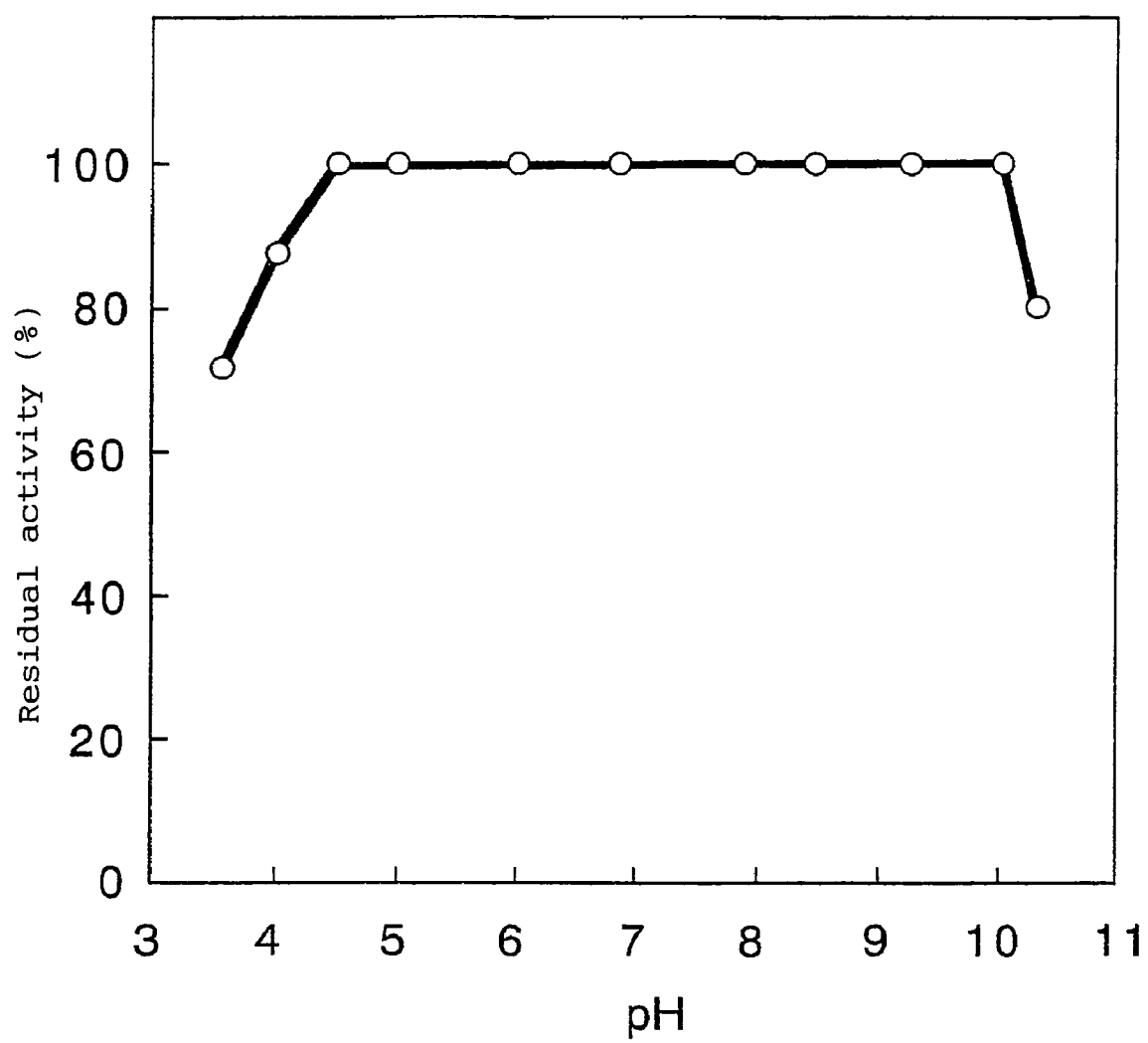
FIG. 28 shows the pH stability of α-isomaltosyl-transferring enzyme from a microorganism of the species *Bacillus globisporus* N75 strain.

The influence of temperature and pH on the activity of α-isomaltosyl-transferring enzyme was examined in accordance with the assay for its enzyme activity. These results are in FIG. 25 (influence of temperature) and FIG. 26 (influence of pH). The optimum temperature of the enzyme was about 50° C. when incubated at pH 6.0 for 30 min. The optimum pH of the enzyme was about 6.0 when incubated at 35° C. for 30 min. The thermal stability of the enzyme was determined by incubating the testing enzyme solutions in the form of 20 mM acetate buffer (pH 6.0) at prescribed temperatures for 60 min, cooling the resulting enzyme solutions with water, and assaying the remaining enzyme activity of each solution. The pH stability of the enzyme was determined by keeping the testing enzyme solutions in the from of 50 mM buffers having prescribed pHs at 4° C. for 24 hours, adjusting the pH of each solution to 6.0, and assaying the remaining enzyme activity of each solution. These results are respectively in FIG. 27 (thermal stability) and FIG. 28 (pH stability). As a result, the enzyme had thermal stability of up to about 45° C. and had pH stability of about 4.5 to about 10.0. The influence of metal ions on the activity of α-isomaltosyl-transferring enzyme was examined in the presence of 1 mM of each metal-ion according to the assay for its enzyme activity. The results are in Table 14.

TABLE 14

| Metal ion | Relative activity (%) | Metal ion | Relative activity (%) |
|---|---|---|---|
| None | 100 | $Hg^{2+}$ | 0.5 |
| $Zn^{2+}$ | 75 | $Ba^{2+}$ | 102 |
| $Mg^{2+}$ | 95 | $Sr^{2+}$ | 91 |
| $Ca^{2+}$ | 100 | $Pb^{2+}$ | 69 |
| $Co^{2+}$ | 92 | $Fe^{2+}$ | 97 |
| $Cu^{2+}$ | 15 | $Fe^{3+}$ | 90 |
| $Ni^{2+}$ | 91 | $Mn^{2+}$ | 101 |
| $Al^{3+}$ | 94 | EDTA | 92 |

As evident form the results in Table 14, the enzyme activity was strongly inhibited by $Hg^{2+}$ and also inhibited by $Cu^{2+}$. It was also found that the enzyme was not activated by $Ca^{2+}$ and not inhibited by EDTA.

Amino acid analysis on the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:3, i.e., isoleucine-aspartic acid-glycine-valine-tyrosine-histidine-alanine-proline-tyrosine-glycine at the N-terminal region. Comparison of the above partial amino acid sequence at the N-terminal region with that derived from the α-isomaltosyl-transferring enzymes from *Bacillus globisporus* C9 strain in Experiment 5-2 and from *Bacillus globisporus* C11 strain in Experiment 8-2 revealed that they had a consensus amino acid sequence of isoleucine-aspartic acid-glycine-valine-tyrosine-histidine-alanine-proline, as shown in SEQ ID NO:4 in their N-terminal regions. Detailed method for assaying amino acid sequence is not shown in this specification because it is disclosed in detail in PCT/JP01/04276 (International Publication No. WO 01/90338), however, the α-isomaltosyl-transferring enzyme obtained in Experiment 11-3 has an amino acid sequence of amino acid residues 30-1093 shown in parallel in SEQ ID NO:24 similarly as the polypeptide disclosed in the specification of PCT/JP01/04276.

EXPERIMENT 13

Internal Amino Acid Sequence of α-isomaltosylglucosaccharide-forming Enzyme and α-isomaltosyl-transferring Enzyme

EXPERIMENT 13-1

Internal Partial Amino Acid Sequence of α-isomaltosylglucosaccharide-forming Enzyme A part of a purified specimen of α-isomaltosylglucosaccharide-forming enzyme, obtained by the method in Experiment 11-2, was dialyzed against 10 mM Tris-HCl buffer (pH 9.0), and the dialyzed solution was diluted with a fresh preparation of the same buffer as used in the above to give a concentration of about one milligram per milliliter. One milliliter of the dilute as a test sample was admixed with 20 μg of "Lysyl Endopeptidase" commercialized by Wako Pure Chemical Industries, Ltd., Tokyo, Japan, and allowed to react at 30° C. for 24 hours to form peptides. The resultant mixture was subjected to reverse-phase HPLC to separate the peptides using "μ-Bondasphere C18 column" having a diameter of 3.9 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 8% (v/v) to 36% (v/v) in 0.1% (v/v) trifluoroacetate over 120 min. The peptides eluted from the column were detected by monitoring the absorbance at a wavelength of 210 nm. Three peptide specimens named PN59 with a retention time of about 59 min, PN67 with a retention time of about 67 min, and PN87 with a retention time of about 87 min, which had been well separated from other peptides, were separately collected and dried in vacuo and then dissolved in 200 μl of a solution of 0.1% (v/v) trifluoroacetate and 50% (v/v) acetonitrile. Each peptide specimen was subjected to a protein sequencer for analyzing amino acid sequence up to eight amino acid residues to obtain amino acid sequences of SEQ ID NOs:12 to 14. The analyzed internal partial amino acid sequences are in Table 15.

TABLE 15

| Peptide name | Internal partial amino acid sequence |
|---|---|
| PN59 | aspartic acid-phenylalanine-serine-asparagine-asparagine-proline-threonine-valine |
| PN67 | tyrosine-threonine-valine-asparagine-alanine-proline-alanine-alanine |
| PN87 | tyrosine-glutamic acid-alanine-glutamic acid-serine-alanine-glutamic acid-leucine |

EXPERIMENT 13-2

Internal Amino Acid Sequence of α-isomaltosyl-transferring Enzyme

A part of a purified specimen of α-isomaltosyl-transferring enzyme, obtained by the method in Experiment 11-3, was dialyzed against 10 mM Tris-HCl buffer (pH 9.0), and the dialyzed solution was diluted with a fresh preparation of the same buffer as used in the above to give a concentration of about one milligram per milliliter. One milliliter of the dilute as a test sample was admixed with 20 µg of "Lysyl Endopeptidase" commercialized by Wako Pure Chemical Industries, Ltd., Tokyo, Japan, and allowed to react at 30° C. for 24 hours to form peptides. The resultant mixture was subjected to reverse-phase HPLC to separate the peptides using "µ-Bondasphere C18 column" having a diameter of 3.9 mm and a length of 150 mm, a product of Waters Chromatography Div., MILLIPORE Corp., Milford, USA, at a flow rate of 0.9 ml/min and at ambient temperature, and using a liner gradient of acetonitrile increasing from 4% (v/v) to 42.4% (v/v) in 0.1% (v/v) trifluoroacetate over 90 min. The peptides eluted from the column were detected by monitoring the absorbance at a wavelength of 210 nm. Three peptide specimens named PN21 with a retention time of about 21 min, PN38 with a retention time of about 38 min, and PN69 with a retention time of about 69 min which had been well separated from other peptides, were separately collected and dried in vacuo and then dissolved in 200 µl of a solution of 0.1% (v/v) trifluoroacetate and 50% (v/v) acetonitrile. Each peptide specimen was subjected to a protein sequencer for analyzing amino acid sequence up to eight amino acid residues, but up to six amino acids residues for PN21, to obtain amino acid sequences of SEQ ID NOs: 15 to 17. The analyzed internal partial amino acid sequences are in Table 16.

TABLE 16

| Peptide name | Internal partial amino acid sequence |
|---|---|
| PN21 | asparagine-tryptophane-tryptophane-methionine-serine-lysine |
| PN38 | threonine-aspartic acid-glycine-glycine-glutamic acid-methionine-valine-tryptophane |
| PN69 | asparagine-isoleucine-tyrosine-leucine-proline-glutamine-glycine-aspartic acid |

EXPERIMENT 14

Production of α-isomaltosylglucosaccharide-forming Enzyme from *Arthrobacter globiformis* A19 Strain A liquid nutrient culture medium, consisting of 4.0% (w/v) of "PINE-DEX #4", a partial starch hydrolyzate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water, was placed in 500-ml Erlenmeyer flasks in a volume of 100 ml each, autoclaved at 121° C. for 20 minutes to effect sterilization, cooled, inoculated with a stock culture of *Arthrobacter globiformis* A19 strain (FERM BP-7590), and incubated at 27° C. for 48 hours under rotary shaking conditions of 230 rpm for use as a seed culture. About 20 L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration-agitation conditions at 27° C. and pH 6.0 to 9.0. The resultant culture, having about 1.1 units/ml of an α-isomaltosylglucosaccharide-forming enzyme activity, about 1.7 units/ml of an α-isomaltosyl-transferring enzyme activity, and about 0.35 unit/ml of a cyclotetrasaccharide-forming enzyme activity, was centrifuged at 10,000 rpm for 30 min to obtain about 18 L of a supernatant. Measurement of the supernatant revealed that it had about 1.06 units/ml of an α-isomaltosylglucosaccharide-forming enzyme activity, i.e., a total enzyme activity of about 19,100 units; about 1.6 units/ml of an α-isomaltosyl-transferring enzyme activity, i.e., a total enzyme activity of about 28,800 units; and about 0.27 unit/ml of a cyclotetrasaccharide-forming enzyme activity, i.e., a total enzyme activity of about 4,860 units. The activity of the α-isomaltosylglucosaccharide-forming enzyme from *Arthrobacter globiformis* A19 strain was similarly assayed as the method in Experiment 3 except for using 100 mM glycine-NaOH buffer (pH 8.4) as a buffer for substrate.

EXPERIMENT 15

Preparation of Enzyme from *Arthrobacter globiformis* A19 Strain

EXPERIMENT 15-1

Purification of Enzyme from *Arthrobacter globiformis* A19 Strain

About 18 L of the supernatant, obtained in Experiment 14, was salted out in a 60% saturated ammonium sulfate solution and allowed to stand at 4° C. for 24 hours. Then, the salted out sediments were collected by centrifugation at 10,000 for 30 min, dissolved in 10 mM phosphate buffer (pH 7.0), dialyzed against a fresh preparation of the same buffer as used in the above to obtain about 850 ml of a crude enzyme solution. The crude enzyme solution was revealed to have 8,210 units of α-isomaltosylglucosaccharide-forming enzyme, about 15,700 units of α-isomaltosyl-transferring enzyme, and about 2,090 units of cyclotetrasaccharide-forming enzyme, followed by subjecting it to ion-exchange chromatography using 380 ml of "DEAE-TOYOPEARL 650S" gel. When eluted with a linear gradient increasing from 0 M to 0.5 M NaCl, α-isomaltosylglucosaccharide-forming enzyme and α-isomaltosyl-transferring enzyme were separately eluted from the gel, the former was eluted at a concentration of about 0.2 M NaCl, while the latter was eluted at a concentration of about 0.3 M NaCl. Under these conditions, fractions with an α-isomaltosylglucosaccharide-forming enzyme activity and those with an α-isomaltosyl-transferring enzyme activity were separately fractionated and collected. Since the facts that no cyclotetrasaccharide-forming activity was found in any fraction obtained in this column chromatography, and an enzyme solution, obtained by mixing the fractions of α-isomaltosylglucosaccharide-forming enzyme and of α-isomaltosyl-transferring enzyme, showed a cyclotetrasaccharide-forming activity, it was revealed that the activity of forming cyclotetrasaccharide from partial starch hydrolyzates is exerted by the coaction of α-isomaltosylglucosaccharide-forming enzyme and α-isomaltosyl-transferring enzyme.

The following experiments describe a method for separately purifying α-isomaltosylglucosaccharide-forming enzyme and α-isomaltosyl-transferring enzyme:

EXPERIMENT 15-2

Purification of α-isomaltosylglucosaccharide-forming Enzyme

Fractions with α-isomaltosylglucosaccharide-forming enzyme, obtained in Experiment 15-1, were pooled and dialyzed against 10 mM phosphate buffer (pH 7.0) containing 1 M ammonium sulfate, and the dialyzed solution was centrifuged to remove insoluble impurities and fed to affinity chromatography using 500 ml of "SEPHACRYL HR S-200" gel. The enzyme was adsorbed on the gel and then eluted therefrom with a linear gradient decreasing from 1 M to 0 M ammonium sulfate. As a result, the α-isomaltosylglucosaccharide-forming enzyme adsorbed on the gel was eluted therefrom at a concentration of about 0.2 M ammonium sulfate, followed by collecting fractions with the enzyme activity and pooling them for use as a finally purified specimen. The amount of enzyme activity, specific activity, and yield of α-isomaltosylglucosaccharide-forming enzyme in each purification step are in Table 17.

TABLE 17

| Purification step | Enzyme* activity (unit) | Specific activity of enzyme* (unit/mg protein) | Yield (%) |
| --- | --- | --- | --- |
| Culture supernatant | 19,100 | 0.11 | 100 |
| Dialyzed solution after salting out with ammonium sulfate | 8,210 | 0.48 | 43.0 |
| Eluate from ion-exchange column chromatography | 6,890 | 4.18 | 36.1 |
| Eluate from affinity column chromatography | 5,220 | 35.1 | 27.3 |

Note:
The symbol "*" means α-isomaltosylglucosaccharide-forming enzyme.

The finally purified α-isomaltosylglucosaccharide-forming enzyme specimen was assayed for purity on gel electrophoresis using a 7.5% (w/v) polyacrylamide gel and detected on the gel as a single protein band, meaning a high purity enzyme specimen.

EXPERIMENT 15-3

Purification of α-isomaltosyl-transferring Enzyme

Fractions of α-isomaltosyl-transferring enzyme, which had been separated from fractions of α-isomaltosylglucosaccharide-forming enzyme by ion-exchange chromatography in Experiment 15-1, were pooled and dialyzed against 10 mM phosphate buffer (pH 7.0) containing 1 M ammonium sulfate, and the dialyzed solution was centrifuged to remove insoluble impurities. The resulting supernatant was fed to affinity column chromatography using 500 ml of "SEPHACRYL HR S-200" gel, a gel commercialized by Amersham Corp., Div., Amersham International, Arlington Heights, Ill., USA. The enzyme was adsorbed on the gel and then eluted therefrom with a linear gradient decreasing from 1 M to 0 M of ammonium sulfate, resulting in an elution of the enzyme from the gel at a concentration of about 0 M ammonium sulfate and collecting the resulting fractions with the enzyme activity for a partially purified specimen. The amount of enzyme activity, specific activity, and yield of α-isomaltosyl-transferring enzyme in each purification step are in Table 18.

TABLE 18

| Purification step | Enzyme* activity (unit) | Specific activity of enzyme* (unit/mg protein) | Yield (%) |
| --- | --- | --- | --- |
| Culture supernatant | 28,800 | 0.18 | 100 |
| Dialyzed solution after salting out with ammonium sulfate | 15,700 | 0.97 | 54.5 |
| Eluate from ion-exchange column chromatography | 7,130 | 4.01 | 24.8 |

TABLE 18-continued

| Purification step | Enzyme* activity (unit) | Specific activity of enzyme* (unit/mg protein) | Yield (%) |
| --- | --- | --- | --- |
| Eluate from affinity column chromatography | 1,440 | 12.1 | 5.0 |

Note:
The symbol "*" means α-isomaltosyl-transferring enzyme.

The partially purified α-isomaltosyl-transferring enzyme specimen was assayed for purity on gel electrophoresis using a 7.5% (w/v) polyacrylamide gel and detected on the gel as a single protein band, meaning a high purity enzyme specimen.

EXPERIMENT 16

Property of α-isomaltosylglucosaccharide-forming Enzyme and α-isomaltosyl-transferring Enzyme

EXPERIMENT 16-1

Property of α-isomaltosylglucosaccharide-forming Enzyme

A purified specimen of α-isomaltosylglucosaccharide-forming enzyme, obtained by the method in Experiment 15-2, was subjected to SDS-PAGE using a 7.5% (w/v) of polyacrylamide gel and then determined for molecular weight by comparing with the dynamics of standard molecular markers electrophoresed in parallel, commercialized by Japan Bio-Rad Laboratories Inc., Tokyo, Japan, revealing that the enzyme had a molecular weight of about 94,000±20,000 daltons.

A portion of the above purified specimen was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 4.3±0.5.

Figure 29:
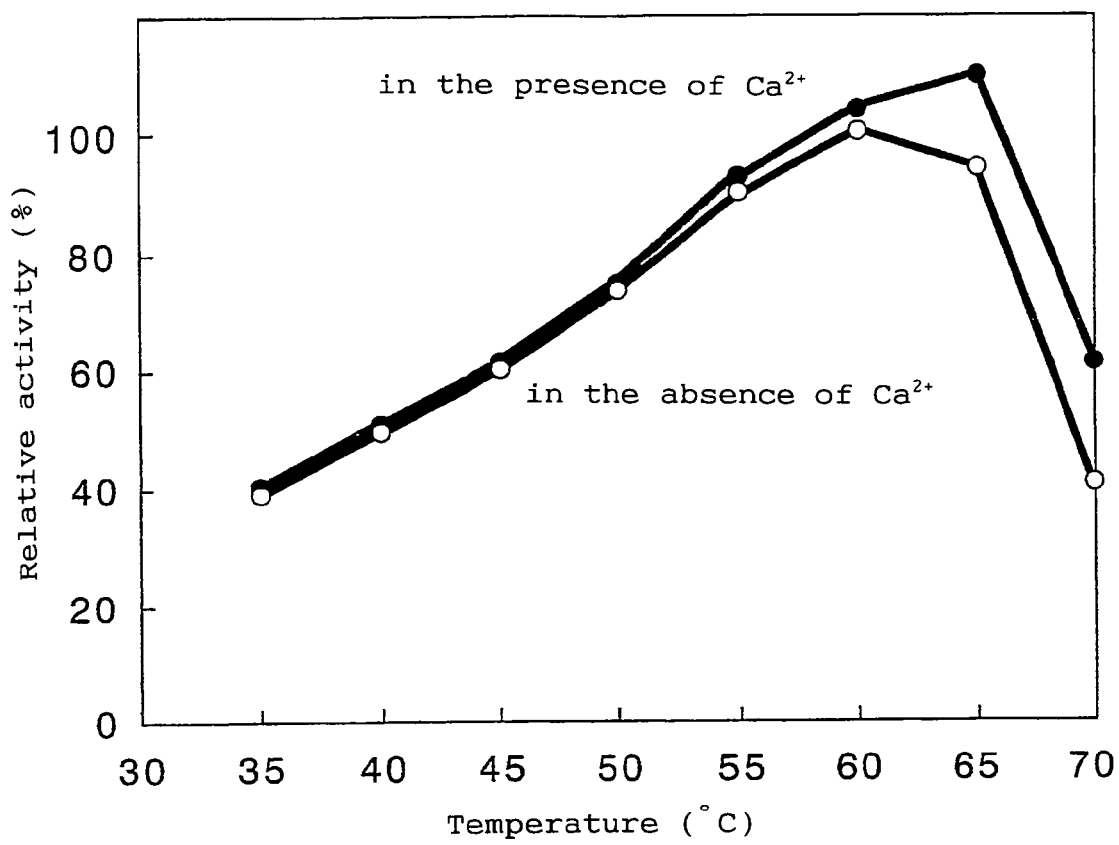
FIG. 29 shows the thermal influence on the enzymatic activity of α-isomaltosylglucosaccharide-forming enzyme from a microorganism of the species *Arthrobacter globiformis* A19 strain.
Figure 30:
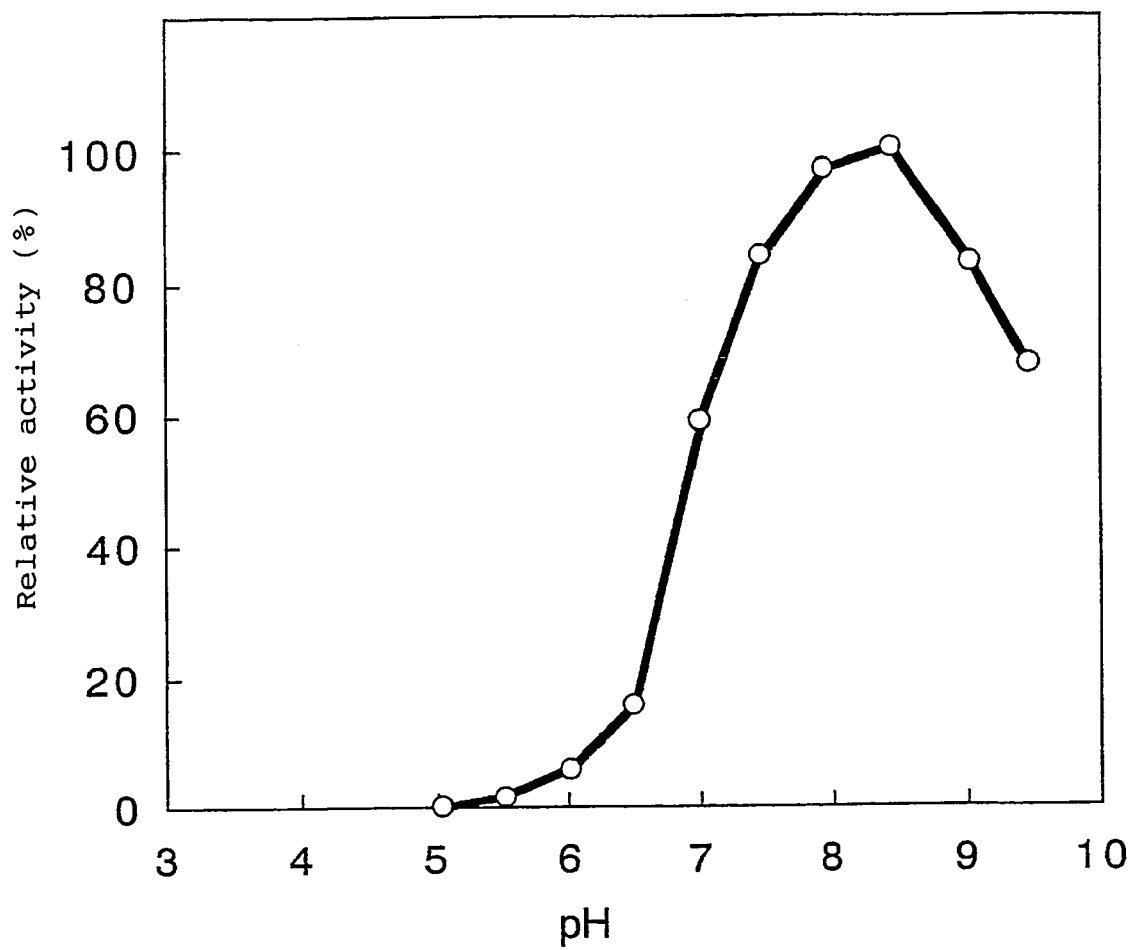
FIG. 30 shows the pH influence on the enzymatic activity of α-isomaltosylglucosaccharide-forming enzyme from a microorganism of the species *Arthrobacter globiformis* A19 strain.
Figure 31:
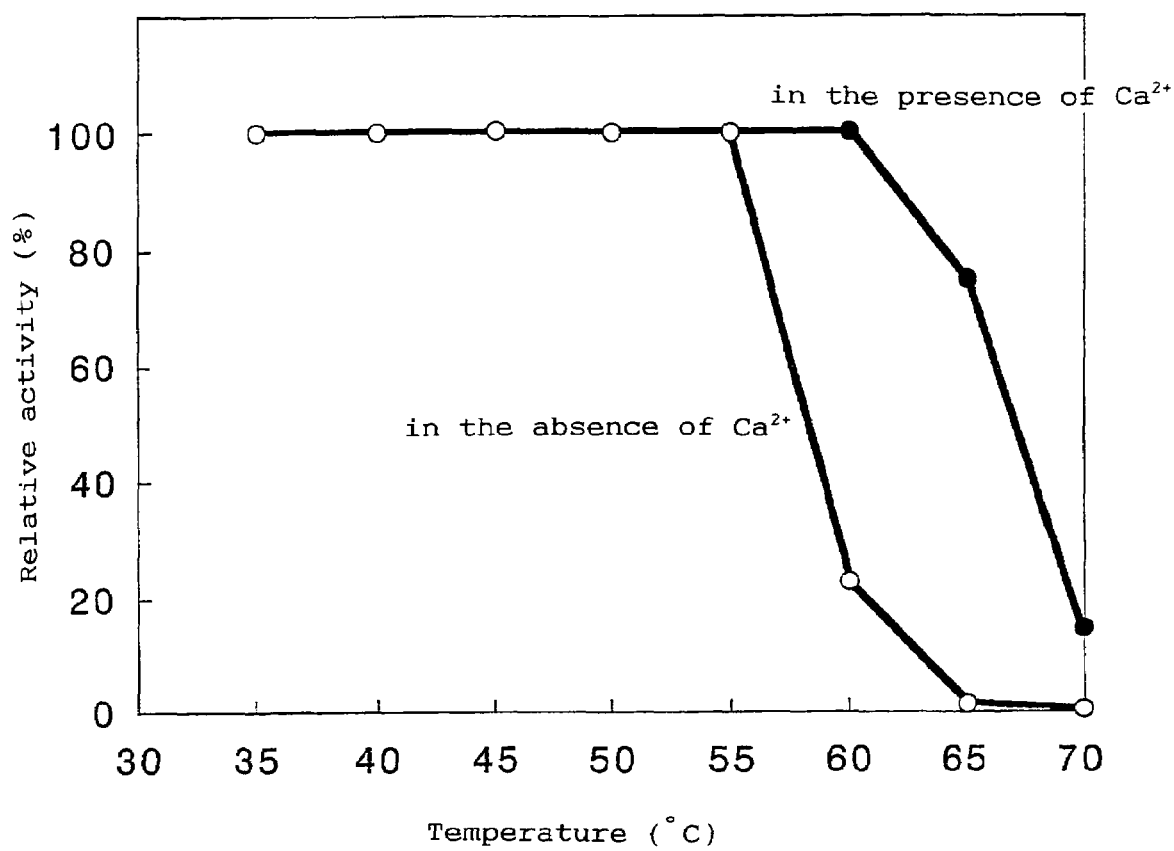
FIG. 31 shows the thermal stability of α-isomaltosylglucosaccharide-forming enzyme from a microorganism of the species *Arthrobacter globiformis* A19 strain.
Figure 32:
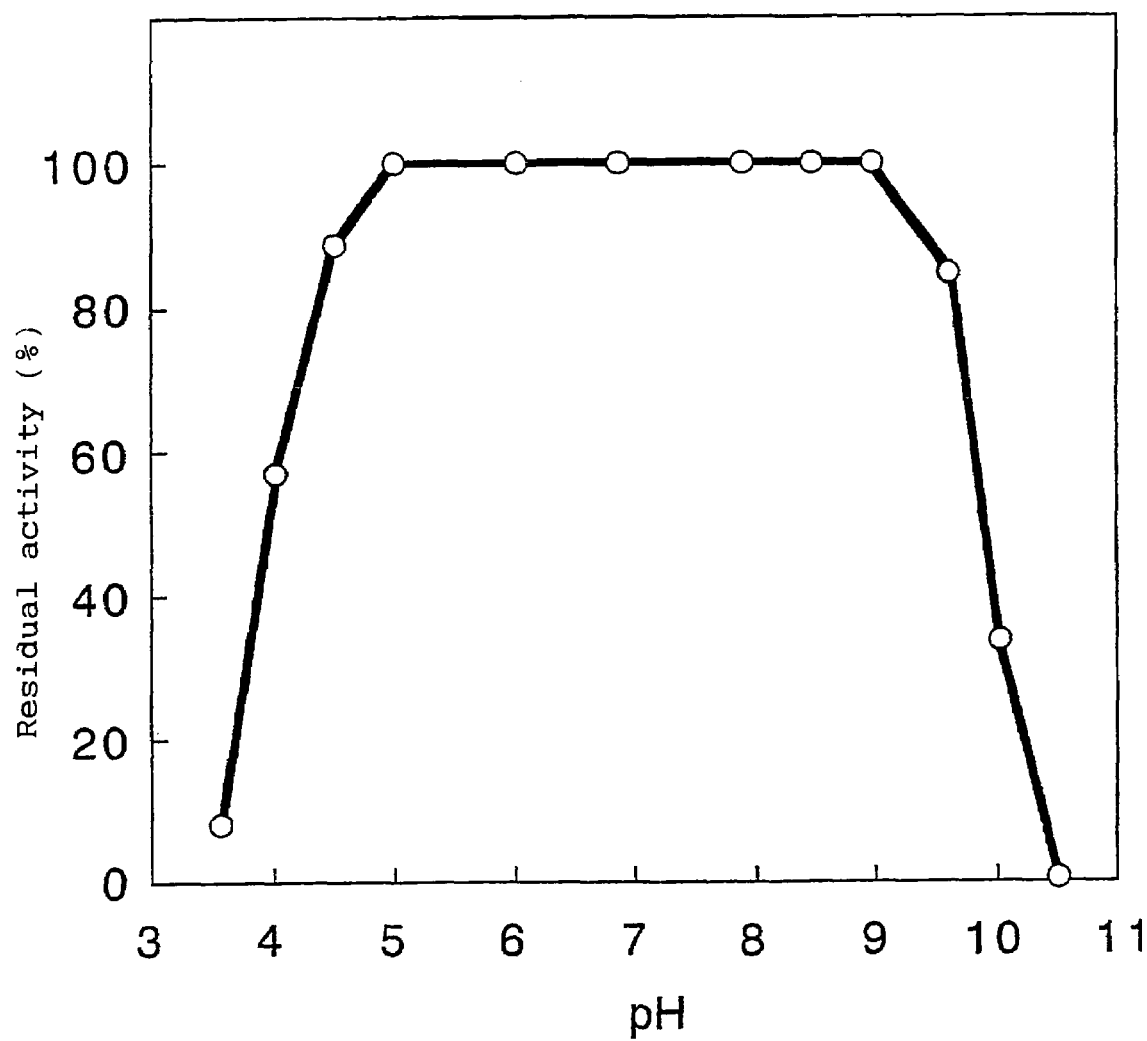
FIG. 32 shows the pH stability of α-isomaltosylglucosaccharide-forming enzyme from a microorganism of the species *Arthrobacter globiformis* A19 strain.

The influence of temperature and pH on the activity of α-isomaltosylglucosaccharide-forming enzyme was examined in accordance with the assay for its enzyme activity. The influence of temperature was determined in the presence of or the absence of 1 mM $Ca^{2+}$. These results are in FIG. 29 (influence of temperature) and FIG. 30 (influence of pH). The optimum temperature of the enzyme was about 60° C. and about 65° C. when incubated at pH 8.4 for 60 min in the absence of and in the presence of 1 mM $Ca^{2+}$, respectively. The optimum pH of the enzyme was about 8.4 when incubated at 35° C. for 60 min. The thermal stability of the enzyme was determined by incubating the testing enzyme solutions in the form of 20 mM glycine-NaOH buffer (pH 8.0) at prescribed temperatures for 60 min in the absence of or the presence of 1 mM $Ca^{2+}$, cooling the resulting enzyme solutions with water, and assaying the remaining enzyme activity of each solution. The pH stability of the enzyme was determined by keeping the testing enzyme in 50 mM buffers having prescribed pHs at 4° C. for 24 hours, adjusting the pH of each solution to 8.0, and assaying the remaining enzyme activity of each solution. These results are respectively in FIG. 31 (thermal stability) and FIG. 32 (pH stability). As a result, the enzyme had thermal stability of up to about 55° C.

and about 60° C. in the absence of and in the presence of 1 mM $Ca^{2+}$, respectively, and had pH stability of about 5.0 to about 9.0.

The influence of metal ions on the activity of α-isomalto-syl-transferring enzyme was examined in the presence of 1 mM of each metal-ion according to the assay for its enzyme activity. The results are in Table 19.

TABLE 19

| Metal ion | Relative activity (%) | Metal ion | Relative activity (%) |
|---|---|---|---|
| None | 100 | $Hg^{2+}$ | 0 |
| $Zn^{2+}$ | 56 | $Ba^{2+}$ | 99 |
| $Mg^{2+}$ | 97 | $Sr^{2+}$ | 102 |
| $Ca^{2+}$ | 106 | $Pb^{2+}$ | 43 |
| $Co^{2+}$ | 93 | $Fe^{2+}$ | 36 |
| $Cu^{2+}$ | 0 | $Fe^{3+}$ | 35 |
| $Ni^{2+}$ | 46 | $Mn^{2+}$ | 98 |
| $Al^{3+}$ | 37 | EDTA | 2 |

As evident form the results in Table 19, it was revealed that the enzyme activity was strongly inhibited by $Hg^{2+}$, $Cu^{2+}$, and EDTA. Amino acid analysis on the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:18, i.e., alanine-proline-leucine-glycine-valine-glutamine-arginine-alanine-glutamine-phenylalanine-glutamine-serine-glycine in the N-terminal region. Detailed method for assaying amino acid sequence is not shown in this specification because it is disclosed in detail in Japanese Patent Application No. 2001-5441 (International Publication No. WO 02/055708), however, the α-isomaltosylglucosaccharide-forming enzyme has an amino acid sequence of amino acid residues 37-965 shown in parallel in SEQ ID NO:25 similarly as the polypeptide disclosed in the specification of the above Japanese Patent Application No. 2001-5441.

EXPERIMENT 16-2

Property of α-isomaltosyl-transferring Enzyme

A purified specimen of α-isomaltosyl-transferring enzyme, obtained by the method in Experiment 15-3, was subjected to SDS-PAGE using a 7.5% (w/v) of polyacrylamide gel and then determined for molecular weight by comparing with the dynamics of standard molecular markers electrophoresed in parallel, commercialized by Japan Bio-Rad Laboratories Inc., Tokyo, Japan, revealing that the enzyme had a molecular weight of about 113,000±20,000 daltons.

A portion of the above purified specimen was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 4.2±0.5.

Figure 33:
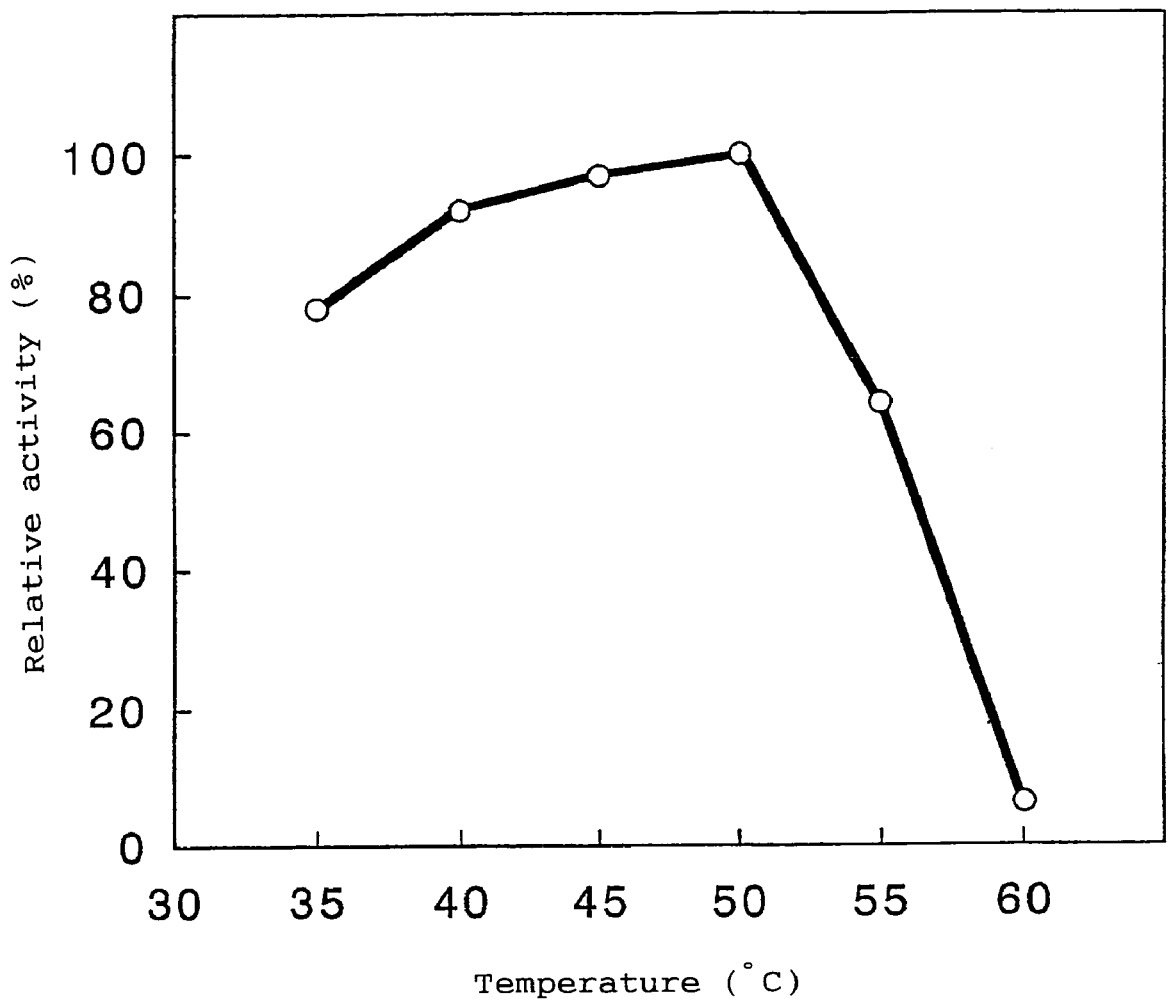
FIG. 33 shows the thermal influence on the enzymatic activity of α-isomaltosyl-transferring enzyme from a microorganism of the species *Arthrobacter globiformis* A19 strain.
Figure 34:
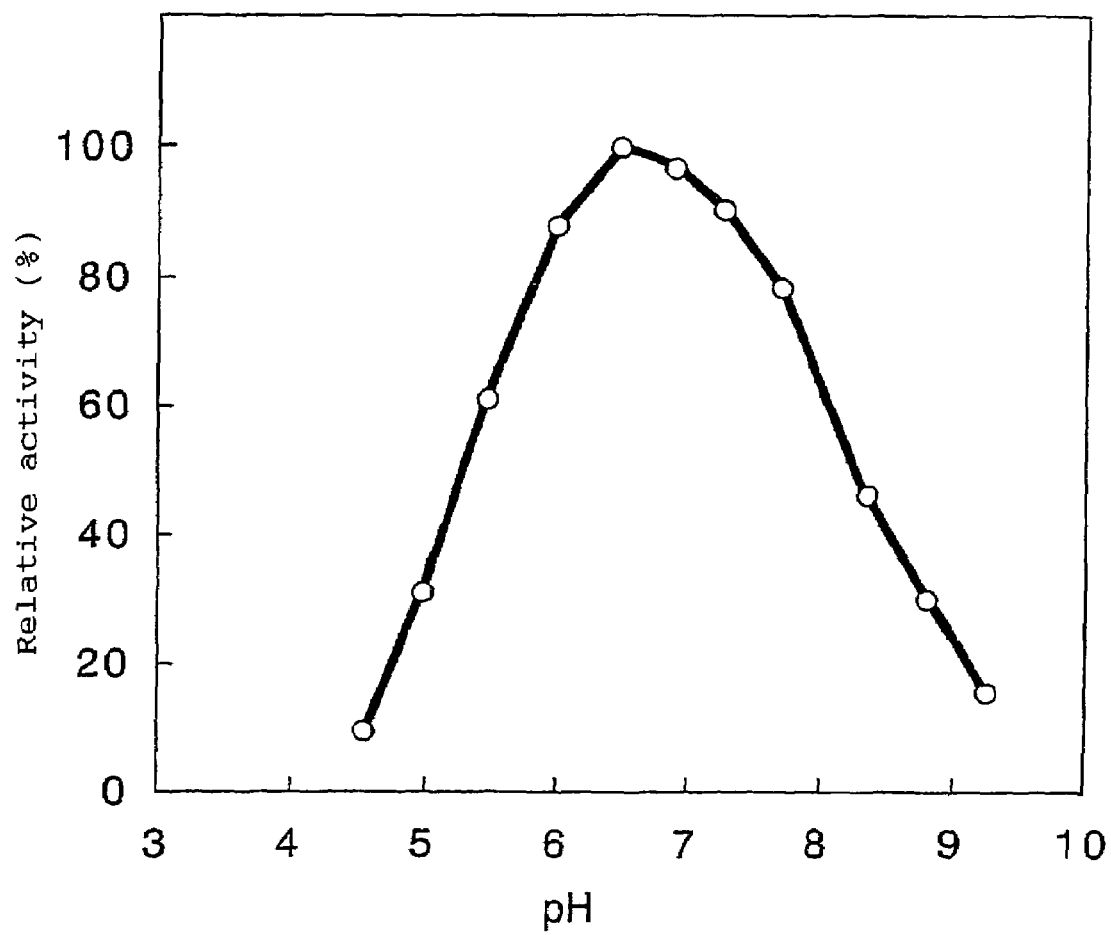
FIG. 34 shows the pH influence on the enzymatic activity of α-isomaltosyl-transferring enzyme from a microorganism of the species *Arthrobacter globiformis* A19 strain.
Figure 35:
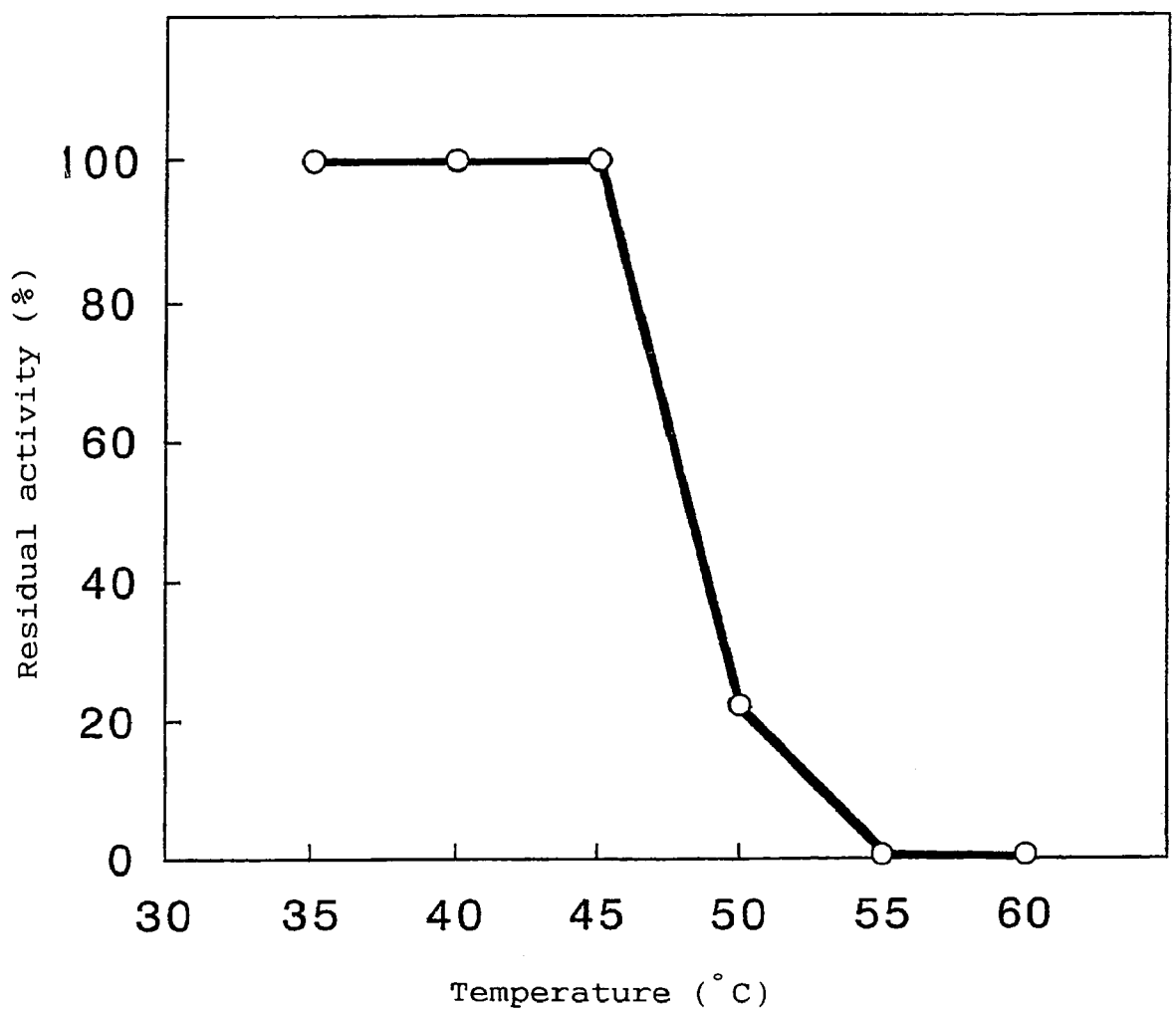
FIG. 35 shows the thermal stability of α-isomaltosyl-transferring enzyme from a microorganism of the species *Arthrobacter globiformis* A19 strain.
Figure 36:
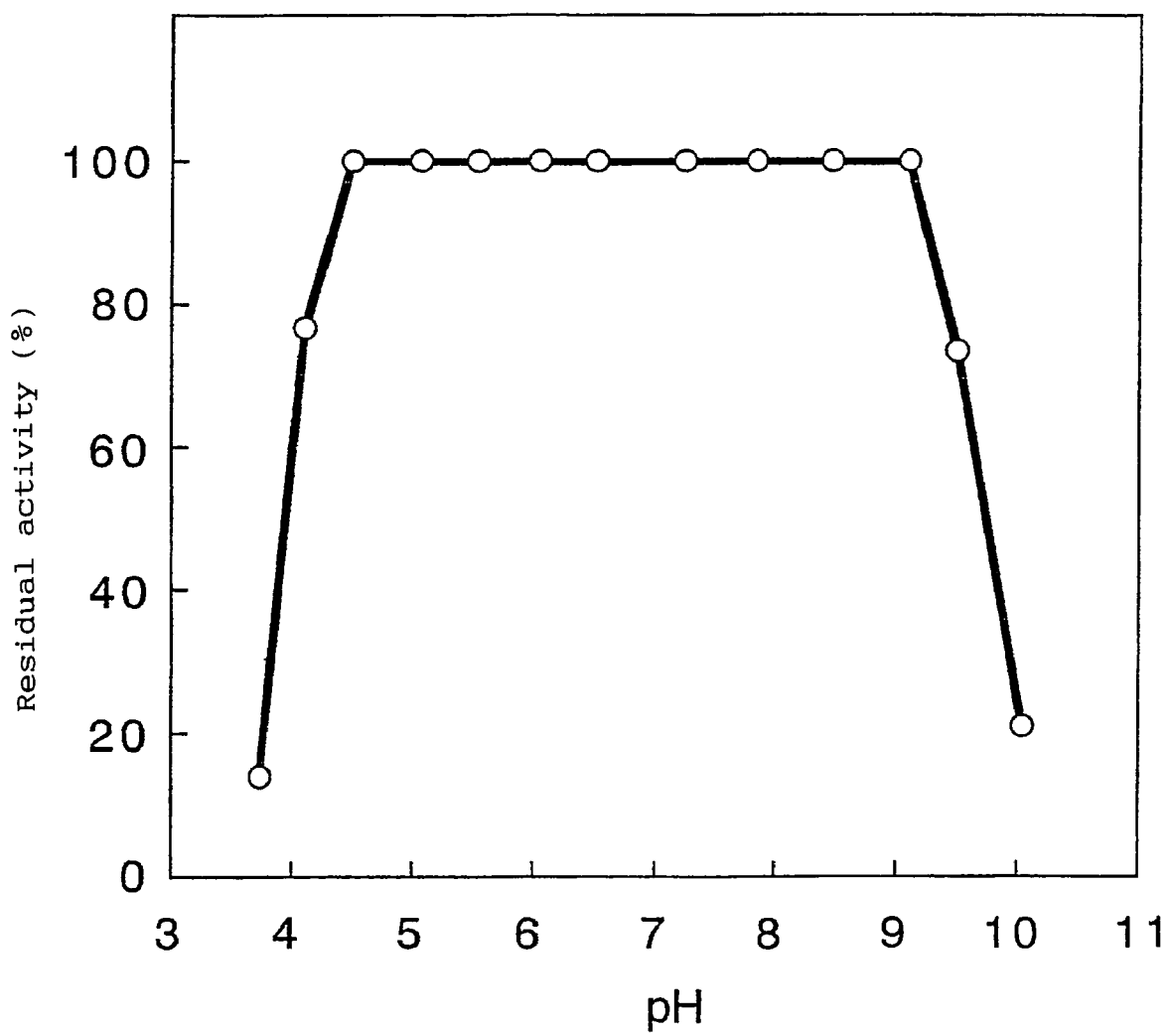
FIG. 36 shows the pH stability of α-isomaltosyl-transferring enzyme from a microorganism of the species *Arthrobacter globiformis* A19 strain.

The influence of temperature and pH on the above enzyme was examined in accordance with the assay for its enzyme activity. These results are in FIG. 33 (influence of temperature) and FIG. 34 (influence of pH). The optimum temperature of the enzyme was about 50° C. when incubated at pH 6.0 for 30 min. The optimum pH of the enzyme was about 6.5 when incubated at 35° C. for 30 min. The thermal stability of the enzyme was determined by incubating the testing enzyme solutions in the form of 20 mM acetate buffer (pH 6.0) at prescribed temperatures for 60 min, cooling the resulting enzyme solutions with water, and assaying the remaining enzyme activity of each solution. The pH stability of the enzyme was determined by keeping the testing enzyme solutions in the form of 50 mM buffers having prescribed pHs at 4° C. for 24 hours, adjusting the pH of each solution to 6.0, and assaying the remaining enzyme activity of each solution. These results are respectively in FIG. 35 (thermal stability) and FIG. 36 (pH stability). As a result, the enzyme had thermal stability of up to about 45° C. and pH stability of about 4.5 to about 9.0. Amino acid analysis on the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:19, i.e., asparagine-threonine-leucine-aspartic acid-glycine-valine-tryptophane-histidine-asparagine-proline-tyrosine-glycine-alanine-aspartic acid-glutamic acid-leucine-tyrosine-alanine-threonine-glutamine in the N-terminal region.

EXPERIMENT 16-3

Total Amino Acid Sequence of α-isomaltosyl-transferring Enzyme

Figure 37:
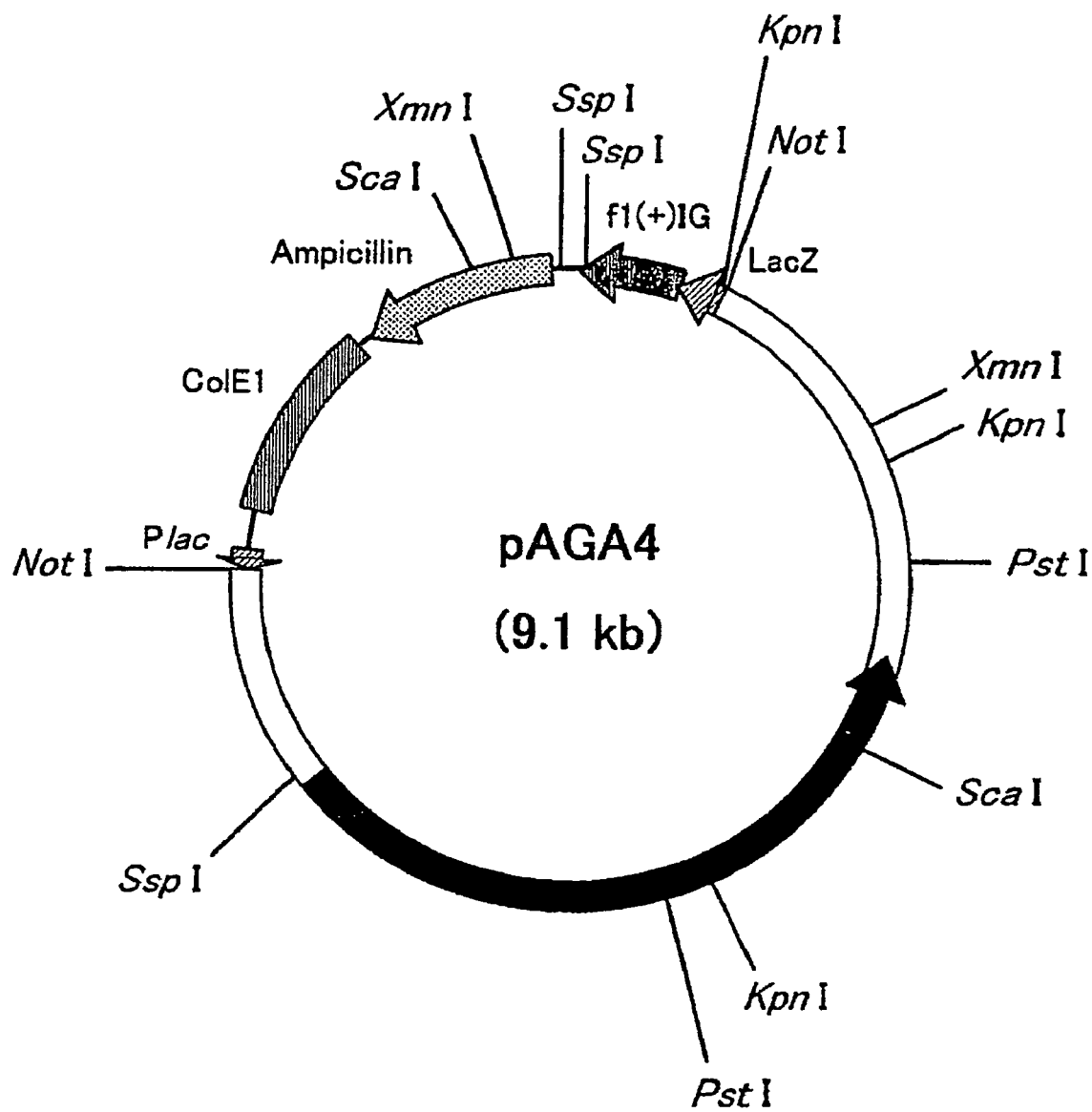
FIG. 37 is a figure for a restriction map of a recombinant DNA "pAGA4", where the part with a bold line is a DNA encoding a polypeptide having an α-isomaltosyl-transferring enzyme activity, derived from a microorganism of the species *Arthrobacter globiformis* A19 strain.

According to the method in Japanese Patent Application No. 2001-5441 (International Publication No. WO 02/055708), chromosomal DNAs (cDNAs) were extracted from *Arthrobacter globiformis* A19 strain and purified. The purified cDNAs were hydrolyzed with a restriction enzyme, Not I, to obtain DNA fragments. While, "Bluescript II SK(+)", a plasmid vector commercialized by Stratagene Cloning Systems, California, USA, was completely cleaved with a restriction enzyme, Not I, and the resulting cleaved plasmid vector and the above DNA fragments using "DNA Ligation Kit" commercialized by Takara Shuzo Co., Ltd., Tokyo, Japan, to obtain a recombinant DNA. "Epicurian Coli XL2-Blue", commercialized by Stratagene Cloning Systems, California, USA, was transformed with the recombinant DNA to obtain a gene library. An oligonucleotide, represented by 5'-AAYACNCTNGAYGGNGTNTGGCAYAAY-CCNTAYGGNGCNGAYGARCTNTGGAC-3', was chemically synthesized based on the amino acid sequence of amino acid residues 1-18 in SEQ ID NO:19, which had been revealed by the method in Experiment 16-2; and labeled with [γ-$^{32}$P]ATP and T4 polynucleotide kinase to obtain a probe. In accordance with the method in Japanese Patent Application No. 2001-5441 (International Publication No. WO 02/055708), the above gene library and the probe were subjected to the colony hybridization method, followed by selecting a transformant that strongly hybridized with the probe. The transformant was named "AGA4". According to conventional manner, a recombinant DNA was prepared from the transformant and analyzed for nucleotide sequence by conventional dideoxy method, revealing that the recombinant DNA thus obtained comprised the DNA of SEQ ID NO:26 consisting of 6153 base pairs, derived from *Arthrobacter globiformis* A19 strain. As shown in FIG. 37, in the recombinant DNA, the above DNA was linked to the downstream of the recognition site of Not I. When an amino acid sequence estimable from the above nucleotide sequence, which is shown in parallel in SEQ ID NO:26, was compared with the N-terminal amino acid sequence of the α-isomaltosyl-transferring enzyme that was confirmed by the method in Experiment 16-2, the amino acid sequence of SEQ ID NO:19 was completely coincided with the amino acid residues 50-69 shown in parallel in SEQ ID NO:26. Since the nucleotide sequence of nucleotide residues 4644-4646 in SEQ ID NO:26 encodes the termination codon (5'-TGA-3'), the C-terminus of α-isomaltosyl-transferring enzyme was revealed to be arginine, corresponding to amino acid residue 1121, shown in parallel in SEQ ID NO:26, which positions just before the termination codon. These results show that the α-isomaltosyl-transferring enzyme obtained in Experiment 15-3 comprises the amino acid residues 50-1121 shown in parallel in SEQ ID NO:26 and is encoded by a DNA comprising the nucleotide residues 1428-4643 shown in parallel in SEQ ID NO:26. A sequence of amino acid residues 1-49 shown in parallel in SEQ ID NO:26 was estimated to be an amino acid sequence of secretory signal for the polypeptide. These data revealed that the precursor peptide of the polypeptide before secretion comprises the amino acid sequence shown in parallel in SEQ ID NO:26 and is encoded by the nucleotide sequence shown in parallel in SEQ ID NO:26. Based on these, the recombinant DNA with its confirmed nucleotide sequence was named "pAGA4".

EXPERIMENT 17

Production of α-isomaltosyl-transferring Enzyme from *Arthrobacter ramosus* S1 Strain A liquid nutrient culture medium, consisting of 4.0% (w/v) of "PINE-DEX #4", a partial starch hydrolyzate, 1.8% (w/v) of "ASAHIMEAST", a yeast extract, 0.1% (w/v) of dipotassium phosphate, 0.06% (w/v) of sodium phosphate dodecahydrate, 0.05% (w/v) magnesium sulfate heptahydrate, and water, was placed in 500-ml Erlenmeyer flasks in a volume of 100 ml each, autoclaved at 121° C. for 20 min to effect sterilization, cooled, inoculated with a stock culture of *Arthrobacter ramosus* S1 strain (FERM BP-7592), and incubated at 27° C. for 48 hours under rotary shaking conditions of 230 rpm for use as a seed culture. About 20 L of a fresh preparation of the same nutrient culture medium as used in the above culture were placed in a 30-L fermentor, sterilized by heating, cooled to 27° C., inoculated with 1% (v/v) of the seed culture, and incubated for about 48 hours while stirring under aeration-agitation conditions at 27° C. and pH 6.0 to 8.0. The resultant culture, having about 0.45 unit/ml of an α-isomaltosyl-transferring activity, was centrifuged at 10,000 rpm for 30 min to obtain about 18 L of a supernatant having about 0.44 unit/ml of an α-isomaltosyl-transferring enzyme activity and a total enzyme activity of about 7,920 units.

EXPERIMENT 18

Purification of α-isomaltosyl-transferring Enzyme from *Arthrobacter ramosus* S1 Strain About 18 L of a supernatant obtained in Experiment 17 were salted out in an 80% (w/v) ammonium sulfate solution at 4° C. for 24 hours, and the resulting sediments were collected by centrifugation at 10,000 rpm for 30 min and dialyzed against 10 mM phosphate buffer (pH 7.0) to obtain about 380 ml of a crude enzyme solution having 6,000 units of α-isomaltosyl-transferring enzyme. The crude enzyme solution was dialyzed against 10 mM phosphate buffer (pH 7.0) containing 1 M ammonium sulfate, and the dialyzed solution was centrifuged to remove insoluble impurities. The resulting supernatant was fed to affinity column chromatography using 500 ml of "SEPHACRYL HR S-200" gel. The enzyme was adsorbed on the gel and then eluted sequentially with a linear gradient decreasing from 1 M to 0 M of ammonium sulfate and with a linear gradient increasing from 0% (w/v) to 5% (w/v) maltotetraose, resulting in an elution of the enzyme from the gel at a concentration of about 2% (w/v) maltotetraose and collecting fractions with the enzyme activity. The fractions were pooled and dialyzed against 10 mM phosphate buffer (pH 7.0) containing 1 M ammonium sulfate, and the dialyzed solution was centrifuged to remove insoluble impurities. The supernatant thus obtained was fed to hydrophobic column chromatography using 380 ml of "BUTYL-TOYO-PEARL 650M" gel. When eluted with a linear gradient decreasing from 1 M to 0 M ammonium sulfate, the α-isomaltosyl-transferring enzyme adsorbed on the gel was eluted therefrom at about 0.3 M ammonium sulfate, followed by collecting fractions with the enzyme activity for a purified enzyme specimen. The amount of enzyme activity, specific activity, and yield of the α-isomaltosyl-transferring enzyme in each purification step are in Table 20.

TABLE 20

| Purification step | Enzyme* activity (unit) | Specific activity of enzyme* (unit/mg protein) | Yield (%) |
|---|---|---|---|
| Culture supernatant | 7,920 | 0.47 | 100 |
| Dialyzed solution after salting out with ammonium sulfate | 6,000 | 3.36 | 75.8 |
| Eluate from affinity column chromatography | 5,270 | 29.9 | 66.5 |
| Eluate from hydrophobic column chromatography | 4,430 | 31.1 | 55.9 |

Note:
The symbol "*" means α-isomaltosyl-transferring enzyme.

The purified α-isomaltosyl-transferring enzyme specimen obtained in this experiment was assayed for purity on gel electrophoresis using a 7.5% (w/v) polyacrylamide gel and detected on the gel as a single protein band, meaning a high purity enzyme specimen.

EXPERIMENT 19

Property of α-Isomaltosyl-transferring Enzyme

A purified specimen of α-isomaltosyl-transferring enzyme, obtained by the method in Experiment 18, was subjected to SDS-PAGE using a 7.5% (w/v) of polyacrylamide gel and then determined for molecular weight by comparing with the dynamics of standard molecular markers electrophoresed in parallel, commercialized by Japan Bio-Rad Laboratories Inc., Tokyo, Japan, revealing that the enzyme had a molecular weight of about 116,000±20,000 daltons.

A portion of the above purified specimen was subjected to isoelectrophoresis using a gel containing 2% (w/v) ampholine commercialized by Amersham Corp., Div., Amersham International, Arlington Heights, Ill., USA, and then measured for pHs of protein bands and gel to determine the isoelectric point of the enzyme, revealing that the enzyme had an isoelectric point of about 4.2±0.5.

Figure 38:
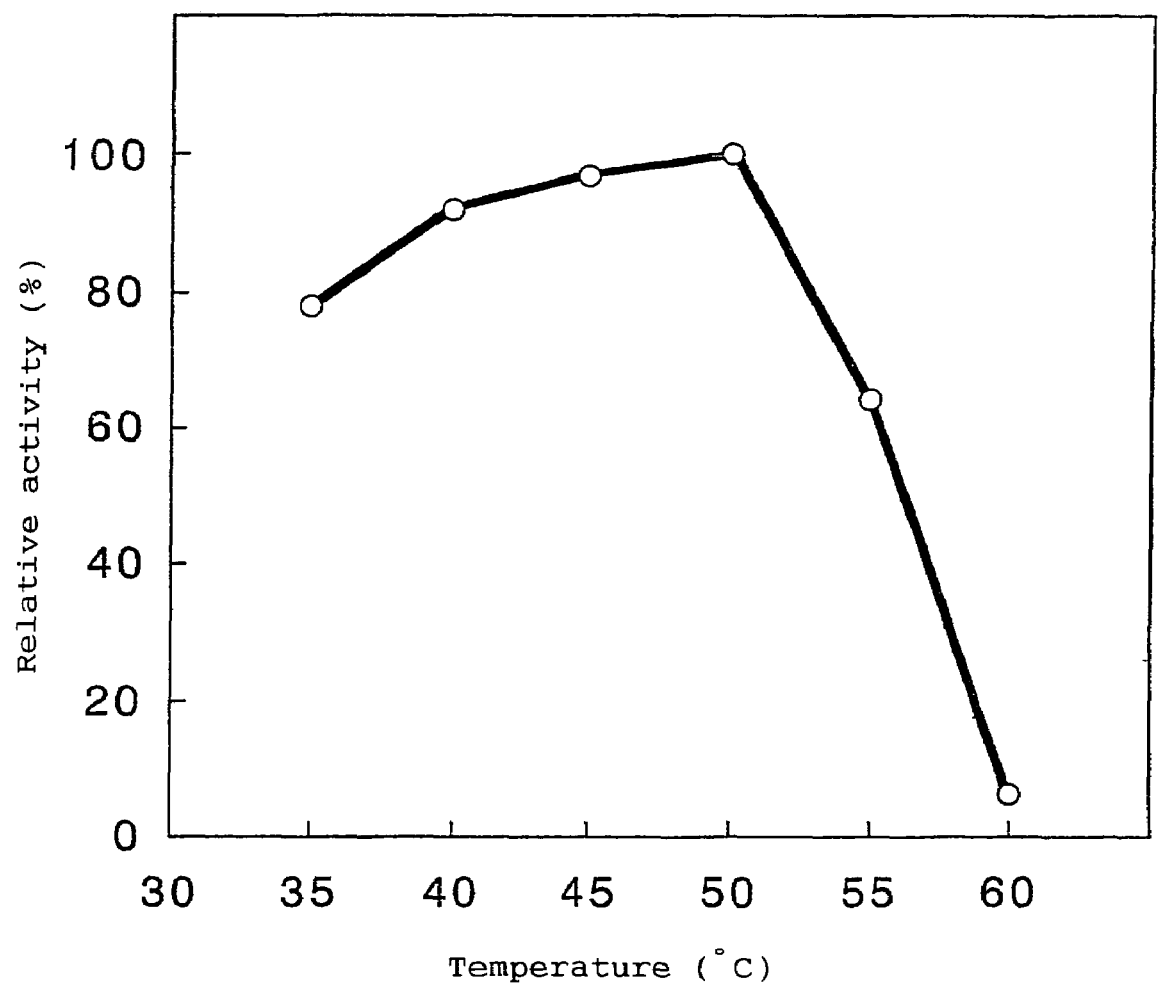
FIG. 38 shows the thermal influence on the enzymatic activity of α-isomaltosyl-transferring enzyme from a microorganism of the species *Arthrobacter ramosus* S1 strain.
Figure 39:
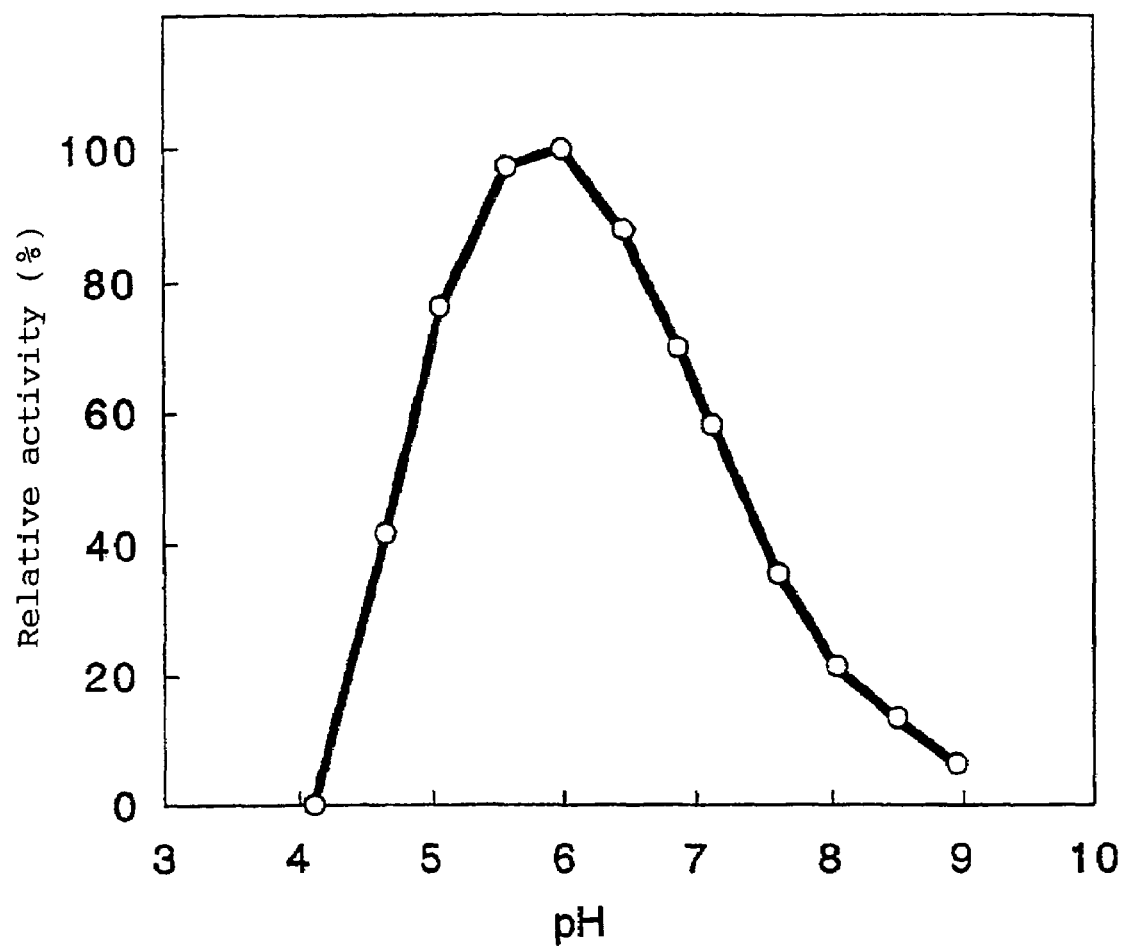
FIG. 39 shows the pH influence on the enzymatic activity of α-isomaltosyl-transferring enzyme from a microorganism of the species *Arthrobacter ramosus* S1 strain.
Figure 40:
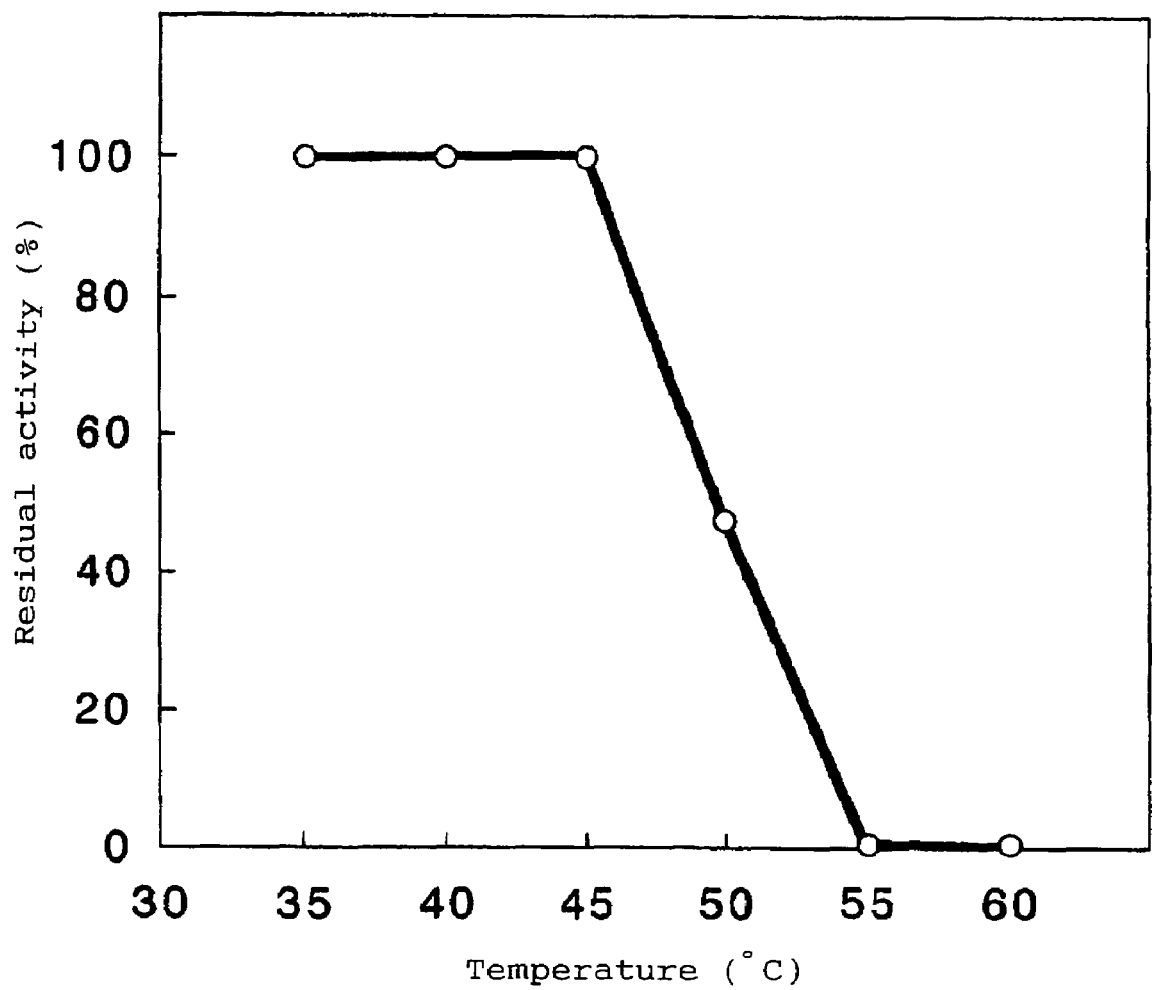
FIG. 40 shows the thermal stability of α-isomaltosyl-transferring enzyme from a microorganism of the species *Arthrobacter ramosus* S1 strain.
Figure 41:
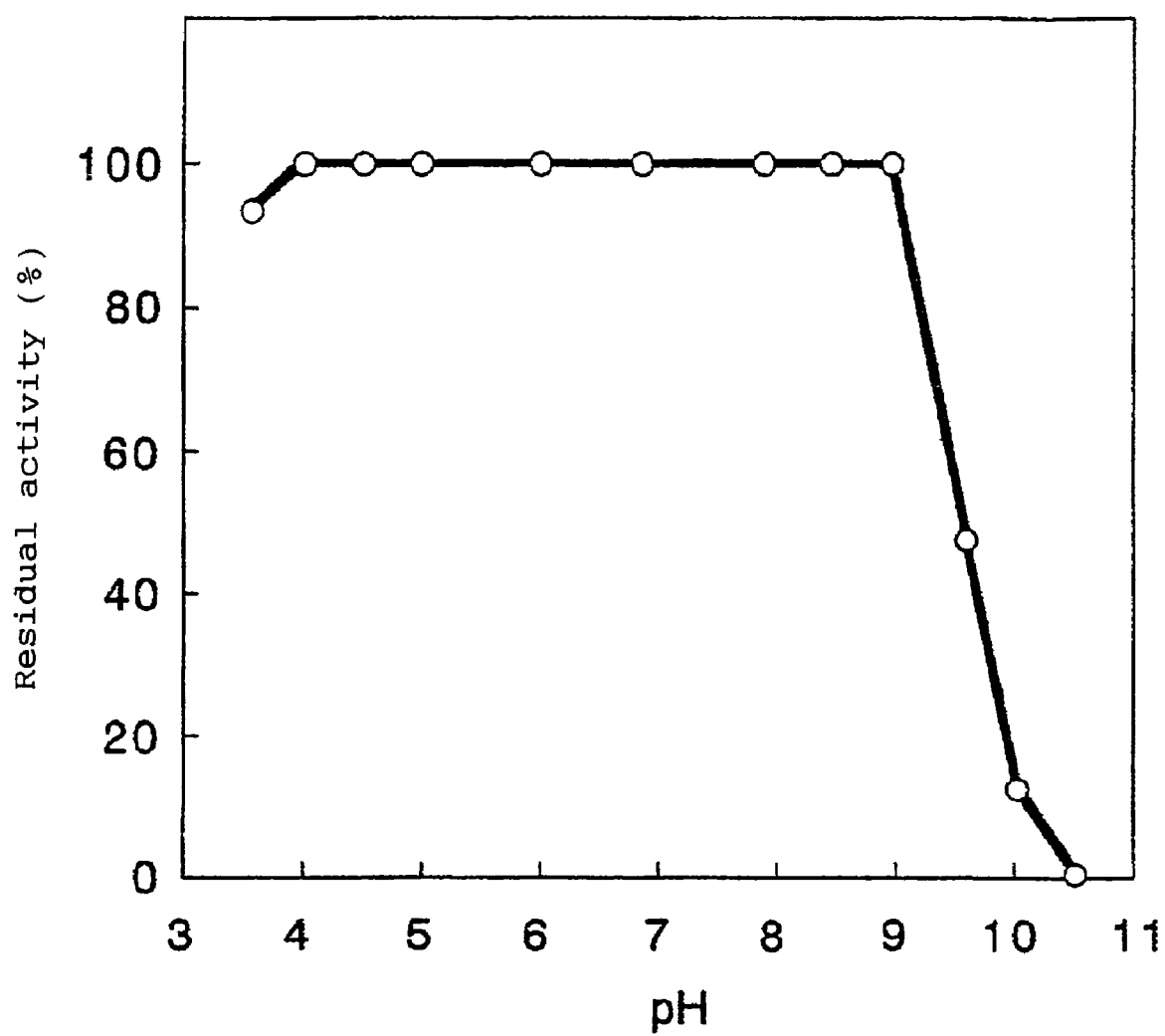
FIG. 41 shows the pH stability of α-isomaltosyl-transferring enzyme from a microorganism of the species *Arthrobacter ramosus* S1 strain.

The influence of temperature and pH on the activity of α-isomaltosyl-transferring enzyme was examined in accordance with the assay for its enzyme activity. These results are in FIG. 38 (influence of temperature) and FIG. 39 (influence of pH). The optimum temperature of the enzyme was about 50° C. when incubated at pH 6.0 for 30 min. The optimum pH of the enzyme was about 6.0 when incubated at 35° C. for 30 min. The thermal stability of the enzyme was determined by incubating the testing enzyme solutions in the form of 20 mM acetate buffers (pH 6.0) at prescribed temperatures for 60 min, cooling the resulting enzyme solutions with water, and assaying the remaining enzyme activity of each solution. The pH stability of the enzyme was determined by keeping the testing enzyme solutions in the from of 50 mM buffers having prescribed pHs at 4° C. for 24 hours, adjusting the pH of each solution to 6.0, and assaying the remaining enzyme activity of each solution. These results are respectively in FIG. 40 (thermal stability) and FIG. 41 (pH stability). As evident from these figures, the enzyme had thermal stability of up to about 45° C. and had pH stability of about 3.6 to about 9.0.

The influence of metal ions on the activity of α-isomaltosyl-transferring enzyme was examined in the presence of 1 mM of each metal-ion according to the assay for its enzyme activity. The results are in Table 21.

TABLE 21

| Metal ion | Relative activity (%) | Metal ion | Relative activity (%) |
|---|---|---|---|
| None | 100 | $Hg^{2+}$ | 0.1 |
| $Zn^{2+}$ | 78 | $Ba^{2+}$ | 97 |
| $Mg^{2+}$ | 99 | $Sr^{2+}$ | 101 |
| $Ca^{2+}$ | 103 | $Pb^{2+}$ | 85 |
| $Co^{2+}$ | 91 | $Fe^{2+}$ | 105 |
| $Cu^{2+}$ | 2 | $Fe^{3+}$ | 75 |
| $Ni^{2+}$ | 87 | $Mn^{2+}$ | 98 |
| $Al^{3+}$ | 93 | EDTA | 91 |

As evident form the results in Table 21, it was revealed that the enzyme activity was strongly inhibited by $Hg^{2+}$ and also inhibited by $Cu^{2+}$. It was also revealed that the enzyme was neither activated by $Ca^{2+}$ nor by EDTA.

Amino acid analysis on the N-terminal amino acid sequence of the enzyme by "PROTEIN SEQUENCER MODEL 473A", an apparatus of Applied Biosystems, Inc., Foster City, USA, revealed that the enzyme had a partial amino acid sequence of SEQ ID NO:20, i.e., aspartic acid-threonine-leucine-serine-glycine-valine-phenylalanine-histidine-glycine-proline at the N-terminal region.

EXPERIMENT 20

Action on Saccharides

It was tested whether any saccharides can be used as substrates for α-isomaltosylglucosaccharide-forming enzyme. For the purpose, a solution of maltose, maltotriose, maltotetraose, maltopentaose, maltohexaose, maltoheptaose, isomaltose, isomaltotriose, panose, isopanose, α,α-trehalose, kojibiose, nigerose, neotrehalose, cellobiose, gentibiose, maltitol, maltotriitol, lactose, sucrose, erlose, selaginose, maltosyl glucoside, or isomaltosyl glucoside was prepared.

To each of the above solutions was added two units/g substrate of a purified specimen of α-isomaltosylglucosaccharide-forming enzyme from either *Bacillus globisporus* C9 strain obtained by the method in Experiment 4-2, *Bacillus globisporus* C11 strain obtained by the method in Experiment 7-2, *Bacillus globisporus* N75 strain obtained by the method in Experiment 11-2, or *Arthrobacter globiformis* A19 strain obtained by the method in Experiment 15-2, and the resulting each solution was adjusted to give a substrate concentration of 2% (w/v) and incubated at 30° C. and pH 6.0 for 24 hours, except for using pH 8.4 for the enzyme from *Arthrobacter globiformis* A19 strain. The enzyme solutions before and after the enzymatic reactions were respectively analyzed on TLC disclosed in Experiment 1 to confirm whether the enzymes acted on these substrates. The results are in Table 22.

TABLE 22

| | Enzymatic action | | | |
|---|---|---|---|---|
| Substrate | Enzyme of C9 strain | Enzyme of C11 strain | Enzyme of N75 strain | Enzyme of A19 strain |
| Maltose | + | + | + | + |
| Maltotriose | ++ | ++ | ++ | ++ |
| Maltotetraose | +++ | +++ | +++ | +++ |
| Maltopentaose | +++ | +++ | +++ | +++ |
| Maltohexaose | +++ | +++ | +++ | +++ |
| Maltoheptaose | +++ | +++ | +++ | +++ |
| Isomaltose | − | − | − | − |
| Isomaltotriose | − | − | − | − |
| Panose | − | − | − | − |
| Isopanose | ++ | ++ | ++ | ++ |
| Trehalose | − | − | − | − |
| Kojibiose | + | + | + | + |
| Nigerose | + | + | + | + |
| Neotrehalose | + | + | + | + |
| Cellobiose | − | − | − | − |
| Gentibiose | − | − | − | − |
| Maltitol | − | − | − | − |
| Maltotriitol | + | + | + | + |
| Lactose | − | − | − | − |
| Sucrose | − | − | − | − |
| Erlose | + | + | + | + |
| Selaginose | − | − | − | − |
| Maltosyl glucoside | ++ | ++ | ++ | ++ |
| Isomaltosyl glucoside | − | − | − | − |

Note:
Before and after the enzymatic reaction, the symbols "−", "+", "++", and "+++", mean that it showed no change, it showed a slight reduction of the color spot of the substrate and the formation of other reaction product, it showed a high reduction of the color spot of the substrate and the formation of other reaction product, and it showed a substantial disappearance of the substrate spot and the formation of other reaction product, respectively.

As evident from the Table 22, it was revealed that the α-isomaltosylglucosaccharide-forming enzymes well acted on saccharides having a glucose polymerization degree of at least three and having a maltose structure at their non-reducing ends, among the saccharides tested. It was also found that the enzymes slightly acted on saccharides, having a glucose polymerization degree of two, such as maltose, kojibiose, nigerose, neotrehalose, maltotriitol, and erlose.

EXPERIMENT 21

Reaction product from Maltooligosaccharide

EXPERIMENT 21-1

Preparation of Reaction Product

To an aqueous solution containing one percent (w/v) of maltose, maltotriose, maltotetraose, or maltopentaose as a substrate was added a purified specimen of α-isomaltosylglucosaccharide-forming enzyme obtained by the method in Experiment 7-2 in an amount of two units/g solid, d.s.b., for the aqueous solutions of maltose and maltotriose; 0.2 unit/g solid, d.s.b., for the aqueous solution of maltotetraose; and 0.1 unit/g solid, d.s.b., for the aqueous solution of maltopentaose, followed by incubation at 35° C. and pH 6.0 for eight hours. After a 10-min incubation at 100° C., the enzymatic reaction was suspended. The resulting reaction solutions were respectively measured for saccharide composition on HPLC using "YMC PACK ODS-AQ303", a column commercialized by YMC Co., Ltd., Tokyo, Japan, at a column temperature of 40° C. and a flow rate of 0.5 ml/min of water, and using as a detector "RI-8012", a differential refractometer commercialized by Tosoh Corporation, Tokyo, Japan. The results are in Table 23.

TABLE 23

| Saccharide as reaction product | Substrate | | | |
|---|---|---|---|---|
| | Maltose | Maltotriose | Maltotetraose | Maltopentaose |
| Glucose | 8.5 | 0.1 | 0.0 | 0.0 |
| Maltose | 78.0 | 17.9 | 0.3 | 0.0 |
| Maltotriose | 0.8 | 45.3 | 22.7 | 1.9 |
| Maltotetraose | 0.0 | 1.8 | 35.1 | 19.2 |
| Maltopentaose | 0.0 | 0.0 | 3.5 | 34.4 |
| Maltohexaose | 0.0 | 0.0 | 0.0 | 4.6 |
| Isomaltose | 0.5 | 0.0 | 0.0 | 0.0 |
| Glucosylmaltose | 8.2 | 1.2 | 0.0 | 0.0 |
| Glucosylmaltotriose | 2.4 | 31.5 | 6.8 | 0.0 |
| X | 0.0 | 2.1 | 30.0 | 11.4 |
| Y | 0.0 | 0.0 | 1.4 | 26.8 |
| Z | 0.0 | 0.0 | 0.0 | 1.7 |
| Others | 0.6 | 0.1 | 0.2 | 0.0 |

Note:
In the table, glucosylmaltose means α-isomaltosylglucose alias $6^2$-O-α-glucosylmaltose or panose;
glucosylmaltotriose means α-isomaltosylglucose alias $6^3$-O-α-glucosylmaltotriose;
X means the α-isomaltosylmaltotriose in Experiment 11-2, alias $6^4$-O-α-glucomaltotetraose;
Y means the α-isomaltosylmaltotetraose in Experiment 11-2, alias $6^5$-O-α-glucosylmaltopentaose; and
Z means an unidentified saccharide.

As evident from the results in Table 23, it was revealed that, after the enzymatic action, glucose and α-isomaltosylglucose alias $6^2$-O-α-glucosylmaltose or panose were mainly formed maltose as a substrate; and maltose and α-isomaltosylglucose alias $6^3$-O-α-glucosylmaltotriose were mainly formed along with small amounts of glucose, maltotetraose, α-isomaltosylglucose alias $6^2$-O-α-glucosylmaltose or panose, and a product X. Also, it was revealed that maltotriose and the product X were mainly formed from maltotetraose as a substrate along with small amounts of maltose, maltopentaose, α-isomaltosylglucose alias $6^3$-O-α-glucosylmaltotriose; and a product Y; and that maltotetraose and the product Y were mainly formed from maltopentaose as a substrate along with small amounts of maltotriose, maltohexaose, and the products X and Z. The product X as a main product from maltotetraose as a substrate and the product Y as a main product from maltopentaose as a substrate were respectively isolated and purified as follows: The products X and Y were respectively purified on HPLC using "YMC PACK ODS-A R355-15S-15 12A", a separatory HPLC column commercialized by YMC Co., Ltd., Tokyo, Japan, to isolate the product X having a purity of at least 99.9% from the reaction product from maltotetraose in a yield of about 8.3%, d.s.b., and the product Y having a purity of at least 99.9% from the reaction product from maltopentaose in a yield of about 11.5%, d.s.b.

EXPERIMENT 21-2

Structural Analysis on Reaction Product

Figure 42:
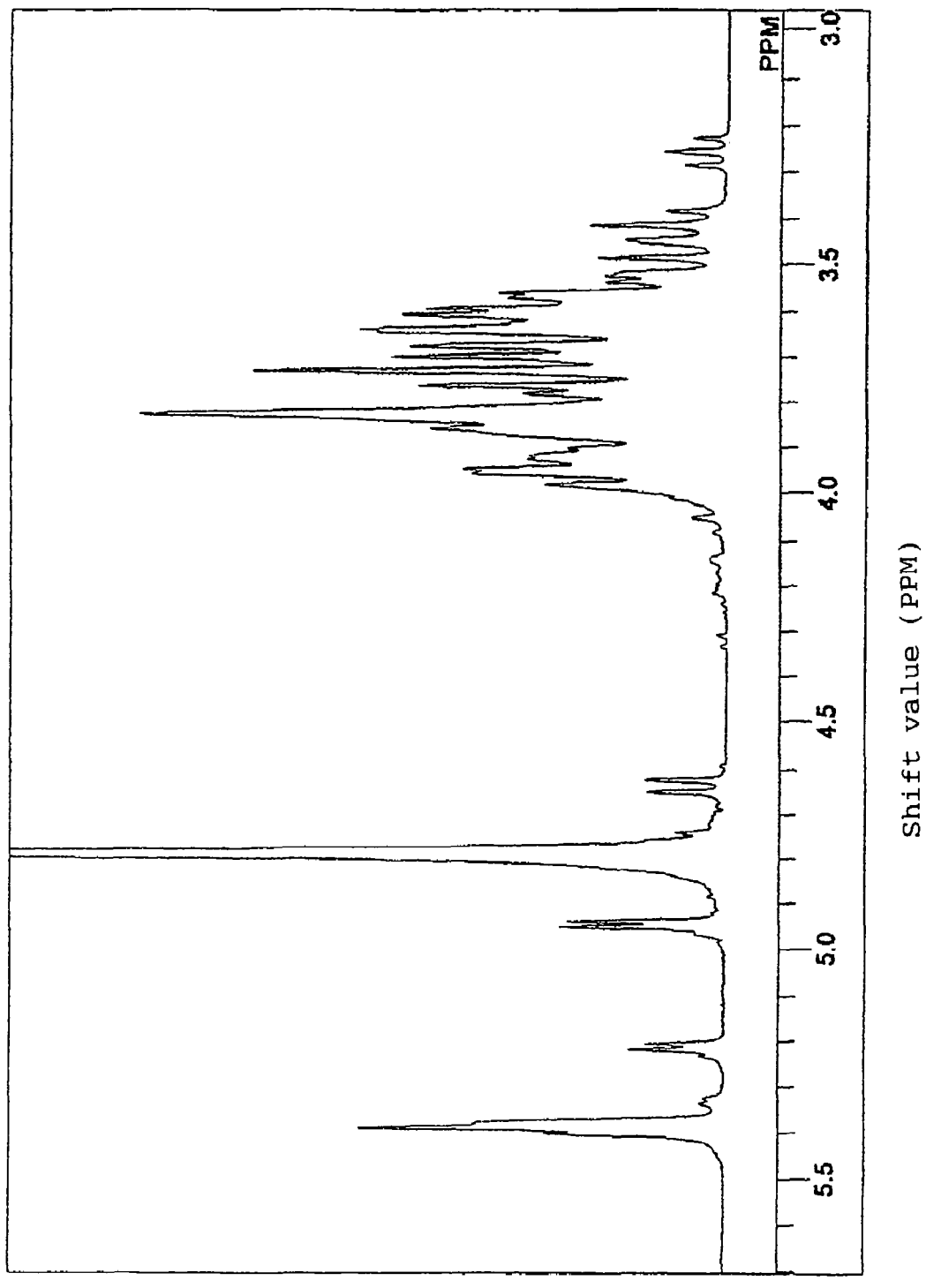
FIG. 42 is a spectrum of nuclear magnetic resonance ($^1$H-NMR) of α-isomaltosylmaltotriose, obtained by the enzymatic reaction using α-isomaltosylglucosaccharide-forming enzyme.
Figure 43:
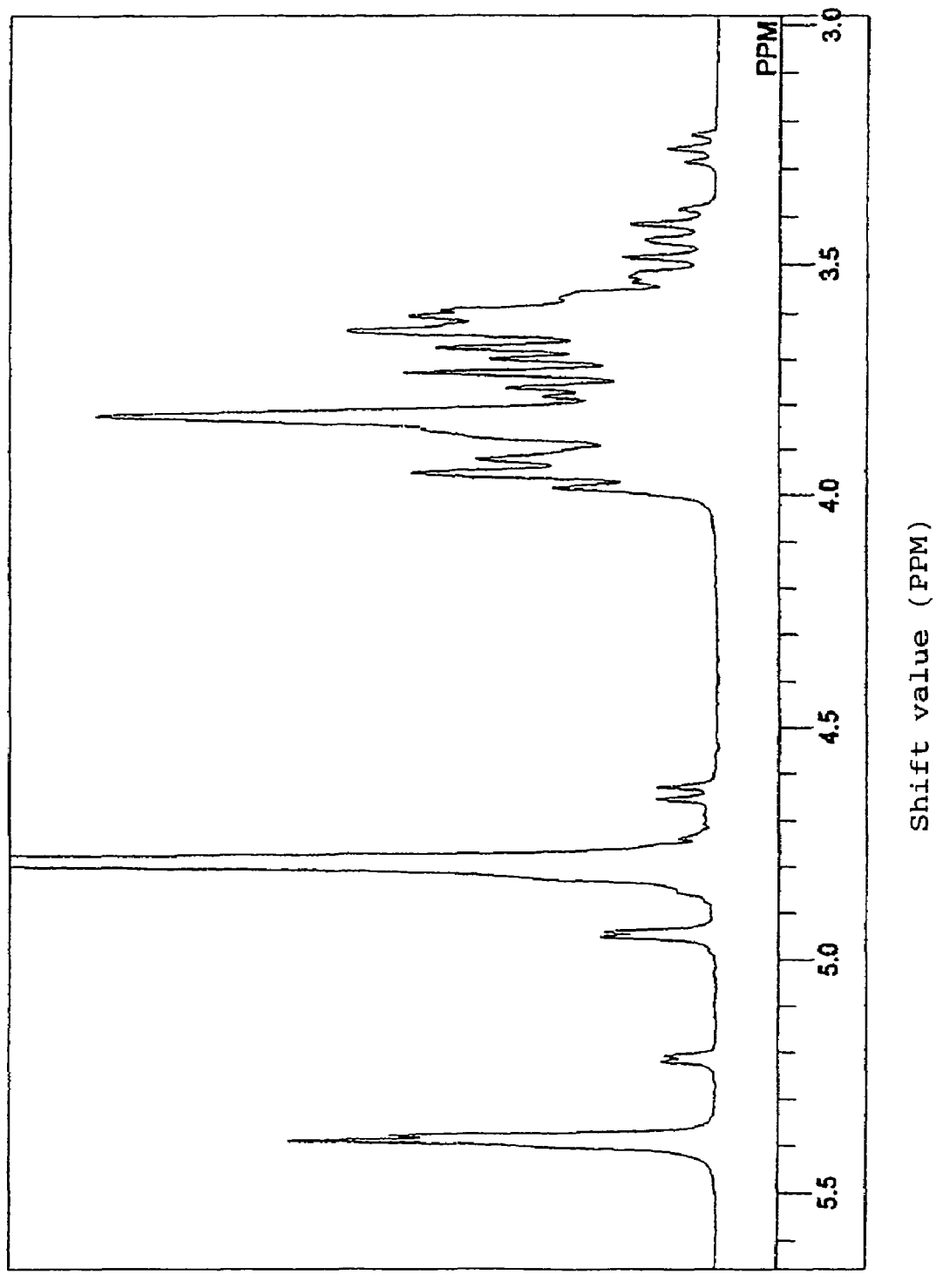
FIG. 43 is a spectrum of nuclear magnetic resonance ($^1$H-NMR) of α-isomaltosylmaltotetraose, obtained by the enzymatic reaction using α-isomaltosylglucosaccharide-forming enzyme.
Figure 44:
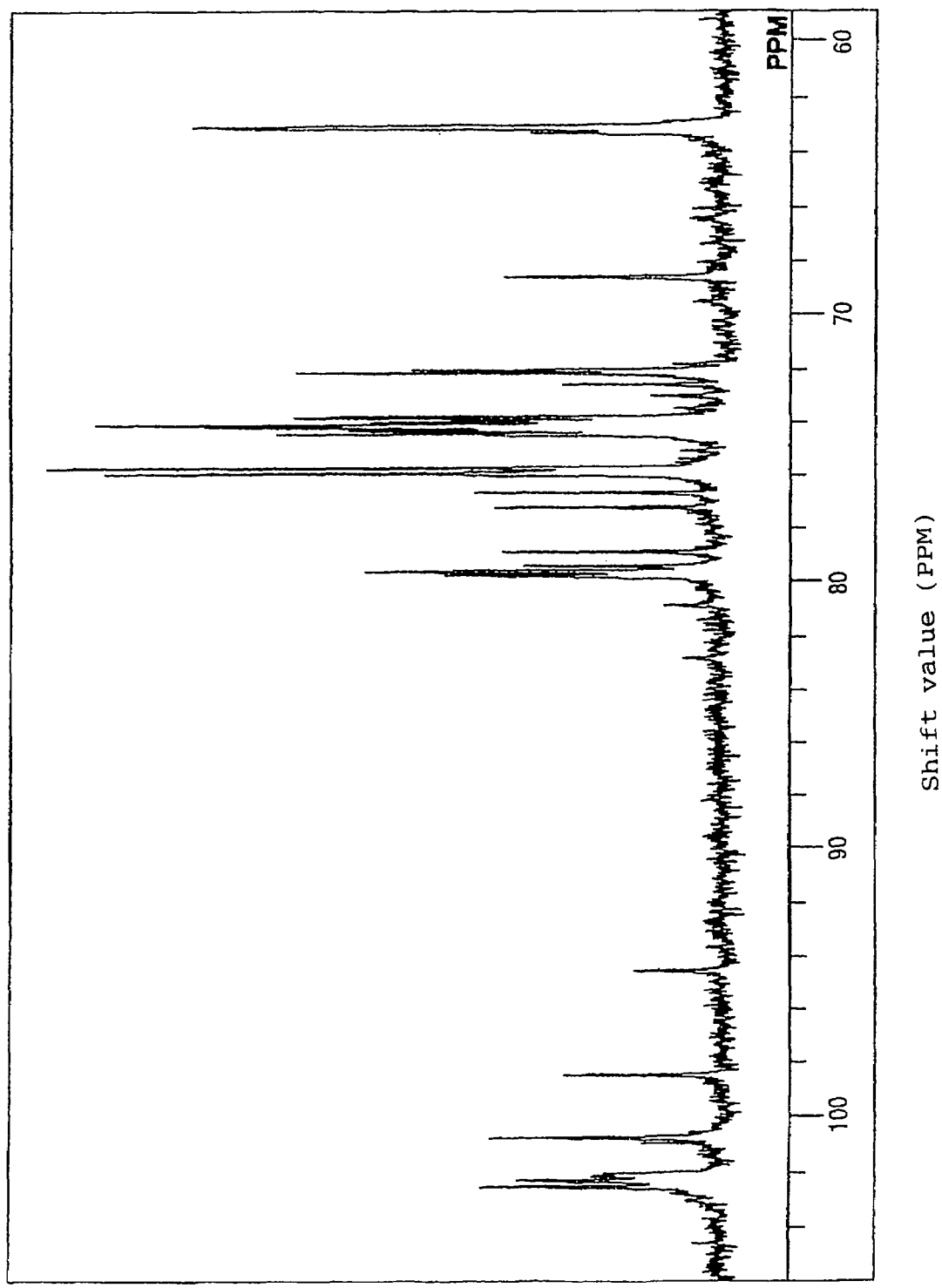
FIG. 44 is a spectrum of nuclear magnetic resonance ($^{13}$C-NMR) of α-isomaltosylmaltotriose, obtained by the enzymatic reaction using α-isomaltosylglucosaccharide-forming enzyme.
Figure 45:
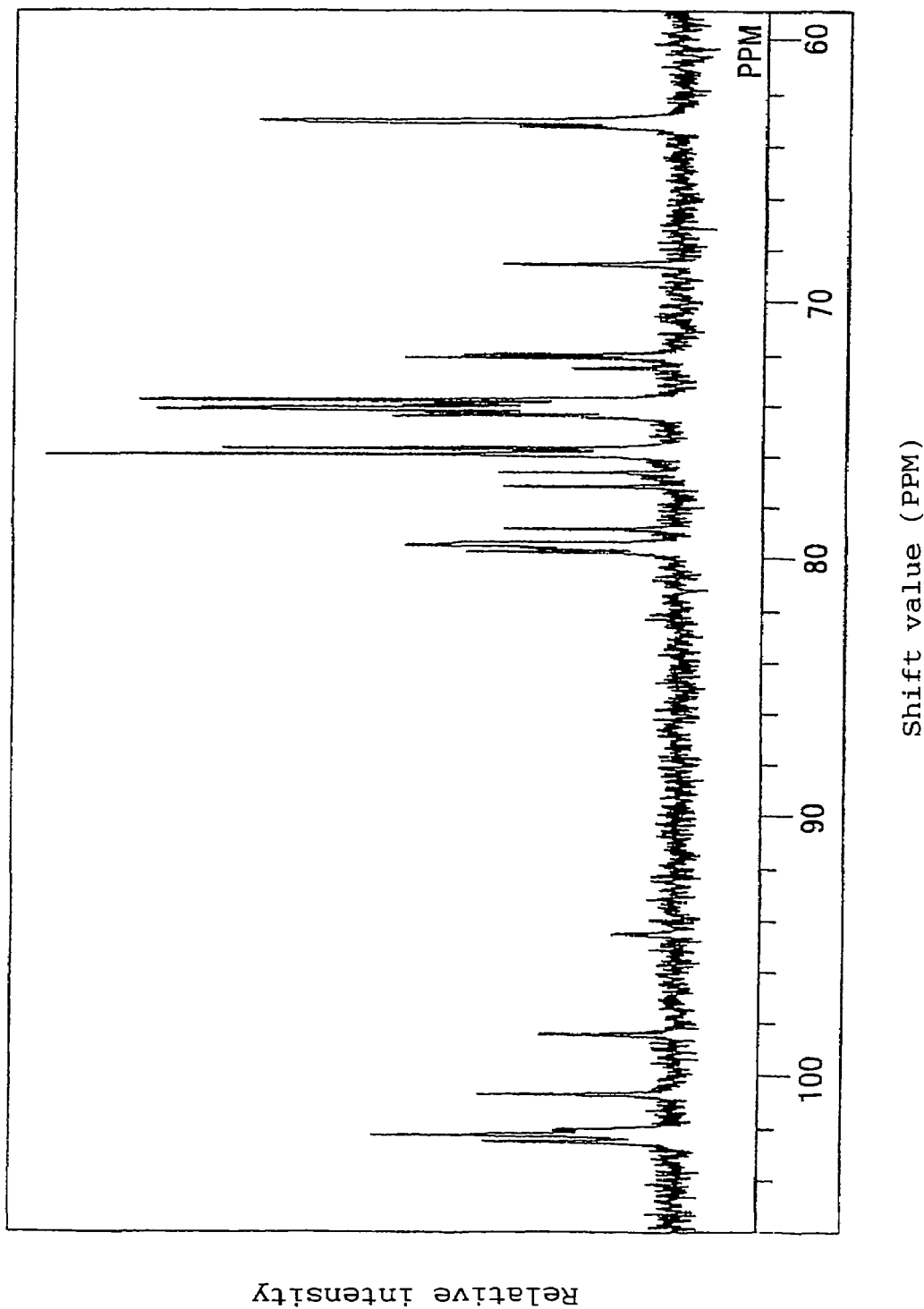
FIG. 45 is a spectrum of nuclear magnetic resonance ($^{13}$C-NMR) of α-isomaltosylmaltotetraose, obtained by the enzymatic reaction using α-isomaltosylglucosaccharide-forming enzyme.

The products X and Y, obtained by the method in Experiment 21-1, were subjected to methyl analysis and NMR analysis in a usual manner. The results on their methyl analyses are in Table 24. Regarding the results on their NMR analyses, FIG. 42 is a $^1$H-NMR spectrum for the product X and FIG. 43 is for the product Y. The $^{13}$C-NMR spectra for the products X and Y are respectively FIGS. 44 and 45. The assignment of the products X and Y are tabulated in Table 25.

TABLE 24

| Analyzed methyl compound | Ratio | |
|---|---|---|
| | Product X | Product Y |
| 2,3,4-Trimethyl compound | 1.00 | 1.00 |
| 2,3,6-Trimethyl compound | 3.05 | 3.98 |
| 2,3,4,6-Tetramethyl compound | 0.82 | 0.85 |

TABLE 25

| Glucose number | Carbon number | Chemical shift on NMR (ppm) | |
|---|---|---|---|
| | | Product X | Product Y |
| a | 1a | 100.8 | 100.8 |
| | 2a | 74.2 | 74.2 |
| | 3a | 75.8 | 75.7 |
| | 4a | 72.2 | 72.2 |
| | 5a | 74.5 | 74.5 |
| | 6a | 63.2 | 63.1 |
| b | 1b | 102.6 | 102.6 |
| | 2b | 74.2 | 74.2 |
| | 3b | 75.8 | 75.7 |
| | 4b | 72.1 | 72.1 |
| | 5b | 74.0 | 74.0 |
| | 6b | 68.6 | 68.6 |
| c | 1c | 102.3 | 102.3 |
| | 2c | 74.2 | 74.2 |
| | 3c | 76.0 | 76.0 |
| | 4c | 79.6 | 79.5 |
| | 5c | 73.9 | 73.9 |
| | 6c | 63.2 | 63.1 |
| d | 1d | 102.2 | 102.3 |
| | 2d | 74.0 (α), 74.4 (β) | 74.2 |
| | 3d | 76.0 | 76.0 |
| | 4d | 79.8 | 79.5 |
| | 5d | 73.9 | 73.9 |
| | 6d | 63.2 | 63.1 |
| e | 1e | 94.6 (α), 98.5 (β) | 102.1 |
| | 2e | 74.2 (α), 76.7 (β) | 74.0 (α), 74.4 (β) |
| | 3e | 75.9 (α), 78.9 (β) | 76.0 |
| | 4e | 79.6 (α), 79.4 (β) | 79.8 |
| | 5e | 72.6 (α), 77.2 (β) | 73.9 |
| | 6e | 63.4 (α), 63.4 (β) | 63.1 |
| f | 1f | | 94.6 (α), 98.5 (β) |
| | 2f | | 74.2 (α), 76.7 (β) |
| | 3f | | 76.0 (α), 78.9 (β) |
| | 4f | | 79.6 (α), 79.5 (β) |
| | 5f | | 72.6 (α), 77.2 (β) |
| | 6f | | 63.3 (α), 63.3 (β) |

Based on these results, the product X, formed from maltotetraose via the action of the α-isomaltosylglucosaccharide-forming enzyme, was revealed as a pentasaccharide, in which a glucose residue is linked via the α-linkage to OH-6 of the glucose positioning at the non-reducing end of maltotetraose, i.e., α-isomaltosylmaltotriose alias $6^6$-O-α-glucosylmaltotetraose, represented by Formula 1.

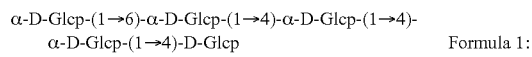

Formula 1:

The product Y formed from maltopentaose was revealed as a hexasaccharide, in which a glucosyl residue is linked via the α-linkage to OH-6 of the glucose at the non-reducing end of maltopentaose, i.e., α-isomaltosylmaltotetraose alias $6^5$-O-α-glucosylmaltopentaose, represented by Formula 2.

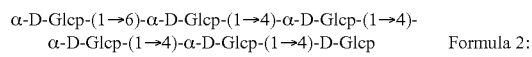

Formula 2:

Based on these results, it was concluded that α-isomaltosylglucosaccharide-forming enzyme acts on maltooligosaccharides as indicated below:

(1) The enzyme acts on as a substrate maltooligosaccharides having a glucose polymerization degree of at least two linked via the α-1,4 linkage, and catalyzes the intermolecular 6-glucosyl-transferring reaction in such a manner of transferring a glucosyl residue at the non-reducing end of a maltooligosaccharide molecule to C-6 of the non-reducing end of other maltooligosaccharide molecule to form both an α-isomaltosylglucosaccharide alias 6-O-α-glucosylmaltooligosaccharide, having a 6-O-α-glucosyl residue and an increased glucose polymerization degree by one as compared with the intact substrate, and a maltooligosaccharide with a reduced glucose polymerization degree by one as compared with the intact substrate molecule; and (2) The enzyme slightly catalyzes the 4-glucosyl-transferring reaction and forms both a maltooligosaccharide molecule, having an increased glucose polymerization degree by one as compared with the intact substrate, and a maltooligosaccharide having a reduced glucose polymerization degree by one as compared with the intact substrate molecule.

EXPERIMENT 22

Test on Reducing-power Formation

The following test was carried out to study whether α-isomaltosylglucosaccharide-formation enzyme had the ability of forming a reducing power. To a 1% (w/v) aqueous solution of maltotetraose as a substrate was added 0.25 unit/g substrate, d.s.b., of either of purified specimens of α-isomaltosylglucosaccharide-forming enzyme from *Bacillus globisporus* C9 strain obtained by the method in Experiment 4-2, *Bacillus globisporus* C11 strain obtained by the method in Experiment 7-2, *Bacillus globisporus* N75 strain obtained by the method in Experiment 11-2, or *Arthrobacter globiformis* A19 strain obtained by the method in Experiment 15-2, and incubated at 35° C. and pH 6.0, except that pH 8.4 was used for the enzyme from *Arthrobacter globiformis* A19 strain. During the enzymatic reaction, a portion of each reaction solution was sampled at prescribed time intervals and measured for reducing powder after keeping the sampled solutions at 100° C. for 10 min to suspend the enzymatic reaction. Before and after the enzymatic reaction, the reducing saccharide content and the total sugar content were respectively quantified by the Somogyi-Nelson's method and the anthrone-sulfuric acid reaction method. The percentage of forming reducing power was calculated by the following equation:

Equation:

$$\text{Percentage of forming reducing power (\%)} = \left(\frac{AR}{AT} - \frac{BR}{BT}\right) \times 100$$

AR: Reducing sugar content after enzymatic reaction.
AT: Total sugar content after enzymatic reaction.
BR: Reducing sugar content before enzymatic reaction.
BT: Total sugar content before enzymatic reaction.

The results are in Table 26.

TABLE 26

| Reaction time (hour) | Percentage of forming reducing power (%) | | | |
| --- | --- | --- | --- | --- |
| | Enzyme of C9 strain | Enzyme of C11 strain | Enzyme of N75 strain | Enzyme of A19 strain |
| 0 | 0.0 | 0.0 | 0.0 | 0.0 |
| 1 | 0.0 | 0.1 | 0.1 | 0.0 |
| 2 | 0.1 | 0.0 | 0.0 | 0.1 |
| 4 | 0.1 | 0.1 | 0.0 | 0.0 |
| 8 | 0.0 | 0.0 | 0.1 | 0.1 |

As evident from the results in Table 26, it was revealed that α-isomaltosylglucosaccharide-forming enzyme did not substantially increase the reducing power of the reaction product when acted on maltotetraose as a substrate; the enzyme did not have any hydrolyzing activity or had only an undetectable level of such activity.

EXPERIMENT 23

Test on Dextran Formation

To examine whether α-isomaltosylglucosaccharide-formation enzyme has the ability of forming dextran, it was tested in accordance with the method in *Bioscience Biotechnology and Biochemistry*, Vol. 56, pp. 169-173 (1992). To a 1% (w/v) aqueous solution of maltotetraose as a substrate was added 0.25 unit/g substrate, d.s.b., of either of purified specimens of α-isomaltosylglucosaccharide-forming enzyme from *Bacillus globisporus* C9 strain obtained by the method in Experiment 4-2, *Bacillus globisporus* C11 strain obtained by the method in Experiment 7-2, *Bacillus globisporus* N75 strain obtained by the method in Experiment 11-2, or *Arthrobacter globiformis* A19 strain obtained by the method in Experiment 15-2, and incubated at 35° C. and pH 6.0, except that pH 8.4 was used for the enzyme from *Arthrobacter globiformis* A19 strain, for four or eight hours. After completion of the enzymatic reaction, the reaction was suspended by heating at 100° C. for 15 min. Fifty microliters of each of the reaction mixtures were placed in a centrifugation tube and then admixed and sufficiently stirred with 3-fold volumes of ethanol, followed by standing at 4° C. for 30 min. Thereafter, each mixture solution was centrifuged at 15,000 rpm for five minutes and, after removing supernatant, the resulting sediment was admixed with one milliliter of 75% ethanol solution and stirred for washing. The resulting each solution was centrifuged to remove supernatant, dried in vacuo, and then admixed and sufficiently stirred with one milliliter of deionized water. The total sugar content, in terms of glucose, of each of the resulting solutions was quantified by the phenol-sulfuric acid method. As a control, the total sugar content was determined similarly as in the above except for using either of purified specimens of α-isomaltosylglucosaccharide-forming enzyme from *Bacillus globisporus* C9 strain, *Bacillus globisporus* C11 strain, *Bacillus globisporus* N75 strain, and *Arthrobacter globiformis* A19 strain, which had been inactivated at 100° C. for 10 min. The content of dextran formed was calculated by the following equation.

Content of dextran formed (mg/ml)=[(Total sugar content for test sample)]−[(Total sugar content for control sample)]×20        Equation The results are in Table 27.

TABLE 27

| Reaction time (hour) | Content of dextran formed (mg/ml) | | | |
|---|---|---|---|---|
| | Enzyme of C9 strain | Enzyme of C11 strain | Enzyme of N75 strain | Enzyme of A19 strain |
| 4 | 0.0 | 0.0 | 0.0 | 0.0 |
| 8 | 0.0 | 0.0 | 0.0 | 0.0 |

As evident from the results in Table 27, it was revealed that α-isomaltosylglucosaccharide-forming enzyme did not substantially have the action of forming dextran or had only an undetectable level of such activity because it did not form dextran when acted on maltotetraose.

EXPERIMENT 24

Transfer-acceptor Specificity

Using various saccharides, it was tested whether the saccharides were used as transferring-acceptors for α-isomaltosylglucosaccharide-forming enzyme. A solution of D-glucose, D-xylose, L-xylose, D-galactose, D-fructose, D-mannose, D-arabinose, D-fucose, D-psicose, L-sorbose, L-rhamnose, methyl-α-glucopyranoside, methyl-β-glucopyranoside, N-acetyl-glucosamine, sorbitol, α,α-trehalose, isomaltose, isomaltotriose, cellobiose, gentibiose, glycerol, maltitol, lactose, sucrose, α-cyclodextrin, β-cyclodextrin, γ-cyclodextrin, or L-ascorbic acid was prepared. To each solution with a saccharide concentration of 1.6% was added "PINE-DEX #100", a partial starch hydrolyzate, as a saccharide donor, to give a concentration of 4%, and admixed with one unit/g saccharide donor, d.s.b., of either of purified specimens of α-isomaltosylglucosaccharide-forming enzyme from *Bacillus globisporus* C9 strain obtained by the method in Experiment 4-2, *Bacillus globisporus* C11 strain obtained by the method in Experiment 7-2, *Bacillus globisporus* N75 strain obtained by the method in Experiment 11-2, or *Arthrobacter globiformis* A19 strain obtained by the method in Experiment 15-2, and incubated at 30° C. and pH 6.0 for 24 hours, except that pH 8.4 was used for the enzyme from *Arthrobacter globiformis* A19 strain. The reaction mixtures of the post-enzymatic reactions were analyzed on gas chromatography (abbreviated as "GLC" hereinafter) for monosaccharides and disaccharides as acceptors, and on HPLC for trisaccharides as acceptors to confirm whether these saccharides could be used as the transfer acceptors of the above enzymes. In the case of performing GLC, the following apparatuses and conditions were used: GLC apparatus, "GC-16A" commercialized by Shimadzu Corporation, Tokyo, Japan; column, a stainless-steel column, 3 mm in diameter and 2 m in length, packed with 2% "SILICONE OV-17/CHROMOSOLV W", commercialized by GL Sciences Inc., Tokyo, Japan; carrier gas, nitrogen gas at a flow rate of 40 ml/min under temperature conditions of increasing from 160° C. to 320° C. at an increasing temperature rate of 7.5° C./min; and detection, a hydrogen flame ionization detector. In the case of performing HPLC analysis, the following apparatuses and conditions were used: HPLC apparatus, "CCPD" commercialized by Tosoh Corporation, Tokyo, Japan; column, "ODS-AQ-303" commercialized by YMC Co., Ltd., Tokyo, Japan; eluent, water at a flow rate of 0.5 ml/min; and detection, a differential refractometer. The results are in Table 28.

TABLE 28

| | Product of transferring reaction | | | |
|---|---|---|---|---|
| Saccharide | Enzyme of C9 strain | Enzyme of C11 strain | Enzyme of N75 strain | Enzyme of A19 strain |
| D-Glucose | + | + | + | + |
| D-Xylose | ++ | ++ | ++ | + |
| L-Xylose | ++ | ++ | ++ | + |
| D-Galactose | + | + | + | ± |
| D-Fructose | + | + | + | + |
| D-Mannose | − | − | − | ± |
| D-Arabinose | ± | ± | ± | ± |
| D-Fucose | + | + | + | ± |
| D-Psicose | + | + | + | + |
| L-Sorbose | + | + | + | + |
| L-Rhamnose | − | − | − | − |
| Methyl-α-glucopyranoside | ++ | ++ | ++ | ++ |
| Methyl-β-glucopyranoside | ++ | ++ | ++ | ++ |
| N-Acetylglucosamine | + | + | + | − |
| Sorbitol | − | − | − | − |
| Trehalose | ++ | ++ | ++ | ++ |
| Isomaltose | ++ | ++ | ++ | + |
| Isomaltotriose | ++ | ++ | ++ | ± |
| Cellobiose | ++ | ++ | ++ | ++ |
| Gentibiose | ++ | ++ | ++ | + |
| Glycerol | + | + | + | + |
| Maltitol | ++ | ++ | ++ | ++ |
| Lactose | ++ | ++ | ++ | ++ |
| Sucrose | ++ | ++ | ++ | ++ |
| α-Cyclodextrin | − | − | − | − |
| β-Cyclodextrin | − | − | − | − |
| γ-Cyclodextrin | − | − | − | − |
| L-Ascorbic acid | + | + | + | + |

Note:
In the table, the symbols "−", "±", "+", and "++" mean that no saccharide-transferred product was detected through transfer reaction to acceptor; a saccharide-transferred product was detected in an amount less than one percent through transfer reaction to acceptor; a saccharide-transferred product was detected in an amount over one percent but less than 10% through transfer reaction to acceptor; and a saccharide-transferred product was detected in an amount over ten percent through transfer reaction to acceptor.

As evident from the results in Table 28, it was revealed that α-isomaltosylglucosaccharide-forming enzymes utilizes different types of saccharides as transfer acceptors; the α-isomaltosylglucosaccharide-forming enzymes from C9, C11 and N75 strains advantageously transfer a saccharide(s), particularly, to D-/L-xylose, methyl-α-glucopyranoside, methyl-β-glucopyranoside, α,α-trehalose, isomaltose, isomaltotriose, cellobiose, gentibiose, maltitol, lactose, and sucrose; then transfer to D-glucose, D-fructose, D-fucose, D-psicose, L-sorbose, N-acetylglucosamine, glycerol, and L-ascorbic acid; and further to D-arabinose. Particularly, the α-isomaltosylglucosaccharide-forming enzyme from A19 strain well transfers a saccharide(s), specifically, to methyl-α-glucopyranoside, methyl-β-glucopyranoside, α,α-trehalose, cellobiose, maltitol, lactose, and sucrose; secondary transfers to D-glucose, D-/L-xylose, D-fructose, D-psicose, L-sorbose, isomaltose, gentibiose, glycerol, and L-ascorbic acid; and thirdly to D-galactose, D-mannose, D-arabinose, D-fucose, and isomaltotriose.

The properties of α-isomaltosylglucosaccharide-transferring enzyme as described above were compared with those of a previously reported enzyme having 6-glucosyl-transferring action; a dextrin dextranase disclosed in "*Bioscience Biotechnology and Biochemistry*", Vol. 56, pp. 169-173 (1992); and a transglucosidase disclosed in "*Nippon Nogeikagaku Kaishi*", Vol. 37, pp. 668-672 (1963). The results are in Table 29.

TABLE 29

| Property | α-Isomaltosyl-glucosaccharide-forming enzyme of the present invention | | | | Dextrin dextranase Control | Transglucosidase Control |
| --- | --- | --- | --- | --- | --- | --- |
| | C9 strain | C11 strain | N75 strain | A19 strain | | |
| Hydrolysis activity | Negative | Negative | Negative | Negative | Negative | Positive |
| Optimum pH | 6.0-6.5 | 6.0 | 6.0 | 8.4 | 4.0 to 4.2 | 3.5 |
| Inhibition by EDTA | Positive | Positive | Positive | Positive | Negative | Negative |

As evident from Table 29, α-isomaltosylglucosaccharide-forming enzyme had outstandingly novel physicochemical properties completely different from those of conventionally known dextrin dextranase and transglucosidase.

EXPERIMENT 25

Formation of Cyclotetrasaccharide

The test on the formation of cyclotetrasaccharide by α-isomaltosylglucosaccharide-forming enzyme and α-isomaltosyl-transferring enzyme was conducted using saccharides. For the test, it was prepared a solution of maltose, maltotriose, maltotetraose, maltopentaose, amylose, soluble starch, "PINE-DEX #100" (a partial starch hydrolyzate commercialized by Matsutani Chemical Ind., Tokyo, Japan), or glycogen from oyster commercialized by Wako Pure Chemical Industries Ltd., Tokyo, Japan.

To each of these solutions with a concentration of 0.5%, one unit/g solid, d.s.b., of a purified specimen of α-isomaltosylglucosaccharide-forming enzyme from C11 strain obtained by the method in Experiment 7-2 and 10 units/g solid, d.s.b., of a purified specimen of α-isomaltosyl-transferring enzyme from C11 strain obtained by the method in Experiment 7-3, and the resulting mixture was subjected to an enzymatic reaction at 30° C. and pH 6.0. The enzymatic conditions were the following four systems:

(1) After the α-isomaltosylglucosaccharide-forming enzyme was allowed to act on a saccharide solution for 24 hours, the enzyme was inactivated by heating, and then the α-isomaltosyl-transferring enzyme was allowed to act on the resulting mixture for 24 hours and then inactivated by heating;

(2) After the α-isomaltosylglucosaccharide-forming enzyme and the α-isomaltosyl-transferring enzyme were simultaneously allowed to act on a saccharide solution for 24 hours, the enzymes were inactivated by heating;

(3) After only the α-isomaltosylglucosaccharide-forming enzyme was allowed to act on a saccharide solution for 24 hours, the enzyme was inactivated by heating; and (4) After only the α-isomaltosyl-transferring enzyme was allowed to act on a saccharide solution for 24 hours, the enzyme was inactivated by heating.

To determine the formation level of cyclotetrasaccharide in each reaction mixture after the inactivation of enzyme(s) by heating, the reaction mixture was treated with α-glucosidase and glucoamylase similarly as in Experiment 1 to hydrolyze the remaining reducing oligosaccharides, followed by the quantitation of cyclotetrasaccharide on HPLC. The results are in Table 30.

TABLE 30

| | Yield of cyclotetrasaccharide (%) | | | |
| --- | --- | --- | --- | --- |
| Substrate | A | B | C | D |
| Maltose | 4.0 | 4.2 | 0.0 | 0.0 |
| Maltotriose | 10.2 | 12.4 | 0.0 | 0.0 |
| Maltotetraose | 11.3 | 21.5 | 0.0 | 0.0 |
| Maltopentaose | 10.5 | 37.8 | 0.0 | 0.0 |
| Amylose | 3.5 | 31.6 | 0.0 | 0.0 |
| Soluble starch | 5.1 | 38.2 | 0.0 | 0.0 |
| Partial starch hydrolyzate | 6.8 | 63.7 | 0.0 | 0.0 |
| Glycogen | 10.2 | 86.9 | 0.0 | 0.0 |

Note:
The symbols "A", "B", "C" and "D" mean that α-isomaltosylglucosaccharide-forming enzyme was first allowed to act on a substrate and then α-isomaltosyl-transferring enzyme was allowed acted on the substrate, the α-isomaltosylglucosaccharide-forming enzyme and α-isomaltosyl-transferring enzyme were allowed to coact on a substrate, only α-isomaltosylglucosaccharide-forming enzyme was allowed to act on a substrate, and only α-isomaltosyl-transferring enzyme was allowed to act on a substrate.

As evident from the results in Table 30, no cyclotetrasaccharide was formed from any of the saccharides tested by the single action of either α-isomaltosylglucosaccharide-forming enzyme or α-isomaltosyl-transferring enzyme, but cyclotetrasaccharide was formed by the coaction of these enzymes. It was revealed that the formation level of cyclotetrasaccharide was relatively low, i.e., about 11% or lower, when α-isomaltosyl-transferring enzyme was allowed to act on the saccharides after the action of α-isomaltosylglucosaccharide-forming enzyme, while the formation level was increased when the enzymes were allowed to coact on any of the saccharides tested, particularly, it was increased to about 87% and about 64% when the enzymes were allowed to coact on glycogen and partial starch hydrolyzate, respectively.

Based on the reaction properties of α-isomaltosylglucosaccharide-forming enzyme and α-isomaltosyl-transferring enzyme, the formation mechanism of cyclotetrasaccharide by the coaction of these enzymes is estimated as follows:

(1) α-Isomaltosylglucosaccharide-forming enzyme acts on a glucose residue at the non-reducing end of an α-1,4 glucan chain of glycogen and partial starch hydrolyzates, etc., and intermolecularly transfers the glucose residue to OH-6 of the glucose residue at the non-reducing end of other α-1,4 glucan chain of glycogen and partial starch hydrolyzates, etc., to form an α-1,4 glucan chain having an α-isomaltosyl residue at the non-reducing end;

(2) α-Isomaltosyl-transferring enzyme acts on the α-1,4 glucan chain having an α-isomaltosyl residue at the non-reducing end and intermolecularly transfers the isomaltosyl residue to C-3 of a glucose residue at the non-reducing end of other α-1,4 glucan chain having an isomaltosyl residue at the non-reducing end to form an α-1,4 glucan chain having an isomaltosyl-1,3-isomaltosyl residue at the non-reducing end;

(3) Then, α-isomaltosyl-transferring enzyme acts on the α-1,4 glucan chain having an isomaltosyl-1,3-isomaltosyl residue at the non-reducing end and releases the isomaltosyl-1,3-isomaltosyl residue from the α-1,4 glucan chain via the intramolecular transferring reaction to cyclize the released isomaltosyl-1,3-isomaltosyl residue into cyclotetrasaccharide;

(4) From the released α-1,4 glucan chain, cyclotetrasaccharide is successively formed through the sequential steps (1) to (3). Thus, it is estimated that the coaction of α-isomaltosylglucosaccharide-forming enzyme and α-isomaltosyl-transferring enzyme increases the formation of cyclotetrasaccharide in such a cyclic manner as indicated above.

EXPERIMENT 26

Influence of Liquefaction Degree of Starch

A 15% corn starch suspension was prepared, admixed with 0.1% calcium carbonate, adjusted to pH 6.0, and then mixed with 0.2 to 2.0% per gram starch of "TERMAMYL 60L™", an α-amylase specimen commercialized by Novo Indutri A/S, Copenhagen, Denmark, followed by an enzymatic reaction at 95° C. for 10 min. Thereafter, the reaction mixture was autoclaved at 120° C. for 20 min, promptly cooled to about 35° C. to obtain a liquefied starch solution with a DE (dextrose equivalent) of 3.2 to 20.5. To the liquefied starch solution were added two units/g solid, d.s.b., of a purified specimen of α-isomaltosylglucosaccharide-forming enzyme from C11 strain obtained by the method in Experiment 7-2, and 20 units/g solid, d.s.b., of a purified specimen of α-isomaltosyl-transferring enzyme from C11 strain obtained by the method in Experiment 7-3, followed by an incubation at 35° C. for 24 hours. After completion of the reaction, the reaction mixture was heated at 100° C. for 15 min to inactivate the remaining enzymes. Then, the reaction mixture thus obtained was treated with α-glucosidase and glucoamylase similarly as in Experiment 1 to hydrolyze the remaining reducing oligosaccharides, followed by quantifying the formed cyclotetrasaccharide on HPLC. The results are in Tale 31.

TABLE 31

| Amount of α-amylase per starch (%) | DE | Yield of cyclotetrasaccharide (%) |
|---|---|---|
| 0.2 | 3.2 | 54.5 |
| 0.4 | 4.8 | 50.5 |
| 0.6 | 7.8 | 44.1 |
| 1.0 | 12.5 | 39.8 |
| 1.5 | 17.3 | 34.4 |
| 2.0 | 20.5 | 30.8 |

As evident from the results in Table 31, it was revealed that the formation of cyclotetrasaccharide by the coaction of α-isomaltosylglucosaccharide-forming enzyme and α-isomaltosyl-transferring enzyme is influenced by the liquefaction degree of starch, i.e., the lower the liquefaction degree or the lower the DE, the more the yield of cyclotetrasaccharide from starch increases. On the contrary, the higher the liquefaction degree or the higher the DE, the lower the yield of cyclotetrasaccharide from starch decreases. It was revealed that a suitable liquefaction degree is a DE of about 20 or lower, preferably, a DE of about 12 or lower, more preferably, a DE of about five or lower.

EXPERIMENT 27

Influence of the Concentration of Partial Starch Hydrolyzate

Aqueous solutions of "PINE-DEX #100", a partial starch hydrolyzate with a DE of about two to about five, having a final concentration of 0.5 to 40%, were prepared and respectively admixed with one unit/g solid, d.s.b., of the purified specimen of α-isomaltosylglucosaccharide-forming enzyme from C11 strain obtained by the method in Experiment 7-2 and 10 units/g solid, d.s.b., of a purified specimen of α-isomaltosyl-transferring enzyme from C11 strain obtained by the method in Experiment 7-3, followed by the coaction of these enzymes at 30° C. and pH 6.0 for 48 hours. After completion of the enzymatic reaction, the reaction mixture was heated at 100° C. for 15 min to inactivate the remaining enzymes, and then treated with α-glucosidase and glucoamylase similarly as in Experiment 1 to hydrolyze the remaining reducing oligosaccharides, followed by quantifying the formed cyclotetrasaccharide on HPLC. The results are in Table 32.

TABLE 32

| Concentration of PINE-DEX (%) | Yield of cyclotetrasaccharide (%) |
|---|---|
| 0.5 | 63.6 |
| 2.5 | 62.0 |
| 5 | 60.4 |
| 10 | 57.3 |
| 15 | 54.6 |
| 20 | 51.3 |
| 30 | 45.9 |
| 40 | 35.9 |

As evident from the results in Table 32, the yield of cyclotetrasaccharide was about 64% at a low concentration of 0.5%, while it was about 40% at a high concentration of 40%. The fact indicates that the yield of cyclotetrasaccharide increases depending on the concentration of partial starch hydrolyzate as a substrate. The result revealed that the yield of cyclotetrasaccharide increased as the decrease of concentration of partial starch hydrolyzate.

EXPERIMENT 28

Influence of the Addition of Cyclodextrin Glucanotransferase

A 15% aqueous solution of "PINE-DEX #100", a partial starch hydrolyzate, was prepared and admixed with one unit/g solid, d.s.b., of the purified specimen of α-isomaltosylglucosaccharide-forming enzyme from C11 strain obtained by the method in Experiment 7-2, 10 units/g solid, d.s.b., of a purified specimen of α-isomaltosyl-transferring enzyme from C11 strain obtained by the method in Experiment 7-3, and 0 to 0.5 unit/g solid, d.s.b., of CGTase from a microorganism of the species *Bacillus stearothermophilus*, followed by the coaction of these enzymes at 30° C. and pH 6.0 for 48 hours. After completion of the reaction, the reaction mixture was heated at 100° C. for 15 min to inactivate the remaining enzymes, and then treated with α-glucosidase and glucoamylase similarly as in Experiment 1 to hydrolyze the remaining reducing oligosaccharides, followed by quantifying the formed cyclotetrasaccharide on HPLC. The results are in Table 33.

TABLE 33

| Amount of CGTase added (unit) | Yield of cyclotetrasaccharide (%) |
|---|---|
| 0 | 54.6 |
| 2.5 | 60.1 |
| 5 | 63.1 |
| 10 | 65.2 |

As evident from the Table 33, it was revealed that the addition of CGTase increased the yield of cyclotetrasaccharide.

EXPERIMENT 29

Preparation of Isomaltose-releasing Enzyme

A liquid medium, consisting of 3.0% (w/v) of dextran, 0.7% (w/v) of peptone, 0.2% (w/v) of dipotassium phosphate, 0.05% (w/v) of magnesium sulfate heptahydrate, and water, was placed in 500-ml Erlenmeyer flasks in a volume of 100 ml each, autoclaved at 121° C. for 20 minutes for sterilization, cooled, inoculated with a stock culture of *Arthrobacter globiformis* T6 strain (IAM 12103), and incubated at 27° C. for 48 hours under rotary shaking conditions of 230 rpm to obtain a seed culture. About 20 L of a fresh preparation of the same nutrient culture medium as used in the above culture were placed in a 30-L fermentor, sterilized by heating, cooled to 27° C., inoculated with 1% (v/v) of the seed culture, and further incubated for about 72 hours while stirring under aeration-agitation conditions at 27° C. and pH 6.0 to 8.0. After completion of the culture, the resultant culture, having about 16.5 units/ml of isomaltodextranase activity, was centrifuged at 10,000 rpm for 30 min to obtain about 18 L of a supernatant, having about 16 units/ml of the enzyme, in a total enzyme activity of about 288,000 units. The activity of isomaltodextranase was assayed by providing, as a substrate solution, four milliliters of 1.25% (w/v) of an aqueous dextran solution in the form of 0.1M acetate buffer (pH 5.5), adding one milliliter of an enzyme solution, subjecting the mixture to an enzymatic reaction at 40° C. for 20 min, sampling one milliliter of the reaction mixture, adding two milliliters of the Somogyi copper solution to suspend the enzymatic reaction, and quantifying the reducing power of the formed isomaltose by the Somogyi-Nelson's method. One unit activity of isomaltodextranase is defined as the enzyme amount that forms a reducing power corresponding to one micromole of isomaltose per minute. About 18 L of the culture supernatant were concentrated with a UF membrane into about two liters, salted out in an 80% ammonium sulfate solution, and allowed to stand at 4° C. for 24 hours. The resulting precipitate was collected by centrifugation at 10,000 rpm for 30 min, dissolved in 5 mM phosphate buffer (pH 6.8), and dialyzed against a fresh preparation of the same buffer as used in the above to obtain about 400 ml of a dialyzed solution. The solution as a crude enzyme solution thus obtained was fed to ion-exchange chromatography using two liters of "SEPABEADS FP-DA13" gel. The component with isomaltodextranase activity did not adsorb on the gel and it was eluted in non-adsorbed fractions. The non-adsorbed fractions with the desired enzyme activity were collected, pooled, salted out in an 80% ammonium sulfate solution, and allowed to stand at 4° C. for 24 hours. The resulting precipitate was collected by centrifugation at 10,000 rpm for 30 min, dissolved in 5 mM phosphate buffer (pH 6.8), and dialyzed against a fresh preparation of the same buffer as used in the above to obtain about 500 ml of a dialyzed solution having an isomaltodextranase activity of 161,000 units.

EXPERIMENT 30

Preparation of Isomaltose from α-isomaltosylglucosaccharide and Cyclotetrasaccharide To a 0.2% aqueous solution of panose, α-isomaltosylmaltose, α-isomaltosyltriose, α-isomaltosyltetraose, or cyclotetrasaccharide was added 100 units/g solid, d.s.b., of an isomaltodextranase specimen, obtained by the method in Experiment 29, where 3,000 units/g solid, d.s.b., of the specimen was also used for the aqueous solution with cyclotetrasaccharide. The mixture was subjected to an enzymatic reaction at 40° C. and pH 5.5 for 24 hours and heated at 100° C. for 20 min to suspend the enzymatic reaction. The saccharide composition of the resulting mixture was analyzed on HPLC using column of "MCIGEL CK04SS", a column commercialized by Mitsubishi Chemical Industries, Ltd., Tokyo, Japan; an inner column temperature of 80° C.; a flow rate of 0.5 ml/min of water as an eluate; and a detector of "RI-8012", a differential refractometer commercialized by Tosoh Corporation, Tokyo, Japan. The results are in Table 34.

TABLE 34

| Substrate | Enzyme (unit) | Saccharide as reaction product (peak area (%) on HPLC) | | | | | |
|---|---|---|---|---|---|---|---|
| | | G1 | IM | G2 | G3 | G4 | A |
| IMG1 | 100 | 35 | 65 | 0 | 0 | 0 | 0 |
| IMG2 | 100 | 0 | 51 | 49 | 0 | 0 | 0 |
| IMG3 | 100 | 0 | 41 | 0 | 59 | 0 | 0 |
| IMG4 | 100 | 0 | 35 | 0 | 0 | 65 | 0 |
| Cyclotetrasaccharide | 100 | 0 | 22 | 0 | 0 | 0 | 78 |
| | 3,000 | 0 | 100 | 0 | 0 | 0 | 0 |

Note:
In the table, the symbols "IMG1", "IMG2", "IMG3" and "IMG4" mean panose, α-isomaltosylmaltose, α-isomaltoglucotriose, and isomaltoglucotetraose, respectively.
The symbols "G1", "G2", "G3" and "G4" mean glucose, isomaltose, maltose, maltotriose, and maltotetraose, respectively.
The symbol "A" means an intermediate formed during the formation of isomaltose from cyclotetrasaccharide.

As evident from the results in Table 34, it was revealed that, when isomaltodextranase was allowed to act on α-isomaltosylglucosaccharides, only glucose and isomaltose were formed from panose as a substrate; only isomaltose and maltose were formed from α-isomaltosylmaltose as a substrate; only isomaltose and maltotriose were formed from α-isomaltosyltriose; and only isomaltose and maltotetraose were formed from α-isomaltosyltetraose as a substrate. It was also found that only isomaltose was formed via the product "A" from cyclotetrasaccharide as a substrate.

Then, the purification and isolation of the above-identified product A were conducted as follows: The product A was subjected to "YMC-PACK ODS-AR355-15S-15 12A", a separatory HPLC column commercialized by YMC Co., Ltd., Tokyo, Japan, for purifying and isolating. Thus, the product A with a purity of at least 98.2% was obtained in a yield of about 7.2% from the reaction product of cyclotetrasaccharide.

Figure 46:
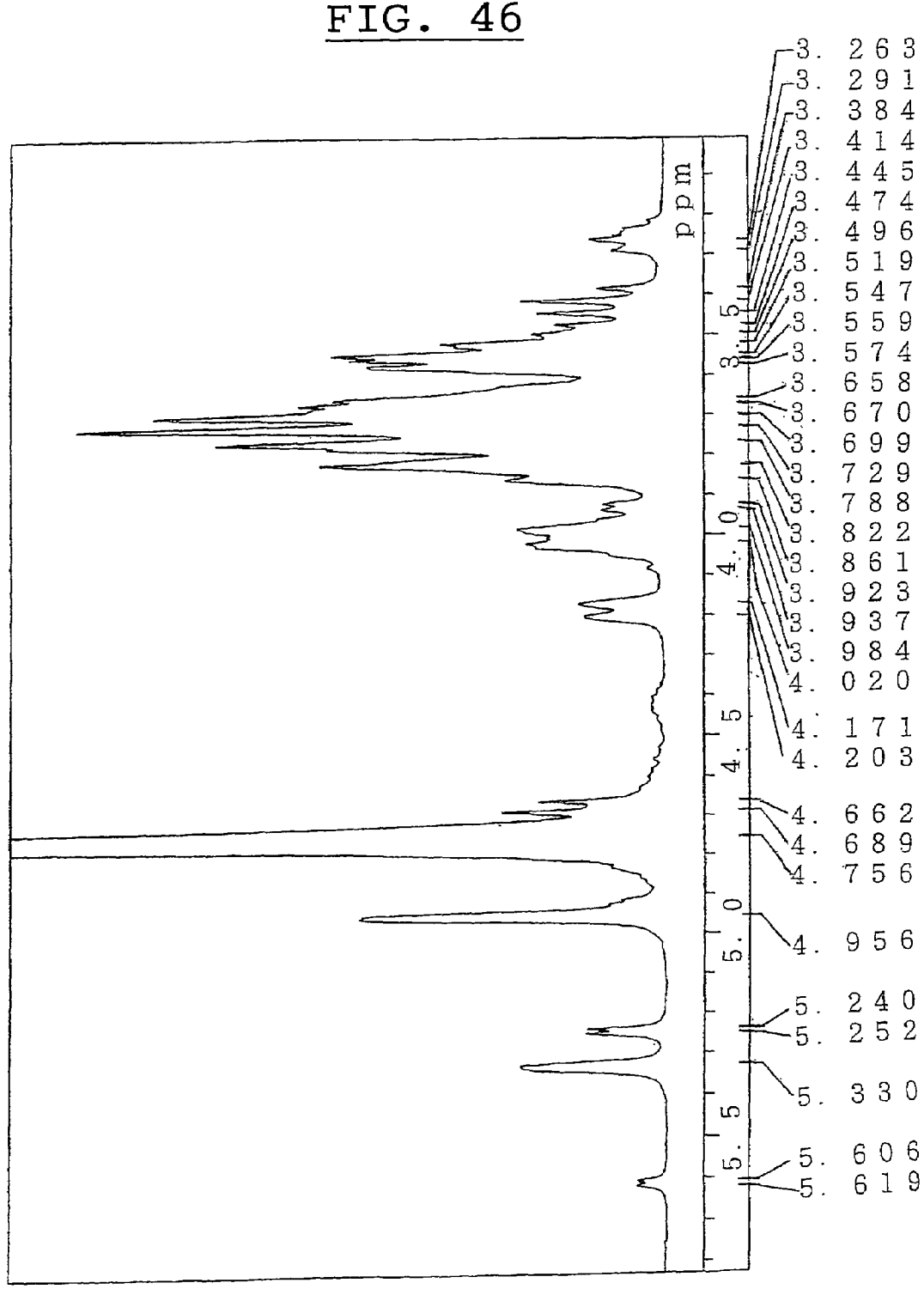
FIG. 46 is a spectrum of nuclear magnetic resonance ($^1$H-NMR) of product A.
Figure 47:
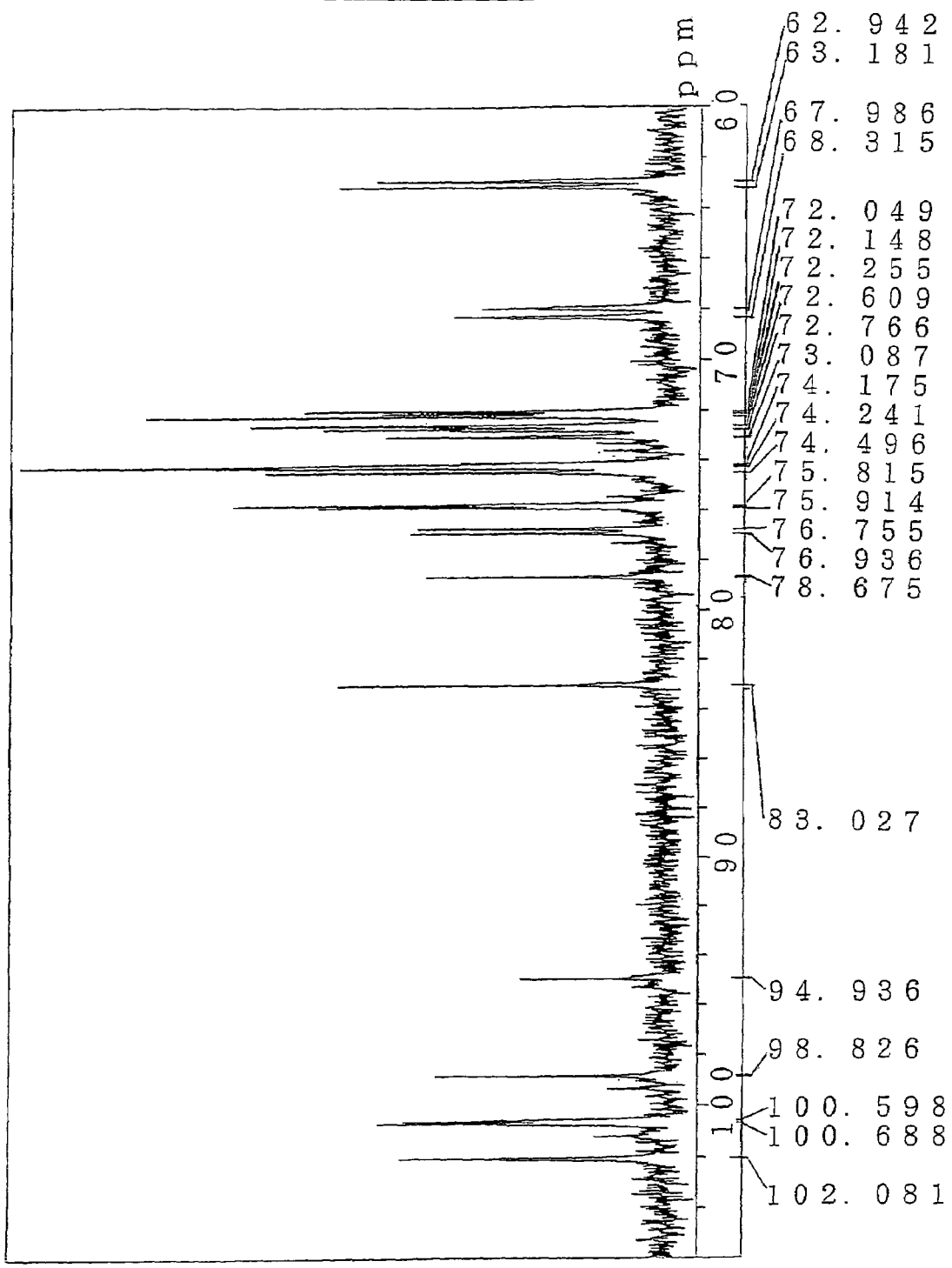
FIG. 47 is a spectrum of nuclear magnetic resonance ($^{13}$C-NMR) of product A.

The product A was subjected to methyl analysis and NMR analysis in a usual manner. The result on the methyl analysis is in Table 35. While the results on the NMR analyses are respectively in FIG. 46 for $^1$H-NMR spectrum and in FIG. 47 for $^{13}$C-NMR spectrum. The data on assignment of the product A is tabulated in Table 36.

TABLE 35

| Analyzed methyl compound | Composition ratio |
| --- | --- |
| 2,3,4-Trimethyl compound | 2.00 |
| 2,3,6-Trimethyl compound | 0.92 |
| 2,3,4,6-Tetramethyl compound | 0.88 |

TABLE 36

| Glucose No. | Carbon No. | NMR chemical shift (ppm) |
| --- | --- | --- |
| a | 1a | 100.7 |
|   | 2a | 74.2 |
|   | 3a | 75.8 |
|   | 4a | 72.3 |
|   | 5a | 74.5 |
|   | 6a | 63.2 |
| b | 1b | 102.1 |
|   | 2b | 74.3 |
|   | 3b | 75.9 |
|   | 4b | 72.6 |
|   | 5b | 74.2 |
|   | 6b | 68.0 |
| c | 1c | 100.6 |
|   | 2c | 72.8 |
|   | 3c | 83.0 |
|   | 4c | 72.0 |
|   | 5c | 73.1 |
|   | 6c | 62.9 |
| e | 1e | 94.9(α), 98.8(β) |
|   | 2e | 74.1(α), 76.6(β) |
|   | 3e | 75.8(α), 78.7(β) |
|   | 4e | 72.1(α), 72.1(β) |
|   | 5e | 72.6(α), 76.9(β) |
|   | 6e | 68.3(α), 68.3(β) |

From these results, the product A, formed as an intermediate during the formation of isomaltose from cyclotetrasaccharide by the action of isomaltodextranase, was revealed as a tetrasaccharide in the form of a ring-opened cyclotetrasaccharide, formed as a result of the hydrolysis of any one of the 1,3-linkages of cyclotetrasaccharide, represented by Formula 3, i.e., α-glucosyl-(1→6)-α-glucosyl-(1→3)-α-glucosyl-(1→6)-glucose (or ring-opened tetrasaccharide).

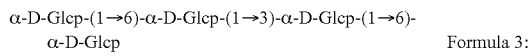

Formula 3:

Based on these results, it can be concluded that the mechanism of the action of isomaltodextranase on α-isomaltosylglucosaccharide is as follows:

Isomaltodextranase acts on an α-isomaltosylglucosaccharide, having a 6-O-α-glucosyl group at the non-reducing end, as a substrate, and specifically hydrolyzes the α-1,4 linkage between the isomaltosyl residue at the non-reducing end and the resting glucose or maltooligosaccharide residue to form isomaltose and glucose or a maltooligosaccharide. Then the enzyme also acts on cyclotetrasaccharide as a substrate and hydrolyzes the α-1,3 linkage for ring-opening to form ring-opened cyclotetrasaccharide as an intermediate, and further acts on the formed ring-opened cyclotetrasaccharide and hydrolyzes the α-1,3 linkage thereof to form isomaltose.

EXPERIMENT 31

Formation of Isomaltose from Different Substrates

Using different saccharides, the formation mechanism of the action of α-isomaltosylglucosaccharide-forming enzyme and isomaltodextranase was examined. Maltose, maltotriose, maltotetraose, maltopentaose, maltohexaose, maltoheptaose, amylose, or "PINE-DEX #100", a partial starch hydrolyzate commercialized by Matsutani Chemical Ind., Tokyo, Japan, was dissolved in water to give a final concentration of five percent. Also, calcium chloride was dissolved in water to give a final concentration of 1 mM. To each of the above aqueous solutions 0.2 unit/g solid, d.s.b., of the purified specimen of α-isomaltosylglucosaccharide-forming enzyme from C11 strain obtained in Experiment 7-2, and 100 units/g solid, d.s.b., of an isomaltodextranase specimen obtained by the method in Experiment 29, followed by an enzymatic reaction at 40° C. and pH 5.5. The reaction conditions used were the following two systems:

(1) After contacting the α-isomaltosylglucosaccharide-forming enzyme with any of the substrates for 65 hours, the enzyme was inactivated by heating, then the isomaltodextranase was allowed to act on the resulting mixture for 65 hours and inactivated by heating.

(2) After contacting the α-isomaltosylglucosaccharide-forming enzyme and the isomaltodextranase with any of the substrates in combination for 65 hours, the enzymes were inactivated by heating.

The resulting heated reaction mixtures were assayed for isomaltose yield on HPLC. The results are in Table 37:

TABLE 37

| | Yield of isomaltose (%) | |
| --- | --- | --- |
| Substrate | Sequential use* | Combination use** |
| Maltose | 6.6 | 7.0 |
| Maltotriose | 15.7 | 18.7 |
| Maltotetraose | 15.8 | 45.4 |
| Maltopentaose | 15.3 | 55.0 |
| Maltohexaose | 10.1 | 58.1 |
| Maltoheptaose | 8.5 | 63.6 |
| Amylose | 4.0 | 64.9 |
| Partial starch hydrolyzate | 3.8 | 62.7 |

Note:
The symbols "*" and "**" mean that α-isomaltosylglucosaccharide-forming enzyme and isomaltodextranase were allowed to act on a substrate in this order and in combination, respectively.

As evident from the results in Table 37, all of the saccharides tested formed isomaltose through the action of α-isomaltosylglucosaccharide-forming enzyme and isomaltodextranase. It was revealed that the sequential use of α-isomaltosylglucosaccharide-forming enzyme and isomaltodextranase in this order only gave a low yield of isomaltose as low as less than about 15%, while the combination use of the enzymes gave an improved yield of isomaltose, particularly, up to a high yield of 60% or higher of isomaltose when the enzymes were allowed to coact on maltoheptaose, amylose, or partial starch hydrolyzate. The isomaltose formation mechanism by the combination use of α-isomaltosylglucosaccharide-forming enzyme and isomaltodextranase is speculated as follows based on their enzymatic reaction properties:

(1) α-Isomaltosylglucosaccharide-forming enzyme acts on the glucose residue at the non-reducing end of an α-1,4 glucan chain such as of amylose and partial starch hydrolyzates, and intermolecularly transfers the glucose residue to the hydroxyl group at C-6 of the glucose residue at the non-reducing end of another α-1,4 glucan chain to form an α-1,4 glucan chain having an α-isomaltosyl group at the non-reducing end.

(2) Isomaltodextranase acts on the formed α-1,4 glucan chain, having an α-isomaltosyl group at the non-reducing end, and hydrolyzes the α-1,4 linkage between the isomaltosyl group and the resting α-1,4 glucan chain to form/release isomaltose and an α-1,4 glucan chain with a reduced glucose polymerization degree by two.

(3) The released α-1,4 glucan chain sequentially receives the enzymatic reactions of (1) and (2) and forms another isomaltose.

As explained above, it can be speculated that, when used in combination, α-Isomaltosylglucosaccharide-forming enzyme and isomaltodextranase repeatedly act on their substrates to form isomaltose and increase the yield.

EXPERIMENT 32

Effect of the Addition of Isoamylase

An aqueous solution of "PINE-DEX #100", a partial starch hydrolyzate, with a final concentration of five percent and 1 mM calcium chloride, was prepared, admixed with 0.2 unit/g starch, d.s.b., of the purified specimen of α-isomaltosylglucosaccharide-forming enzyme from C11 strain obtained in Experiment 7-2, 100 units/g starch, d.s.b., of an isomaltodextranase specimen obtained by the method in Experiment 29, and 0 to 250 units/g starch, d.s.b., of an isoamylase specimen of a microorganism of the species *Pseudomonas amyloderamosa* commercialized by Hayashibara Biochemical Laboratories, Inc., Okayama, Japan, followed by an enzymatic reaction at 40° C. and pH 5.5 for 65 hours. Thereafter, the resulting mixture was heated at 100° C. for 15 min to inactivate the remaining enzymes. The formed isomaltose was quantified by HPLC. The results are in Table 38.

TABLE 38

| Isoamylase added (unit) | Yield of isomaltose (%) |
|---|---|
| 0 | 62.7 |
| 50 | 65.1 |
| 250 | 71.1 |

As evident from the results in Table 38, it was revealed that the addition of isoamylase increases the yield of isomaltose.

EXPERIMENT 33

Influence of the Concentration of Partial Starch Hydrolyzate

Eight types of aqueous solutions, having different concentrations of "PINE-DEX #100", a partial starch hydrolyzate, with a DE of about two to about five, having a final concentration of 1 to 40%, and containing 1 mM calcium chloride, were prepared, admixed with 0.2 unit/g starch, d.s.b., of the purified specimen of α-isomaltosylglucosaccharide-forming enzyme from C11 strain obtained in Experiment 7-2, 100 units/g starch, d.s.b., of an isomaltodextranase specimen obtained by the method in Experiment 29, and 250 units/g starch, d.s.b., of an isoamylase specimen of a microorganism of the species *Pseudomonas amyloderamosa* commercialized by Hayashibara Biochemical Laboratories, Inc., Okayama, Japan, followed by an enzymatic reaction at 40° C. and pH 5.5 for 65 hours. Thereafter, the resulting mixture was heated at 100° C. for 15 min to inactivate the remaining enzymes. The formed isomaltose was quantified by HPLC. The results are in Table 39.

TABLE 39

| Concentration of "PINE DEX 100" (%) | Yield of isomaltose (%) |
|---|---|
| 1 | 73.0 |
| 2.5 | 72.8 |
| 5 | 71.1 |
| 10 | 67.0 |
| 15 | 63.7 |
| 20 | 60.7 |
| 30 | 55.4 |
| 40 | 50.7 |

As evident from the results in Table 39, it was revealed that the yield of isomaltose increased up to about 73% at a low concentration of one percent of partial starch hydrolyzate, but decreased to about 51% at a concentration of 40% of partial starch hydrolyzate, meaning that the yield of isomaltose varies depending on the concentration of partial starch hydrolyzate as a substrate.

EXPERIMENT 34

Influence of the Degree of Liquefied Starch

A 15% corn starch suspension was prepared, admixed with 0.1% calcium carbonate, adjusted to pH 6.0, and then mixed with 0.2 to 2.0% per gram starch of "TERMAMYL 60L™", an α-amylase specimen commercialized by Novo Indutri A/S, Copenhagen, Denmark, followed by an enzymatic reaction at 95° C. for 10 min. Thereafter, the reaction mixture was autoclaved at 120° C., promptly cooled to about 40° C. to obtain a liquefied starch solution with a DE of 3.2 to 20.5. The liquefied starch solution was adjusted to give a final starch concentration of 5% and to pH 5.5, and then mixed with 0.2 unit/g solid, d.s.b., of a purified specimen of α-isomaltosylglucosaccharide-forming enzyme from C11 strain obtained by the method in Experiment 7-2, 100 units/g solid, d.s.b., of a purified specimen of isomaltodextranase obtained by the method in Experiment 29, and 250 units/g solid, d.s.b., of an isoamylase specimen from *Pseudomonas amyloderamosa* commercialized by Hayashibara Biochemical laboratories, Inc., Okayama, Japan, followed by an incubation at 40° C. for 65 hours. After completion of the reaction, the reaction mixture was heated at 100° C. for 15 min to inactivate the remaining enzymes. The formed isomaltose was quantified by HPLC. The results are in Table 40.

TABLE 40

| Amount of α-amylase per g starch (%) | DE | Yield of isomaltose (%) |
|---|---|---|
| 0.2 | 3.2 | 71.5 |
| 0.4 | 4.8 | 71.0 |
| 0.6 | 7.8 | 66.2 |
| 1.0 | 12.5 | 59.8 |
| 1.5 | 17.3 | 53.2 |
| 2.0 | 20.5 | 47.9 |

As evident from the results in Table 40, it was revealed that the formation of isomaltose by the coaction of α-isomaltosylglucosaccharide-forming enzyme and isomaltodextranase is influenced by the liquefaction degree of starch, i.e., the lower the liquefaction degree or the lower the DE, the higher the yield of isomaltose from starch increases. On the contrary, the higher the liquefaction degree or the higher the DE, the lower the yield of isomaltose from starch decreases. It was revealed that a suitable liquefaction degree is a DE of about 20 or lower, preferably, a DE of about 12 or lower, more preferably, a DE of about five or lower.

EXPERIMENT 35

Effect of the Addition of CGTase and Glucoamylase

An aqueous solution, containing 20% of "PINE-DEX #100", a partial starch hydrolyzate, and 1 mM calcium chloride, was prepared, mixed with 0.2 unit/g solid, d.s.b., of a purified specimen of α-isomaltosylglucosaccharide-forming enzyme from C11 strain obtained by the method in Experiment 7-2, 100 units/g solid, d.s.b., of a purified specimen of isomaltodextranase obtained by the method in Experiment 29, and 0 to 0.5 unit/g solid, d.s.b., of a CGTase specimen from *Bacillus stearothermophilus* commercialized by Hayashibara Biochemical laboratories, Inc., Okayama, Japan, followed by incubating the mixture at 40° C. and pH 5.5 for 65 hours and heating the resulting mixture at 100° C. for 15 min to inactivate the remaining enzymes. To the mixture thus obtained was added 20 units/g starch, d.s.b., of "XL-4™", a glucoamylase specimen commercialized by Nagase Biochemicals, Ltd., Kyoto, Japan, incubated at 50° C. for 24 hours, and heated at 100° C. for 20 min to inactivate the remaining enzyme. The formed isomaltose was quantified on HPLC. The results are in Table 41.

TABLE 41

| Amount of CGTase added (unit/g solid, d.s.b.) | Yield of isomaltose (%) |
| --- | --- |
| 0 | 60.7 |
| 0.1 | 62.9 |
| 0.25 | 65.0 |
| 0.5 | 66.4 |

As evident from the results in Table 41, it was revealed that the addition of CGTase to the enzymatic reaction system of isomaltodextranase and α-isomaltosylglucosaccharide-forming enzyme increased the yield of isomaltose. In the above enzymatic reaction system, the glucoamylase was used to form isomaltose from saccharides, composed of isomaltose linked with one or more D-glucose residues, and to release the D-glucose residue(s) therefrom, resulting in an increased yield of isomaltose.

EXPERIMENT 36

Formation of Isomaltose

About one hundred liters of an aqueous solution of phytoglycogen from corn, commercialized by Q.P. Corporation, Tokyo, Japan, were adjusted to give a concentration of 4% (w/v) and pH 6.0, heated to 30° C., admixed with one unit/g solid, d.s.b., of a purified specimen of α-isomaltosylglucosaccharide-forming enzyme from C11 strain obtained by the method in Experiment 7-2, 10 units/g solid, d.s.b., of a purified specimen of α-isomaltosyl-transferring enzyme from C11 strain obtained by the method in Experiment 7-3, followed by incubating the mixture for 48 hours and heating the resulting mixture at 100° C. for 10 min to inactivate the remaining enzymes. The mixture thus obtained was sampled for quantifying the yield of cyclotetrasaccharide on HPLC, revealing that it had about 84% of cyclotetrasaccharide in terms of sugar composition, where HPLC was carried out using "SHOWDEX KS-801™ column", Showa Denko K.K., Tokyo, Japan, at a column temperature of 60° C. and a flow rate of 0.5 ml/min of water, and using "RI-8012™", a differential refractometer commercialized by Tosoh Corporation, Tokyo, Japan. The above mixture was adjusted to pH 5.0 and 45° C., admixed with 1,500 units/g starch, d.s.b. of "TRANSGLUCOSIDASE L AMANO™", an α-glucosidase commercialized by Amano Pharmaceutical Co., Ltd., Aichi, Japan, and 75 units/g starch, d.s.b., of "XL-4™", a glucoamylase specimen commercialized by Nagase Biochemicals, Ltd., Kyoto, Japan, incubated for 24 hours to hydrolyze the remaining reducing oligosaccharides, etc. The resulting mixture was adjusted to pH 5.8, kept at 90° C. for one hour to inactivate the remaining enzymes, and filtered to remove insoluble substances. The filtrate was concentrated to give a concentration of about 16% with "HOLLOSEP® HR 5155PI", a reverse osmotic membrane, Toyobo Co., Ltd., Tokyo, Japan, and in a usual manner decolored, desalted, filtered, and concentrated to obtain about 6.2 kg of a saccharide solution with a solid content of about 3,700 g, d.s.b. The saccharide solution was fed to a column packed with about 225 L of "AMBERLITE CR-1310 (Na+-form)", a strong-acid cation exchange resin commercialized by Japan Organo Co., Ltd., Tokyo, Japan, and chromatographed at a column temperature of 60° C. and a flow rate of about 45 L/h. While the saccharide composition of eluate from the column was monitoring by the above-identified HPLC, fractions of cyclotetrasaccharide with a purity of at least 98% were collected, and in a usual manner desalted, decolored, filtered, and concentrated to obtain about 7.5 kg of a saccharide solution with a solid content of about 2,500 g, d.s.b. HPLC analysis for saccharide composition of the solution thus obtained revealed that it contained cyclotetrasaccharide with a purity of about 99.5%. The resulting saccharide solution with cyclotetrasaccharide was concentrated into an about 50% solution by an evaporator, and about five kilograms of which were placed in a cylindrical plastic vessel, cooled from 65° C. to 20° C. over about 20 hours under gentle stirring conditions to crystallize cyclotetrasaccharide. Then, the resulting massecuite was centrifugally separated to collect 1,360 g of crystalline cyclotetrasaccharide by wet weight, and dried at 60° C. for three hours to obtain 1,170 g of a crystalline cyclotetrasaccharide powder. HPLC analysis for saccharide composition of the powder revealed that it had a purity of cyclotetrasaccharide crystal as high as at least about 99.9%.

The above crystalline cyclotetrasaccharide powder was dissolved in deionized water, adjusted to give a concentration of one percent, pH 5.5 and 50° C., admixed with 500 units/g solids, d.s.b., of an isomaltodextranase specimen prepared by the method in Experiment 29, and enzymatically reacted at pH 5.5 and 50° C. for 70 hours. Thereafter, the resulting mixture was heated to and kept at 95° C. for 10 min, cooled, and filtered. The filtrate was in a usual manner decolored with an activated charcoal, desalted for purification with ion-exchange resins in H- and OH-forms, and concentrated to give a concentration of about 50%. Thus, a high isomaltose content syrup was obtained in a yield of about 95%, d.s.b., to the solid contents. HPLC analysis for saccharide composition of the syrup revealed that it contained 96.1% of isomaltose, 2.8% of ring-opened tetrasaccharide, and 1.1% of other saccharides.

Four hundred grams of the above syrup were in a usual manner placed in an autoclave with 0.1 g/solids, d.s.b., of "N154™", an alkaline-developed Raney nickel catalyst commercialized by Nikki Chemical Co., Ltd., Yokohama, Japan, stirred at 100° C. for four hours while keeping the inner hydrogen pressure at 100 kg/cm$^2$, and stirred at 120° C. for another two hours to effect hydrogenation. After standing to cool, the hydrogenated products were collected from the autoclave and passed through an activated charcoal layer about 1-cm thick to remove the Raney nickel catalyst. The filtrate was in a usual manner desalted, purified, and concentrated to give a concentration of about 73%. The concentrate was placed in a cylindrical plastic vessel, admixed with 0.1% to the solids, d.s.b., of a crystalline isomaltitol powder as a seed, cooled to 35° C. over about 20 hours under gentle stirring conditions to crystallize isomaltitol. Then, the resulting mixture was separated by a centrifuge to collect isomaltitol crystal, and dried in vacuo at 80° C. for 20 hours to obtain about 168 g of isomaltitol crystal.

Figure 48:
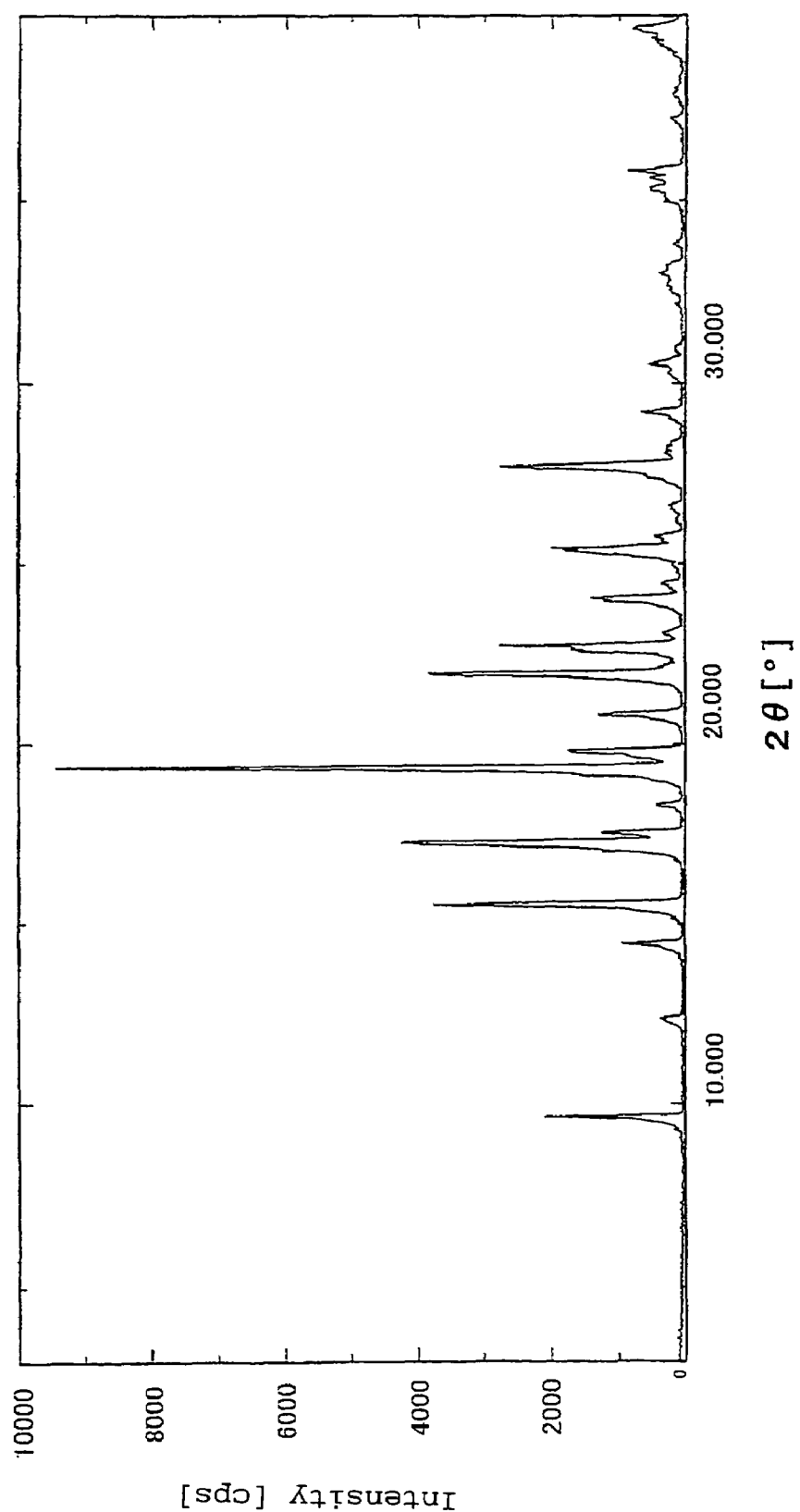
FIG. 48 is an x-ray powder diffraction pattern of isomaltitol crystal obtained by the method of the present invention.
Figure 49:
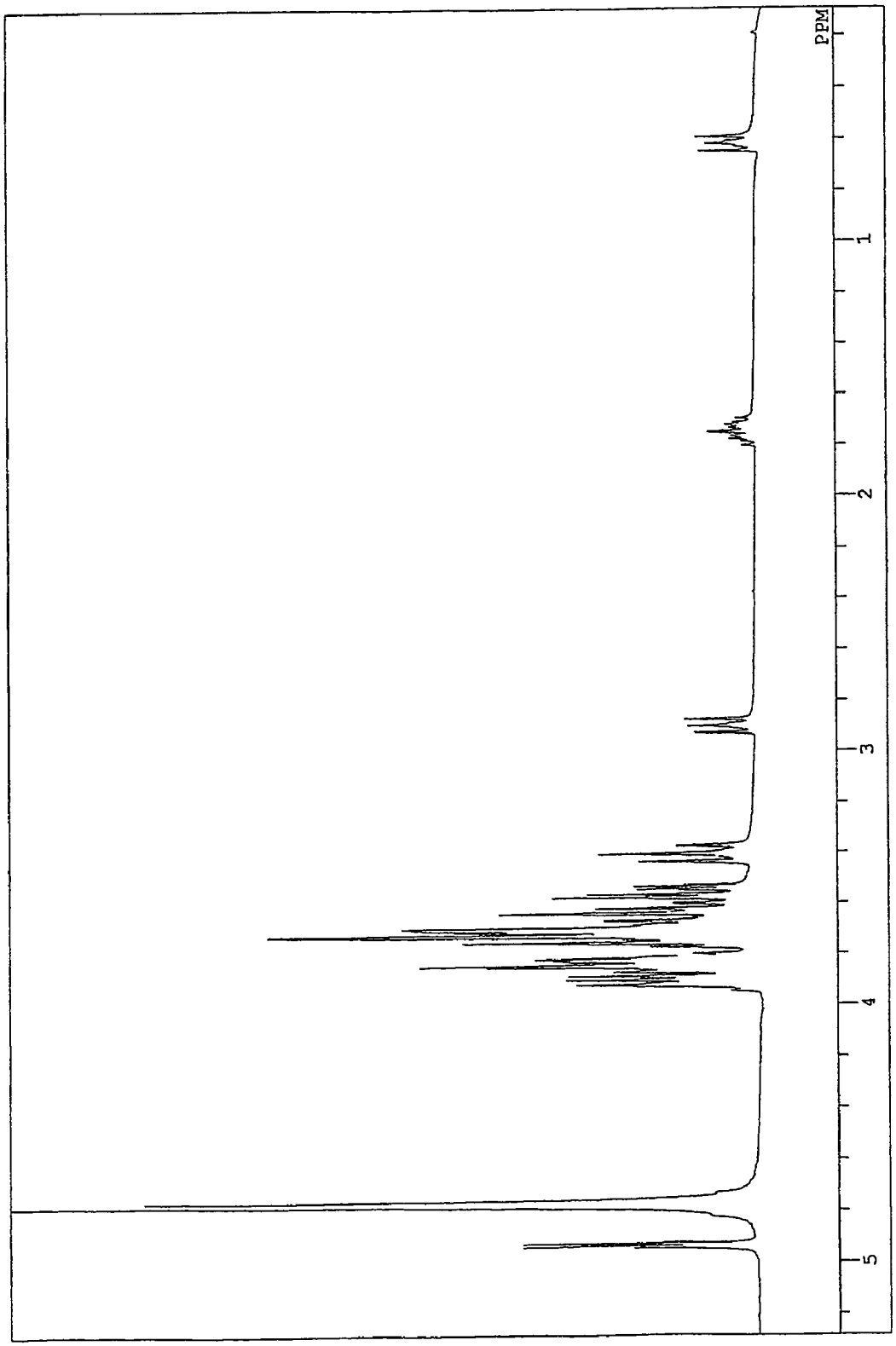
FIG. 49 is a spectrum of nuclear magnetic resonance ($^1$H-NMR) of isomaltitol crystal obtained by the method of the present invention.
Figure 50:
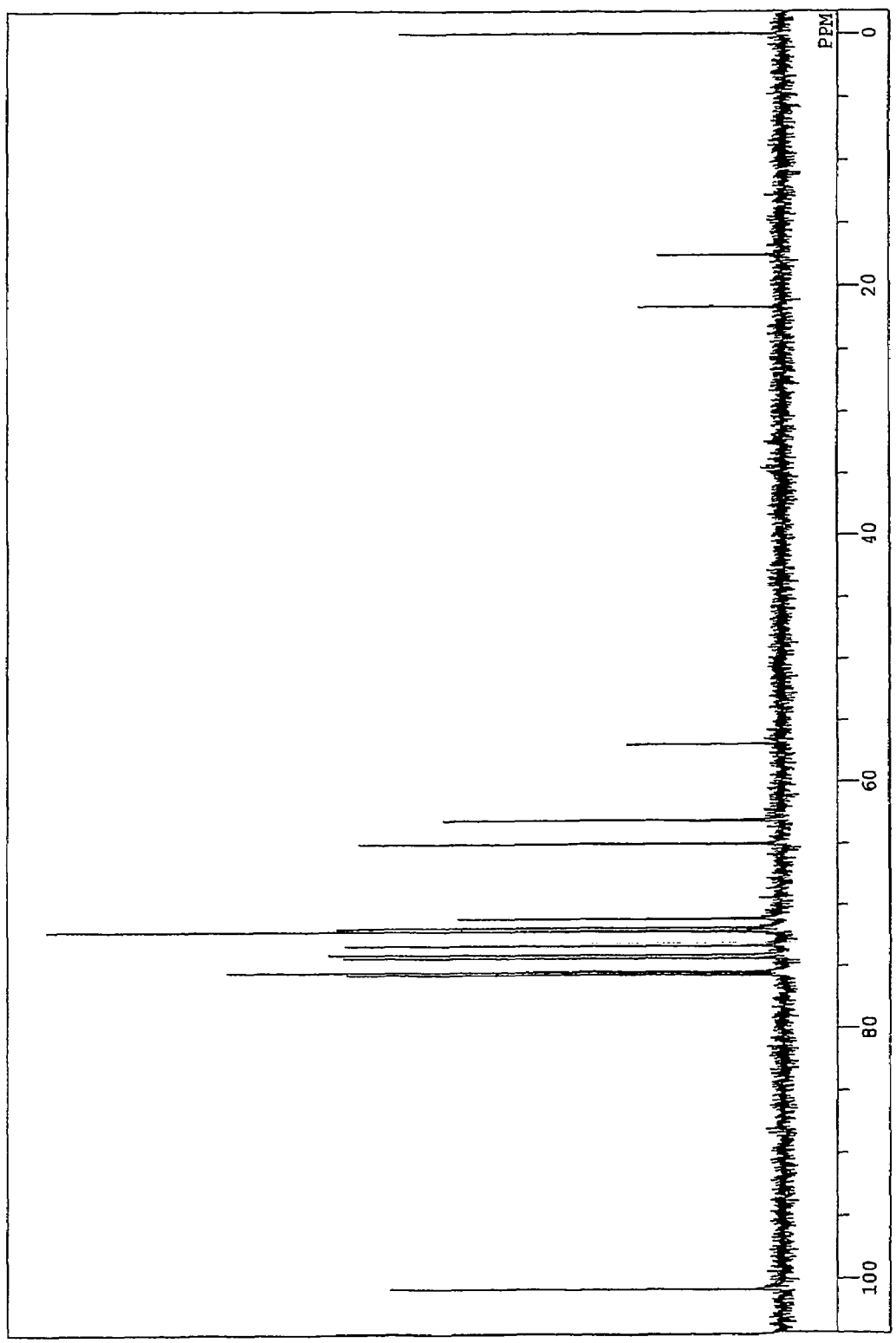
FIG. 50 is a spectrum of nuclear magnetic resonance ($^{13}$C-NMR) of isomaltitol crystal obtained by the method of the present invention.

The product had an isomaltitol purity of about 99.9% or higher, d.s.b. The results on x-ray powder diffraction pattern, $^1$H-NMR spectrum, and $^{13}$C-NMR spectrum of the product are respectively shown in FIGS. 48 to 50. Based on the data, the product was judged to be isomaltitol.

The following Example A explains isomaltose or saccharides comprising the same and the process for producing isomaltitol and/or saccharides comprising the same; and Example B explains the uses of isomaltitol and/or saccharides comprising the same:

EXAMPLE A-1

About one hundred liter of an aqueous solution of phytoglycogen from corn commercialized by Q.P. Corporation, Tokyo, Japan, was adjusted to give a concentration of 4% (w/v) and pH 6.0, heated to 30° C., and admixed with one unit/g starch of a purified specimen of α-isomaltosylglucosaccharide-forming enzyme from *Bacillus globisporus* N75 strain obtained by the method in Experiment 11-2, and 12 units/g starch of a purified specimen of α-isomaltosyltransferring enzyme from *Bacillus globisporus* N75 strain obtained by the method in Experiment 11-3, followed by an enzymatic reaction for 48 hours and a heat treatment at 100° C. for 10 min to inactivate the remaining enzymes. The mixture thus obtained was sampled for quantifying the yield of cyclotetrasaccharide on HPLC, revealing that it had about 80% of cyclotetrasaccharide in terms of sugar composition, where HPLC was carried out using "SHOWDEX™ KS-801 column", Showa Denko K.K., Tokyo, Japan, at a column temperature of 60° C. and a flow rate of 0.5 ml/min of water, and "RI-8012", a differential refractometer commercialized by Tosoh Corporation, Tokyo, Japan. The above mixture was adjusted to pH 5.0 and 45° C., admixed with 1,500 units/g starch, d.s.b. of "TRANSGLUCOSIDASE L AMANO™", an α-glucosidase commercialized by Amano Pharmaceutical Co., Ltd., Aichi, Japan, and 75 units/g starch, d.s.b., of "XL-4™", a glucoamylase specimen commercialized by Nagase Biochemicals, Ltd., Kyoto, Japan, incubated for 24 hours to hydrolyze the remaining reducing oligosaccharides, etc. The resulting mixture was adjusted to pH 5.8, kept at 90° C. for one hour to inactivate the remaining enzymes, and filtered to remove insoluble substances. The filtrate was concentrated to give a concentration of about 16% with "HOLLOSEP® HR 5155PI", a reverse osmotic membrane, Toyobo Co., Ltd., Tokyo, Japan, and in a usual manner decolored, desalted, filtered, and concentrated to obtain about 6.0 kg of a saccharide solution with a solid content of about 3,500 g, d.s.b. The saccharide solution was fed to a column packed with about 225 L of "AMBERLITE CR-1310 (Na$^+$-form)", a strong-acid cation exchange resin commercialized by Japan Organo Co., Ltd., Tokyo, Japan, and chromatographed at a column temperature of 60° C. and a flow rate of about 45 L/h. While the saccharide composition of eluate from the column was monitoring by the above-identified HPLC, fractions of cyclotetrasaccharide with a purity of at least 80% were collected, and in a usual manner desalted, decolored, filtered, and concentrated into a saccharide solution.

HPLC analysis for saccharide composition of the saccharide solution thus obtained revealed that it contained cyclotetrasaccharide with a purity of about 95.5%. The resulting saccharide solution with cyclotetrasaccharide was concentrated in vacuo into a powder containing cyclotetrasaccharide. The powder was dissolved in deionized water, adjusted to give a concentration of one percent, pH 5.5 and 50° C., and admixed with 80 units/g solids, d.s.b., of an isomaltose-releasing enzyme obtained by the method in Experiment 29, followed by an enzymatic reaction at pH 5.5 and 50° C. for 70 hours. Thereafter, the resulting mixture was sequentially heated to 95° C., kept at the temperature for 10 min, cooled, and filtered. The filtrate was in a usual manner decolored with an activated charcoal, desalted for purification with ion-exchange resins in H- and OH-forms, and concentrated to give a concentration of about 43.0%. Thus, a high isomaltose content syrup was obtained in a yield of about 95%, d.s.b., to the solid contents. HPLC analysis for saccharide composition of the syrup revealed thus obtained that it contained 43.1% of isomaltose, 37.8% of ring-opened tetrasaccharide, and 13.8% of cyclotetrasaccharide.

The product has a satisfactory moisture-retaining ability, low sweetness, osmosis-controlling ability, filler-imparting ability, gloss-imparting ability, viscosity-imparting ability, ability of preventing crystallization of other saccharides, insubstantial fermentability, ability of preventing the retrogradation of starch, etc., it can be arbitrarily used in various food products, health foods, feeds, pet foods including bait for fish, cosmetics, pharmaceuticals, and favorite foods.

EXAMPLE A-2

A powder containing cyclotetrasaccharide, obtained by the method in Example A-1, was dissolved in deionized water, adjusted to give a concentration of one percent, pH 5.5 and 50° C., and admixed with 500 units/g solids, d.s.b., of an isomaltose-releasing enzyme obtained by the method in Experiment 29, followed by an enzymatic reaction at pH 5.5 and 50° C. for 70 hours. Thereafter, the resulting mixture was sequentially heated to 95° C., kept at the temperature for 10 min, cooled, and filtered. The filtrate was in a usual manner decolored with an activated charcoal, desalted for purification with ion-exchange resins in H- and OH-forms, and concentrated to give a concentration of about 75%. Thus, a high isomaltose content syrup was obtained in a yield of about 90%, d.s.b., to the solid contents. HPLC analysis for saccharide composition of the syrup revealed that it contained 92.8% of isomaltose, 2.7% of ring-opened tetrasaccharide, and 4.5% of other saccharides.

The product has a satisfactory moisture-retaining ability, low sweetness, osmosis-controlling ability, filler-imparting ability, gloss-imparting ability, viscosity-imparting ability, ability of preventing crystallization of other saccharides, insubstantial fermentability, ability of preventing the retrogradation of starch, etc., it can be arbitrarily used in various food products, health foods, feeds, pet foods including bait for fish, cosmetics, pharmaceuticals, and favorite foods.

EXAMPLE A-3

An about 20% corn starch suspension was prepared, admixed with 0.1% calcium carbonate, adjusted to pH 6.5, and then mixed with 0.3% per gram starch of "TERMAMYL 60L™", an α-amylase specimen commercialized by Novo Indutri A/S, Copenhagen, Denmark, followed by an enzymatic reaction at 95° C. for 15 min. Thereafter, the reaction mixture was autoclaved at 120° C. for 20 min, and promptly cooled to about 50° C. to obtain a liquefied starch solution with a DE of about four. To the liquefied solution were added 0.2 unit/g solid, d.s.b., of a purified specimen of α-isomaltosylglucosaccharide-forming enzyme from N75 strain obtained by the method in Experiment 11-2, 100 units/g solid, d.s.b., of an isomaltodextranase specimen obtained by the method in Experiment 29, 250 units/g solid, d.s.b., of an isoamylase specimen from *Pseudomonas amyloderamosa* commercialized by Hayashibara Biochemical laboratories, Inc., Okayama, Japan, and 0.5 unit/g starch of a CGTase specimen from *Bacillus stearothermophilus* commercialized by Hayashibara Biochemical laboratories, Inc., Okayama, Japan, followed by an incubation at 50° C. and pH 5.5 for 65 hours. After completion of the reaction, the reaction mixture was heated at 100° C. for 15 min to inactivate the remaining enzymes. To the resulting mixture was added 20 units/g starch of "XL-4™", a glucoamylase specimen commercialized by Nagase Biochemicals, Ltd., Kyoto, Japan, incubated at 50° C. for 24, and heated at 100° C. for 20 min to inactivate the remaining enzyme. The reaction mixture was cooled and filtered. The filtrate was in a usual manner decolored with an activated charcoal, desalted for purification with ion-exchange resins in H- and OH-forms, and concentrated to give a concentration of about 60%. Thus, a high isomaltose content syrup was obtained in a yield of about 95%, d.s.b., to the solid contents. HPLC analysis for saccharide composition of the syrup revealed that it contained 62.9% of isomaltose, 30.1% of glucose, and 7.0% of other saccharides.

The product has a satisfactory moisture-retaining ability, low sweetness, osmosis-controlling ability, filler-imparting ability, gloss-imparting ability, viscosity-imparting ability, ability of preventing crystallization of other saccharides, insubstantial fermentability, ability of preventing the retrogradation of starch, etc., it can be arbitrarily used in various food products, health foods, feeds, pet foods including bait for fish, cosmetics, pharmaceuticals, and favorite foods.

EXAMPLE A-4

A high isomaltose content syrup, obtained by the method in Example A-3, as a saccharide solution, was column chromatographed to increase the concentration of isomaltose using "AMBERLITE CR-1310 (Na$^+$-form)", a strong-acid cation exchange resin commercialized by Japan Organo Co., Ltd., Tokyo, Japan, in such a manner of packing the above resin to 10 stainless-steel columns equipped with an inner jacket having 12.5 cm in diameter, cascading the columns in series to give a total column bed depth of 16 m, applying the above syrup in a volume of 1.5% (v/v) to the volume of resin, fractionating and purifying the syrup by feeding hot water heated to 40° C. to the columns at a space velocity (SV) of 0.2, collecting fractions rich in isomaltose while monitoring the sugar composition of the eluates, and concentrating the pooled eluates up to give a concentration of 75% to obtain a high isomaltose content syrup, consisting of, on a dry solid basis, 4.3% glucose, 90.5% isomaltose, 3.5% of other saccharides, and 1.7% of trisaccharide or higher, in a yield of about 45%.

The product has a satisfactory moisture-retaining ability, low sweetness, osmosis-controlling ability, filler-imparting ability, gloss-imparting ability, viscosity-imparting ability, ability of preventing crystallization of other saccharides, insubstantial fermentability, ability of preventing the retrogradation of starch, etc., it can be arbitrarily used in various food products, health foods, feeds, pet foods including bait for fish, cosmetics, pharmaceuticals, and favorite foods.

EXAMPLE A-5

An isomaltose content syrup, obtained by the method in Example A-1, was hydrogenated in accordance with the method in Experiment 36, and the resulting mixture was in a usual manner decolored with an activated charcoal, desalted for purification with ion-exchange resins in H- and OH-forms, and concentrated to give a concentration of about 73%. The concentrate was spray dried in a usual manner to obtain a high isomaltitol content powder, containing 43.3% of isomaltitol, 37.8% of ring-opened tetrasaccharide, 13.8% of cyclotetrasaccharide, and 3.5% of other sugar alcohols, in a yield of about 80%.

The product is substantially a non-reducing saccharide which does not substantially cause the Maillard reaction and substantially has non-hygroscopicity, low sweetness, osmosis-controlling ability, filler-imparting ability, gloss-imparting ability, moisture-retaining ability, viscosity-imparting ability, ability of preventing crystallization of other saccharides, insubstantial fermentability, ability of preventing the retrogradation of starch, etc., it can be arbitrarily used in various food products, health foods, health supplements, feeds, pet foods including bait for fish, cosmetics, pharmaceuticals, and favorite foods.

EXAMPLE A-6

A 20% tapioca starch suspension was prepared, admixed with 0.1% calcium carbonate, adjusted to pH 6.5, and then mixed with 0.3% per gram starch of "TERMAMYL 60L™", an α-amylase specimen commercialized by Novo Indutri A/S, Copenhagen, Denmark, followed by an enzymatic reaction at 95° C. for 15 min. Thereafter, the reaction mixture was autoclaved at 120° C. for 20 min, and promptly cooled to about 40° C. to obtain a liquefied starch solution with a DE of about four. To the liquefied starch solution were added 0.2 unit/g solid, d.s.b., of a purified specimen of α-isomaltosylglucosaccharide-forming enzyme from C9 strain obtained by the method in Experiment 4-2, 100 units/g solid, d.s.b., of a purified specimen of α-isomaltodextranase obtained by the method in Experiment 29, 250 units/g of an isoamylase specimen commercialized by Hayashibara Biochemical Laboratories, Inc., Okayama, Japan, and 0.5 unit/g of a CGTase specimen commercialized by Hayashibara Biochemical Laboratories, Inc., Okayama, Japan, followed by an incubation at pH 5.5 and 40° C. for 64 hours. After completion of the reaction, the reaction mixture was sequentially heated at 95° C. for 30 min, cooled to 50° C., admixed with 10 units/g of "GLUCOZYME™", a glucoamylase specimen commercialized by Nagase Biochemicals, Ltd., Kyoto, Japan, subjected to an enzymatic reaction for 24 hours, heated to 95° C., incubated at 95° C. for 30 min, cooled, and filtered. The filtrate was in a usual manner decolored with an activated charcoal, desalted for purification with ion-exchange resins in H- and OH-forms, and concentrated to give a concentration of about 50% (w/v). Thus, a high isomaltose content syrup, containing 11.0% of glucose, 66.5% of isomaltose, 2.4% of disaccharide other than isomaltose, and 20.1% of trisaccharide or higher, was obtained in a yield of about 95%, d.s.b.

The high isomaltose content syrup thus obtained was hydrogenated in accordance with the method in Experiment 36, followed by removing the Raney Nickel catalyst from the mixture. The resulting mixture was decolored with an activated charcoal, desalted for purification with ion-exchange resins in H- and OH-forms, concentrated, and dried in vacuo to obtain a high isomaltitol content powder in a yield of about 85%.

The powder contained 12.3% of sorbitol, 66.7% of isomaltitol, and 21.0% of other sugar alcohols.

The product substantially does not have reducibility and does not cause the Maillard reaction, and it has a relatively low sweetness, osmosis-controlling ability, filler-imparting ability, gloss-imparting ability, moisture-retaining ability, viscosity-imparting ability, ability of preventing crystallization of other saccharides, insubstantial fermentability, ability of preventing the retrogradation of starch, etc. Thus the product can be arbitrarily used in various food products, health foods, feeds, pet foods including bait for fish, cosmetics, pharmaceuticals, and favorite foods.

EXAMPLE A-7

In accordance with the method in Experiment 1, *Bacillus globisporus* C9 strain (FERM BP-7143) was cultured in a fermentor for 48 hours. Thereafter, the culture was membrane filtered to remove the cells to collect about 18 L of a filtrate which was then concentrated with a UF membrane to yield about one liter of an enzyme concentrate containing 8.8 units/ml of α-isomaltosylglucosaccharide-forming enzyme and 26.7 units/ml of α-isomaltosyl-transferring enzyme. While, an about 27% corn starch suspension was prepared, admixed with 0.1% calcium carbonate, adjusted to pH 6.5, and then mixed with 0.3% per gram starch of "TERMAMYL 60L™", an α-amylase specimen commercialized by Novo Indutri A/S, Copenhagen, Denmark, followed by an enzymatic reaction at 95° C. for 15 min. Thereafter, the reaction mixture was autoclaved at 120° C. for 20 min and promptly cooled to about 40° C. to obtain a liquefied starch solution with a DE of about four. To the liquefied starch solution were added 0.25 ml of the above enzyme solution of α-isomaltosylglucosaccharide-forming enzyme and α-isomaltosyl-transferring enzyme, 100 units/g starch of an isomaltodextranase specimen obtained by the method in Experiment 29, 250 units/g starch of an isoamylase specimen commercialized by Hayashibara Biochemical Laboratories, Inc., Okayama, Japan, and 0.5 unit/g starch of a CGTase specimen commercialized by Hayashibara Biochemical Laboratories, Inc., Okayama, Japan, followed by an incubation at pH 5.5 and 40° C. for 70 hours. After completion of the reaction, the reaction mixture was sequentially heated to 95° C., incubated at 95° C. for 10 min, adjusted to 50° C., admixed with 20 units/g starch of "GLU-COZYME™", a glucoamylase specimen commercialized by Nagase Biochemicals, Ltd., Kyoto, Japan, enzymatically reacted for 24, and heated to and incubated at 95° C. for 30 min. The resulting mixture was cooled and filtered. The filtrate was in a usual manner decolored with an activated charcoal, desalted for purification with ion-exchange resins in H- and OH-forms, and concentrated to give a concentration of about 50%. Thus, a high isomaltose content syrup, containing 32.6% glucose, 59.4% of isomaltose, 1.2% of disaccharide other than isomaltose, 6.8% of trisaccharide or higher, was obtained in a yield of about 95%, d.s.b.

The high isomaltose content syrup thus obtained was hydrogenated in accordance with the method in Experiment 36, followed by removing the Raney Nickel catalyst from the mixture in a usual manner. The resulting mixture was decolored with an activated charcoal, desalted for purification with ion-exchange resins in H- and OH-forms, concentrated to give a concentration of about 50%. Thus, a high isomaltitol content syrup was obtained in a yield of about 85%, d.s.b.

The product contained 33.4% of sorbitol, 59.1% of isomaltitol, 6.4% of sugar alcohols other than sorbitol and isomaltitol, and 1.1% of cyclotetrasaccharide. The product substantially does not has reducibility and does not cause the Maillard reaction, and it has a relatively low sweetness, osmosis-controlling ability, filler-imparting ability, gloss-imparting ability, moisture-retaining ability, viscosity-imparting ability, ability of preventing crystallization of other saccharides, insubstantial fermentability, ability of preventing the retrogradation of starch, etc. Thus the product can be arbitrarily used in various food products, health foods, feeds, pet foods including bait for fish, cosmetics, pharmaceuticals, and favorite foods.

EXAMPLE A-8

A high isomaltose content syrup, obtained by the method in Example A-7, as a saccharide solution, was column chromatographed to increase the content of isomaltose using "AMBERLITE CR-1310 (Na$^+$-form)", a strong-acid cation exchange resin commercialized by Japan Organo Co., Ltd., Tokyo, Japan, in such a manner of packing the above resin to 10 stainless-steel columns equipped with an inner jacket having 12.5 cm in diameter, cascading the columns in series to give a total column bed depth of 16 m, applying the above syrup in a volume of 1.5% (v/v) to the volume of resin, fractionating and purifying the syrup by feeding hot water heated to 40° C. to the columns at SV 0.2, collecting fractions rich in isomaltose while monitoring the sugar composition of the eluates, and concentrating the pooled eluates up to give a concentration of 55% to obtain a high isomaltose content syrup, consisting of, on a dry solid basis, 4.8% glucose, 88.0% isomaltose, 4.1% of other saccharides, and 3.1% of trisaccharide or higher, in a yield of about 55%.

The high isomaltose content syrup thus obtained was hydrogenated in accordance with the method in Experiment 36, followed by removing the Raney Nickel catalyst from the mixture in a usual manner. The resulting mixture was decolored with an activated charcoal and desalted for purification with ion-exchange resins in H- and OH-forms to obtain a high isomaltitol content syrup, consisting of, on a dry solid basis, 4.9% sorbitol, 88.1% isomaltitol, and 7.0% of other sugar alcohols, in a yield of about 90%.

The high isomaltitol content syrup thus obtained was concentrated to give a concentration of about 73%, and the concentrate was placed in a crystallizer, admixed with a crystalline isomaltitol powder as a seed in an amount of 0.1%, d.s.b., to the solid contents, and allowed to crystallize maltitol at 25° C. for about 20 hours. The mixture was separated by a centrifuge, followed by separately collecting the resulting isomaltitol crystal and syrup. The isomaltitol crystal thus obtained was dried in vacuo at 80° C. for 20 hours to obtain a crystalline maltitol powder in a yield of about 39%, d.s.b. In accordance with the above method, the above syrup was column chromatographed using a strong-acid cation exchange resin, followed collecting high isomaltitol content fractions with an isomaltitol content of about 88%, d.s.b. The fractions were pooled, purified, concentrated, crystallized, and separated to collect isomaltitol crystal which was then aged and dried in vacuo to obtain a crystalline isomaltitol powder in a yield of about 20%, d.s.b. By combining the powder thus obtained and the previously obtained powder, a crystalline isomaltitol powder was obtained in a total yield of about 59%, d.s.b.

The product contained, on a dry solid basis, 0.7% sorbitol, 98.0% isomaltitol, and 1.3% sugar alcohol. The product has non-reducibility, non-hygroscopicity, low sweetness, osmosis-controlling ability, filler-imparting ability, gloss-imparting ability, moisture-retaining ability, viscosity-imparting ability, ability of preventing crystallization of other saccharides, insubstantial fermentability, ability of preventing the retrogradation of starch, etc., it can be arbitrarily used in various food products, health foods, health supplements, feeds, pet foods including bait for fish, cosmetics, pharmaceuticals, and favorite foods.

EXAMPLE A-9

About one hundred liter of an aqueous solution of phytoglycogen from corn commercialized by Q.P. Corporation, Tokyo, Japan, was adjusted to give a concentration of 4% (w/v) and pH 6.0, heated to 30° C., and admixed with one unit/g starch of a purified specimen of α-isomaltosylglucosaccharide-forming enzyme from *Bacillus globisporus* N75 strain obtained by the method in Experiment 11-2, and 12 units/g starch of a purified specimen of α-isomaltosyl-transferring enzyme from *Bacillus globisporus* N75 strain obtained by the method in Experiment 11-3, followed by an enzymatic reaction for 48 hours and a heat treatment at 100° C. for 10 min to inactivate the remaining enzymes. The mixture thus obtained was sampled for quantifying the yield of cyclotetrasaccharide on HPLC, revealing that it contained about 80% of cyclotetrasaccharide in terms of sugar composition, where HPLC was carried out using "SHOWDEX KS-80™ column", Showa Denko K.K., Tokyo, Japan, at a column temperature of 60° C. and a flow rate of 0.5 ml/min of water, and "RI-8012™", a differential refractometer commercialized by Tosoh Corporation, Tokyo, Japan. The above mixture was adjusted to pH 5.0 and 45° C., admixed with 1,500 units/g starch, d.s.b., of "TRANSGLUCOSIDASE L AMANO™", an α-glucosidase commercialized by Amano Pharmaceutical Co., Ltd., Aichi, Japan, and 75 units/g starch, d.s.b., of "XL-4™", a glucoamylase specimen commercialized by Nagase Biochemicals, Ltd., Kyoto, Japan, incubated for 24 hours to hydrolyze the remaining reducing oligosaccharides, etc. The resulting mixture was adjusted to pH 5.8, kept at 90° C. for one hour to inactivate the remaining enzymes, and filtered to remove insoluble substances. The filtrate was concentrated to give a concentration of about 16% (w/v) with "HOLLOSEP® HR 5155PI", a reverse osmotic membrane, Toyobo Co., Ltd., Tokyo, Japan, and in a usual manner decolored, desalted, filtered, and concentrated into a saccharide solution. Then, the saccharide solution was adjusted to give concentration of about one percent, pH 5.5, and 50° C., admixed with 80 units/g solids of an isomaltodextranase specimen prepared by the method in Experiment 29, and subjected to an enzymatic reaction at pH 5.5 and 50° C. for 70 hours. Thereafter, the reaction mixture was heated to and incubated at 95° C. for 10 min, cooled, and filtered. The filtrate was in a usual manner decolored with an activated charcoal, desalted for purification with ion-exchange resins in H- and OH-forms, and concentrated to give a concentration of about 43% (w/v). Thus, an isomaltose content syrup was obtained in a yield of about 95%, d.s.b. HPLC analysis for saccharide composition of the syrup revealed that it contained 35.5% of isomaltose. The isomaltose content syrup thus obtained was hydrogenated in accordance with the method in Experiment 36, followed by removing the Raney Nickel catalyst from the mixture in a usual manner. The resulting mixture was decolored with an activated charcoal, desalted for purification with ion-exchange resins in H- and OH-forms, and concentrated to give a concentration of about 40%. The resulting concentrate was column chromatographed using a column packed with about 225 L of "AMBERLITE CR-1310 ($Na^+$-form)", a strong-acid cation exchange resin commercialized by Japan Organo Co., Ltd., Tokyo, Japan, at a column temperature of 60° C. and a flow rate of about 45 L/h, followed by collecting fractions containing isomaltitol with a purity of at least 50% while monitoring the saccharide composition on the above-identified HPLC. The fractions were pooled, and in a usual manner desalted for purification with ion-exchange resins in H- and OH-forms, decolored, filtered, and concentrated to give a concentration of about 50%, d.s.b. Thus a high isomaltitol content syrup, containing 65.3% of isomaltitol, 13.8% of reduced ring-opened cyclotetrasaccharide, 5.2% of cyclotetrasaccharide, and 15.7% of sugar alcohols such as sorbitol, was obtained in a yield of about 78%, d.s.b.

The product is substantially free of the Maillard reaction, and it has a satisfactory osmosis-controlling ability, filler-imparting ability, gloss-imparting ability, moisture-retaining ability, viscosity-imparting ability, non-fermentability, ability of preventing the retrogradation of starch, etc. Thus the product can be arbitrarily used in various food products, health foods, feeds, pet foods including bait for fish, cosmetics, pharmaceuticals, and favorite foods.

EXAMPLE A-10

An high isomaltitol content syrup, consisting of 4.9% sorbitol, 88.1% of isomaltitol, and 7.0% of other sugar alcohols, was concentrated to give a concentration of about 88%. The concentrate was placed in a crystallizer, admixed with crystalline isomaltitol powder in an amount of two percent to the contents, d.s.b., heated to 50° C., incubated for two hours under gentle stirring conditions, transferred to a vat, allowed to stand at 20° C. for four days to crystallize and solidify the contents. The resulting solid product was pulverized by a cutter and dried to obtain a crystalline isomaltitol powder in a yield of about 90%.

The product has non-reducibility, non-hygroscopicity, low sweetness, osmosis-controlling ability, filler-imparting ability, gloss-imparting ability, moisture-retaining ability, viscosity-imparting ability, ability of preventing crystallization of other saccharides, insubstantial fermentability, ability of preventing the retrogradation of starch, etc., it can be arbitrarily used in various food products, health foods, health supplements, feeds, pet foods including bait for fish, cosmetics, pharmaceuticals, and favorite foods.

EXAMPLE B-1

Sweetener.

To 0.8 part by weight of a crystalline isomaltitol powder, obtained by the method in Example A-8, were added to homogeneity 0.2 part by weight of "TREHA®", an α,α-trehalose product commercialized by Hayashibara Shoji, Inc., Okayama, Japan, 0.01 part by weight of "αG SWEET™", an α-glycosyl stevioside commercialized by Toyo Sugar Refining Co., Ltd., Tokyo, Japan, and 0.01 part by weight of "ASPARTAME™" or L-aspartyl phenylalanine methyl ester.

The mixture was subjected to a granulator to obtain a granular sweetener. The product, which does not substantially has hygroscopicity but has satisfactory moisture-retaining ability and low sweetness, is a stable sweetener containing isomaltitol free from causing deterioration even when stored at ambient temperature.

EXAMPLE B-2

Hard Candy

To 100 parts by weight of a 55% sucrose solution were added 50 parts by weight of a high isomaltitol content syrup obtained by the method in Example A-7, and the mixture was concentrated by heating under a reduced pressure to give a moisture content of less than two percent. The concentrate was admixed with 0.6 part by weight of citric acid and adequate amounts of a lemon flavor and a color, followed by shaping the resulting mixture into a hard candy. The product, which is only less colored by the Maillard reaction and is satisfactory in biting property, flavor, and taste, is a stable, high quality hard candy free from causing crystallization of sucrose and having lesser hygroscopicity.

EXAMPLE B-3

Chewing Gum

Three parts by weight of a gum base were melted by heating to an extent to be softened and then admixed with two parts by weight of anhydrous crystalline maltitol, two parts by weight of xylitol, two parts by weight of a high isomaltitol content syrup obtained by the method in Example A-7, and one part by weight of hydrous crystalline α,α-trehalose, monohydrate, and further mixed with adequate amounts of a flavor and a color. The mixture was in a usual manner kneaded by a roll and then shaped and packed to obtain a chewing gum. The product is a relatively low cariogenic, caloric chewing gum having a satisfactory texture, flavor, and taste.

EXAMPLE B-4

Chocolate

Forty parts by weight of a cacao paste, 10 parts by weight of a cacao butter, and 50 parts by weight of a crystalline isomaltitol obtained by the method in Example A-8 were mixed, and the mixture was fed to a refiner to reduce the granular size and then placed in a conche and kneaded at 50° C. over two days and nights. During the processing, 0.5 part by weight of lecithin was added to the kneaded mixture and well dispersed therein. Thereafter, the resulting mixture was adjusted to 31° C. with a thermo controller, and then poured into a mold just before solidification of the butter, deairated by a vibrator, and solidified by passing through a cooling tunnel kept at 10° C. over 20 min. The solidified contents were removed from the mold and packed to obtain a chocolate.

The product substantially has no hygroscopicity but has satisfactory color, gloss, and internal texture; smoothly melts in the mouth; and has a high quality sweetness and a mild taste and flavor. The product can be useful as a low caloric, cariogenic chocolate.

EXAMPLE B-5

Powdery Peptide

One part by weight of 40% of "HINUTE S™", a peptide solution of edible soy beans commercialized by Fuji Oil Co., Ltd., Tokyo, Japan, was mixed with two parts by weight of a high isomaltitol content syrup obtained by the method in Example A-6, and the resultant mixture was placed in a plastic vat, dried in vacuo at 50° C., and pulverized to obtain a powdery peptide. The product, which is only less colored by the Maillard reaction, is useful as a material for low caloric confectionery and also as a material for controlling intestinal function, health food, and hardly assimilable dietary fiber for oral or tube fed liquid diets.

EXAMPLE B-6

Bath Salt

One part by weight of a peel juice of "yuzu" (a Chinese lemon) was admixed with 10 parts by weight of a crystalline isomaltitol powder obtained in accordance with the method in Example A-10, and 10 parts by weight of anhydrous crystalline cyclotetrasaccharide, followed by crystallizing hydrous cyclotetrasaccharide crystal, penta- or hexa-hydrate, aging the crystal and pulverizing the aged crystal to obtain an isomaltitol and cyclotetrasaccharide powder with a yuzu extract.

To five parts by weight of the powder thus obtained were added 90 parts by weight of roast salt, two parts by weight of hydrous crystalline α,α-trehalose, one part by weight of silicic anhydride, and 0.5 part by weight of "αG HESPERIDIN™", α-glucosyl hesperidin commercialized by Hayashibara Shoji, Inc., Okayama, Japan, to obtain a bath salt.

The product is a high quality bath salt enriched with yuzu flavor and used by diluting in a bathtub with hot water by 100-10,000 folds, and it moisturizes and smooths the skin and does not make you feel cold after a bath.

EXAMPLE B-7

Cosmetic Cream

Two parts by weight of polyoxyethylene glycol monostearate, five parts by weight of glyceryl monostearate, self-emulsifying, two parts by weight of a high isomaltitol content syrup obtained by the method in Example A-7, one part by weight of "αG RUTIN™", α-glucosyl rutin commercialized by Hayashibara Shoji, Inc., Okayama, Japan, one part by weight of liquid petrolatum, 10 parts by weight of glyceryl tri-2-ethylhexanoate, and an adequate amount of an antiseptic were dissolved by heating in a usual manner. The resultant solution was admixed with two parts by weight of L-lactic acid, five parts by weight of 1,3-butylene glycol, and 66 parts by weight of refined water, and the resultant mixture was emulsified by a homogenizer and admixed with an adequate amount of a flavor while stirring to obtain a cosmetic cream. The product exhibits an antioxidant activity and has a relatively high stability, and these render it advantageously useful as a high quality sunscreen, skin-refining agent, and skin-whitening agent.

EXAMPLE B-8

Toothpaste

A toothpaste was obtained by mixing 45 parts by weight of calcium secondary phosphate, 1.5 parts by weight of sodium lauryl sulfate, 25 parts by weight of glycerine, 0.5 part by weight of polyoxyethylene sorbitan laurate, 15 parts by weight of a high isomaltitol content syrup obtained by the method in Example A-2, 0.02 part by weight of saccharine, 0.05 part by weight of an antiseptic, and 13 parts by weight of water. The product has an improved after taste and satisfactory feeling after use without lowering the detergent power of the surfactant.

EXAMPLE B-9

Solid Preparation for Fluid Diet

A composition was prepared by mixing 100 parts by weight of a high isomaltitol content powder obtained by the method in Example A-5, 200 parts by weight of hydrous crystalline α,α-trehalose, 200 parts by weight of a high maltotetraose content powder, 270 parts by weight of an egg yolk powder, 209 parts by weight of a skim milk powder, 4.4 parts by weight of sodium chloride, 1.8 parts by weight of potassium chloride, four parts by weight of magnesium sulfate, 0.01 part by weight of thiamine, 0.1 part by weight of sodium L-ascorbate, 0.6 part by weight of vitamin E acetate, and 0.04 part by weight of nicotinamide. Twenty-five gram aliquots of the composition were injected into moisture-proof laminated small bags which were then heat-sealed to obtain the desired product.

The product is a fluid diet having a satisfactory action of improving intestinal function. In use, one bag of the product is dissolved in about 150 to about 300 ml of water into a fluid diet and arbitrarily administered orally or administered intubationally into the nasal cavity, stomach, intestines, etc.

EXAMPLE B-10

Tablet

Fifty parts by weight of aspirin were sufficiently mixed with 14 parts by weight of a crystalline isomaltitol powder obtained by the method in Example A-7, and four parts by weight of corn starch. The resulting mixture was in a usual manner tabletted by a tabletting machine to obtain a tablet, 680 mg and 5.25 mm in thickness.

The tablet, processed by using the filler-imparting ability of isomaltitol, has substantially no hygroscopicity, but has a sufficient physical strength and satisfactory degradability in water.

EXAMPLE B-11

Sugar Coated Tablet

A crude tablet as a core, 150 mg weight, was sugar coated with a first solution, consisting of 40 parts by weight of a crystalline isomaltitol obtained by the method in Experiment 36, two parts by weight of pullulan having an average molecular weight of 200,000, 30 parts by weight of water, 25 parts by weight of talc, and three parts by weight of titanium oxide until the total weight increased to about 230 mg. The resultant tablet was further sugar coated with a second solution, consisting of 65 parts by weight of a powder of hydrous crystalline cyclotetrasaccharide, penta- or hexa-hydrate, one part by weight of pullulan, and 34 parts by weight of water. Then, the resulting tablet was glossed with a liquid wax into a sugar coated tablet having a satisfactory gloss and appearance. The product has a relatively high shock tolerance and retains its initial high quality for a relatively-long period of time.

EXAMPLE B-12

Ointment for Treating Trauma

To 100 parts by weight of a high isomaltitol content syrup, obtained by the method in Example A-7, and 300 parts by weight of maltose were added 50 parts by weight of methanol dissolving three parts by weight of iodine, and further added 200 parts by weight of a 10% (w/v) aqueous pullulan solution to obtain the desired product with an adequate extensibility and adhesiveness. The product is a high-valued ointment in which the volatilization of iodine and methanol is well inhibited by isomaltitol and is relatively less in property change during storage.

Because the product exerts a sterilizing action by iodine and acts as an energy-supplementing agent on living cells due to maltose, it shortens the curing term and well cures the affected parts and surfaces.

INDUSTRIAL APPLICABILITY

As described above, the present invention relates to a novel method for producing isomaltose and isomaltitol, more particularly, to a process for producing isomaltose, which comprises the steps of contacting a saccharide, having the α-1,4 glucosidic linkage as the linkage of non-reducing end and a glucose polymerization degree of at least two, with one or more α-isomaltosylglucosaccharide-forming enzymes derived from *Bacillus globisporus* N75 strain (FERM BP-7591), *Arthrobacter globiformis* A19 strain (FERM BP-7590) and *Arthrobacter ramosus* S1 strain (FERM BP-7592) in the presence or the absence of an α-isomaltosyl-transferring enzyme derived from *Bacillus globisporus* N75 strain (FERM BP-7591) and/or *Arthrobacter globiformis* A19 strain (FERM BP-7590) to form α-isomaltosylglucosaccharides having the α-1,6 glucosidic linkage as the linkage of non-reducing end and the α-1,4 glucosidic linkage other than the above linkage, and/or to form a saccharide with the structure of cyclo{→6)-α-D-glucopyranosyl-(1→3)-α-D-glucopyranosyl-(1→6)-α-D-glucopyranosyl-(1→3)-α-D-glucopyranosyl-(1→}; contacting the resulting mixture with isomaltose-releasing enzyme to form isomaltose; and collecting the produced isomaltose. The present invention also relates to a method for producing isomaltitol, which comprises the steps of contacting a saccharide, having the α-1,4 glucosidic linkage as the linkage of non-reducing end and a glucose polymerization degree of at least two, with α-isomaltosylglucosaccharide-forming enzyme to form α-isomaltosylglucosaccharides having the α-1,6 glucosidic linkage as the linkage of non-reducing end and the α-1,4 glucosidic linkage other than the above linkage, and/or to form a saccharide with the structure of cyclo{→6)-α-D-glucopyranosyl-(1→3)-α-D-glucopyranosyl-(1→6)-α-D-glucopyranosyl-(1→3)-α-D-glucopyranosyl-(1→}; contacting the resulting mixture with isomaltose-releasing enzyme to form isomaltose; hydrogenating either the resulting mixture directly or the isomaltose separated from the mixture to form isomaltitol; and collecting the formed isomaltitol. The present invention further relates to saccharide compositions containing isomaltose and/or isomaltitol, and uses thereof. According to the present invention, saccharide compositions containing isomaltose and/or isomaltitol, which are useful in this art, can be produced on an industrial scale, at a relatively low cost and in a relatively high yield. The saccharide compositions of the present invention can be arbitrarily used in various food products, health foods, health supplements, feeds, pet foods including bait for fish, cosmetics, pharmaceuticals, and favorite foods because the compositions, which are substantially free of reducibility and the Maillard reaction, have satisfactory low sweetness, osmosis-controlling ability, filler-imparting ability, gloss-imparting ability, moisture-retaining ability, viscosity-imparting ability, ability of preventing crystallization of other saccharides, insubstantial fermentability, ability of preventing the retrogradation of starch, etc.

The present invention with these outstanding functions and effects is a significant invention that greatly contributes to this art.

The invention claimed is:

1. A process for producing isomaltitol, comprising the steps of:

(a) allowing an α-isomaltosylglucosaccharide-forming enzyme, which forms an α-isomaltosylglucosaccharide with a glucose polymerization degree of at least three and having both the α-1,6 glucosidic linkage as the linkage at the non-reducing end and the α-1,4 glucosidic linkage other than the above linkage, via the α-glucosyl-transfer from a material saccharide having a glucose polymerization degree of at least two and having the α-1,4 glucosidic linkage as the linkage at the non-reducing end, without substantially increasing the reducing power of the material saccharide, to act on a saccharide with a glucose polymerization degree of at least two and having the α-1,4 glucosidic linkage as the linkage of non-reducing end to form said α-isomaltosylglucosaccharide wherein said α-isomaltosylglucosaccharide-forming enzyme has the following physicochemical properties:

(1) Molecular weight

Having a molecular weight of about 117,000 to about 160,000 daltons when determined on SDS-PAGE (sodium dodecyl sulfate polyacrylamide gel electrophoresis);

(2) Isoelectric point

Having an isoelectric point of about 4.7 to about 5.7 when determined on isoelectrophoresis using ampholine;

(3) Optimum temperature

Having an optimum temperature of about 40° C. to about 45° C. when incubated at a pH of 6.0 for 60 min;

Having an optimum temperature of about 45° C. to about 50° C. when incubated at a pH of 6.0 for 60 min in the presence of 1 mM Ca$^{2+}$;

(4) Optimum pH

Having optimum pH of about 6.0 to about 6.5 when incubated at 35° C. or 60 min;

(5) Thermal stability

Being stable up to a temperature of about 35° C. to 40° C. when incubated at a pH of 6.0 for 60 min, Being stable up to a temperature of about 40° C. to 45° C. when incubated at a pH of 6.0 for 60 min in the presence of 1 mM Ca$^{2+}$, (6) pH Stability Having a stable pH range at about 4.5 to about 10.0 when incubated at 4° C. for 24 hours;

(b) allowing an isomaltodextranase to act on the resulting mixture in the step (a) to form isomaltose;

(c) hydrogenating either the resulting mixture in the step (b) directly or the isomaltose, which has been separated from the mixture to form isomaltitol; and (d) collecting the formed isomaltitol.

2. The process of claim 1, wherein one or more enzymes selected from the group consisting of α-isomaltosyl-transferring enzyme, which forms a cyclotetrasaccharide having the structure of cyclo{→6) -α-D-glucopyranosyl- (1→3) -α-D-glucopyranosyl- (1→6) -α-D-glucopyranosyl- (1→3) -α-D-glucopyranosyl- (1→} from said α-isomaltosylglucosaccharide and has the following physicochemical properties:

(1) Molecular weight

Having a molecular weight of about 82,000 to about 136,000 daltons when determined on SDS-PAGE;

(2) Isoelectic point (pI)

Having a pI about 5.0 to about 6.1 when determined on isoelectrophoresis using ampholine;

(3) Optimum temperature

Having an optimum temperature of about 45° C. to about 50° C. when incubated at a pH of 6.0 for 30 min;

(4) Optimum pH

Having an optimum pH of about 5.5 to about 6.0 when incubated at 35° C. for 30 min;

(5) Thermal stability

Being stable up to a temperature of about 40° C. when incubated at a pH of 6.0 for 60 min; and (6) pH Stability Having a stable pH range at about 4.0 to about 9.0 when incubated at 4° C. for 24 hours;

cyclomaltodextrin glucanotransferase and starch debranching enzyme are further allowed to act on said saccharide with a glucose polymerization degree of at least two and having the α-1,4 glucosidic linkage as the linkage of non-reducing end in the step (a).

3. The process of claim 1, wherein glucoamylases is further allowed to act on the reaction mixture after the enzymatic reaction of said isomaltodextranase in the step (b).

4. A process of claim 1, wherein said saccharide, having the α-1,4 glucosidic linkage as the linkage of non-reducing end and a glucose polymerization degree of at least two, is one or more saccharides selected from the group consisting of maltooligosaccharides, maltodextrins, amylodextrins, amyloses, amylopectins, soluble starches, liquefied starches, gelatinized starches, and glycogens.

5. The process of claim 1, characterized in that it employs a column chromatography using an alkaline metal- and/or alkaline earth metal-strong-acid-cation-exchange-resin and optionally employs a step of pulverization or crystallization in the step (d).

6. The process of claim 1, wherein said isomaltitol is collected in the form of a syrup, powder, or crystal in the step (d).

7. The process of claim 1, wherein the collected isomaltitol in the step (d) is a high isomaltitol content syrup comprising isomaltitol in an amount of at least 40% (w/w), on a dry solid basis.

* * * * *

SEQUENCE LISTING

```
<160> NUMBER OF SEQ ID NOS: 26

<210> SEQ ID NO 1
<211> LENGTH: 9
<212> TYPE: PRT
<213> ORGANISM: Bacillus globisporus

<400> SEQUENCE: 1

Tyr Val Ser Ser Leu Gly Asn Leu Ile
1               5

<210> SEQ ID NO 2
<211> LENGTH: 10
<212> TYPE: PRT
<213> ORGANISM: Bacillus globisporus

<400> SEQUENCE: 2

Ile Asp Gly Val Tyr His Ala Pro Asn Gly
1               5                   10

<210> SEQ ID NO 3
<211> LENGTH: 10
<212> TYPE: PRT
<213> ORGANISM: Bacillus globisporus

<400> SEQUENCE: 3

Ile Asp Gly Val Tyr His Ala Pro Tyr Gly
1               5                   10

<210> SEQ ID NO 4
<211> LENGTH: 8
<212> TYPE: PRT
<213> ORGANISM: Bacillus globisporus

<400> SEQUENCE: 4

Ile Asp Gly Val Tyr His Ala Pro
1               5

<210> SEQ ID NO 5
<211> LENGTH: 8
<212> TYPE: PRT
<213> ORGANISM: Bacillus globisporus

<400> SEQUENCE: 5

Asp Ala Ser Ala Asn Val Thr Thr
1               5

<210> SEQ ID NO 6
<211> LENGTH: 8
<212> TYPE: PRT
<213> ORGANISM: Bacillus globisporus

<400> SEQUENCE: 6

Trp Ser Leu Gly Phe Met Asn Phe
```

```
1               5

<210> SEQ ID NO 7
<211> LENGTH: 8
<212> TYPE: PRT
<213> ORGANISM: Bacillus globisporus

<400> SEQUENCE: 7

Asn Tyr Thr Asp Ala Trp Met Phe
1               5

<210> SEQ ID NO 8
<211> LENGTH: 8
<212> TYPE: PRT
<213> ORGANISM: Bacillus globisporus

<400> SEQUENCE: 8

Gly Asn Glu Met Arg Asn Gln Tyr
1               5

<210> SEQ ID NO 9
<211> LENGTH: 8
<212> TYPE: PRT
<213> ORGANISM: Bacillus globisporus

<400> SEQUENCE: 9

Ile Thr Thr Trp Pro Ile Glu Ser
1               5

<210> SEQ ID NO 10
<211> LENGTH: 8
<212> TYPE: PRT
<213> ORGANISM: Bacillus globisporus

<400> SEQUENCE: 10

Trp Ala Phe Gly Leu Trp Met Ser
1               5

<210> SEQ ID NO 11
<211> LENGTH: 9
<212> TYPE: PRT
<213> ORGANISM: Bacillus globisporus

<400> SEQUENCE: 11

His Val Ser Ala Leu Gly Asn Leu Leu
1               5

<210> SEQ ID NO 12
<211> LENGTH: 8
<212> TYPE: PRT
<213> ORGANISM: Bacillus globisporus

<400> SEQUENCE: 12

Asp Phe Ser Asn Asn Pro Thr Val
1               5

<210> SEQ ID NO 13
<211> LENGTH: 8
<212> TYPE: PRT
<213> ORGANISM: Bacillus globisporus

<400> SEQUENCE: 13

Tyr Thr Val Asn Ala Pro Ala Ala
1               5
```

```
<210> SEQ ID NO 14
<211> LENGTH: 8
<212> TYPE: PRT
<213> ORGANISM: Bacillus globisporus

<400> SEQUENCE: 14

Tyr Glu Ala Glu Ser Ala Glu Leu
1               5

<210> SEQ ID NO 15
<211> LENGTH: 6
<212> TYPE: PRT
<213> ORGANISM: Bacillus globisporus

<400> SEQUENCE: 15

Asn Trp Trp Met Ser Lys
1               5

<210> SEQ ID NO 16
<211> LENGTH: 8
<212> TYPE: PRT
<213> ORGANISM: Bacillus globisporus

<400> SEQUENCE: 16

Thr Asp Gly Gly Glu Met Val Trp
1               5

<210> SEQ ID NO 17
<211> LENGTH: 8
<212> TYPE: PRT
<213> ORGANISM: Bacillus globisporus

<400> SEQUENCE: 17

Asn Ile Tyr Leu Pro Gln Gly Asp
1               5

<210> SEQ ID NO 18
<211> LENGTH: 13
<212> TYPE: PRT
<213> ORGANISM: Arthrobacter globiformis

<400> SEQUENCE: 18

Ala Pro Leu Gly Val Gln Arg Ala Gln Phe Gln Ser Gly
1               5                   10

<210> SEQ ID NO 19
<211> LENGTH: 20
<212> TYPE: PRT
<213> ORGANISM: Arthrobacter globiformis

<400> SEQUENCE: 19

Asn Thr Leu Asp Gly Val Trp His Asn Pro Tyr Gly Ala Asp Glu Leu
1               5                   10                  15

Tyr Ala Thr Gln
            20

<210> SEQ ID NO 20
<211> LENGTH: 10
<212> TYPE: PRT
<213> ORGANISM: Arthrobacter ramosus

<400> SEQUENCE: 20

Asp Thr Leu Ser Gly Val Phe His Gly Pro
1               5                   10
```

```
<210> SEQ ID NO 21
<211> LENGTH: 5180
<212> TYPE: DNA
<213> ORGANISM: Bacillus globisporus
<220> FEATURE:
<221> NAME/KEY: CDS
<222> LOCATION: (877)..(4728)

<400> SEQUENCE: 21
atctaccggt ttttgtgaag tttggcagta ttcttccgat gaatttgaac gcgcaatatc      60
aagtgggcgg gaccattggc aacagcttga cgagctacac gaatctcgcg ttccgcattt     120
atccgcttgg gacaacaacg tacgactgga atgatgatat tggcggttcg gtgaaaacca     180
taacttctac agagcaatat gggttgaata agaaaccgt gactgttcca gcgattaatt      240
ctaccaagac attgcaagtg tttacgacta agccttcctc tgtaacggtg gtggttctg      300 tgatgacaga gtacagtact ttaactgccc taacgggagc gtcgacaggc tggtactatg     360
atactgtaca gaaattcact tacgtcaagc ttggttcaag tgcatctgct caatccgttg     420
tgctaaatgg cgttaataag gtggaatatg aagcagaatt cggcgtgcaa gcggcgtttt     480
caacgaacac gaaccatgca ggttatactg gtacaggatt tgtggacggc tttgagactc     540
ttggagacaa tgttgctttt gatgtttccg tcaaagccgc aggtacttat acgatgaagg     600
ttcggtattc atccggtgca ggcaatggct caagagccat ctatgtgaat aacaccaaag     660
tgacggacct tgccttgccg caaacaacaa gctgggatac atgggggact gctacgttta     720
gcgtctcgct gagtacaggt ctcaacacgg tgaaagtcag ctatgatggt accagttcac     780
ttggcattaa tttcgataac atcgcgattg tagagcaata aaaggtcggg agggcaagtc     840
cctcccttaa tttctaatcg aaagggagta tccttg atg cgt cca cca aac aaa      894
                                        Met Arg Pro Pro Asn Lys
                                         1               5 gaa att cca cgt att ctt gct ttt ttt aca gcg ttt acg ttg ttt ggt      942
Glu Ile Pro Arg Ile Leu Ala Phe Phe Thr Ala Phe Thr Leu Phe Gly
         10                  15                  20 tca acc ctt gcc ttg ctt cct gct ccg cct gcg cat gcc tat gtc agc      990
Ser Thr Leu Ala Leu Leu Pro Ala Pro Pro Ala His Ala Tyr Val Ser
     25                  30                  35 agc cta gga aat ctc att tct tcg agt gtc acc gga gat acc ttg acg     1038
Ser Leu Gly Asn Leu Ile Ser Ser Ser Val Thr Gly Asp Thr Leu Thr
 40                  45                  50 cta act gtt gat aac ggt gcg gag ccg agt gat gac ctc ttg att gtt     1086
Leu Thr Val Asp Asn Gly Ala Glu Pro Ser Asp Asp Leu Leu Ile Val
55                  60                  65                  70 caa gcg gtg caa aac ggt att ttg aag gtg gat tat cgt cca aat agc     1134
Gln Ala Val Gln Asn Gly Ile Leu Lys Val Asp Tyr Arg Pro Asn Ser
                 75                  80                  85 ata acg ccg agc gcg aag acg ccg atg ctg gat ccg aac aaa act tgg     1182
Ile Thr Pro Ser Ala Lys Thr Pro Met Leu Asp Pro Asn Lys Thr Trp
             90                  95                 100 tca gct gta gga gct acg att aat acg aca gcc aat cca atg acc atc     1230
Ser Ala Val Gly Ala Thr Ile Asn Thr Thr Ala Asn Pro Met Thr Ile
        105                 110                 115 acg act tcc aat atg aag att gag att acc aag aat cca gta cga atg     1278
Thr Thr Ser Asn Met Lys Ile Glu Ile Thr Lys Asn Pro Val Arg Met
    120                 125                 130 acg gtc aag aag gcg gac ggc act acg cta ttc tgg gaa cca tca ggc     1326
Thr Val Lys Lys Ala Asp Gly Thr Thr Leu Phe Trp Glu Pro Ser Gly
135                 140                 145                 150
```

```
gga ggg gta ttc tca gac ggt gtg cgc ttc ctt cat gcc aca ggg gat    1374
Gly Gly Val Phe Ser Asp Gly Val Arg Phe Leu His Ala Thr Gly Asp
            155                 160                 165 aat atg tat ggc atc cgg agc ttc aat gct ttt gat agc ggg ggt gac    1422
Asn Met Tyr Gly Ile Arg Ser Phe Asn Ala Phe Asp Ser Gly Gly Asp
        170                 175                 180 ctg ctg cgg aat tcg tcc aat cat gcc gcc cat gcg ggt gaa cag gga    1470
Leu Leu Arg Asn Ser Ser Asn His Ala Ala His Ala Gly Glu Gln Gly
                185                 190                 195 gat tcc ggt ggt ccg ctt att tgg agt acg gca gga tat gga cta tta    1518
Asp Ser Gly Gly Pro Leu Ile Trp Ser Thr Ala Gly Tyr Gly Leu Leu
    200                 205                 210 gtc gat agc gat ggc ggc tac ccc tat aca gat agc aca acc ggt caa    1566
Val Asp Ser Asp Gly Gly Tyr Pro Tyr Thr Asp Ser Thr Thr Gly Gln
215                 220                 225                 230 atg gag ttt tat tat ggt ggg acc cct cct gag gga cgt cgt tat gcg    1614
Met Glu Phe Tyr Tyr Gly Gly Thr Pro Pro Glu Gly Arg Arg Tyr Ala
                235                 240                 245 aaa caa aac gtg gaa tat tat att atg ctc gga acc ccc aag gaa att    1662
Lys Gln Asn Val Glu Tyr Tyr Ile Met Leu Gly Thr Pro Lys Glu Ile
        250                 255                 260 atg acc gac gta ggg gaa atc aca ggg aaa ccg cct atg ctg cct aag    1710
Met Thr Asp Val Gly Glu Ile Thr Gly Lys Pro Pro Met Leu Pro Lys
            265                 270                 275 tgg tcg ctt gga ttc atg aac ttt gag tgg gat acg aat caa acg gag    1758
Trp Ser Leu Gly Phe Met Asn Phe Glu Trp Asp Thr Asn Gln Thr Glu
280                 285                 290 ttt acg aat aat gtg gat acg tat cgt gcc aaa aat atc ccc ata gat    1806
Phe Thr Asn Asn Val Asp Thr Tyr Arg Ala Lys Asn Ile Pro Ile Asp
295                 300                 305                 310 gct tac gcc ttc gac tat gac tgg aaa aag tac ggg gaa acc aac tat    1854
Ala Tyr Ala Phe Asp Tyr Asp Trp Lys Lys Tyr Gly Glu Thr Asn Tyr
                315                 320                 325 ggt gaa ttc gcg tgg aat acg act aat ttc cct tct gcg tca acg act    1902
Gly Glu Phe Ala Trp Asn Thr Thr Asn Phe Pro Ser Ala Ser Thr Thr
            330                 335                 340 tct tta aag tca aca atg gat gct aaa ggc atc aaa atg atc gga att    1950
Ser Leu Lys Ser Thr Met Asp Ala Lys Gly Ile Lys Met Ile Gly Ile
        345                 350                 355 aca aaa ccc cgc atc gtt acg aag gat gct tca gcg aat gtg acg acc    1998
Thr Lys Pro Arg Ile Val Thr Lys Asp Ala Ser Ala Asn Val Thr Thr
    360                 365                 370 caa ggg acg gac gcg aca aat ggc ggt tat ttt tat cca ggc cat aac    2046
Gln Gly Thr Asp Ala Thr Asn Gly Gly Tyr Phe Tyr Pro Gly His Asn
375                 380                 385                 390 gag tat cag gat tat ttc att ccc gta act gtg cgt agt atc gat cct    2094
Glu Tyr Gln Asp Tyr Phe Ile Pro Val Thr Val Arg Ser Ile Asp Pro
                395                 400                 405 tac aat gct aac gaa cgt gct tgg ttc tgg aat cat tcc aca gat gcg    2142
Tyr Asn Ala Asn Glu Arg Ala Trp Phe Trp Asn His Ser Thr Asp Ala
            410                 415                 420 ctt aat aaa ggg atc gta ggt tgg tgg aat gac gag acg gat aaa gta    2190
Leu Asn Lys Gly Ile Val Gly Trp Trp Asn Asp Glu Thr Asp Lys Val
        425                 430                 435 tct tcg ggt gga gcg tta tat tgg ttt ggc aat ttc aca aca ggc cac    2238
Ser Ser Gly Gly Ala Leu Tyr Trp Phe Gly Asn Phe Thr Thr Gly His
    440                 445                 450 atg tct cag acg atg tac gaa ggg ggg cgg gct tac acg agt gga gcg    2286
Met Ser Gln Thr Met Tyr Glu Gly Gly Arg Ala Tyr Thr Ser Gly Ala
```

```
                455                 460                 465                 470
cag cgt gtt tgg caa acg gct aga acc ttc tac cca ggt gcc cag cgg       2334
Gln Arg Val Trp Gln Thr Ala Arg Thr Phe Tyr Pro Gly Ala Gln Arg
            475                 480                 485 tat gcg act acg ctt tgg tct ggc gat att ggc att caa tac aat aaa       2382
Tyr Ala Thr Thr Leu Trp Ser Gly Asp Ile Gly Ile Gln Tyr Asn Lys
            490                 495                 500 ggc gaa cgg atc aat tgg gct gcc ggg atg cag gag caa agg gca gtt       2430
Gly Glu Arg Ile Asn Trp Ala Ala Gly Met Gln Glu Gln Arg Ala Val
            505                 510                 515 atg cta tcc tcc gtg aac aat ggc cag gtg aaa tgg ggc atg gat acc       2478
Met Leu Ser Ser Val Asn Asn Gly Gln Val Lys Trp Gly Met Asp Thr
        520                 525                 530 ggc gga ttc aat cag cag gat ggc acg acg aac aat ccg aat ccc gat       2526
Gly Gly Phe Asn Gln Gln Asp Gly Thr Thr Asn Asn Pro Asn Pro Asp
535                 540                 545                 550 tta tac gct cgg tgg atg cag ttc agt gcc cta acg cct gtt ttc cga       2574
Leu Tyr Ala Arg Trp Met Gln Phe Ser Ala Leu Thr Pro Val Phe Arg
                555                 560                 565 gtg cat ggg aac aac cat cag cag cgc cag cca tgg tac ttc gga tcg       2622
Val His Gly Asn Asn His Gln Gln Arg Gln Pro Trp Tyr Phe Gly Ser
            570                 575                 580 act gcg gag gag gcc tcc aaa gag gca att cag ctg cgg tac tcc ctg       2670
Thr Ala Glu Glu Ala Ser Lys Glu Ala Ile Gln Leu Arg Tyr Ser Leu
            585                 590                 595 atc cct tat atg tat gcc tat gag aga agt gct tac gag aat ggg aat       2718
Ile Pro Tyr Met Tyr Ala Tyr Glu Arg Ser Ala Tyr Glu Asn Gly Asn
        600                 605                 610 ggg ctc gtt cgg cca ttg atg caa gcc tat cca aca gat gcg gcc gtc       2766
Gly Leu Val Arg Pro Leu Met Gln Ala Tyr Pro Thr Asp Ala Ala Val
615                 620                 625                 630 aaa aat tac acg gat gct tgg atg ttt ggt gac tgg ctg ctg gct gca       2814
Lys Asn Tyr Thr Asp Ala Trp Met Phe Gly Asp Trp Leu Leu Ala Ala
                635                 640                 645 cct gtg gta gat aaa cag cag acg agt aag gat atc tat tta ccg tct       2862
Pro Val Val Asp Lys Gln Gln Thr Ser Lys Asp Ile Tyr Leu Pro Ser
            650                 655                 660 ggg tca tgg att gac tat gcg cga ggc aat gca ata act ggc ggt caa       2910
Gly Ser Trp Ile Asp Tyr Ala Arg Gly Asn Ala Ile Thr Gly Gly Gln
            665                 670                 675 acc atc cga tat tcg gtt aat ccg gac acg ttg aca gac atg cct ctc       2958
Thr Ile Arg Tyr Ser Val Asn Pro Asp Thr Leu Thr Asp Met Pro Leu
        680                 685                 690 ttt att aaa aaa ggt gcc att att cca aca cag aaa gtg cag gat tac       3006
Phe Ile Lys Lys Gly Ala Ile Ile Pro Thr Gln Lys Val Gln Asp Tyr
695                 700                 705                 710 gta ggg cag gct tcc gtc act tcc gtt gat gtg gat gtg ttt ccg gat       3054
Val Gly Gln Ala Ser Val Thr Ser Val Asp Val Asp Val Phe Pro Asp
                715                 720                 725 acg acg cag tcg agt ttc acg tac tac gat gat gat ggc gcc agt tat       3102
Thr Thr Gln Ser Ser Phe Thr Tyr Tyr Asp Asp Asp Gly Ala Ser Tyr
            730                 735                 740 aac tat gag agc ggc act tat ttt aag caa aat atg act gct cag gat       3150
Asn Tyr Glu Ser Gly Thr Tyr Phe Lys Gln Asn Met Thr Ala Gln Asp
        745                 750                 755 aat ggg tca ggc tcg tta agt ttt act tta gga gca aag agt ggc agt       3198
Asn Gly Ser Gly Ser Leu Ser Phe Thr Leu Gly Ala Lys Ser Gly Ser
            760                 765                 770 tac acg ccg gct ctc caa tcc tat atc gtt aag ctg cac ggt tct gct       3246
```

```
Tyr Thr Pro Ala Leu Gln Ser Tyr Ile Val Lys Leu His Gly Ser Ala
775                 780                 785                 790 gga act tct gtt acg aat aac agc gca gct atg aca tct tat gca agc    3294
Gly Thr Ser Val Thr Asn Asn Ser Ala Ala Met Thr Ser Tyr Ala Ser
                795                 800                 805 ttg gaa gca tta aaa gct gct gct ggg gaa ggc tgg gcg act ggg aag    3342
Leu Glu Ala Leu Lys Ala Ala Ala Gly Glu Gly Trp Ala Thr Gly Lys
            810                 815                 820 gac att tat ggg gat gtc acc tat gtg aaa gtg acg gca ggt aca gct    3390
Asp Ile Tyr Gly Asp Val Thr Tyr Val Lys Val Thr Ala Gly Thr Ala
        825                 830                 835 tct tct aaa tct att gct gtt aca ggt gtt gct gcc gtg agc gca act    3438
Ser Ser Lys Ser Ile Ala Val Thr Gly Val Ala Ala Val Ser Ala Thr
    840                 845                 850 act tcg caa tac gaa gct gag gat gca tcg ctt tct ggc aat tcg gtt    3486
Thr Ser Gln Tyr Glu Ala Glu Asp Ala Ser Leu Ser Gly Asn Ser Val
855                 860                 865                 870 gct gca aag gcg tcc ata aac acg aat cat acc gga tat acg gga act    3534
Ala Ala Lys Ala Ser Ile Asn Thr Asn His Thr Gly Tyr Thr Gly Thr
                875                 880                 885 gga ttt gta gat ggt ttg ggg aat gat ggc gct ggt gtc acc ttc tat    3582
Gly Phe Val Asp Gly Leu Gly Asn Asp Gly Ala Gly Val Thr Phe Tyr
            890                 895                 900 cca aag gtg aaa act ggc ggt gac tac aat gtc tcc ttg cgt tat gcg    3630
Pro Lys Val Lys Thr Gly Gly Asp Tyr Asn Val Ser Leu Arg Tyr Ala
        905                 910                 915 aat gct tca ggc acg gct aag tca gtc agt att ttt gtt aat gga aaa    3678
Asn Ala Ser Gly Thr Ala Lys Ser Val Ser Ile Phe Val Asn Gly Lys
    920                 925                 930 aga gtg aag tcc acc tcg ctc gct aat ctc gca aat tgg gac act tgg    3726
Arg Val Lys Ser Thr Ser Leu Ala Asn Leu Ala Asn Trp Asp Thr Trp
935                 940                 945                 950 tct aca caa tct gag aca ctg ccg ttg acg gca ggt gtg aat gtt gtg    3774
Ser Thr Gln Ser Glu Thr Leu Pro Leu Thr Ala Gly Val Asn Val Val
                955                 960                 965 acc tat aaa tat tac tcc gat gcg gga gat aca ggc aat gtt aac atc    3822
Thr Tyr Lys Tyr Tyr Ser Asp Ala Gly Asp Thr Gly Asn Val Asn Ile
            970                 975                 980 gac aac atc acg gta cct ttt gcg cca att atc ggt aag tat gaa gca    3870
Asp Asn Ile Thr Val Pro Phe Ala Pro Ile Ile Gly Lys Tyr Glu Ala
        985                 990                 995 gag agt gct gag ctt tct ggt ggc agc tca ttg aac acg aac cat        3915
Glu Ser Ala Glu Leu Ser Gly Gly Ser Ser Leu Asn Thr Asn His
    1000                1005                1010 tgg tac tac agt ggt acg gct ttt gta gac ggt ttg agt gct gta        3960
Trp Tyr Tyr Ser Gly Thr Ala Phe Val Asp Gly Leu Ser Ala Val
    1015                1020                1025 ggc gcg cag gtg aaa tac aac gtg aat gtc cct agc gca gga agt        4005
Gly Ala Gln Val Lys Tyr Asn Val Asn Val Pro Ser Ala Gly Ser
    1030                1035                1040 tat cag gta gcg ctg cga tat gcg aat ggc agt gca gcg acg aaa        4050
Tyr Gln Val Ala Leu Arg Tyr Ala Asn Gly Ser Ala Ala Thr Lys
    1045                1050                1055 acg ttg agt act tat atc aat gga gcc aag ctg ggg caa acc agt        4095
Thr Leu Ser Thr Tyr Ile Asn Gly Ala Lys Leu Gly Gln Thr Ser
    1060                1065                1070 ttt acg agt cct ggt acg aat tgg aat gtt tgg cag gat aat gtg        4140
Phe Thr Ser Pro Gly Thr Asn Trp Asn Val Trp Gln Asp Asn Val
    1075                1080                1085
```

```
caa acg gtg acg tta aat gca ggg gca aac acg att gcg ttt aaa       4185
Gln Thr Val Thr Leu Asn Ala Gly Ala Asn Thr Ile Ala Phe Lys
    1090                1095                1100 tac gac gcc gct gac agc ggg aac atc aac gta gat cgt ctg ctt       4230
Tyr Asp Ala Ala Asp Ser Gly Asn Ile Asn Val Asp Arg Leu Leu
1105                1110                1115 ctt tca act tcg gca gcg gga acg ccg gtt tct gag cag aac ctg       4275
Leu Ser Thr Ser Ala Ala Gly Thr Pro Val Ser Glu Gln Asn Leu
    1120                1125                1130 cta gac aat ccc ggt ttc gag cgt gac acg agt caa acc aat aac       4320
Leu Asp Asn Pro Gly Phe Glu Arg Asp Thr Ser Gln Thr Asn Asn
1135                1140                1145 tgg att gag tgg cat cca ggc acg caa gct gtt gct ttt ggc gtt       4365
Trp Ile Glu Trp His Pro Gly Thr Gln Ala Val Ala Phe Gly Val
    1150                1155                1160 gat agc ggc tca acc acc aat ccg ccg gaa tcc ccg tgg tcg ggt       4410
Asp Ser Gly Ser Thr Thr Asn Pro Pro Glu Ser Pro Trp Ser Gly
1165                1170                1175 gat aag cgt gcc tac ttc ttt gca gca ggt gcc tat caa caa agc       4455
Asp Lys Arg Ala Tyr Phe Phe Ala Ala Gly Ala Tyr Gln Gln Ser
    1180                1185                1190 atc cat caa acc att agt gtt cct gtt aat aat gta aaa tac aaa       4500
Ile His Gln Thr Ile Ser Val Pro Val Asn Asn Val Lys Tyr Lys
1195                1200                1205 ttt gaa gcc tgg gtc cgc atg aag aat acg acg ccg acg acg gca       4545
Phe Glu Ala Trp Val Arg Met Lys Asn Thr Thr Pro Thr Thr Ala
    1210                1215                1220 aga gcc gaa att caa aac tat ggc gga tca gcc att tat gcg aac       4590
Arg Ala Glu Ile Gln Asn Tyr Gly Gly Ser Ala Ile Tyr Ala Asn
1225                1230                1235 ata agt aac agc ggt gtt tgg aaa tat atc agc gta agt gat att       4635
Ile Ser Asn Ser Gly Val Trp Lys Tyr Ile Ser Val Ser Asp Ile
    1240                1245                1250 atg gtg acc aat ggt cag ata gat gtt gga ttt tac gtg gat tca       4680
Met Val Thr Asn Gly Gln Ile Asp Val Gly Phe Tyr Val Asp Ser
1255                1260                1265 cct ggt gga act acg ctt cac att gat gat gtg cgc gta acc aaa       4725
Pro Gly Gly Thr Thr Leu His Ile Asp Asp Val Arg Val Thr Lys
    1270                1275                1280 caa taaacaaaca accagctctc ccgttaatgg gagggctggt tgtttgttat        4778
Gln gataatccat ctatttagag tggattaaac gttttgaagt gcttgctgaa cttcttgcac    4838
aatggataac gccgcggtgc gggcacttga gaaagcacgt tctgcaagct ctcccttacc   4898
tgtacagccg tctccgcaga agtagaaagg aacgttttcc acgcgtatcg gcagcagatt   4958
attggaagca atgttttca cgctggaaac catcgctttc ttggaaaccc gtttcacggc    5018
tgtgacatcg cgccagcctg gataatgttt atcaaataag gcttccattt ggaggttctt   5078
ctcttccagg tacgctttgc gctgctcctc gttatcaaag cggtcgctta agtatgcgat   5138
accttgcagc agctgcccgc cttctggtac tagtgtgtga tc                     5180

<210> SEQ ID NO 22
<211> LENGTH: 3869
<212> TYPE: DNA
<213> ORGANISM: Bacillus globisporus
<220> FEATURE:
<221> NAME/KEY: CDS
<222> LOCATION: (241)..(3522)

<400> SEQUENCE: 22
```

-continued

```
tcatcgctac tggcaatcgg attcaaacaa atggctgcag ctcgcacaga cgattgtgga     60
aagggaatat ctgatttaac catacggcgg tcgcgattga ttgaatagga ttcgtggccg    120
cctaatattg aaaggggga tgcgtggagc agcgcatgca cggcgaggaa taactgttgt     180
tggagcctct aagtcattca tgtttagcaa acaaatttcg gtacgaaagg ggaaatgttt    240
```

| | | | | | | | | | | | | | | | | |
|---|---|---|---|---|---|---|---|---|---|---|---|---|---|---|---|---|
| atg | tat | gta | agg | aat | cta | aca | ggt | tca | ttc | cga | ttt | tct | ctc | tct | ttt | 288 |
| Met | Tyr | Val | Arg | Asn | Leu | Thr | Gly | Ser | Phe | Arg | Phe | Ser | Leu | Ser | Phe | |
| 1 | | | | 5 | | | | | 10 | | | | | 15 | | |

| ttg | ctc | tgt | ttc | tgt | ctc | ttc | gtc | ccc | tct | att | tat | gcc | att | gat | ggt | 336 |
|---|---|---|---|---|---|---|---|---|---|---|---|---|---|---|---|---|
| Leu | Leu | Cys | Phe | Cys | Leu | Phe | Val | Pro | Ser | Ile | Tyr | Ala | Ile | Asp | Gly | |
| | | | 20 | | | | | 25 | | | | | 30 | | | |

| gtt | tat | cat | gcg | cca | tac | gga | atc | gat | gat | ctg | tac | gag | att | cag | gcg | 384 |
|---|---|---|---|---|---|---|---|---|---|---|---|---|---|---|---|---|
| Val | Tyr | His | Ala | Pro | Tyr | Gly | Ile | Asp | Asp | Leu | Tyr | Glu | Ile | Gln | Ala | |
| | | 35 | | | | | 40 | | | | | 45 | | | | |

| acg | gag | cgg | agt | cca | aga | gat | ccc | gtt | gca | ggc | gat | act | gtg | tat | atc | 432 |
|---|---|---|---|---|---|---|---|---|---|---|---|---|---|---|---|---|
| Thr | Glu | Arg | Ser | Pro | Arg | Asp | Pro | Val | Ala | Gly | Asp | Thr | Val | Tyr | Ile | |
| | 50 | | | | | 55 | | | | | 60 | | | | | |

| aag | ata | aca | acg | tgg | ccc | att | gaa | tca | gga | caa | acg | gct | tgg | gtg | acc | 480 |
|---|---|---|---|---|---|---|---|---|---|---|---|---|---|---|---|---|
| Lys | Ile | Thr | Thr | Trp | Pro | Ile | Glu | Ser | Gly | Gln | Thr | Ala | Trp | Val | Thr | |
| 65 | | | | | 70 | | | | | 75 | | | | | 80 | |

| tgg | acg | aaa | aac | ggt | gtc | aat | caa | gct | gct | gtc | gga | gca | gca | ttc | aaa | 528 |
|---|---|---|---|---|---|---|---|---|---|---|---|---|---|---|---|---|
| Trp | Thr | Lys | Asn | Gly | Val | Asn | Gln | Ala | Ala | Val | Gly | Ala | Ala | Phe | Lys | |
| | | | | 85 | | | | | 90 | | | | | 95 | | |

| tac | aac | agc | ggc | aac | aac | act | tac | tgg | gaa | gcg | aac | ctt | ggc | act | ttt | 576 |
|---|---|---|---|---|---|---|---|---|---|---|---|---|---|---|---|---|
| Tyr | Asn | Ser | Gly | Asn | Asn | Thr | Tyr | Trp | Glu | Ala | Asn | Leu | Gly | Thr | Phe | |
| | | | 100 | | | | | 105 | | | | | 110 | | | |

| gca | aaa | ggg | gac | gtg | atc | agt | tat | acc | gtt | cat | ggc | aac | aag | gat | ggc | 624 |
|---|---|---|---|---|---|---|---|---|---|---|---|---|---|---|---|---|
| Ala | Lys | Gly | Asp | Val | Ile | Ser | Tyr | Thr | Val | His | Gly | Asn | Lys | Asp | Gly | |
| | | 115 | | | | | 120 | | | | | 125 | | | | |

| gcg | aat | gag | aag | gtt | atc | ggt | cct | ttt | act | ttt | acc | gta | acg | gga | tgg | 672 |
|---|---|---|---|---|---|---|---|---|---|---|---|---|---|---|---|---|
| Ala | Asn | Glu | Lys | Val | Ile | Gly | Pro | Phe | Thr | Phe | Thr | Val | Thr | Gly | Trp | |
| | 130 | | | | | 135 | | | | | 140 | | | | | |

| gaa | tcc | gtt | agc | agt | atc | agc | tct | att | acg | gat | aac | acg | aac | cgt | gtt | 720 |
|---|---|---|---|---|---|---|---|---|---|---|---|---|---|---|---|---|
| Glu | Ser | Val | Ser | Ser | Ile | Ser | Ser | Ile | Thr | Asp | Asn | Thr | Asn | Arg | Val | |
| 145 | | | | | 150 | | | | | 155 | | | | | 160 | |

| gtg | ctg | aat | gcg | gtg | ccg | aat | aca | ggc | aca | ttg | aag | cca | aag | atc | aac | 768 |
|---|---|---|---|---|---|---|---|---|---|---|---|---|---|---|---|---|
| Val | Leu | Asn | Ala | Val | Pro | Asn | Thr | Gly | Thr | Leu | Lys | Pro | Lys | Ile | Asn | |
| | | | | 165 | | | | | 170 | | | | | 175 | | |

| ctt | tcc | ttt | acg | gcg | gat | gat | gtc | ctc | cgc | gta | cag | gtt | tct | cca | acc | 816 |
|---|---|---|---|---|---|---|---|---|---|---|---|---|---|---|---|---|
| Leu | Ser | Phe | Thr | Ala | Asp | Asp | Val | Leu | Arg | Val | Gln | Val | Ser | Pro | Thr | |
| | | | 180 | | | | | 185 | | | | | 190 | | | |

| gga | aca | gga | acg | tta | agc | agt | gga | ctt | agt | aat | tac | aca | gtt | tca | gat | 864 |
|---|---|---|---|---|---|---|---|---|---|---|---|---|---|---|---|---|
| Gly | Thr | Gly | Thr | Leu | Ser | Ser | Gly | Leu | Ser | Asn | Tyr | Thr | Val | Ser | Asp | |
| | | 195 | | | | | 200 | | | | | 205 | | | | |

| acc | gcc | tca | acc | act | tgg | ctt | aca | act | tcc | aag | ctg | aag | gtg | aag | gtg | 912 |
|---|---|---|---|---|---|---|---|---|---|---|---|---|---|---|---|---|
| Thr | Ala | Ser | Thr | Thr | Trp | Leu | Thr | Thr | Ser | Lys | Leu | Lys | Val | Lys | Val | |
| | 210 | | | | | 215 | | | | | 220 | | | | | |

| gat | aag | aat | cca | ttc | aaa | ctt | agt | gtg | tat | aag | cct | gat | gga | acg | acg | 960 |
|---|---|---|---|---|---|---|---|---|---|---|---|---|---|---|---|---|
| Asp | Lys | Asn | Pro | Phe | Lys | Leu | Ser | Val | Tyr | Lys | Pro | Asp | Gly | Thr | Thr | |
| 225 | | | | | 230 | | | | | 235 | | | | | 240 | |

| ttg | att | gcc | cgt | caa | tat | gac | agc | act | acg | aat | cgt | aac | att | gcc | tgg | 1008 |
|---|---|---|---|---|---|---|---|---|---|---|---|---|---|---|---|---|
| Leu | Ile | Ala | Arg | Gln | Tyr | Asp | Ser | Thr | Thr | Asn | Arg | Asn | Ile | Ala | Trp | |
| | | | 245 | | | | | 250 | | | | | 255 | | | |

| tta | acc | aat | ggc | agt | aca | atc | atc | gac | aag | gta | gaa | gat | cat | ttt | tat | 1056 |
|---|---|---|---|---|---|---|---|---|---|---|---|---|---|---|---|---|
| Leu | Thr | Asn | Gly | Ser | Thr | Ile | Ile | Asp | Lys | Val | Glu | Asp | His | Phe | Tyr | |
| | | 260 | | | | | 265 | | | | | 270 | | | | |

| tca | ccg | gct | tcc | gag | gag | ttt | ttt | ggc | ttt | gga | gag | cat | tac | aac | aac | 1104 |
|---|---|---|---|---|---|---|---|---|---|---|---|---|---|---|---|---|
| Ser | Pro | Ala | Ser | Glu | Glu | Phe | Phe | Gly | Phe | Gly | Glu | His | Tyr | Asn | Asn | |

-continued

|     |     | 275 |     |     |     | 280 |     |     |     | 285 |     |     |     |      |
|-----|-----|-----|-----|-----|-----|-----|-----|-----|-----|-----|-----|-----|-----|------|
| ttc | cgt | aaa | cgc | gga | aat | gat | gtg | gac | acc | tat | gtg | ttc | aac cag tat | 1152 |
| Phe | Arg | Lys | Arg | Gly | Asn | Asp | Val | Asp | Thr | Tyr | Val | Phe | Asn Gln Tyr | |
| | 290 | | | | 295 | | | | 300 | | | | | |

```
aag aat caa aat gac cgc acc tac atg gca att cct ttt atg ctt aac      1200
Lys Asn Gln Asn Asp Arg Thr Tyr Met Ala Ile Pro Phe Met Leu Asn
305                 310                 315                 320 agc agc ggt tat ggc att ttc gta aat tca acg tat tat tcc aaa ttt      1248
Ser Ser Gly Tyr Gly Ile Phe Val Asn Ser Thr Tyr Tyr Ser Lys Phe
            325                 330                 335 cgg ttg gca acc gaa cgc acc gat atg ttc agc ttt acg gct gat aca      1296
Arg Leu Ala Thr Glu Arg Thr Asp Met Phe Ser Phe Thr Ala Asp Thr
        340                 345                 350 ggg ggt agt gcc gcc tcg atg ctg gat tat tat ttc att tac ggt aat      1344
Gly Gly Ser Ala Ala Ser Met Leu Asp Tyr Tyr Phe Ile Tyr Gly Asn
    355                 360                 365 gat ttg aaa aat gtg gtg agt aac tac gct aac att acc ggt aag cca      1392
Asp Leu Lys Asn Val Val Ser Asn Tyr Ala Asn Ile Thr Gly Lys Pro
370                 375                 380 aca gcg ctg ccg aaa tgg gct ttc ggg tta tgg atg tca gct aac gag      1440
Thr Ala Leu Pro Lys Trp Ala Phe Gly Leu Trp Met Ser Ala Asn Glu
385                 390                 395                 400 tgg gat cgt caa acc aag gtg aat aca gcc att aat aac gcg aac tcc      1488
Trp Asp Arg Gln Thr Lys Val Asn Thr Ala Ile Asn Asn Ala Asn Ser
            405                 410                 415 aat aat att ccg gct aca gcg gtt gtg ctc gaa cag tgg agt gat gag      1536
Asn Asn Ile Pro Ala Thr Ala Val Val Leu Glu Gln Trp Ser Asp Glu
        420                 425                 430 aac acg ttt tat att ttc aat gat gcc acc tat acc ccg aaa acg ggc      1584
Asn Thr Phe Tyr Ile Phe Asn Asp Ala Thr Tyr Thr Pro Lys Thr Gly
    435                 440                 445 agt gct gcg cat gcc tat acc gat ttc act ttc ccg aca tct ggg aga      1632
Ser Ala Ala His Ala Tyr Thr Asp Phe Thr Phe Pro Thr Ser Gly Arg
450                 455                 460 tgg acg gat cca aaa gcg atg gca gac aat gtg cat aac aat ggg atg      1680
Trp Thr Asp Pro Lys Ala Met Ala Asp Asn Val His Asn Asn Gly Met
465                 470                 475                 480 aag ctg gtg ctt tgg cag gtc cct att cag aaa tgg act tca acg ccc      1728
Lys Leu Val Leu Trp Gln Val Pro Ile Gln Lys Trp Thr Ser Thr Pro
            485                 490                 495 tat acc cag aaa gat aat gat gaa gcc tat atg acg gct cag aat tat      1776
Tyr Thr Gln Lys Asp Asn Asp Glu Ala Tyr Met Thr Ala Gln Asn Tyr
        500                 505                 510 gca gtt ggc aac ggt agc gga ggc cag tac agg ata cct tca gga caa      1824
Ala Val Gly Asn Gly Ser Gly Gly Gln Tyr Arg Ile Pro Ser Gly Gln
    515                 520                 525 tgg ttc gag aac agt ttg ctg ctt gat ttt acg aat acg gcc gcc aaa      1872
Trp Phe Glu Asn Ser Leu Leu Leu Asp Phe Thr Asn Thr Ala Ala Lys
530                 535                 540 aac tgg tgg atg tct aaa cgc gct tat ctg ttt gat ggt gtg ggt atc      1920
Asn Trp Trp Met Ser Lys Arg Ala Tyr Leu Phe Asp Gly Val Gly Ile
545                 550                 555                 560 gac ggc ttc aaa aca gat ggc ggt gaa atg gta tgg ggt cgc tca aat      1968
Asp Gly Phe Lys Thr Asp Gly Gly Glu Met Val Trp Gly Arg Ser Asn
            565                 570                 575 act ttc tca aac ggt aag aaa ggc aat gaa atg cgc aat caa tac ccg      2016
Thr Phe Ser Asn Gly Lys Lys Gly Asn Glu Met Arg Asn Gln Tyr Pro
        580                 585                 590 aat gag tat gtg aaa gcc tat aac gag tac gcg cgc tcg aag aaa gcc      2064
```

```
                Asn Glu Tyr Val Lys Ala Tyr Asn Glu Tyr Ala Arg Ser Lys Lys Ala
                        595                 600                 605 gat gcg gtc tcc ttt agc cgt tcc ggc acg caa ggc gca cag gcg aat            2112
Asp Ala Val Ser Phe Ser Arg Ser Gly Thr Gln Gly Ala Gln Ala Asn
610                 615                 620 cag att ttc tgg tcc ggt gac caa gag tcg acg ttt ggt gct ttt caa            2160
Gln Ile Phe Trp Ser Gly Asp Gln Glu Ser Thr Phe Gly Ala Phe Gln
625                 630                 635                 640 caa gct gtg aat gca ggg ctt acg gca agt atg tct ggc gtt cct tat            2208
Gln Ala Val Asn Ala Gly Leu Thr Ala Ser Met Ser Gly Val Pro Tyr
                645                 650                 655 tgg agc tgg gat atg gca ggc ttt aca ggc act tat cca acg gct gag            2256
Trp Ser Trp Asp Met Ala Gly Phe Thr Gly Thr Tyr Pro Thr Ala Glu
                660                 665                 670 ttg tac aaa cgt gct act gaa atg gct gct ttt gca ccg gtc atg cag            2304
Leu Tyr Lys Arg Ala Thr Glu Met Ala Ala Phe Ala Pro Val Met Gln
                675                 680                 685 ttt cat tcc gag tct aac ggc agc tct ggt atc aac gag gaa cgt tct            2352
Phe His Ser Glu Ser Asn Gly Ser Ser Gly Ile Asn Glu Glu Arg Ser
        690                 695                 700 cca tgg aac gca caa gcg cgt aca ggc gac aat acg atc att agt cat            2400
Pro Trp Asn Ala Gln Ala Arg Thr Gly Asp Asn Thr Ile Ile Ser His
705                 710                 715                 720 ttt gcc aaa tat acg aat acg cgc atg aat ttg ctt cct tat att tat            2448
Phe Ala Lys Tyr Thr Asn Thr Arg Met Asn Leu Leu Pro Tyr Ile Tyr
                725                 730                 735 agc gaa gcg aag atg gct agt gat act ggc gtt ccc atg atg cgc gcc            2496
Ser Glu Ala Lys Met Ala Ser Asp Thr Gly Val Pro Met Met Arg Ala
                740                 745                 750 atg gcg ctt gaa tat ccg aag gac acg aac acg tac ggt ttg aca caa            2544
Met Ala Leu Glu Tyr Pro Lys Asp Thr Asn Thr Tyr Gly Leu Thr Gln
                755                 760                 765 cag tat atg ttc gga ggt aat tta ctt att gct cct gtt atg aat cag            2592
Gln Tyr Met Phe Gly Gly Asn Leu Leu Ile Ala Pro Val Met Asn Gln
        770                 775                 780 gga gaa aca aac aag agt att tat ctt ccg cag ggg gat tgg atc gat            2640
Gly Glu Thr Asn Lys Ser Ile Tyr Leu Pro Gln Gly Asp Trp Ile Asp
785                 790                 795                 800 ttc tgg ttc ggt gct cag cgt cct ggc ggt cga aca atc agc tac acg            2688
Phe Trp Phe Gly Ala Gln Arg Pro Gly Gly Arg Thr Ile Ser Tyr Thr
                805                 810                 815 gcc ggc atc gat gat cta ccg gtt ttt gtg aag ttt ggc agt att ctt            2736
Ala Gly Ile Asp Asp Leu Pro Val Phe Val Lys Phe Gly Ser Ile Leu
                820                 825                 830 ccg atg aat ttg aac gcg caa tat caa gtg ggc ggg acc att ggc aac            2784
Pro Met Asn Leu Asn Ala Gln Tyr Gln Val Gly Gly Thr Ile Gly Asn
        835                 840                 845 agc ttg acg agc tac acg aat ctc gcg ttc cgc att tat ccg ctt ggg            2832
Ser Leu Thr Ser Tyr Thr Asn Leu Ala Phe Arg Ile Tyr Pro Leu Gly
        850                 855                 860 aca aca acg tac gac tgg aat gat gat att ggc ggt tcg gtg aaa acc            2880
Thr Thr Thr Tyr Asp Trp Asn Asp Asp Ile Gly Gly Ser Val Lys Thr
865                 870                 875                 880 ata act tct aca gag caa tat ggg ttg aat aaa gaa acc gtg act gtt            2928
Ile Thr Ser Thr Glu Gln Tyr Gly Leu Asn Lys Glu Thr Val Thr Val
                885                 890                 895 cca gcg att aat tct acc aag aca ttg caa gtg ttt acg act aag cct            2976
Pro Ala Ile Asn Ser Thr Lys Thr Leu Gln Val Phe Thr Thr Lys Pro
                900                 905                 910
```

```
tcc tct gta acg gtg ggt ggt tct gtg atg aca gag tac agt act tta      3024
Ser Ser Val Thr Val Gly Gly Ser Val Met Thr Glu Tyr Ser Thr Leu
            915                 920                 925 act gcc cta acg gga gcg tcg aca ggc tgg tac tat gat act gta cag      3072
Thr Ala Leu Thr Gly Ala Ser Thr Gly Trp Tyr Tyr Asp Thr Val Gln
        930                 935                 940 aaa ttc act tac gtc aag ctt ggt tca agt gca tct gct caa tcc gtt      3120
Lys Phe Thr Tyr Val Lys Leu Gly Ser Ser Ala Ser Ala Gln Ser Val
945                 950                 955                 960 gtg cta aat ggc gtt aat aag gtg gaa tat gaa gca gaa ttc ggc gtg      3168
Val Leu Asn Gly Val Asn Lys Val Glu Tyr Glu Ala Glu Phe Gly Val
                965                 970                 975 caa agc ggc gtt tca acg aac acg aac cat gca ggt tat act ggt aca      3216
Gln Ser Gly Val Ser Thr Asn Thr Asn His Ala Gly Tyr Thr Gly Thr
            980                 985                 990 gga ttt gtg gac ggc ttt gag act  ctt gga gac aat gtt  gct ttt gat    3264
Gly Phe Val Asp Gly Phe Glu Thr  Leu Gly Asp Asn Val  Ala Phe Asp
            995                 1000                1005 gtt tcc  gtc aaa gcc gca ggt  act tat acg atg aag  gtt cgg tat       3309
Val Ser  Val Lys Ala Ala Gly  Thr Tyr Thr Met Lys  Val Arg Tyr
    1010                1015                 1020 tca tcc  ggt gca ggc aat ggc  tca aga gcc atc tat  gtg aat aac       3354
Ser Ser  Gly Ala Gly Asn Gly  Ser Arg Ala Ile Tyr  Val Asn Asn
    1025                1030                 1035 acc aaa  gtg acg gac ctt gcc  ttg ccg caa aca aca  agc tgg gat       3399
Thr Lys  Val Thr Asp Leu Ala  Leu Pro Gln Thr Thr  Ser Trp Asp
    1040                1045                 1050 aca tgg  ggg act gct acg ttt  agc gtc tcg ctg agt  aca ggt ctc       3444
Thr Trp  Gly Thr Ala Thr Phe  Ser Val Ser Leu Ser  Thr Gly Leu
    1055                1060                 1065 aac acg  gtg aaa gtc agc tat  gat ggt acc agt tca  ctt ggc att       3489
Asn Thr  Val Lys Val Ser Tyr  Asp Gly Thr Ser Ser  Leu Gly Ile
    1070                1075                 1080 aat ttc  gat aac atc gcg att  gta gag caa taa aaggtcggga             3532
Asn Phe  Asp Asn Ile Ala Ile  Val Glu Gln
    1085                1090 gggcaagtcc ctcccttaat ttctaatcga aagggagtat ccttgatgcg tccaccaaac    3592
aaagaaattc cacgtattct tgcttttttt acagcgttta cgttgtttgg ttcaaccctt    3652
gccttgcttc ctgctccgcc tgcgcatgcc tatgtcagca gcctagggga aaatctcatt    3712
tcttcgagtg tcaccggaga taccttgacg ctaactgttg ataacggtgc gccgagtgat    3772
gacctcttga ttgttcaagc ggtgcaaaac ggtattttga aggtggatta tcgtccaaat    3832
agcataacgc cgagcgcgaa gacgccgatg ctggatc                             3869

<210> SEQ ID NO 23
<211> LENGTH: 4991
<212> TYPE: DNA
<213> ORGANISM: Bacillus globisporus
<220> FEATURE:
<221> NAME/KEY: CDS
<222> LOCATION: (466)..(4326)

<400> SEQUENCE: 23
ggtaccggct tgtcgacgg cttcgatgcg gcaggcgatg cagtgacctt cgacgtatcc      60
gtcaaagcgg ccggcacgta tgcgctcaag gtccggtacg cttccgctgg tggcaacgct    120
tcacgcgcta tctatgtcaa caacgccaag gtgaccgatc tggcgcttcc ggcaacggcc    180
aactgggaca cctgggggac ggcaaccgtc aacgtagcct taaacgccgg ctacaactcg    240
```

-continued

| | |
|---|---|
| atcaaggtca gctacgacaa caccaatacg ctcggcatta atctcgataa cattgcgatc | 300 |
| gtggagcatt gacagcagga atcttcgcga ggaatgagtt agcgaagagt tcatgcaggc | 360 |
| agagggtta cccataattg taaagcccgg cgcagccagg caccaagtat gcccgggagg | 420 |
| gccgccggcc ctccctttat ttcaatgatg aaaggcggca tcgat atg ggt cta tgg<br>                           Met Gly Leu Trp<br>                              1 | 477 |
| aac aaa cga gtc act cgc atc ctc tcc gta ctc gca gca agc gcg ctg<br>Asn Lys Arg Val Thr Arg Ile Leu Ser Val Leu Ala Ala Ser Ala Leu<br>5         10         15         20 | 525 |
| atc ggc tct acc gta cct tct cta gcc cca cct ccc gct caa gcc cat<br>Ile Gly Ser Thr Val Pro Ser Leu Ala Pro Pro Pro Ala Gln Ala His<br>           25         30         35 | 573 |
| gtg agc gcg ctg ggc aac ctg ctt tcc tcg gcg gtg acc ggg gat acg<br>Val Ser Ala Leu Gly Asn Leu Leu Ser Ser Ala Val Thr Gly Asp Thr<br>    40          45         50 | 621 |
| ctc acg ctg acg atc gat aac ggc gcg gaa ccg aat gac gat att cta<br>Leu Thr Leu Thr Ile Asp Asn Gly Ala Glu Pro Asn Asp Asp Ile Leu<br>    55          60         65 | 669 |
| gtt ctg caa gca gtc cag aac ggt att ctg aag gtg gac tac cgg ccg<br>Val Leu Gln Ala Val Gln Asn Gly Ile Leu Lys Val Asp Tyr Arg Pro<br>70         75         80 | 717 |
| aac ggt gta gct cca agc gcg gat acg ccg atg ctg gat ccc aat aaa<br>Asn Gly Val Ala Pro Ser Ala Asp Thr Pro Met Leu Asp Pro Asn Lys<br>85         90         95         100 | 765 |
| acc tgg ccg tcc ata ggc gcc gtt atc aat aca gcc tct aat ccg atg<br>Thr Trp Pro Ser Ile Gly Ala Val Ile Asn Thr Ala Ser Asn Pro Met<br>         105        110        115 | 813 |
| acg atc aca acg ccg gcg atg aag att gag att gcc aaa aat ccg gtg<br>Thr Ile Thr Thr Pro Ala Met Lys Ile Glu Ile Ala Lys Asn Pro Val<br>      120         125        130 | 861 |
| cgc ctg acc gtg aaa aaa ccg gac ggc acc gct ctg tta tgg gaa ccc<br>Arg Leu Thr Val Lys Lys Pro Asp Gly Thr Ala Leu Leu Trp Glu Pro<br>      135         140        145 | 909 |
| ccg acc ggc ggc gtc ttc tcg gac ggc gtc cgt ttc ttg cac ggg acg<br>Pro Thr Gly Gly Val Phe Ser Asp Gly Val Arg Phe Leu His Gly Thr<br>150         155         160 | 957 |
| ggc gac aat atg tac ggc atc cgc agc ttc aat gct ttt gac agc ggc<br>Gly Asp Asn Met Tyr Gly Ile Arg Ser Phe Asn Ala Phe Asp Ser Gly<br>165         170        175        180 | 1005 |
| ggg gat ctg ctg cgc aac agc tcc acc caa gcc gcc cgt gca ggc gac<br>Gly Asp Leu Leu Arg Asn Ser Ser Thr Gln Ala Ala Arg Ala Gly Asp<br>      185         190        195 | 1053 |
| cag ggc aac tcc ggc ggc ccg ctg atc tgg agc aca gcc ggg tac ggg<br>Gln Gly Asn Ser Gly Gly Pro Leu Ile Trp Ser Thr Ala Gly Tyr Gly<br>      200         205        210 | 1101 |
| gtg ctc gtt gac agc gac ggt ggg tat ccg ttc acg gac gag gct acc<br>Val Leu Val Asp Ser Asp Gly Gly Tyr Pro Phe Thr Asp Glu Ala Thr<br>    215         220        225 | 1149 |
| ggc aag ctg gag ttc tat tac ggc ggc acg cct ccg gaa ggc cgg cgc<br>Gly Lys Leu Glu Phe Tyr Tyr Gly Gly Thr Pro Pro Glu Gly Arg Arg<br>    230         235        240 | 1197 |
| tat acg aag cag gat gtg gag tac tac atc atg ctc ggc acg ccg aaa<br>Tyr Thr Lys Gln Asp Val Glu Tyr Tyr Ile Met Leu Gly Thr Pro Lys<br>245         250        255        260 | 1245 |
| gag atc atg tcc ggc gtc ggg gaa att acg ggc aaa ccg ccg atg ctg<br>Glu Ile Met Ser Gly Val Gly Glu Ile Thr Gly Lys Pro Pro Met Leu<br>         265        270        275 | 1293 |
| ccc aag tgg tcc ctg ggc ttt atg aac ttc gag tgg gat ctg aat gaa | 1341 |

```
                Pro Lys Trp Ser Leu Gly Phe Met Asn Phe Glu Trp Asp Leu Asn Glu
                        280                 285                 290 gct gag ctc aag aac cat gtg gat acg tac cgg gcc aaa aat att ccg              1389
Ala Glu Leu Lys Asn His Val Asp Thr Tyr Arg Ala Lys Asn Ile Pro
        295                 300                 305 atc gac ggc tat gcg atc gat ttc gat tgg aag aag tac ggc gag aat              1437
Ile Asp Gly Tyr Ala Ile Asp Phe Asp Trp Lys Lys Tyr Gly Glu Asn
310                 315                 320 aat tac ggc gaa ttc gct tgg aat acg gcc aat ttc cct tcc gcc gcc              1485
Asn Tyr Gly Glu Phe Ala Trp Asn Thr Ala Asn Phe Pro Ser Ala Ala
325                 330                 335                 340 acg acg gcg ctg aag tcg cag atg gac gcc aag ggc att aaa atg atc              1533
Thr Thr Ala Leu Lys Ser Gln Met Asp Ala Lys Gly Ile Lys Met Ile
                345                 350                 355 ggc ata acc aag cct cgc atc gcg acg aag gat ttt tcg aac aat cct              1581
Gly Ile Thr Lys Pro Arg Ile Ala Thr Lys Asp Phe Ser Asn Asn Pro
            360                 365                 370 acc gtg cag gga acg gac gcg gcg agc ggc ggt tat ttt tat ccg gga              1629
Thr Val Gln Gly Thr Asp Ala Ala Ser Gly Gly Tyr Phe Tyr Pro Gly
        375                 380                 385 cat agc gaa tac aag gac tac ttc atc ccg gtc ttt gtg cgc agc atc              1677
His Ser Glu Tyr Lys Asp Tyr Phe Ile Pro Val Phe Val Arg Ser Ile
    390                 395                 400 gac cct tat aac cct gct gca cgc tcc tgg ttc tgg aac cac tcc aag              1725
Asp Pro Tyr Asn Pro Ala Ala Arg Ser Trp Phe Trp Asn His Ser Lys
405                 410                 415                 420 gat gcg ttc gat aaa ggc atc gta ggc tgg tgg aac gac gag acg gat              1773
Asp Ala Phe Asp Lys Gly Ile Val Gly Trp Trp Asn Asp Glu Thr Asp
                425                 430                 435 gcg gta tcg tcg gga ggg gcc tcc tac tgg ttc ggc aat ttt acg acc              1821
Ala Val Ser Ser Gly Gly Ala Ser Tyr Trp Phe Gly Asn Phe Thr Thr
            440                 445                 450 ggc cat atg tcc cag gcg ctt tac gag gga cag cgg gca tat acg tcg              1869
Gly His Met Ser Gln Ala Leu Tyr Glu Gly Gln Arg Ala Tyr Thr Ser
        455                 460                 465 aac gcc cag cgc gtc tgg cag aca gcg cgc acg ttc tat ccc ggg gcg              1917
Asn Ala Gln Arg Val Trp Gln Thr Ala Arg Thr Phe Tyr Pro Gly Ala
    470                 475                 480 cag cgt tat gcg acg acg ctc tgg tcg gga gac atc ggg att cag tat              1965
Gln Arg Tyr Ala Thr Thr Leu Trp Ser Gly Asp Ile Gly Ile Gln Tyr
485                 490                 495                 500 acc aag ggg gaa aga atc aac tgg gct gcc ggc atg cag gag cag cgg              2013
Thr Lys Gly Glu Arg Ile Asn Trp Ala Ala Gly Met Gln Glu Gln Arg
                505                 510                 515 gcg gtg atg ctt tct tcg atc aac aac ggc cag gtc aaa tgg gga atg              2061
Ala Val Met Leu Ser Ser Ile Asn Asn Gly Gln Val Lys Trp Gly Met
            520                 525                 530 gac aca ggc ggc ttc aac cag cag gac ggc acg acg aac aat ccg aat              2109
Asp Thr Gly Gly Phe Asn Gln Gln Asp Gly Thr Thr Asn Asn Pro Asn
        535                 540                 545 ccg gac ctg tac gcc aga tgg atg cag ttc agc gcg ctg act ccg gtg              2157
Pro Asp Leu Tyr Ala Arg Trp Met Gln Phe Ser Ala Leu Thr Pro Val
    550                 555                 560 ttc cgc gtg cat ggc aac aat cac cag cag cgc cag cct tgg tat tat              2205
Phe Arg Val His Gly Asn Asn His Gln Gln Arg Gln Pro Trp Tyr Tyr
565                 570                 575                 580 ggc tcg aca gcc gag gag gca tcc aag gaa gcg ctc cag ctc cgt tac              2253
Gly Ser Thr Ala Glu Glu Ala Ser Lys Glu Ala Leu Gln Leu Arg Tyr
                585                 590                 595
```

```
tcc ctg att cct tat atg tat gct tac gaa aga agc gcc tac gag aac    2301
Ser Leu Ile Pro Tyr Met Tyr Ala Tyr Glu Arg Ser Ala Tyr Glu Asn
        600                 605                 610 ggt aac gga ctt gtc cgg ccg ctg atg cag gaa tac cct gcc gat gcc    2349
Gly Asn Gly Leu Val Arg Pro Leu Met Gln Glu Tyr Pro Ala Asp Ala
            615                 620                 625 aac gcc aaa aac tat ctc gat gcc tgg atg ttc ggc gat tgg ctg ctg    2397
Asn Ala Lys Asn Tyr Leu Asp Ala Trp Met Phe Gly Asp Trp Leu Leu
630                 635                 640 gcg gcg cct gtg gtc gag aag cag cag acc tcc aag gaa atc tat ctc    2445
Ala Ala Pro Val Val Glu Lys Gln Gln Thr Ser Lys Glu Ile Tyr Leu
645                 650                 655                 660 cct gca ggc act tgg att gac tac aac cgg ggc acg gtg ctc acc ggc    2493
Pro Ala Gly Thr Trp Ile Asp Tyr Asn Arg Gly Thr Val Leu Thr Gly
                665                 670                 675 ggc cag aag atc agc tac gcc gtc aat ccc gac acg ctg acg gat att    2541
Gly Gln Lys Ile Ser Tyr Ala Val Asn Pro Asp Thr Leu Thr Asp Ile
            680                 685                 690 ccg ctc ttc att aag aag ggc gcg att atc cct tcg cag aag gtg cag    2589
Pro Leu Phe Ile Lys Lys Gly Ala Ile Ile Pro Ser Gln Lys Val Gln
        695                 700                 705 gac tac gtg ggc cag gct ccc gtc caa acg gtg gat gtg gat gta ttc    2637
Asp Tyr Val Gly Gln Ala Pro Val Gln Thr Val Asp Val Asp Val Phe
    710                 715                 720 ccg aat acg gca caa tcg agc ttt acc tat tat gac gat gac ggc agc    2685
Pro Asn Thr Ala Gln Ser Ser Phe Thr Tyr Tyr Asp Asp Asp Gly Ser
725                 730                 735                 740 agc tac aat tat gaa agc gga gct tac ttc aag caa ttg atg acg gct    2733
Ser Tyr Asn Tyr Glu Ser Gly Ala Tyr Phe Lys Gln Leu Met Thr Ala
                745                 750                 755 cag gac aac gga tcc ggt gcg ctg agc ttt acg ctg ggc gcc aaa acc    2781
Gln Asp Asn Gly Ser Gly Ala Leu Ser Phe Thr Leu Gly Ala Lys Thr
            760                 765                 770 ggc acg tac agc ccc gca ctg caa tcc tat atc gtc aag ctt cac ggg    2829
Gly Thr Tyr Ser Pro Ala Leu Gln Ser Tyr Ile Val Lys Leu His Gly
        775                 780                 785 gcc gca ggc gcg tcg gtg aca agc aat ggg gcg gcg ctg gcc tcc tat    2877
Ala Ala Gly Ala Ser Val Thr Ser Asn Gly Ala Ala Leu Ala Ser Tyr
    790                 795                 800 gcc agc ctg caa gcg ctg aaa gcc tca gcc agt gaa ggc tgg gcc aag    2925
Ala Ser Leu Gln Ala Leu Lys Ala Ser Ala Ser Glu Gly Trp Ala Lys
805                 810                 815                 820 ggc aag gac atc tac ggc gat gtc acg tat gtc aag cta tcc gcg ggg    2973
Gly Lys Asp Ile Tyr Gly Asp Val Thr Tyr Val Lys Leu Ser Ala Gly
                825                 830                 835 gca gcg gcg gcc aag gcg att gcc gtc acc ggc aac agc ccg gtc agc    3021
Ala Ala Ala Ala Lys Ala Ile Ala Val Thr Gly Asn Ser Pro Val Ser
            840                 845                 850 gtg gcg gat gtg cag tac gaa gcc gaa gaa gct tcg ctg tcc ggc aat    3069
Val Ala Asp Val Gln Tyr Glu Ala Glu Glu Ala Ser Leu Ser Gly Asn
        855                 860                 865 acg aca gca acc aag gcg acc gtg aat acg aac cac gca ggc tac acg    3117
Thr Thr Ala Thr Lys Ala Thr Val Asn Thr Asn His Ala Gly Tyr Thr
    870                 875                 880 ggc agc ggc ttc gtg gat gga ctg agt aat ccg gga gcg gcg gtt acg    3165
Gly Ser Gly Phe Val Asp Gly Leu Ser Asn Pro Gly Ala Ala Val Thr
885                 890                 895                 900 ttc tat ccg aag gtg aaa acg ggc gga gac tac aat gtc tcg ctg cgc    3213
Phe Tyr Pro Lys Val Lys Thr Gly Gly Asp Tyr Asn Val Ser Leu Arg
                905                 910                 915
```

-continued

| | | |
|---|---|---|
| tac gct aat tcg acg gga gcg gca aag agc gtc agc atc ttc gtt aac<br>Tyr Ala Asn Ser Thr Gly Ala Ala Lys Ser Val Ser Ile Phe Val Asn<br>               920                         925                        930 | 3261 |
| ggc aag cgc gtc aaa tcc acg tcg ctg gcg aac ctg ccg aac tgg gat<br>Gly Lys Arg Val Lys Ser Thr Ser Leu Ala Asn Leu Pro Asn Trp Asp<br>               935                         940                        945 | 3309 |
| acg tgg ggg acg cag gct gag aca ctg ccg ctg acg gcg ggg acg aac<br>Thr Trp Gly Thr Gln Ala Glu Thr Leu Pro Leu Thr Ala Gly Thr Asn<br>               950                         955                        960 | 3357 |
| gtt gtc acc tac aag ttc tac tcg gat gcc gga gat acg ggc tcg gtt<br>Val Val Thr Tyr Lys Phe Tyr Ser Asp Ala Gly Asp Thr Gly Ser Val<br>965                        970                        975                        980 | 3405 |
| aac ctg gac aac atc acg gtg ccc ttc gct ccg gcc atc ggc aaa tac<br>Asn Leu Asp Asn Ile Thr Val Pro Phe Ala Pro Ala Ile Gly Lys Tyr<br>               985                         990                        995 | 3453 |
| gag gcg gag agc gcc gag ctg agc ggc ggc agc acg gtc aac cag<br>Glu Ala Glu Ser Ala Glu Leu Ser Gly Gly Ser Thr Val Asn Gln<br>              1000                      1005                     1010 | 3498 |
| aat cat tgg ttc tac agc ggc acg gca ttt gta gat ggc tta acc<br>Asn His Trp Phe Tyr Ser Gly Thr Ala Phe Val Asp Gly Leu Thr<br>              1015                      1020                     1025 | 3543 |
| gca ccg ggc gcc caa gtc aaa tat acc gtg aac gcc ccg gcc gca<br>Ala Pro Gly Ala Gln Val Lys Tyr Thr Val Asn Ala Pro Ala Ala<br>              1030                      1035                     1040 | 3588 |
| ggc agc tac cag atc gcg ctt cgc tat gcg aac ggc acg ggt gct<br>Gly Ser Tyr Gln Ile Ala Leu Arg Tyr Ala Asn Gly Thr Gly Ala<br>              1045                      1050                     1055 | 3633 |
| gcg aag acg ctc agc acg tat gtg aac ggg acg aag ctg ggg caa<br>Ala Lys Thr Leu Ser Thr Tyr Val Asn Gly Thr Lys Leu Gly Gln<br>              1060                      1065                     1070 | 3678 |
| acg gcc ttc gcc agc cct ggc ggc aac tgg aac gtg tgg cag gac<br>Thr Ala Phe Ala Ser Pro Gly Gly Asn Trp Asn Val Trp Gln Asp<br>              1075                      1080                     1085 | 3723 |
| agc gtg cag acc gtc gcg ctc gcc gcc ggt acg aac acg atc gcg<br>Ser Val Gln Thr Val Ala Leu Ala Ala Gly Thr Asn Thr Ile Ala<br>              1090                      1095                     1100 | 3768 |
| ttc aag tac gat gcc ggc gac agc ggc agc ggc agc gtc aat ctg<br>Phe Lys Tyr Asp Ala Gly Asp Ser Gly Ser Gly Ser Val Asn Leu<br>              1105                      1110                     1115 | 3813 |
| gac cgt ctg ttg ctc tct gcc gca gcg cca ggc gtg ccc gtg tcc<br>Asp Arg Leu Leu Leu Ser Ala Ala Ala Pro Gly Val Pro Val Ser<br>              1120                      1125                     1130 | 3858 |
| gag cag aac ctg ctc gat aac ggg ggc ttt gaa cgc gat ccg tcg<br>Glu Gln Asn Leu Leu Asp Asn Gly Gly Phe Glu Arg Asp Pro Ser<br>              1135                      1140                     1145 | 3903 |
| cag agc agc aac tgg acc gag tgg cat ccg gct tcg cag gcg att<br>Gln Ser Ser Asn Trp Thr Glu Trp His Pro Ala Ser Gln Ala Ile<br>              1150                      1155                     1160 | 3948 |
| gct tac ggc atc gac agc ggc tcc ggg atg aat ccg cct gaa tcg<br>Ala Tyr Gly Ile Asp Ser Gly Ser Gly Met Asn Pro Pro Glu Ser<br>              1165                      1170                     1175 | 3993 |
| cca tgg gca ggc gat aag cgc gcc tat ttc tat gcg gca ggc ccg<br>Pro Trp Ala Gly Asp Lys Arg Ala Tyr Phe Tyr Ala Ala Gly Pro<br>              1180                      1185                     1190 | 4038 |
| tat cag caa agc atc cat caa aca gtc agc gtg cct gtc aat aat<br>Tyr Gln Gln Ser Ile His Gln Thr Val Ser Val Pro Val Asn Asn<br>              1195                      1200                     1205 | 4083 |
| gcc aag tac aag ttc gaa gcc tgg gta ttg ctg aag aat aca aca<br>Ala Lys Tyr Lys Phe Glu Ala Trp Val Leu Leu Lys Asn Thr Thr | 4128 |

-continued

```
              1210                1215                1220
ccg aca acg gcc cgg gtg gag att caa aat tac ggc ggt tcg ccg         4173
Pro Thr Thr Ala Arg Val Glu Ile Gln Asn Tyr Gly Gly Ser Pro
            1225                1230                1235 atc ttc acg aac atc agt aaa gac ggc gtc tgg aaa tac atc agc         4218
Ile Phe Thr Asn Ile Ser Lys Asp Gly Val Trp Lys Tyr Ile Ser
            1240                1245                1250 gtc agc gat att cag gtc acg aac ggc caa atc gat att ggc ttc         4263
Val Ser Asp Ile Gln Val Thr Asn Gly Gln Ile Asp Ile Gly Phe
            1255                1260                1265 tat gtg gat tcg ccc gga ggc acc acg ctc cac atc gac gat gtg         4308
Tyr Val Asp Ser Pro Gly Gly Thr Thr Leu His Ile Asp Asp Val
            1270                1275                1280 cgg gtc acc aag caa taa tccggtaaca ctagccctcc cccgccttgc            4356
Arg Val Thr Lys Gln
            1285 ggcaggaggg cttttttgctt ctgtaggttg tgaaggcgat accgagcgat gagaattcga   4416
ttctgaacag ctcgccctgt gtcctgctaa attcctctcc tccctggcag ggaagccgct    4476
tccacatgtc gaattgggga ggtactatga aagttagta ctaccgtctg caacggcttt     4536
cgctacaatg gaaccaataa gacatcgcga aggtttggga ggattcggca tgcagagacg   4596
cgaggttaaa gtaataggca cgggcaaata tttgcccgcc catcgagtga ctgcgcagga   4656
gatggaccgg cggctaggag tgcccgacgg atgggtgctg aagaagtcgg atgtggccgt   4716
tcgttatttc gccggtacgg agaaggcctc ggagatgggg gcgagagcgg ctgaggcggc   4776
gctggcttcc gcaggcctgg ccttcacgga tatcgactgc ctgatgtgcg ccagcgggac   4836
gatgaacag ccgattccat gcacggcggc gctcattcag aaggcgatag ccaaggaca    4896
ctccggagtg ccggcactgg atttgaatac aacctgtctg agctttgtgg cggctctgga   4956
catggtttct tatatggtga cggcgggaag gtacc                              4991
```

<210> SEQ ID NO 24
<211> LENGTH: 4986
<212> TYPE: DNA
<213> ORGANISM: Bacillus globisporus
<220> FEATURE:
<221> NAME/KEY: CDS
<222> LOCATION: (667)..(3948)

<400> SEQUENCE: 24

```
gagctcggga agaacccgtc cctgcaagct tggacgcagg cggtggagga ggcgggagtc    60
tacatcgctt ccgctatggc aggggctggg ggaggtgcat acggcttgat cggccactgc   120
tggggagggc tgctggcgtt cgagaccggc cactggctga aggcttgcgg gatgcaggag   180
ccgacgcatc tgttcgtgtc cgggtgcagc ccgccccatc tgctgcaagc gcggccggac   240
ttgggaacgg gaccatccgg cccggctccg ctccccgatg cctgccggat cgcccaagcg   300
taccgtatgc cttccaggcg cgggccgctg cttgcccggc tgagtgtatt cgccggccgc   360
cgagacccgg gcgtgtatgt ggatagtttg gccgaatggg gccgctatac ggcccgcata   420
tgcgatgttc atattggcga gggcgggcat gcagattggg gacctgatgc agaccgttgg   480
ctgccattcg tgcaaatgat tgcggagagg gaatattcgt cttcttgaag ccaggtgacc   540
tcagataaga tgtcgcacta agctgtatag tttcggaagg gaggtgaggc agagaagcgc   600
accatgagct gttagcttga cgtttaacgg tcaaaaccaa ttttactttg gaaggagca    660
     agattt atg cat gga aga aac ata ccg aga ccc atc aag ctc att gtt    708
           Met His Gly Arg Asn Ile Pro Arg Pro Ile Lys Leu Ile Val
```

```
            1               5                   10
tct tgg ctg ctg att ttc ttt tta atg gtg cca agc atc tat gca att      756
Ser Trp Leu Leu Ile Phe Phe Leu Met Val Pro Ser Ile Tyr Ala Ile
 15              20                  25                  30 gac ggc gta tac cac gcg cct tac ggg atc gac gat ctt tat gag att      804
Asp Gly Val Tyr His Ala Pro Tyr Gly Ile Asp Asp Leu Tyr Glu Ile
                 35                  40                  45 cag gcg acg gag cgc agt ccg aga gac cct gtg gcc ggg gag acg gtg      852
Gln Ala Thr Glu Arg Ser Pro Arg Asp Pro Val Ala Gly Glu Thr Val
             50                  55                  60 tat atc aaa atc aca aca tgg ccg atc gag ccc gga cag acg gca tgg      900
Tyr Ile Lys Ile Thr Thr Trp Pro Ile Glu Pro Gly Gln Thr Ala Trp
         65                  70                  75 gtg acc tgg acg aaa aac ggc gtc gcc cag ccg gcg gtc ggt gcc gcc      948
Val Thr Trp Thr Lys Asn Gly Val Ala Gln Pro Ala Val Gly Ala Ala
     80                  85                  90 tac aag tac aac agc ggc aac aac acc tac tgg gag gcg aac ctg ggc      996
Tyr Lys Tyr Asn Ser Gly Asn Asn Thr Tyr Trp Glu Ala Asn Leu Gly
 95                 100                 105                 110 agc ttc gcc aaa gga gac gta att tcc tac acc gtt cgc ggc aat aag     1044
Ser Phe Ala Lys Gly Asp Val Ile Ser Tyr Thr Val Arg Gly Asn Lys
                115                 120                 125 gac ggt gcc aat gaa aaa acg gcc gga ccg ttc acc ttt acc gta acc     1092
Asp Gly Ala Asn Glu Lys Thr Ala Gly Pro Phe Thr Phe Thr Val Thr
            130                 135                 140 gac tgg gaa tac gtc agc agc atc ggc tcg gtc acg aat aac acg aac     1140
Asp Trp Glu Tyr Val Ser Ser Ile Gly Ser Val Thr Asn Asn Thr Asn
        145                 150                 155 cgt gtc ctg ctg aat gcg gtg ccg aac acg ggg acg ctg tcc ccc aag     1188
Arg Val Leu Leu Asn Ala Val Pro Asn Thr Gly Thr Leu Ser Pro Lys
    160                 165                 170 atc aac att tcg ttc acg gcg gac gat gtg ttc cgc gtt cag ctc tcc     1236
Ile Asn Ile Ser Phe Thr Ala Asp Asp Val Phe Arg Val Gln Leu Ser
175                 180                 185                 190 cct acg gga tcg ggg acg ttg agc acg ggc ctg agt aat ttt acc gtc     1284
Pro Thr Gly Ser Gly Thr Leu Ser Thr Gly Leu Ser Asn Phe Thr Val
                195                 200                 205 acg gac agt gcg tcc acg gcc tgg atc tct aca tcc aaa tta aag ctg     1332
Thr Asp Ser Ala Ser Thr Ala Trp Ile Ser Thr Ser Lys Leu Lys Leu
            210                 215                 220 aag gtg gat aag aat ccg ttc aaa ctg agc gtg tac aag ccg gac ggc     1380
Lys Val Asp Lys Asn Pro Phe Lys Leu Ser Val Tyr Lys Pro Asp Gly
        225                 230                 235 acg acg ctg atc gcg cgc cag tat gac agc acg gcc aac cgc aat ctc     1428
Thr Thr Leu Ile Ala Arg Gln Tyr Asp Ser Thr Ala Asn Arg Asn Leu
    240                 245                 250 gct tgg ctg acc aat ggc agc act gtc atc aat aaa atc gag gac cac     1476
Ala Trp Leu Thr Asn Gly Ser Thr Val Ile Asn Lys Ile Glu Asp His
255                 260                 265                 270 ttc tac tcg ccg gcg tcc gag gag ttt ttc ggc ttc ggg gag cgc tac     1524
Phe Tyr Ser Pro Ala Ser Glu Glu Phe Phe Gly Phe Gly Glu Arg Tyr
                275                 280                 285 aac aac ttc cgc aag cgc gga acc gac gtg gac acg tat gtc tac aat     1572
Asn Asn Phe Arg Lys Arg Gly Thr Asp Val Asp Thr Tyr Val Tyr Asn
            290                 295                 300 cag tac aaa aat caa aac gac cgc acc tat atg gca atc ccc ttc atg     1620
Gln Tyr Lys Asn Gln Asn Asp Arg Thr Tyr Met Ala Ile Pro Phe Met
        305                 310                 315 ctg aac agc agc ggg tac ggt atc ttc gta aac tcc acg tac tac tcc     1668
```

```
Leu Asn Ser Ser Gly Tyr Gly Ile Phe Val Asn Ser Thr Tyr Tyr Ser
    320                 325                 330 aaa ttc cgc ttg gca act gag cgc tcc gat atg tac agt ttt acg gcc      1716
Lys Phe Arg Leu Ala Thr Glu Arg Ser Asp Met Tyr Ser Phe Thr Ala
335                 340                 345                 350 gat acc ggg ggc agc gcc aat tcg acg ctg gat tac tac ttt att tac      1764
Asp Thr Gly Gly Ser Ala Asn Ser Thr Leu Asp Tyr Tyr Phe Ile Tyr
                355                 360                 365 ggc aat gac ttg aag ggc gtc gtc agc aat tat gcg aac atc aca ggc      1812
Gly Asn Asp Leu Lys Gly Val Val Ser Asn Tyr Ala Asn Ile Thr Gly
370                 375                 380 aag ccg gct gct ctg ccc aaa tgg gcg ttt ggc ctc tgg atg tcg gcc      1860
Lys Pro Ala Ala Leu Pro Lys Trp Ala Phe Gly Leu Trp Met Ser Ala
                385                 390                 395 aat gag tgg gac cgg caa tcc aaa gta gcg act gcg atc aat aac gcc      1908
Asn Glu Trp Asp Arg Gln Ser Lys Val Ala Thr Ala Ile Asn Asn Ala
        400                 405                 410 aat acg aac aac atc ccg gcg acg gcc gtc gtg ctg gag cag tgg agt      1956
Asn Thr Asn Asn Ile Pro Ala Thr Ala Val Val Leu Glu Gln Trp Ser
415                 420                 425                 430 gac gag aat acg ttc tat atg ttc aac gat gcg cag tat acg gcc aaa      2004
Asp Glu Asn Thr Phe Tyr Met Phe Asn Asp Ala Gln Tyr Thr Ala Lys
                435                 440                 445 cct ggc ggc agc aca cac tcc tat acg gac tat atc ttc ccg gcg gcc      2052
Pro Gly Gly Ser Thr His Ser Tyr Thr Asp Tyr Ile Phe Pro Ala Ala
                450                 455                 460 ggc cgt tgg ccg aat ccg aag caa atg gcg gat aat gta cac agt aac      2100
Gly Arg Trp Pro Asn Pro Lys Gln Met Ala Asp Asn Val His Ser Asn
            465                 470                 475 ggg atg aag ctg gtg ctg tgg cag gtg ccg att cag aaa tgg acc gcc      2148
Gly Met Lys Leu Val Leu Trp Gln Val Pro Ile Gln Lys Trp Thr Ala
        480                 485                 490 gct cct cat ctg cag aag gac aac gac gaa agc tat atg atc gcg caa      2196
Ala Pro His Leu Gln Lys Asp Asn Asp Glu Ser Tyr Met Ile Ala Gln
495                 500                 505                 510 aat tat gcc gta ggc aac ggc agc gga ggc cag tac cgc atc cct agc      2244
Asn Tyr Ala Val Gly Asn Gly Ser Gly Gly Gln Tyr Arg Ile Pro Ser
                515                 520                 525 ggg caa tgg ttt gag aac agc ctg ctg ctg gac ttc acg aac ccg agc      2292
Gly Gln Trp Phe Glu Asn Ser Leu Leu Leu Asp Phe Thr Asn Pro Ser
            530                 535                 540 gcc aaa aac tgg tgg atg tcc aag cgc gcc tat ctg ttt gat ggc gtc      2340
Ala Lys Asn Trp Trp Met Ser Lys Arg Ala Tyr Leu Phe Asp Gly Val
        545                 550                 555 ggc atc gac ggg ttc aag acg gac gga ggg gag atg gtc tgg ggc cgc      2388
Gly Ile Asp Gly Phe Lys Thr Asp Gly Gly Glu Met Val Trp Gly Arg
560                 565                 570 tgg aac acg ttc gcc aat ggc aaa aaa ggc gat gaa atg cgc aac cag      2436
Trp Asn Thr Phe Ala Asn Gly Lys Lys Gly Asp Glu Met Arg Asn Gln
575                 580                 585                 590 tac ccg aac gat tac gtg aag gcc tac aac gaa tat gcg cgc tcg aag      2484
Tyr Pro Asn Asp Tyr Val Lys Ala Tyr Asn Glu Tyr Ala Arg Ser Lys
                595                 600                 605 aaa agc gat gcc gtc agc ttc agc cgt tcg ggc acg caa ggg gcg caa      2532
Lys Ser Asp Ala Val Ser Phe Ser Arg Ser Gly Thr Gln Gly Ala Gln
            610                 615                 620 gcg aat cag atc ttc tgg tcc ggt gac cag gaa tcg acg ttc ggt gcc      2580
Ala Asn Gln Ile Phe Trp Ser Gly Asp Gln Glu Ser Thr Phe Gly Ala
625                 630                 635
```

```
ttc cag caa gcc gtc cag gcg gga ctg acc gca ggc ttg tcc ggc gtt     2628
Phe Gln Gln Ala Val Gln Ala Gly Leu Thr Ala Gly Leu Ser Gly Val
        640                 645                 650 ccg tat tgg agc tgg gac ttg gct gga ttc acc ggc gct tat ccg tcg     2676
Pro Tyr Trp Ser Trp Asp Leu Ala Gly Phe Thr Gly Ala Tyr Pro Ser
655                 660                 665                 670 gcc gag cta tat aaa cgc gcg acg gca atg tcg gca ttt gcc ccg att     2724
Ala Glu Leu Tyr Lys Arg Ala Thr Ala Met Ser Ala Phe Ala Pro Ile
                675                 680                 685 atg cag ttc cac tcc gaa gcc aac ggc agt tcc ggc atc aat gag gag     2772
Met Gln Phe His Ser Glu Ala Asn Gly Ser Ser Gly Ile Asn Glu Glu
        690                 695                 700 cgg tcc ccg tgg aat gct cag gcc cgg act ggc gac aac acg atc atc     2820
Arg Ser Pro Trp Asn Ala Gln Ala Arg Thr Gly Asp Asn Thr Ile Ile
705                 710                 715 agc cat ttt gcc aag tat acg aac acc cgg atg aac ctg ctt cct tat     2868
Ser His Phe Ala Lys Tyr Thr Asn Thr Arg Met Asn Leu Leu Pro Tyr
        720                 725                 730 att tac agc gag gct aaa gca gca agc gat act ggc gtg ccg atg atg     2916
Ile Tyr Ser Glu Ala Lys Ala Ala Ser Asp Thr Gly Val Pro Met Met
735                 740                 745                 750 cgc gcg atg gcg ctg gag tat ccg agc gat acc cag acg tac gga ttg     2964
Arg Ala Met Ala Leu Glu Tyr Pro Ser Asp Thr Gln Thr Tyr Gly Leu
                755                 760                 765 acg cag cag tac atg ttc ggc ggc agc ctg ctg gtg gcg cct gtc ttg     3012
Thr Gln Gln Tyr Met Phe Gly Gly Ser Leu Leu Val Ala Pro Val Leu
        770                 775                 780 aac caa ggc gag acg aat aag aat atc tac ctt ccg caa gga gat tgg     3060
Asn Gln Gly Glu Thr Asn Lys Asn Ile Tyr Leu Pro Gln Gly Asp Trp
                785                 790                 795 atc gac ttc tgg ttc ggc gcg cag cgt ccg ggc ggg cga acg atc agc     3108
Ile Asp Phe Trp Phe Gly Ala Gln Arg Pro Gly Gly Arg Thr Ile Ser
800                 805                 810 tac tac gcg ggc gtg gac gat ctt ccc gtc ttc gtg aag tcc ggc agc     3156
Tyr Tyr Ala Gly Val Asp Asp Leu Pro Val Phe Val Lys Ser Gly Ser
815                 820                 825                 830 atc ctg ccg atg aat ctg aac ggg cag tat cag gtt ggc ggc acg atc     3204
Ile Leu Pro Met Asn Leu Asn Gly Gln Tyr Gln Val Gly Gly Thr Ile
                835                 840                 845 ggc aac agc ttg acc gcc tac aac aac ctg acg ttc cgg att tat cca     3252
Gly Asn Ser Leu Thr Ala Tyr Asn Asn Leu Thr Phe Arg Ile Tyr Pro
        850                 855                 860 ctg ggt acg acg acg tac agc tgg aat gat gac atc ggc ggc tcg gtg     3300
Leu Gly Thr Thr Thr Tyr Ser Trp Asn Asp Asp Ile Gly Gly Ser Val
                865                 870                 875 aag acg att acg tcg aca gag cag tat gga ctg aat aaa gag acg gtg     3348
Lys Thr Ile Thr Ser Thr Glu Gln Tyr Gly Leu Asn Lys Glu Thr Val
880                 885                 890 acg ctt ccg gcg atc aac tcg gcg aag acg ctc cag gtg ttc acg acc     3396
Thr Leu Pro Ala Ile Asn Ser Ala Lys Thr Leu Gln Val Phe Thr Thr
895                 900                 905                 910 aag ccg tcg tcg gtg acg ctg ggc ggc acg gcc ctc acc gcg cat agc     3444
Lys Pro Ser Ser Val Thr Leu Gly Gly Thr Ala Leu Thr Ala His Ser
                915                 920                 925 aca tta agc gca ttg atc ggc gct tcc tcc ggc tgg tat tac gat acg     3492
Thr Leu Ser Ala Leu Ile Gly Ala Ser Ser Gly Trp Tyr Tyr Asp Thr
        930                 935                 940 gtg caa aag ctc gcc tat gtg aag ctc ggc gcc agc tca tcg gcg caa     3540
Val Gln Lys Leu Ala Tyr Val Lys Leu Gly Ala Ser Ser Ser Ala Gln
945                 950                 955
```

-continued

| | | |
|---|---|---|
| acc gtc gtg ctt gac ggc gtc aac aag gtc gag tat gag gct gag ttc<br>Thr Val Val Leu Asp Gly Val Asn Lys Val Glu Tyr Glu Ala Glu Phe<br>960                            965                          970 | | 3588 |
| ggc aca ctt acc ggc gtc acg acc aat acg aat cat gcc ggc tat atg<br>Gly Thr Leu Thr Gly Val Thr Thr Asn Thr Asn His Ala Gly Tyr Met<br>975                            980                          985                          990 | | 3636 |
| ggt acc ggc ttt gtc gac ggc ttc gat gcg gca ggc gat gca gtg  acc<br>Gly Thr Gly Phe Val Asp Gly Phe Asp Ala Ala Gly Asp Ala Val  Thr<br>                        995                            1000                          1005 | | 3684 |
| ttc gac gta tcc gtc aaa gcg gcc ggc  acg tat gcg ctc aag  gtc<br>Phe Asp Val Ser Val Lys Ala Ala Gly  Thr Tyr Ala Leu Lys  Val<br>                       1010                           1015                         1020 | | 3729 |
| cgg tac gct tcc gct ggt ggc aac gct  tca cgc gct atc tat  gtc<br>Arg Tyr Ala Ser Ala Gly Gly Asn Ala  Ser Arg Ala Ile Tyr  Val<br>                       1025                           1030                         1035 | | 3774 |
| aac aac gcc aag gtg acc gat ctg gcg  ctt ccg gca acg gcc  aac<br>Asn Asn Ala Lys Val Thr Asp Leu Ala  Leu Pro Ala Thr Ala  Asn<br>                       1040                           1045                         1050 | | 3819 |
| tgg gac acc tgg ggg acg gca acc gtc  aac gta gcc tta aac  gcc<br>Trp Asp Thr Trp Gly Thr Ala Thr Val  Asn Val Ala Leu Asn  Ala<br>                       1055                           1060                         1065 | | 3864 |
| ggc tac aac tcg atc aag gtc agc tac  gac aac acc aat acg  ctc<br>Gly Tyr Asn Ser Ile Lys Val Ser Tyr  Asp Asn Thr Asn Thr  Leu<br>                       1070                           1075                         1080 | | 3909 |
| ggc att aat ctc gat aac att gcg atc  gtg gag cat tga cagcaggaat<br>Gly Ile Asn Leu Asp Asn Ile Ala Ile  Val Glu His<br>                       1085                           1090 | | 3958 |
| cttcgcgagg aatgagttag cgaagagttc atgcaggcag aggggttacc cataattgta | | 4018 |
| aagcccggcg cagccaggca ccaagtatgc ccggagggc cgccggccct ccctttattt | | 4078 |
| caatgatgaa aggcggcatc gatatgggtc tatggaacaa acgagtcact cgcatcctct | | 4138 |
| ccgtactcgc agcaagcgcg ctgatcggct ctaccgtacc ttctctagcg ccacctcccg | | 4198 |
| ctcaagccca tgtgagcgcg ctgggcaacc tgctttcctc ggcggtgacc ggggatacgc | | 4258 |
| tcacgctgac gatcgataac ggcgcggaac cgaatgacga tattctagtt ctgcaagcag | | 4318 |
| tccagaacgg tattctgaag gtggactacc ggccgaacgg tgtagctcca agcgcggata | | 4378 |
| cgccgatgct ggatcccaat aaaacctggc cgtccatagg cgccgttatc aatacagcct | | 4438 |
| ctaatccgat gacgatcaca acgccggcga tgaagattga gattgccaaa aatccggtgc | | 4498 |
| gcctgaccgt gaaaaaaccg gacggcaccg ctctgttatg ggaaccccg accggcggcg | | 4558 |
| tcttctcgga cggcgtccgt tcttgcacg ggacgggcga caatatgtac ggcatccgca | | 4618 |
| gcttcaatgc ttttgacagc ggcggggatc tgctgcgcaa cagctccacc caagccgccc | | 4678 |
| gtgcaggcga ccagggcaac tccggcggcc cgctgatctg gagcacagcc gggtacgggg | | 4738 |
| tgctcgttga cagcgacggt gggtatccgt tcacggacga ggctaccggc aagctggagt | | 4798 |
| tctattacgg cggcacgcct ccggaaggcc ggcgctatac gaagcaggat gtggagtact | | 4858 |
| acatcatgct cggcacgccg aaagagatca tgtccggcgt cggggaaatt acgggcaaac | | 4918 |
| cgccgatgct gcccaagtgg tccctgggct ttatgaactt cgagtgggat ctgaatgaag | | 4978 |
| ctgagctc | | 4986 |

<210> SEQ ID NO 25
<211> LENGTH: 5811
<212> TYPE: DNA
<213> ORGANISM: Arthrobacter globiformis
<220> FEATURE:

<221> NAME/KEY: CDS
<222> LOCATION: (1655)..(4552)

<400> SEQUENCE: 25

```
ggtacctcgt cgaggagctc ggtgtcgacg gcttcaagac cgacgggagc gaggcgctct      60
tcgggcgtga cctgatcgtc agcgacgggc cgcggtga cgagatgcac aacgcctacc       120
cgaacgagta cacctccgcc tacaacgact tcgtgcagga gacgacgggc gccgacggca     180
cgatcttcag ccgggcgggc acctccggcg gccagagcga atccatcttc tgggccgggg     240
accaggcgtc gacgttcggc gctttccagg aggccgtccg ggccgggcag agcgcgggcc     300
agtcgggagt gccgttctgg gcctgggacc tcggcggctt caccgggtcg ttcccaagcg     360
cggagctgta tctgcgctcg accgctcagg cggtgttctc gccgatcatg cagtaccact     420
cggagaaggc cgaccccagt ccgtccgagg cgcgcacgcc ctggaacgtg caggcgcgca     480
ccgggaacac cactgtcgtc ccaccttcg cccgttacgc gaacgtacgg atgaacctcg      540
tgccctatct gtacacggag gcggacgaca cgcgacgac gggtgtgccg atgatgcgcg     600
cgatgagcct cgcgttcccc gacgaccgg atgccgcgca gtacgaccag cagtacatgt      660
tcgggtctca gctgctggtc gcaccgatta cgaaccaggg ccagaccgtg aaagacgtct     720
acctgcccgc gggcgagtgg tacgacttct ggaacggcgg acgcgcgagc ggcgagggcg     780
tgaagatgta cgacgccgga cccgacggca tccccgtata cgctcgcgcc ggagcggtca     840
tcccgctcaa cctcaacgac gcgtatgagg tgggcggcac gatcggcaac gacgtggaga     900
gctacgacaa ccttgtgttc cgcgtttacc cctccggtga gagcagctac gagtacttcg     960
aagaccaagc gaacgcgcac cgccggatcg atgtctcggc cgaccgcgca gcgcgcacgg    1020
tcgaggtgtc tgctcccgcg ctcacgaccg cgagcacctt ccaggtgtcg ggcaccaagc    1080
ccgacaccgt gaccgtcgcg ggctcggcac tgcctgaggt caacagcgtg agcgcgctgg    1140
ccgcatccac cgaggcctgg tactgggatg cgaagcagca gctgacgtac gtgaaggtcg    1200
gtgcgagcac cggcgagcgc acgatcctcc tgctgggcgt cgacaaggcc gggtacgagg    1260
ccgagttcgc gggtcatacg gccgtctcga cgaacgccga ccacccgggc tacaccgggc    1320
tcggcttcgt cgacggcttc gcgaacgcag gagacgcggt ggagttcgac gtgtgggccg    1380
aggagaacgg cgcgcaccag ctccgcttcc gctacggaaa cggagcggcg acccccgcca    1440
cccgcacgat ccgggtcgac ggagcgcctc tgggaacgct gtcgcttccg cccaccgggt    1500
cgtggagttc gtggggcacg gcctcgatcg acgtgaccct cccacccgga cgccacgccg    1560
tacggatcga gtacgccgga ggcgattccg gcggcgtcaa cctcgacaac ctcgtcctcg    1620
cgcgctgagc gcacacggga aagggagaag aacc atg cct gct ctt ccg tgg cgc    1675
                                     Met Pro Ala Leu Pro Trp Arg
                                      1               5
```

```
cgc acg acg gcg ctc gcg ctc acc acg gcg gtg acg gcc gcg acc ctg      1723
Arg Thr Thr Ala Leu Ala Leu Thr Thr Ala Val Thr Ala Ala Thr Leu
         10                  15                  20
```

```
gtc gcc gtc ggg gtg aac gac gcc ggt cag gcg gcg gct gct ccc ctg      1771
Val Ala Val Gly Val Asn Asp Ala Gly Gln Ala Ala Ala Ala Pro Leu
 25                  30                  35
```

```
ggc gtg caa cgc gcg cag ttc cag tcg ggg tcg agc tac ctc gtc gtc      1819
Gly Val Gln Arg Ala Gln Phe Gln Ser Gly Ser Ser Tyr Leu Val Val
 40                  45                  50                  55
```

```
gag gtg ctc gat gac gac ctc gtc cac ttc gag ctg gcc ggg ggc ggc      1867
Glu Val Leu Asp Asp Asp Leu Val His Phe Glu Leu Ala Gly Gly Gly
                 60                  65                  70
```

```
acc gcc ccc ggc acg ggc tcc ccg ctg ttc acg acg cct cag gtc gcg    1915
Thr Ala Pro Gly Thr Gly Ser Pro Leu Phe Thr Thr Pro Gln Val Ala
             75                  80                  85 aag cac gac tac gcg gga ccc gac gtg ttc acc cag acc ggg tct gtt    1963
Lys His Asp Tyr Ala Gly Pro Asp Val Phe Thr Gln Thr Gly Ser Val
         90                  95                 100 ctg cag acc gcg gcg atg cgc atc gag gtc gat ccc gcg gat ctg tgc    2011
Leu Gln Thr Ala Ala Met Arg Ile Glu Val Asp Pro Ala Asp Leu Cys
    105                 110                 115 gtg acg gcc acc gac atc acc cgc acc ccg aac ctt gta ctg cac gag    2059
Val Thr Ala Thr Asp Ile Thr Arg Thr Pro Asn Leu Val Leu His Glu
120                 125                 130                 135 gcg tgt ccc gcc gac ctc ggc cag gcg tgg aag ggg ctg aac atc acg    2107
Ala Cys Pro Ala Asp Leu Gly Gln Ala Trp Lys Gly Leu Asn Ile Thr
                140                 145                 150 agg tcg gcg atg gag aac gcc tac ggt ctc ggg cag cag ttc ttc acg    2155
Arg Ser Ala Met Glu Asn Ala Tyr Gly Leu Gly Gln Gln Phe Phe Thr
            155                 160                 165 ggc ggc agc gcg gac ggc gac tgg gtg ggc cgc acc cgc acc ccg ggt    2203
Gly Gly Ser Ala Asp Gly Asp Trp Val Gly Arg Thr Arg Thr Pro Gly
        170                 175                 180 ggc acc tac ggc aac gcg atg gtg ttc gac ccc gag aac ggg ccg gtc    2251
Gly Thr Tyr Gly Asn Ala Met Val Phe Asp Pro Glu Asn Gly Pro Val
    185                 190                 195 ggc aac acg cag atc ccg gtg ctc ttc gcg gtc ggc gat gac aac gcg    2299
Gly Asn Thr Gln Ile Pro Val Leu Phe Ala Val Gly Asp Asp Asn Ala
200                 205                 210                 215 aac tac ggg ctg ttc gtc gat cag ctg tac aag cag gaa tgg aac ctc    2347
Asn Tyr Gly Leu Phe Val Asp Gln Leu Tyr Lys Gln Glu Trp Asn Leu
                220                 225                 230 acc ggc gac ccg tgg acg gtg cgc atg tgg ggc gac cag gtg cgc tgg    2395
Thr Gly Asp Pro Trp Thr Val Arg Met Trp Gly Asp Gln Val Arg Trp
            235                 240                 245 tac ctc atg agc ggc gac gac ctg ccc gac ctt cgc cac gac tac atg    2443
Tyr Leu Met Ser Gly Asp Asp Leu Pro Asp Leu Arg His Asp Tyr Met
        250                 255                 260 gag ctg acg ggc acc ccg ccc gtg ccg ccg aag aag gcg ttc ggg ctc    2491
Glu Leu Thr Gly Thr Pro Pro Val Pro Pro Lys Lys Ala Phe Gly Leu
    265                 270                 275 tgg gtg tcg gag ttc ggc tac gac aac tgg agc gag gtc gac aat acg    2539
Trp Val Ser Glu Phe Gly Tyr Asp Asn Trp Ser Glu Val Asp Asn Thr
280                 285                 290                 295 atc gcg ggc ctg cgc tcg gcc gac ttt ccg gtc gat ggc gcg atg ctc    2587
Ile Ala Gly Leu Arg Ser Ala Asp Phe Pro Val Asp Gly Ala Met Leu
                300                 305                 310 gac gta cag tgg ttc ggg ggc gtc acc gcc gac tcg gac gac acc cgc    2635
Asp Val Gln Trp Phe Gly Gly Val Thr Ala Asp Ser Asp Asp Thr Arg
            315                 320                 325 atg ggc acc ctc gat tgg gac acg tcg agg ttt ccc gac cct gcg gga    2683
Met Gly Thr Leu Asp Trp Asp Thr Ser Arg Phe Pro Asp Pro Ala Gly
        330                 335                 340 aag atc gcc gac ctc gcc gag gac ggc gtc ggc atc atc ccg atc gag    2731
Lys Ile Ala Asp Leu Ala Glu Asp Gly Val Gly Ile Ile Pro Ile Glu
    345                 350                 355 gag tcg tac gtc ggt cgc aac ctg ccg gag cac gcc cgg atg gcg gcg    2779
Glu Ser Tyr Val Gly Arg Asn Leu Pro Glu His Ala Arg Met Ala Ala
360                 365                 370                 375 gac ggt tac ctc gtg cgc tcc ggc tgc gct acg tgc ccg ccg gtg tac    2827
Asp Gly Tyr Leu Val Arg Ser Gly Cys Ala Thr Cys Pro Pro Val Tyr
                380                 385                 390
```

```
ctg acg ggg aac ccc tgg tgg ggc aag ggc ggg atg atc gac tgg acg       2875
Leu Thr Gly Asn Pro Trp Trp Gly Lys Gly Gly Met Ile Asp Trp Thr
            395                 400                 405 cag ccg gaa gcc ggc gcc gtc tgg cac gac gag cag cgc cag cat ctc       2923
Gln Pro Glu Ala Gly Ala Val Trp His Asp Glu Gln Arg Gln His Leu
    410                 415                 420 gtc gac gag ggc gta ctg ggc cac tgg ctc gat ctc ggc gaa ccg gag       2971
Val Asp Glu Gly Val Leu Gly His Trp Leu Asp Leu Gly Glu Pro Glu
425                 430                 435 atg tac gac ccg aac gac tgg acc gcc ggc gtc atc ccc ggc aag cac       3019
Met Tyr Asp Pro Asn Asp Trp Thr Ala Gly Val Ile Pro Gly Lys His
440                 445                 450                 455 gcg cac gcc gac tat cac aac gcg tac aac ctg ctg tgg gcg cag agc       3067
Ala His Ala Asp Tyr His Asn Ala Tyr Asn Leu Leu Trp Ala Gln Ser
                460                 465                 470 atc gcc gac ggg tac gcc gac aac ggc gtg cag aag cgt ccc ttc atg       3115
Ile Ala Asp Gly Tyr Ala Asp Asn Gly Val Gln Lys Arg Pro Phe Met
            475                 480                 485 ctg acg cgc gcc gcg gcc gcc ggc atc cag cgt cat ggc gcg ggc atg       3163
Leu Thr Arg Ala Ala Ala Ala Gly Ile Gln Arg His Gly Ala Gly Met
    490                 495                 500 tgg tca gcc gac atc ggg tcg acc atg aag gcg ctc ggg agc cag cag       3211
Trp Ser Ala Asp Ile Gly Ser Thr Met Lys Ala Leu Gly Ser Gln Gln
505                 510                 515 aac gcg cag atg cac atg tcg atg tcg ggg atc gac tat tac ggc tcc       3259
Asn Ala Gln Met His Met Ser Met Ser Gly Ile Asp Tyr Tyr Gly Ser
520                 525                 530                 535 gac atc ggc ggg ttc cgg cgg gag atg gcc gac ggc gac gtg aac gag       3307
Asp Ile Gly Gly Phe Arg Arg Glu Met Ala Asp Gly Asp Val Asn Glu
            540                 545                 550 ctc tac acc cag tgg ttc gcc gac agc gcg tgg ttc gac act ccg ctc       3355
Leu Tyr Thr Gln Trp Phe Ala Asp Ser Ala Trp Phe Asp Thr Pro Leu
    555                 560                 565 cgg ccg cac acc gac aat ctc tgc aac tgc ctc gag acg agc ccc gac       3403
Arg Pro His Thr Asp Asn Leu Cys Asn Cys Leu Glu Thr Ser Pro Asp
570                 575                 580 tcg atc ggc gac gtc gcg agc aac cgc gag aac ctg gtg cgc cgc tac       3451
Ser Ile Gly Asp Val Ala Ser Asn Arg Glu Asn Leu Val Arg Arg Tyr
585                 590                 595 gag ctg gct ccg tac tac tac tcg ctc gcg cac cgc gct cac cag ttc       3499
Glu Leu Ala Pro Tyr Tyr Tyr Ser Leu Ala His Arg Ala His Gln Phe
600                 605                 610                 615 ggc gag ccg ctc gct ccc ccg ctc gtg tac tac tac cag aac gac gac       3547
Gly Glu Pro Leu Ala Pro Pro Leu Val Tyr Tyr Tyr Gln Asn Asp Asp
            620                 625                 630 cac gtt cgc gag atg ggg cat cag aag atg ctc ggg cgc gac ctg ctg       3595
His Val Arg Glu Met Gly His Gln Lys Met Leu Gly Arg Asp Leu Leu
    635                 640                 645 atc gcg atc gtc gcc gga gag ggc gag cgg gaa cgc gac gtg tac ctt       3643
Ile Ala Ile Val Ala Gly Glu Gly Glu Arg Glu Arg Asp Val Tyr Leu
650                 655                 660 ccg gcg ggc gag tgg atc gac atc cac acg aac gag cgc atc cag agc       3691
Pro Ala Gly Glu Trp Ile Asp Ile His Thr Asn Glu Arg Ile Gln Ser
665                 670                 675 acg ggt cag tgg atc gac aac gtg ccg ctg tgg cgt gac ggc gtc ttc       3739
Thr Gly Gln Trp Ile Asp Asn Val Pro Leu Trp Arg Asp Gly Val Phe
680                 685                 690                 695 acc ctg ccg gcg tac gcc cgg gcg ggg gcg atc atc ccg aag gcc ttc       3787
Thr Leu Pro Ala Tyr Ala Arg Ala Gly Ala Ile Ile Pro Lys Ala Phe
```

-continued

```
                700                 705                 710
gtc gac gcc tcc acg aag gac atc acc ggc aag cgc gag gat gcc gcg     3835
Val Asp Ala Ser Thr Lys Asp Ile Thr Gly Lys Arg Glu Asp Ala Ala
            715                 720                 725 gtg cgc aac gag ctg atc gca acc gtt tac gcc gac gac gtc gcg agc     3883
Val Arg Asn Glu Leu Ile Ala Thr Val Tyr Ala Asp Asp Val Ala Ser
        730                 735                 740 gac ttc acc ctg tac gag gat gac ggc gcg acg acc gca tac gcc gac     3931
Asp Phe Thr Leu Tyr Glu Asp Asp Gly Ala Thr Thr Ala Tyr Ala Asp
    745                 750                 755 ggg gct gtc agg acc acg cag atc agc caa tcg ctc acg aac ggc gtg     3979
Gly Ala Val Arg Thr Thr Gln Ile Ser Gln Ser Leu Thr Asn Gly Val
760                 765                 770                 775 gcc acg gtg acg gtg gga gcg gca tct gga acc tac tcc ggt gcg ccc     4027
Ala Thr Val Thr Val Gly Ala Ala Ser Gly Thr Tyr Ser Gly Ala Pro
                780                 785                 790 tcc acc cgt ccc acg gtc gtc gag ctt gtc act gac ggc acg cag gcc     4075
Ser Thr Arg Pro Thr Val Val Glu Leu Val Thr Asp Gly Thr Gln Ala
            795                 800                 805 tcg acc gtc tcc ctc ggc agc gtt ccg ctg acg gag cac gcg aac aag     4123
Ser Thr Val Ser Leu Gly Ser Val Pro Leu Thr Glu His Ala Asn Lys
        810                 815                 820 gcg gcg ttc gac gcg gcg agc agc ggc tgg tac aac gcc ggc ggg ggg     4171
Ala Ala Phe Asp Ala Ala Ser Ser Gly Trp Tyr Asn Ala Gly Gly Gly
    825                 830                 835 ctc gtt gtg gcc aag gcg gcg agc agt tcg gtg aac acc gcc aag acc     4219
Leu Val Val Ala Lys Ala Ala Ser Ser Ser Val Asn Thr Ala Lys Thr
840                 845                 850                 855 ttc tcg ttc acg ctc ggt gag gag tcg gtc tgg gcg acg ttc tcc tgc     4267
Phe Ser Phe Thr Leu Gly Glu Glu Ser Val Trp Ala Thr Phe Ser Cys
                860                 865                 870 gag aac gcc acg acg acc ttc ggt cag tca gtg tac gtc gtc gga aat     4315
Glu Asn Ala Thr Thr Thr Phe Gly Gln Ser Val Tyr Val Val Gly Asn
            875                 880                 885 gtt ccg cag ctc ggc aac tgg tcg ccg gcg gat gcc gtg aag ctc gag     4363
Val Pro Gln Leu Gly Asn Trp Ser Pro Ala Asp Ala Val Lys Leu Glu
        890                 895                 900 ccg agc gcc tac ccc acc tgg acc ggg gtg gtg cgg aac ctg ccg ccg     4411
Pro Ser Ala Tyr Pro Thr Trp Thr Gly Val Val Arg Asn Leu Pro Pro
    905                 910                 915 tcg agc acg gtc gaa tgg aag tgc atc aaa cgt cag gag gcc ggc ctg     4459
Ser Ser Thr Val Glu Trp Lys Cys Ile Lys Arg Gln Glu Ala Gly Leu
920                 925                 930                 935 ccg aac acg gcg gat gcg tgg gag ccc ggc ggg aac aac atc ctc tcg     4507
Pro Asn Thr Ala Asp Ala Trp Glu Pro Gly Gly Asn Asn Ile Leu Ser
                940                 945                 950 acg cca cct tcc ggc tcg gcg ggg ata acc acc ggc gcc ttc tga         4552
Thr Pro Pro Ser Gly Ser Ala Gly Ile Thr Thr Gly Ala Phe
            955                 960                 965 cccagggggg ctcgatcccg gtcgccagcg caagcgcggc gcccggggtc gacgcgtgtt   4612
aggccagtac gcgaaggaac cagccctcta cgacaccggc ctcgaccccg ccgaaggact   4672
ctggcaccgg tcaggctgga tcggacaaca ctgacacgcc ccgacgccat ccactctttt   4732
tggcctacaa cccgttgtcg cacgtgcgcc tcttggcccg gcacgacga aaccccgcg    4792 atccagggat cggcgggggt tcggatggc ggtgacggtg ggatttgaac ccacggtagg    4852
gggttaccct acacaacttt tcgagagttg caccttcggc cgctcggaca cgtcaccggg   4912
gtcgagttta cgcgacgttc tcctggcgcg ccaatcggcg gcgccccgcc cgcgagaatc   4972
```

| caggcccgcg | ccgagaatcc | gcgggcgcct | ggattctcag | cacggggatg | gattctcgcc | 5032 |
| gctcatccga | gccccgcggc | gagcgggctc | agtgctcgtc | ctccatgagc | atgccgaccg | 5092 |
| aggtggcgca | ggcgtcgccg | cgccaggcct | cgatgccctc | gcgcacggcg | aaggcggcga | 5152 |
| tgatgaggcc | ggtgatcgcg | tcggcccacc | accagcccag | gaggctgttg | agcacgaggc | 5212 |
| ccgcgagcac | ggccgccgac | aggtaggtgc | agatgagggt | ctgcttcgag | tcggccacgg | 5272 |
| cggtggccga | tccgagctcg | cggccggcgc | ggcgctcggc | gaacgacagg | aacggcatga | 5332 |
| tcgccacgct | gagcgccgtg | atgacgatgc | cgagcgtcga | gtgctccacg | tccgcgccgc | 5392 |
| cgacgagggc | caggaccgac | gtgacggtga | cgtacgcggc | gagcgcgaag | aaggccacgg | 5452 |
| cgatgacgcg | cagcgtgccg | cgctcccagc | gctccgggtc | gcgccgcgtg | aactgccacg | 5512 |
| cgacggcggc | ggccgagagc | acctcgatgg | tcgagtccag | gccgaacgcg | acgagcgcgg | 5572 |
| ccgacgaggc | cgcagctccc | gcggcgatcg | cgacgaccgc | ctcgacgacg | ttataggcga | 5632 |
| tggtcgcggc | gacgatccag | cggatgcgcc | gctgcaggac | ggatcgccga | tcggcagacg | 5692 |
| cggtggcggt | catgcgcagg | tgcagctctc | tccggcgcag | cagccgggct | cgacgtacag | 5752 |
| gacgacgcgc | agcagctcgt | cgagcgcggg | cgcgaggtgg | gcgtcggcca | gccggtacc | 5811 |

<210> SEQ ID NO 26
<211> LENGTH: 6153
<212> TYPE: DNA
<213> ORGANISM: Arthrobacter globiformis
<220> FEATURE:
<221> NAME/KEY: CDS
<222> LOCATION: (1281)..(4646)

<400> SEQUENCE: 26

| gcggccgctc | cctgggccca | ccggtcgtcc | tgccaggtct | cgaccgcgac | ggggatcgcc | 60 |
| ctgttgcgcg | ggatgagccc | ggcccggaac | gcgggctcga | agccgaacga | ccagtgcgtc | 120 |
| cacgcctccg | ccccttcgcc | gagcaggatg | acgatctccg | ggtcgatcag | gttcaccacc | 180 |
| cccgccagca | cccggccgag | caggtgcccg | gcctgcgaga | actgctgctg | cgcggctgga | 240 |
| tcgccgccat | cggcgagcgc | ctttagggcc | gggtagccgt | cgccgtcgcc | gaggattccc | 300 |
| tgctcgcggg | cgcgccgcac | gagcgcttcc | tggccgatga | cgcctcgag | gcatccgttg | 360 |
| ccgccgcact | gacagggcgg | accgtcctcc | tccaccggga | tgtggccgat | ctctccggct | 420 |
| ccccccgctgc | gtccgcggag | cacgcggccc | tcggagatga | ggccggcgcc | ggcacccgtt | 480 |
| ccgatcgtga | tcacgagcac | gtcctcgtgt | ccgcgggcct | gaccgtgcag | ggcctccgcg | 540 |
| ctggcgaggg | cgttgacgtt | gttctcgacg | aggacgggca | ggtcgagctc | gcgccggagc | 600 |
| agctcgccga | gaggcacccg | cagccagccc | agctccgtcg | agtcgaccgt | gccgaccgcc | 660 |
| tggtcgtcga | cgttgccggg | cacgcccacg | ccgagaccga | gcaggggac | gccgtcgccg | 720 |
| gcggcgatga | acgagcggag | catgtcgctg | agcttcgcga | tcgcggtgcc | cgttccggcg | 780 |
| tcgaagggct | cggtgagcga | tcgctgcacc | cggccgtcga | tgctgacctc | gaccgcggtg | 840 |
| atgtggtcgc | tacgaccctt | aacgccgacg | gcacggccgg | cgtcggcgac | gagaccgagc | 900 |
| agccgcgcgg | gacgtccacc | ctgcgagggg | cggtgatcca | gctcgaccag | caggccatcg | 960 |
| gcgatgagct | cccgggtgtg | ctgcgtgacg | agcgccggcg | agacgccgag | ctcgcgcgcg | 1020 |
| aggtggcccc | gcgaggtcgg | gccattgctg | ccgatgtggg | cgagcatggc | cgatcgcgtc | 1080 |
| agatcggtgc | gtggattcgg | gtgggccaca | ggaaccccctt | tgttcaggac | tgaaagaacg | 1140 |
| gtagagcaca | gcgagggcga | acgtcaactc | acagcctgat | ctcccggggcc | gagagcccgg | 1200 |

```
cggccgaact cacctcttga cgagcccgtt cgactacgga atattcccgg ctaaatacag    1260
acccgaacaa aggggttccc atg tct gat gcc gtc ggc gct ccc cgc gcg ctg    1313
                      Met Ser Asp Ala Val Gly Ala Pro Arg Ala Leu
                       1               5                      10 aac gat ccg cac cgc tcg cgt ctc gcc gcg ctt ccg cgc cgg acc gcg     1361
Asn Asp Pro His Arg Ser Arg Leu Ala Ala Leu Pro Arg Arg Thr Ala
             15                  20                  25 gga ttc gtc ctg gca ctg gtc gcg ggg ctg gtc ttc acg ctg ctc gcc     1409
Gly Phe Val Leu Ala Leu Val Ala Gly Leu Val Phe Thr Leu Leu Ala
         30                  35                  40 gct ccg ccc gcc cac gcc aac aca ctc gac ggg gtc tgg cac aac ccg     1457
Ala Pro Pro Ala His Ala Asn Thr Leu Asp Gly Val Trp His Asn Pro
     45                  50                  55 tac ggg gcc gac gag ctg tat gcg acg cag ccg acg gag cgt tca cca     1505
Tyr Gly Ala Asp Glu Leu Tyr Ala Thr Gln Pro Thr Glu Arg Ser Pro
 60              65                  70                  75 cgc gac ccg atg gcc ggc gac aac gtc acc gtc cgg gcg acg acg tgg     1553
Arg Asp Pro Met Ala Gly Asp Asn Val Thr Val Arg Ala Thr Thr Trp
                 80                  85                  90 ccg gtg gcg ccg ggc cag tcg gtc tgg gtg acg tgg agc gtg aac ggc     1601
Pro Val Ala Pro Gly Gln Ser Val Trp Val Thr Trp Ser Val Asn Gly
             95                 100                 105 gtc gcg cag act ccg cgc ggg gca tcc tgg gac tac aac tcc ggc aac     1649
Val Ala Gln Thr Pro Arg Gly Ala Ser Trp Asp Tyr Asn Ser Gly Asn
         110                 115                 120 aac acg tat tgg aag ctc gat ctg ggt tcc ttc gcc cgg ggc gac gtc     1697
Asn Thr Tyr Trp Lys Leu Asp Leu Gly Ser Phe Ala Arg Gly Asp Val
     125                 130                 135 gtc gag tac acg gtt cac gcc gac gtc aac ggc ggt ggg cag cgc agc     1745
Val Glu Tyr Thr Val His Ala Asp Val Asn Gly Gly Gly Gln Arg Ser
 140                 145                 150                 155 tca ggg ccg ttc tcc ttc acc acg aca tcc tgg agc acg gtc acc gac     1793
Ser Gly Pro Phe Ser Phe Thr Thr Thr Ser Trp Ser Thr Val Thr Asp
                 160                 165                 170 gtc acg tcg gtc gtc gac aac ggc act tcc gtc gac atc gtc acg gga     1841
Val Thr Ser Val Val Asp Asn Gly Thr Ser Val Asp Ile Val Thr Gly
             175                 180                 185 gac agc gct ggc gat ttc acg ccg aag gtg cgc ttc gcc ttc ccg cgc     1889
Asp Ser Ala Gly Asp Phe Thr Pro Lys Val Arg Phe Ala Phe Pro Arg
         190                 195                 200 ctc gac ggc ttc gac gtg cag atc gca ccc acg ggc gcg ggg ctc gag     1937
Leu Asp Gly Phe Asp Val Gln Ile Ala Pro Thr Gly Ala Gly Leu Glu
     205                 210                 215 ctg agc ggg ctg ccg gac tac acc gtc acc gac ggc gcg agc cag gtc     1985
Leu Ser Gly Leu Pro Asp Tyr Thr Val Thr Asp Gly Ala Ser Gln Val
 220                 225                 230                 235 gag atc gcc acc gac gag ctc gtc ctc cgg atc gac aag aac ccc tat     2033
Glu Ile Ala Thr Asp Glu Leu Val Leu Arg Ile Asp Lys Asn Pro Tyr
                 240                 245                 250 cgc ctg tcg gtc tac gag ggc gac ggc acg acg ctc atc acc cgc cag     2081
Arg Leu Ser Val Tyr Glu Gly Asp Gly Thr Thr Leu Ile Thr Arg Gln
             255                 260                 265 tac gac ccc gcg gtc ttc cgg aac atc ggt tgg gcg agc gac ggc gaa     2129
Tyr Asp Pro Ala Val Phe Arg Asn Ile Gly Trp Ala Ser Asp Gly Glu
         270                 275                 280 acg act gtg acc cgc atc gag gat cac ttc ctc aca ccc acg ggc gaa     2177
Thr Thr Val Thr Arg Ile Glu Asp His Phe Leu Thr Pro Thr Gly Glu
     285                 290                 295
```

```
cgg ttc gag ggg ttc ggc gaa cgg tac gac cgg ctc gac cac cgg gga      2225
Arg Phe Glu Gly Phe Gly Glu Arg Tyr Asp Arg Leu Asp His Arg Gly
300             305                 310                 315 acc gac gtg cac aac tac gtc tac aac cag tac cag gac cag ggc gcg      2273
Thr Asp Val His Asn Tyr Val Tyr Asn Gln Tyr Gln Asp Gln Gly Ala
                320                 325                 330 acg cgc cgc acc tac tac tcg gtg ccg tac ttc gcc aac tcc gcc ggc      2321
Thr Arg Arg Thr Tyr Tyr Ser Val Pro Tyr Phe Ala Asn Ser Ala Gly
            335                 340                 345 tac ggc atc cac gtg ccg agc acg cgc tat gcg atc ttc aat ctc gcg      2369
Tyr Gly Ile His Val Pro Ser Thr Arg Tyr Ala Ile Phe Asn Leu Ala
        350                 355                 360 acg cac ctc gac gac atg gcc gga ttc acg gtc gac acg gga ggc gcc      2417
Thr His Leu Asp Asp Met Ala Gly Phe Thr Val Asp Thr Gly Gly Ala
365                 370                 375 ctg gac tcc acg ctg acg tac cag ttc ttc acc ggc gac cag acc gag      2465
Leu Asp Ser Thr Leu Thr Tyr Gln Phe Phe Thr Gly Asp Gln Thr Glu
380                 385                 390                 395 atg ctc gac gac ttc acg gcc gag acc ggc cgt ccg ctc ctt ccg ccg      2513
Met Leu Asp Asp Phe Thr Ala Glu Thr Gly Arg Pro Leu Leu Pro Pro
                400                 405                 410 aag tgg gcg ttt gga ctc tgg ggc tcc gcc aac gag tgg aac aac cag      2561
Lys Trp Ala Phe Gly Leu Trp Gly Ser Ala Asn Glu Trp Asn Asn Gln
            415                 420                 425 gcc gag gtc gag gcc tgg ctc gac cag gtg gag agc tcc ggc atc ccg      2609
Ala Glu Val Glu Ala Trp Leu Asp Gln Val Glu Ser Ser Gly Ile Pro
        430                 435                 440 cac agc gtg ctc gtg ctc gag cag tgg agc gac gag gcg acg ttc tac      2657
His Ser Val Leu Val Leu Glu Gln Trp Ser Asp Glu Ala Thr Phe Tyr
445                 450                 455 ctc tgg aag gac gcg cag tac acc ccc acc gac ggc agc acg ccg ctg      2705
Leu Trp Lys Asp Ala Gln Tyr Thr Pro Thr Asp Gly Ser Thr Pro Leu
460                 465                 470                 475 cag tac gac gac ctc acg ttc ccc agc gga ggt gcg tgg agc gac ccc      2753
Gln Tyr Asp Asp Leu Thr Phe Pro Ser Gly Gly Ala Trp Ser Asp Pro
                480                 485                 490 aag cag atg att gcc gag gcg cac gcc cag aac gtc aag gtg ctc ctc      2801
Lys Gln Met Ile Ala Glu Ala His Ala Gln Asn Val Lys Val Leu Leu
            495                 500                 505 tgg cag att ccg gtg ctg aag gag aac ttc acc tcc aac ccg gcc acg      2849
Trp Gln Ile Pro Val Leu Lys Glu Asn Phe Thr Ser Asn Pro Ala Thr
        510                 515                 520 gcg ccg cag cag cac ctc aac gac aag gcg tat gcg cag gcc cag ggc      2897
Ala Pro Gln Gln His Leu Asn Asp Lys Ala Tyr Ala Gln Ala Gln Gly
525                 530                 535 tac ctg gtc gac gac ggc gcg ggg cag ccg tac cgc atc ccc acc gga      2945
Tyr Leu Val Asp Asp Gly Ala Gly Gln Pro Tyr Arg Ile Pro Thr Gly
540                 545                 550                 555 cag tgg ttt gga gac agc acg gtg ccc gac ttc aca gat gcc gag gcc      2993
Gln Trp Phe Gly Asp Ser Thr Val Pro Asp Phe Thr Asp Ala Glu Ala
                560                 565                 570 acg gac tgg tgg atg gac aag cgg cgg tac ctc gtc gag gag ctc ggt      3041
Thr Asp Trp Trp Met Asp Lys Arg Arg Tyr Leu Val Glu Glu Leu Gly
            575                 580                 585 gtc gac ggc ttc aag acc gac ggg agc gag gcg ctc ttc ggg cgt gac      3089
Val Asp Gly Phe Lys Thr Asp Gly Ser Glu Ala Leu Phe Gly Arg Asp
        590                 595                 600 ctg atc gtc agc gac ggg cgc cgc ggt gac gag atg cac aac gcc tac      3137
Leu Ile Val Ser Asp Gly Arg Arg Gly Asp Glu Met His Asn Ala Tyr
605                 610                 615
```

| | | |
|---|---|---|
| ccg aac gag tac acc tcc gcc tac aac gac ttc gtg cag gag acg acg<br>Pro Asn Glu Tyr Thr Ser Ala Tyr Asn Asp Phe Val Gln Glu Thr Thr<br>620                        625                        630                      635 | 3185 |
| ggc gcc gac ggc acg atc ttc agc cgg gcg ggc acc tcc ggc ggc cag<br>Gly Ala Asp Gly Thr Ile Phe Ser Arg Ala Gly Thr Ser Gly Gly Gln<br>                  640                        645                        650 | 3233 |
| agc gaa tcc atc ttc tgg gcc ggg gac cag gcg tcg acg ttc ggc gct<br>Ser Glu Ser Ile Phe Trp Ala Gly Asp Gln Ala Ser Thr Phe Gly Ala<br>655                        660                        665 | 3281 |
| ttc cag gag gcc gtc cgg gcc ggg cag agc gcg ggc cag tcg gga gtg<br>Phe Gln Glu Ala Val Arg Ala Gly Gln Ser Ala Gly Gln Ser Gly Val<br>                  670                        675                        680 | 3329 |
| ccg ttc tgg gcc tgg gac ctc ggc ggc ttc acc ggg tcg ttc cca agc<br>Pro Phe Trp Ala Trp Asp Leu Gly Gly Phe Thr Gly Ser Phe Pro Ser<br>685                        690                        695 | 3377 |
| gcg gag ctg tat ctg cgc tcg acc gct cag gcg gtg ttc tcg ccg atc<br>Ala Glu Leu Tyr Leu Arg Ser Thr Ala Gln Ala Val Phe Ser Pro Ile<br>700                        705                        710                        715 | 3425 |
| atg cag tac cac tcg gag aag gcc gac ccc agt ccg tcc gag gcg cgc<br>Met Gln Tyr His Ser Glu Lys Ala Asp Pro Ser Pro Ser Glu Ala Arg<br>                  720                        725                        730 | 3473 |
| acg ccc tgg aac gtg cag gcg cgc acc ggg aac acc act gtc gtc ccc<br>Thr Pro Trp Asn Val Gln Ala Arg Thr Gly Asn Thr Thr Val Val Pro<br>                  735                        740                        745 | 3521 |
| acc ttc gcc cgt tac gcg aac gta cgg atg aac ctc gtg ccc tat ctg<br>Thr Phe Ala Arg Tyr Ala Asn Val Arg Met Asn Leu Val Pro Tyr Leu<br>          750                        755                        760 | 3569 |
| tac acg gag gcg gac gac agc gcg acg acg ggt gtg ccg atg atg cgc<br>Tyr Thr Glu Ala Asp Asp Ser Ala Thr Thr Gly Val Pro Met Met Arg<br>765                        770                        775 | 3617 |
| gcg atg agc ctc gcg ttc ccc gac gac ccg gat gcc gcg cag tac gac<br>Ala Met Ser Leu Ala Phe Pro Asp Asp Pro Asp Ala Ala Gln Tyr Asp<br>780                        785                        790                        795 | 3665 |
| cag cag tac atg ttc ggg tct cag ctg ctg gtc gca ccg att acg aac<br>Gln Gln Tyr Met Phe Gly Ser Gln Leu Leu Val Ala Pro Ile Thr Asn<br>                  800                        805                        810 | 3713 |
| cag ggc cag acc gtg aaa gac gtc tac ctg ccc gcg ggc gag tgg tac<br>Gln Gly Gln Thr Val Lys Asp Val Tyr Leu Pro Ala Gly Glu Trp Tyr<br>                  815                        820                        825 | 3761 |
| gac ttc tgg aac ggc gga cgc gcg agc ggc gag ggc gtg aag atg tac<br>Asp Phe Trp Asn Gly Gly Arg Ala Ser Gly Glu Gly Val Lys Met Tyr<br>          830                        835                        840 | 3809 |
| gac gcc gga ccc gac ggc atc ccc gta tac gct cgc gcc gga gcg gtc<br>Asp Ala Gly Pro Asp Gly Ile Pro Val Tyr Ala Arg Ala Gly Ala Val<br>845                        850                        855 | 3857 |
| atc ccg ctc aac ctc aac gac gcg tat gag gtg ggc ggc acg atc ggc<br>Ile Pro Leu Asn Leu Asn Asp Ala Tyr Glu Val Gly Gly Thr Ile Gly<br>860                        865                        870                        875 | 3905 |
| aac gac gtg gag agc tac gac aac ctt gtg ttc cgc gtt tac ccc tcc<br>Asn Asp Val Glu Ser Tyr Asp Asn Leu Val Phe Arg Val Tyr Pro Ser<br>                  880                        885                        890 | 3953 |
| ggt gag agc agc tac gag tac ttc gaa gac caa gcg aac gcg cac cgc<br>Gly Glu Ser Ser Tyr Glu Tyr Phe Glu Asp Gln Ala Asn Ala His Arg<br>                  895                        900                        905 | 4001 |
| cgg atc gat gtc tcg gcc gac cgc gca gcg cgc acg gtc gag gtg tct<br>Arg Ile Asp Val Ser Ala Asp Arg Ala Ala Arg Thr Val Glu Val Ser<br>          910                        915                        920 | 4049 |
| gct ccc gcg ctc acg acc gcg agc acc ttc cag gtg tcg ggc acc aag<br>Ala Pro Ala Leu Thr Thr Ala Ser Thr Phe Gln Val Ser Gly Thr Lys | 4097 |

```
                      925                 930                 935
ccc gac acc gtg acc gtc gcg ggc tcg gca ctg cct gag gtc aac agc    4145
Pro Asp Thr Val Thr Val Ala Gly Ser Ala Leu Pro Glu Val Asn Ser
940                 945                 950                 955 gtg agc gcg ctg gcc gca tcc acc gag gcc tgg tac tgg gat gcg aag    4193
Val Ser Ala Leu Ala Ala Ser Thr Glu Ala Trp Tyr Trp Asp Ala Lys
                960                 965                 970 cag cag ctg acg tac gtg aag gtc ggt gcg agc acc ggc gag cgc acg    4241
Gln Gln Leu Thr Tyr Val Lys Val Gly Ala Ser Thr Gly Glu Arg Thr
            975                 980                 985 atc ctc ctg ctg ggc gtc gac aag gcc ggg tac gag gcc gag ttc gcg    4289
Ile Leu Leu Leu Gly Val Asp Lys Ala Gly Tyr Glu Ala Glu Phe Ala
        990                 995                 1000 ggt cat acg gcc gtc tcg acg aac gcc gac cac ccg ggc tac acc        4334
Gly His Thr Ala Val Ser Thr Asn Ala Asp His Pro Gly Tyr Thr
    1005                1010                1015 ggg ctc ggc ttc gtc gac ggc ttc gcg aac gca gga gac gcg gtg        4379
Gly Leu Gly Phe Val Asp Gly Phe Ala Asn Ala Gly Asp Ala Val
1020                1025                1030 gag ttc gac gtg tgg gcc gag gag aac ggc gcg cac cag ctc cgc        4424
Glu Phe Asp Val Trp Ala Glu Glu Asn Gly Ala His Gln Leu Arg
1035                1040                1045 ttc cgc tac gga aac gga gcg gcg acc ccc gcc acc cgc acg atc        4469
Phe Arg Tyr Gly Asn Gly Ala Ala Thr Pro Ala Thr Arg Thr Ile
1050                1055                1060 cgg gtc gac gga gcg cct ctg gga acg ctg tcg ctt ccg ccc acc        4514
Arg Val Asp Gly Ala Pro Leu Gly Thr Leu Ser Leu Pro Pro Thr
1065                1070                1075 ggg tcg tgg agt tcg tgg ggc acg gcc tcg atc gac gtg acc ctc        4559
Gly Ser Trp Ser Ser Trp Gly Thr Ala Ser Ile Asp Val Thr Leu
1080                1085                1090 cca ccc gga cgc cac gcc gta cgg atc gag tac gcc gga ggc gat        4604
Pro Pro Gly Arg His Ala Val Arg Ile Glu Tyr Ala Gly Gly Asp
1095                1100                1105 tcc ggc ggc gtc aac ctc gac aac ctc gtc ctc gcg cgc tga            4646
Ser Gly Gly Val Asn Leu Asp Asn Leu Val Leu Ala Arg
1110                1115                1120 gcgcacacgg gaaagggaga agaaccatgc ctgctcttcc gtggcgccgc acgacggcgc    4706
tcgcgctcac cacggcggtg acggccgcga ccctggtcgc cgtcggggtg aacgacgccg    4766
gtcaggcggc ggctgctccc ctgggcgtgc aacgcgcgca gttccagtcg ggtcgagct     4826
acctcgtcgt cgaggtgctc gatgacgacc tcgtccactt cgagctggcc gggggcggca    4886
ccgcccccgg cacgggctcc ccgctgttca cgacgcctca ggtcgcgaag cacgactacg    4946
cgggacccga cgtgttcacc cagaccgggt ctgttctgca gaccgcggcg atgcgcatcg    5006
aggtcgatcc cgcggatctg tgcgtgacgg ccaccgacat cacccgcacc ccgaaccttg    5066
tactgcacga ggcgtgtccc gccgacctcg gccaggcgtg gaaggggctg aacatcacga    5126
ggtcggcgat ggagaacgcc tacggtctcg gcagcagtt cttcacgggc ggcagcgcgg    5186
acggcgactg ggtgggccgc acccgcaccc cgggtggcac ctacggcaac gcgatggtgt    5246
tcgaccccga gaacgggccg gtcggcaaca cgcagatccc ggtgctcttc gcggtcggcg    5306
atgcaaacgc gaactacggg ctgttcgtcg atcagctgta caagcaggaa tggaacctca    5366
ccggcgaccc gtggacggtg cgcatgtggg cgaccaggt gcgctggtac ctcatgagcg     5426
gcgacgacct gcccgacctt cgccacgact acatggagct gacgggcacc ccgcccgtgc    5486
cgccgaagaa ggcgttcggg ctctgggtgt cggagttcgg ctacgacaac tggagcgagg    5546
```

```
tcgacaatac gatcgcgggc ctgcgctcgg ccgactttcc ggtcgatggc gcgatgctcg    5606
acgtacagtg gttcggggc gtcaccgccg actcggacga cacccgcatg ggcaccctcg     5666
attgggacac gtcgaggttt cccgaccctg cgggaaagat cgccgacctc gccgaggacg    5726
gcgtcggcat catcccgatc gaggagtcgt acgtcggtcg caacctgccg gagcacgccc    5786
ggatggcggc ggacggttac ctcgtgcgct ccggctgcgc tacgtgcccg ccggtgtacc    5846
tgacggggaa cccctggtgg ggcaagggcg ggatgatcga ctggacgcag ccggaagccg    5906
gcgccgtctg gcacgacgag cagcgccagc atctcgtcga cgagggcgta ctgggccact    5966
ggctcgatct cggcgaaccg gagatgtacg acccgaacga ctggaccgcc ggcgtcatcc    6026
ccggcaagca cgcgcacgcc gactatcaca acgcgtacaa cctgctgtgg gcgcagagca    6086
tcgccgacgg gtacgccgac aacggcgtgc agaagcgtcc cttcatgctg acgcgcgccg    6146
cggccgc                                                               6153
```